United States Patent
Webber et al.

(10) Patent No.: US 11,806,407 B2
(45) Date of Patent: Nov. 7, 2023

(54) REFILLABLE DRUG DELIVERY BY AFFINITY HOMING

(71) Applicant: UNIVERSITY OF NOTRE DAME DU LAC, Notre Dame, IN (US)

(72) Inventors: Matthew J. Webber, South Bend, IN (US); Lei Zou, South Bend, IN (US)

(73) Assignee: UNIVERSITY OF NOTRE DAME DU LAC, South Bend, IN (US)

( * ) Notice: Subject to any disclaimer, the term of this patent is extended or adjusted under 35 U.S.C. 154(b) by 0 days.

(21) Appl. No.: 17/045,469

(22) PCT Filed: Apr. 5, 2019

(86) PCT No.: PCT/US2019/026063
§ 371 (c)(1),
(2) Date: Oct. 5, 2020

(87) PCT Pub. No.: WO2019/195728
PCT Pub. Date: Oct. 10, 2019

(65) Prior Publication Data
US 2021/0154322 A1     May 27, 2021

Related U.S. Application Data

(60) Provisional application No. 62/653,661, filed on Apr. 6, 2018.

(51) Int. Cl.
| *A61K 47/69* | (2017.01) |
| *A61P 35/04* | (2006.01) |
| *A61K 9/00* | (2006.01) |
| *A61K 9/06* | (2006.01) |
| *A61K 9/107* | (2006.01) |
| *A61K 31/167* | (2006.01) |
| *A61K 31/573* | (2006.01) |
| *A61K 31/704* | (2006.01) |

(52) U.S. Cl.
CPC ........ *A61K 47/6903* (2017.08); *A61K 9/0024* (2013.01); *A61K 9/06* (2013.01); *A61K 9/1075* (2013.01); *A61K 31/167* (2013.01); *A61K 31/573* (2013.01); *A61K 31/704* (2013.01); *A61P 35/04* (2018.01)

(58) Field of Classification Search
CPC .... A61K 47/6903; A61K 9/0024; A61K 9/06; A61K 9/1075; A61K 31/167; A61K 31/573; A61K 31/704; A61K 47/10; A61K 47/32; A61P 35/04; A61P 23/02; A61P 25/04; A61P 35/00
See application file for complete search history.

(56) References Cited

U.S. PATENT DOCUMENTS

| 7,413,752 B2 | 8/2008 | Sawhney |
| 7,850,992 B2 | 12/2010 | Kim et al. |
| 8,378,059 B2 | 2/2013 | Rauwald et al. |
| 8,999,916 B2 | 4/2015 | Hauser et al. |
| 9,067,084 B2 | 6/2015 | Hauser et al. |
| 9,120,841 B2 | 9/2015 | Hauser et al. |
| 9,326,934 B2 | 5/2016 | Gravett et al. |
| 9,687,591 B2 | 6/2017 | Hauser et al. |
| 9,925,307 B2 | 3/2018 | Hauser et al. |
| 2012/0220518 A1 | 8/2012 | von Recum et al. |
| 2017/0119892 A1 | 5/2017 | Brudno et al. |

FOREIGN PATENT DOCUMENTS

WO    WO2005112919 A2    12/2015

OTHER PUBLICATIONS

Ahn et al., "Supramolecular velcro for reversible underwater adhesion", Angewandte Chemie 2013, 52 (11), pp. 3140-3144.
Alley et al., "Antibody-drug conjugates: targeted drug delivery for cancer", Curr Opin Chem Biol, 2010, 14 (4), pp. 529-537.
Amorena et al., "Antibiotic susceptibility assay for Staphylococcus aureus in biofilms developed in vitro", J Antimicrob Chemother., 1999, 44 (1), pp. 43-55.
Anderson, "Mechanisms of Inflammation and Infection with Implanted Devices", Cardiovasc Pathol, 1993, 2 (3), pp. S33-S41.
Assaf et al., "Cucurbiturils: from synthesis to high-affinity binding and catalysis", Chem Soc Rev, 2015, 44 (2), pp. 394-418.
Ayhan et al., "Comprehensive Synthesis of Monohydroxy-Cucurbit[n]urils (n = 5, 6, 7, 8): High Purity and High Conversions", Journal of the American Chemical Society, 2015, p. 10238-10245.
Bryers et al., "Engineering biomaterials to integrate and heal: the biocompatibility paradigm shifts", Biotechnol Bioeng, 2012, 109 (8), pp. 1898-1911.
Burdick et al., Hyaluronic acid hydrogels for biomedical applications. Adv Mater, 2011, 23 (12), pp. H41-H56.
Cao et al., "Cucurbit[7]urilguest pair with an attomolar dissociation constant", Angewandte Chemie 2014, 53 (4), pp. 1006-1011.
Chen et al., "Reactivity of functional groups on the protein surface: development of epoxide probes for protein labeling", Journal of the American Chemical Society, 2003, 125 (27), pp. 8130-8133.
Chinai et al., "Molecular recognition of insulin by a synthetic receptor", Journal of the American Chemical Society, 2011, 133 (23), pp. 8810-8813.
Cho et al., "Therapeutic nanoparticles for drug delivery in cancer", Clin Cancer Res, 2008, 14 (5), pp. 1310-1316.
Darouiche, "Treatment of infections associated with surgical implants", N Engl J Med, 2004, 350 (14), pp. 1422-1429.
Ferrari, "Cancer nanotechnology: opportunities and challenges", Nat Rev Cancer, 2005, 5 (3), pp. 161-171.
Hermanson, Chapter 20—Antibody Modification and Conjugation. In Bioconjugate Techniques, Academic Press: Boston, 2013; pp. 867-920.

(Continued)

*Primary Examiner* — Matthew P Coughlin
*Assistant Examiner* — Thurman Wheeler
(74) *Attorney, Agent, or Firm* — Michael Best & Friedrich LLP

(57) ABSTRACT

Described herein are compositions and methods for a novel drug delivery platform using affinity homing. Also disclosed herein are a drug delivery system, methods for using the novel drug delivery platform and a kit.

33 Claims, 69 Drawing Sheets

(56) References Cited

OTHER PUBLICATIONS

Hilderbrand et al., "Near-infrared fluorescence: application to in vivo molecular imaging", Curr Opin Chem Biol, 2010, 14 (1), pp. 71-79.

Hoffman, "The origins and evolution of "controlled" drug delivery systems", J Control Release, 2008, 132 (3), pp. 153-163.

Jeon et al., Complexation of ferrocene derivatives by the cucurbit[7]uril host: a comparative study of the cucurbituril and cyclodextrin host families. J Am Chem Soc, 2005, 127 (37), pp. 12984-12989.

Jia et al., "Mechanisms of drug combinations: interaction and network perspectives", Nat Rev Drug Discov, 2009, 8 (2), pp. 111-128.

Kennecke et al., "Metastatic behavior of breast cancer subtypes", J Clin Oncol., 2010, 28 (20), pp. 3271-3277.

Lee et al., "Supramolecular fishing for plasma membrane proteins using an ultrastable synthetic host-guest binding pair", Nat Chem, 2011, 3 (2), pp. 154-159.

Lin et al., "Mechanistic investigation of the Staudinger ligation", Journal of the American Chemical Society, 2005, 127 (8), pp. 2686-2695.

Liu et al., "The cucurbit[n]uril family: Prime components for self-sorting systems", Journal of the American Chemical Society, 2005, 127 (45), pp. 15959-15967.

Loi et al., "Prognostic and predictive value of tumor-infiltrating lymphocytes in a phase III randomized adjuvant breast cancer trial in node-positive breast cancer comparing the addition of docetaxel to doxorubicin with doxorubicin-based chemotherapy: BIG 02-98", J Clin Oncol 2013, 31 (7), pp. 1-9.

Malam et al., "Liposomes and nanoparticles: nanosized vehicles for drug delivery in cancer", Trends Pharmacol Sci, 2009, 30 (11), pp. 592-599.

Malhotra et al., "Neoadjuvant and adjuvant chemotherapy with doxorubicin and docetaxel in locally advanced breast cancer", Clin Breast Cancer, 2004, 5 (5), pp. 377-384.

Pai et al., "Cardiotoxicity of chemotherapeutic agents: incidence, treatment and prevention", Drug Saf, 2000, 22 (4), pp. 263-302.

Paludan et al., "Immune Sensing of DNA", Immunity, 2013, 38 (5), pp. 870-880.

Rautio et al., "Prodrugs: design and clinical applications", Nature Reviews Drug Discovery, 2008, 7 (3), pp. 255-270.

Schreiber, "Organic chemistry: Molecular diversity by design", Nature, 2009, 457 (7226), pp. 153-154.

Schreiber, Target-oriented and diversity-oriented organic synthesis in drug discovery. Science, 2000, vol. 287, No. 5460, pp. 1964-1969.

Shachaf et al., "The biocompatibility of Pluronic (R) F127 fibrinogen-based hydrogels", Biomaterials, 2010, 31 (10), pp. 2836-2847.

Shaikh et al., "Complexation of acridine orange by cucurbit[7]uril and beta-cyclodextrin: photophysical effects and pKa shifts", Photochemical & photobiological sciences: Official journal of the European Photochemistry Association and the European Society for Photobiology, 2008, 7 (4), pp. 408-414.

Singh et al., "Recent trends in targeted anticancer prodrug and conjugate design", Curr Med Chem, 2008, 15 (18), pp. 1802-1826.

Szakacs et al., "Targeting multidrug resistance in cancer", Nature Reviews Drug Discovery, 2006, 5 (3), pp. 219-234.

Tong et al., "*Staphylococcus aureus* infections: epidemiology, pathophysiology, clinical manifestations, and management", Clin Microbiol Rev, 2015, 28 (3), pp. 603-661.

Vinciguerra et al., "Synthesis and Self-Assembly Processes of Monofunctionalized Cucurbit[7]uril", Journal of the American Chemical Society, 2012, 134 (31), pp. 13133-13140.

Volkova et al., "Anthracycline cardiotoxicity: prevalence, pathogenesis and treatment", Curr Cardiol Rev, 2011, 7 (4), pp. 214-220.

Walker et al., "The Potential of Cucurbit[n]urils in Drug Delivery", Isr J Chem, 2011, 51 (5-6), pp. 616-624.

Wang et al., "Antibody structure, instability, and formulation", J Pharm Sci-Us, 2007, 96 (1), pp. 1-26.

Webber et al., "Controlled release of dexamethasone from peptide nanofiber gels to modulate inflammatory response", Biomaterials, 2012, 33 (28), pp. 6823-6832.

Webber et al., "Switching of self-assembly in a peptide nanostructure with a specific enzyme", Soft Matter, 2011, 7 (20), pp. 9665-9672.

Westphal et al., "A phase 3 trial of local chemotherapy with biodegradable carmustine (BCNU) wafers (Gliadel wafers) in patients with primary malignant glioma", Neuro Oncol, 2003, 5 (2), pp. 79-88.

Zhang et al., "Drug-induced regeneration in adult mice", Science translational medicine, 2015, 7 (290), pp. 290-292.

Zhang et al., "Surface modification of stainless steel by grafting of poly(ethylene glycol) for reduction in protein adsorption", Biomaterials, 2001, 22 (12), pp. 1541-1548.

Brudno et al., "In Vivo Targeting through Click Chemistry", ChemMedChem, vol. 10, 2015, pp. 617-620.

Brudno et al., "Refilling drug delivery depots through the blood", PNAS, vol. 111, No. 35, Sep. 2014, pp. 12722-12727.

Thatiparti et al., "Cyclodextrin-based device coatings for affinity-based release of antibiotics", Biomaterials, vol. 31, 2010, pp. 2335-2347.

Webber et al., "Drug Delivery by supramolecular design", Chem Soc Rev, vol. 46, 2017, pp. 6600-6620.

Duan et al., "pH-Responsive Supramolecular Vesicles Based on Water-Soluble Pillar[6]arene and Ferrocene Derivative for Drug Delivery", J. Am. Chem. Soc., vol. 135, 2013, p. 10542-10549.

Park et al., "Cucurbituril-based nanoparticles: a new efficient vehicle for targeted intracellular delivery of hydrophobic drugs", ChemCommun., 2009, pp. 71-73.

Saboktakin et al., "Supramolecular hydrogels as drug delivery systems", International Journal of Biological Macromolecules, vol. 75, 2015, pp. 426-436.

International Search Report and Written Opinion for Application No. PCT/US19/26063 dated Jun. 20, 2019 (14 pages).

REFILLABLE DRUG DELIVERY BY AFFINITY HOMING

CROSS-REFERENCE TO RELATED APPLICATIONS

This application is a U.S. national stage entry of International Patent Application No. PCT/US2019/026063, filed on Apr. 5, 2019, which claims priority to U.S. Provisional Patent Application No. 62/653,661, filed on Apr. 6, 2018, the entire contents of each of which are fully incorporated herein by reference.

TECHNICAL FIELD

The present disclosure relates to compositions and methods for a novel drug delivery platform using affinity homing.

BACKGROUND OF THE INVENTION

When thinking about the future of medicine, one assumes continued advancement in the ability to shrink medical interventions without any loss of control or precision. This was dramatized in the 1966 movie "Fantastic Voyage" by a miniature submarine that enters the blood stream on a mission to repair damage in the brain of a scientist. Yet, 50 years later, pharmaceutical practice still suffers from poor regional selectivity in drug action. This is juxtaposed with a continued expansion in the discovery of small molecule therapeutic entities, made possible by work in chemical biology, diversity-oriented synthesis, and medicinal chemistry. The process for discovery in these fields typically identifies drugs from promising activity in vitro. However, delivering these molecules to their site of action in the body remains a challenge due to issues related to poor solubility or toxic off-target activity. In the best-case scenario, poor regional selectivity of a pharmaceutical compound may entail escalation of the required dose to achieve effect. However, as the adage in toxicology goes: "the dose makes the poison." In chemotherapy, for example, there are many well-known side-effects that range in severity from mild fatigue to severe cardiotoxicity. Treatment-associated morbidities dramatically impact the quality of life for many patients, limit the dose of drug that can be administered, and in some cases can be lethal.

Approaches that have been evaluated toward these goals have included systemically administered carriers or drug delivery devices with targeting to diseased tissue often mediated using biological recognition (e.g., antibodies). Unfortunately, approaches using antibody-drug conjugates have shown that very little of these (0.001-0.01%) agents actually target to the sites of disease, in spite of affinities ranging from $\sim 10^8$-$10^{12}$ $M^{-1}$ Thus, there is an urgent need for improved strategies for targeting and localizing drug to sites within the body to improve small molecule drug practice.

BRIEF SUMMARY OF THE INVENTION

In one aspect, the disclosure provides a thermoresponsive hydrogel comprising a cucurbit[n]uril moiety, wherein n is an integer from 5-8 and a polymer. The thermoresponsive hydrogel may have a gelation temperature between 25° C. and 35° C.

In another aspect, the disclosure provides a drug delivery system comprising a thermoresponsive hydrogel a described herein and at least one therapeutic agent reversibly bound to the thermoresponsive hydrogel.

In another aspect, the disclosure provides a kit comprising a thermoresponsive hydrogel as described herein and at least one therapeutic agent.

In another aspect, the disclosure provides a method for treating a disease or disorder in a subject in need thereof. The method may comprise implanting the thermoresponsive hydrogel as described herein at a desired location in a subject and administering at least one dose of a first therapeutic agent to the subject. The first therapeutic agent may reversibly bind to the thermoresponsive hydrogel.

Other aspects and embodiments of the disclosure will become apparent in light of the following description and drawings.

BRIEF DESCRIPTIONS OF THE DRAWINGS

The patent or application file contains at least one drawing executed in color. Copies of this patent or patent application publication with color drawings will be provided by the Office upon request and payment of the necessary fee.

FIG. 1 is a schematic showing the use of supramolecular homing in order to drive accumulation of small molecules to desired sites in the body, so as to improve biomedical device practice or bias distribution of systemically administered drugs to sites of diseased tissue in cancer applications.

FIG. 2A, FIG. 2B, FIG. 2C and FIG. 2D are synthetic schemes and spectra of the generation of CB[7] analogues. FIG. 2A is the synthetic strategies used to generate different monofunctional CB[7] with reactive handles for "click" chemistry (Azide), reaction with amines (Epoxide) or reaction with thiols (Maleimide). FIG. 2B and FIG. 2C show the NMR (FIG. 2B) and ESI-MS (FIG. 2C) used to characterize the production of CB[7]-$N_3$, in both cases using a guest probe to assist in characterization. FIG. 2D shows the scheme to use CB[7] analogues to modify medical devices based on biopolymers or metals.

Figure 4A:
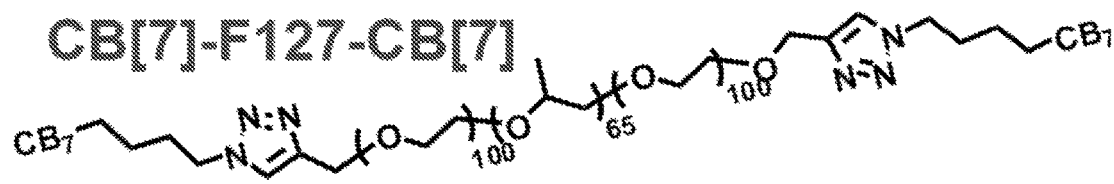
Figure 4B:
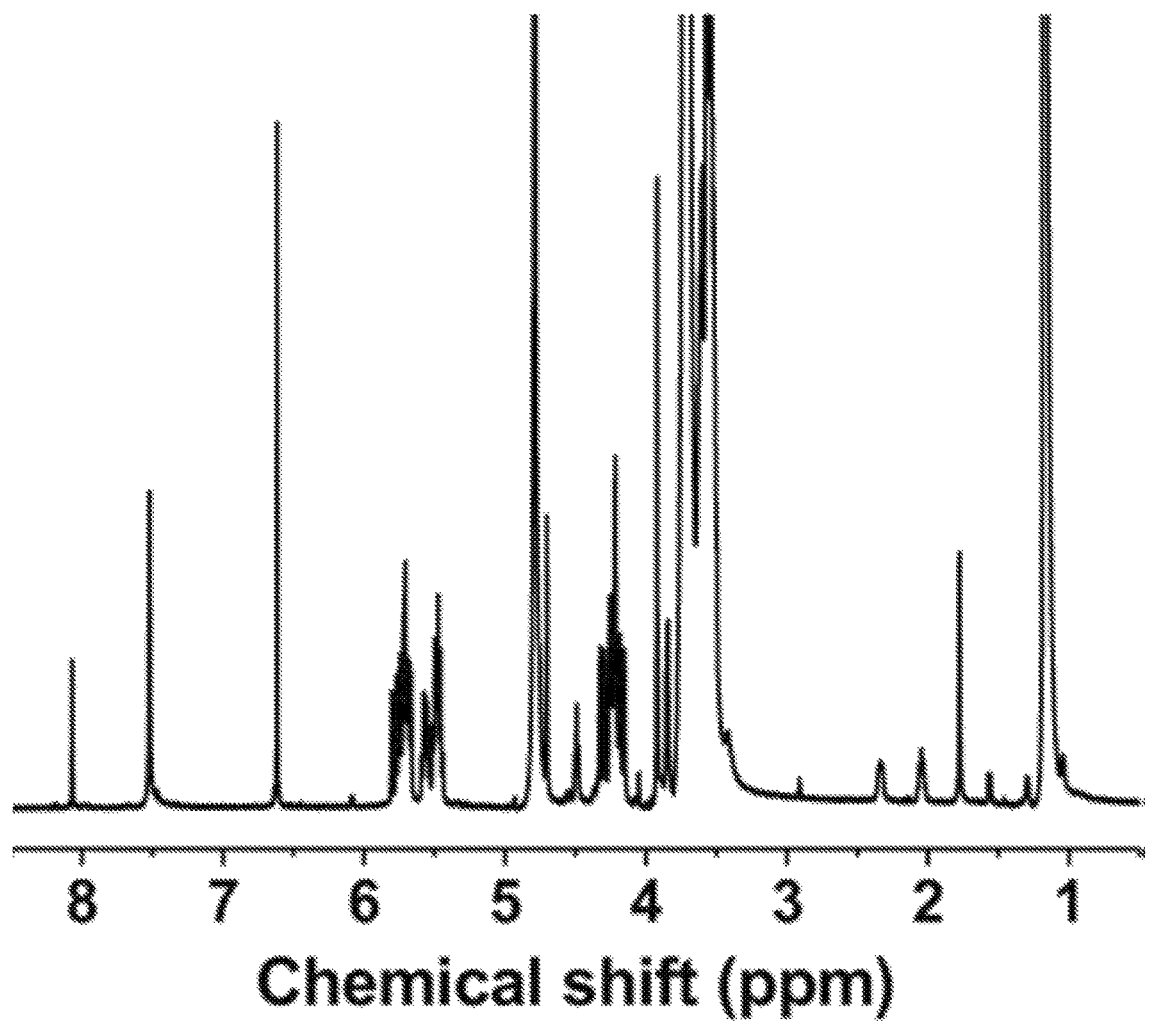
Figure 4C:
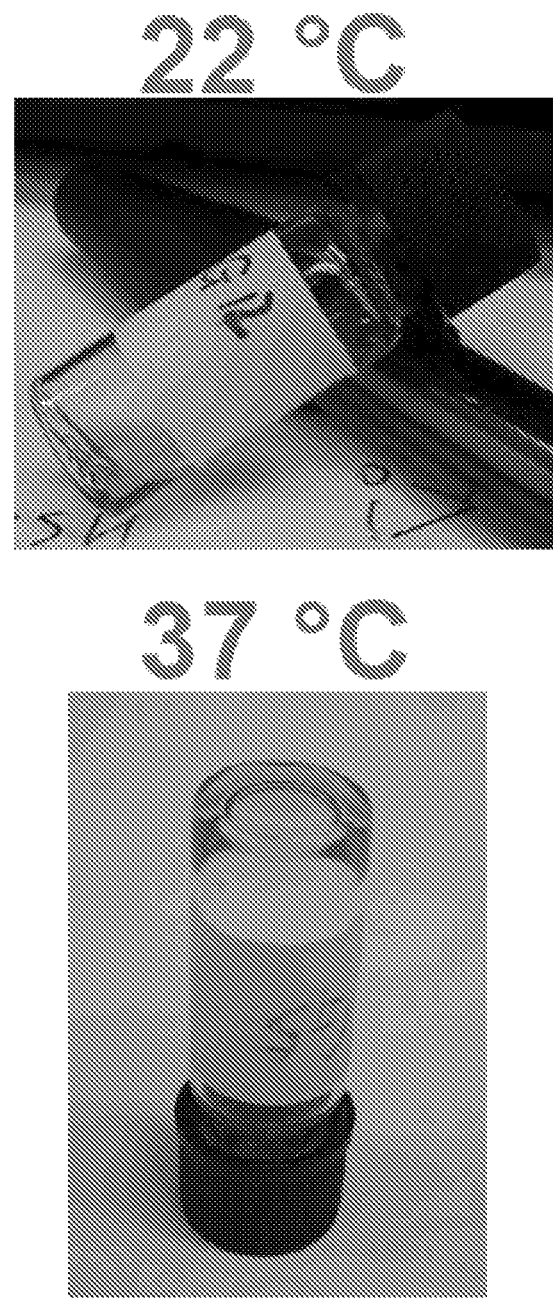

FIG. 4A, FIG. 4B, and FIG. 4C show the structure of a thermoresponsive CB[7]-containing polymer (FIG. 4A), the NMR spectra of the polymer (FIG. 4B), and photographs of physical characteristics at 22° C. and 37° C. when combined with a 4-arm PEG-linker, demonstrating thermoresponsive gelation.

Figure 4D:
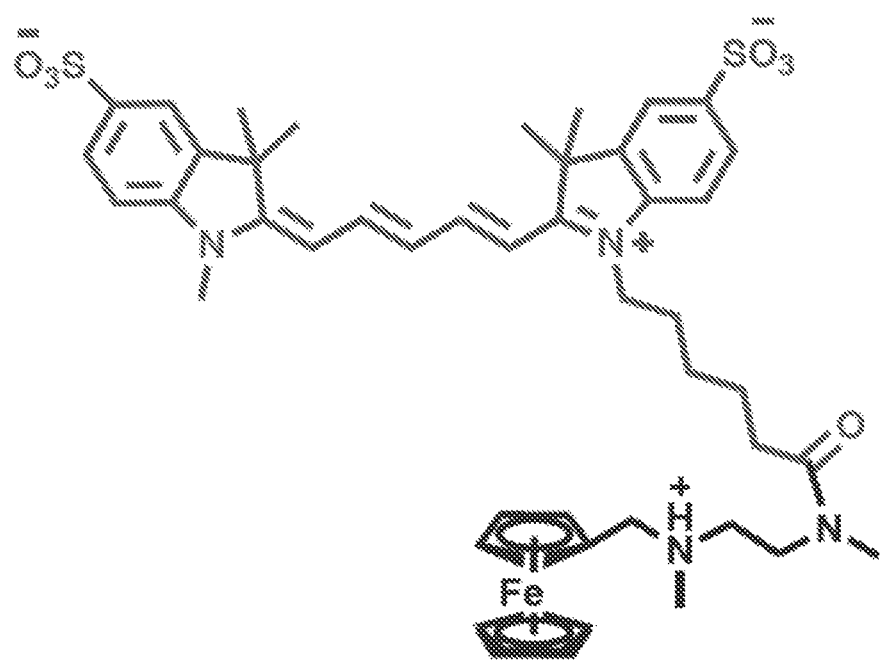
Figure 4E:
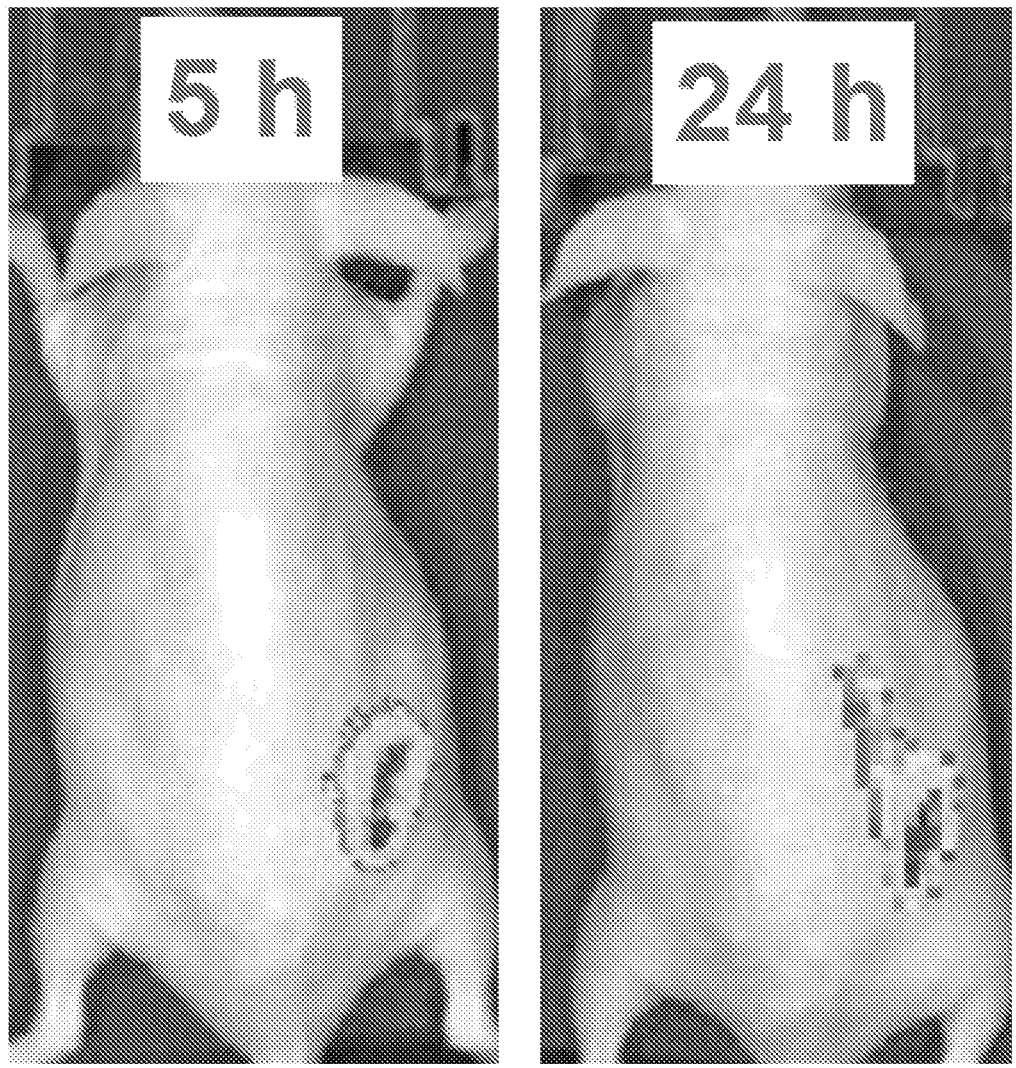

FIG. 4D and FIG. 4E show the structure of a model Cy5 prodrug created from fusing a Cy5 dye to a ferrocene guest (FIG. 4D) the site-specific homing to the implanted CB[7] hydrogel over time following Cy5 prodrug systemic administration (FIG. 4E).

Figure 5:
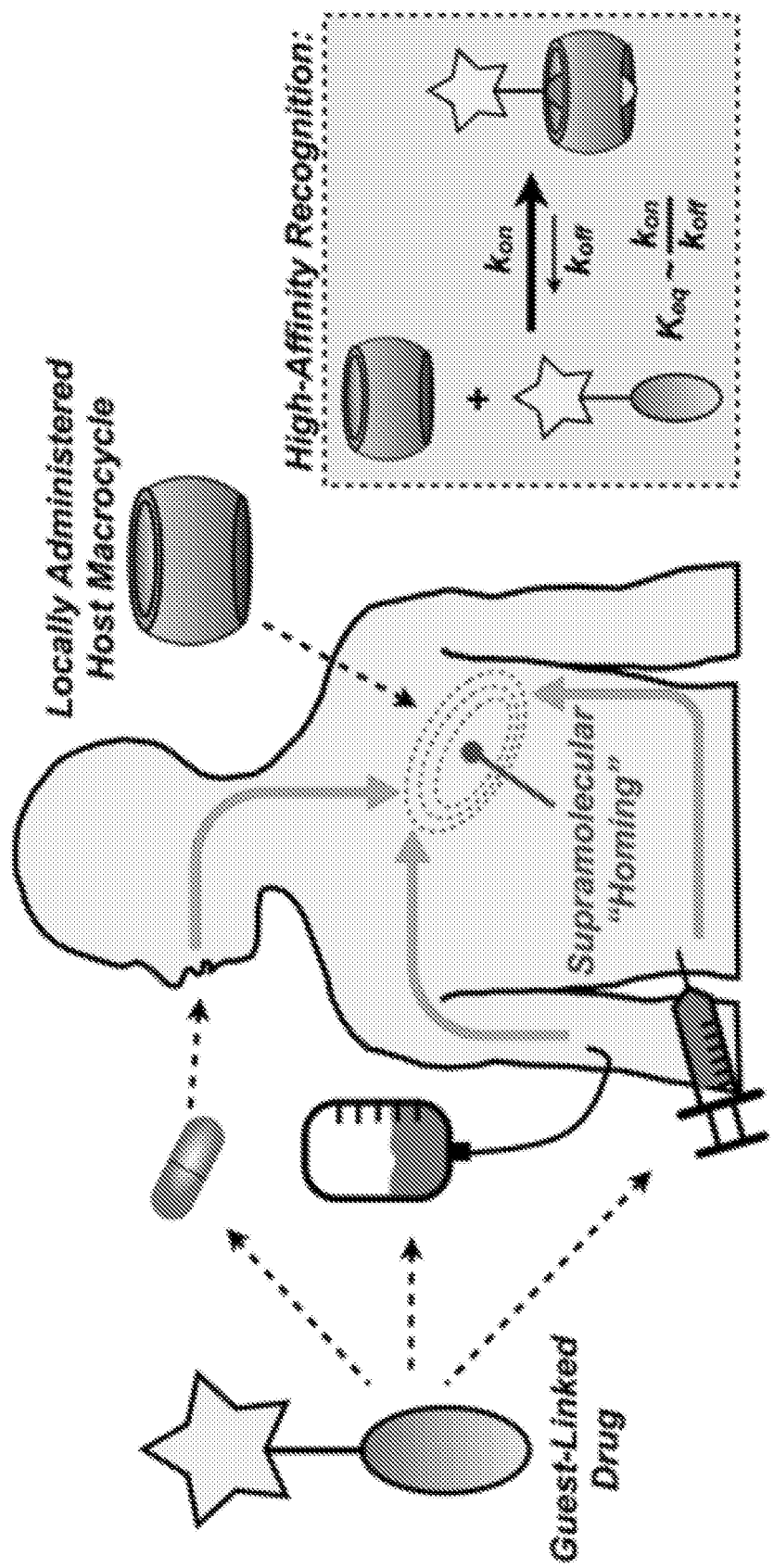

FIG. 5 is a schematic of the approach for supramolecular homing of guest-appended small molecules on the basis of affinity for locally applied host macrocycles.

Figure 6A:
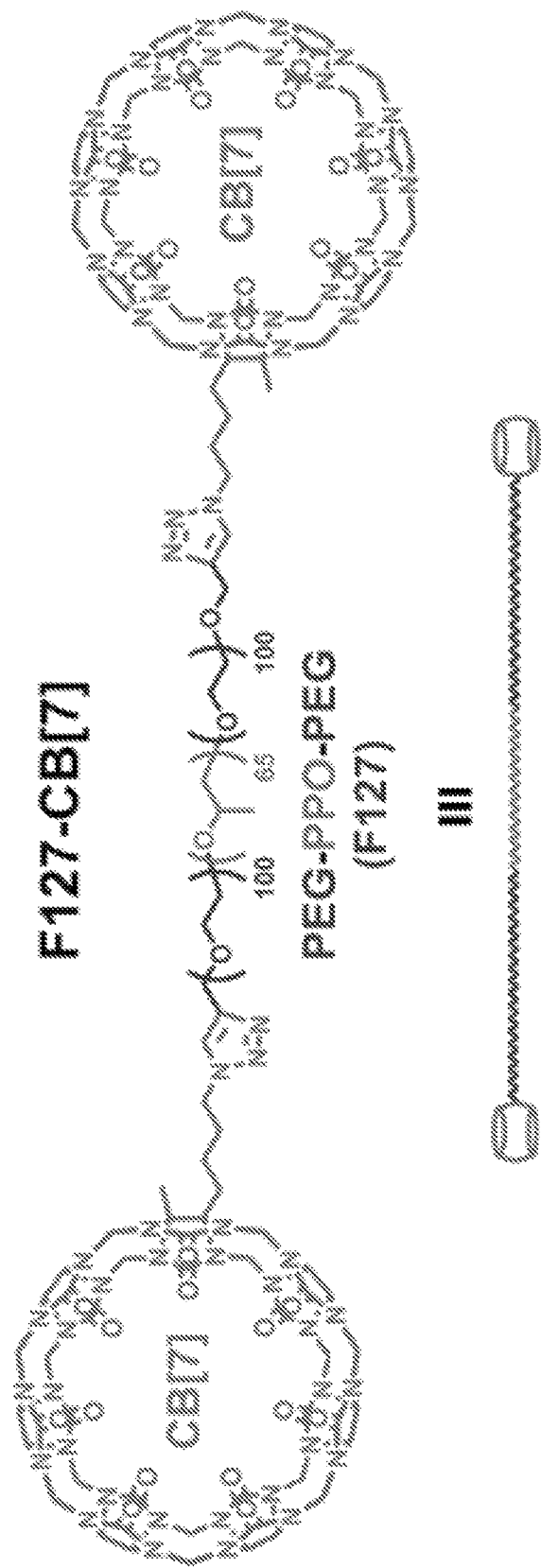
Figure 6B:
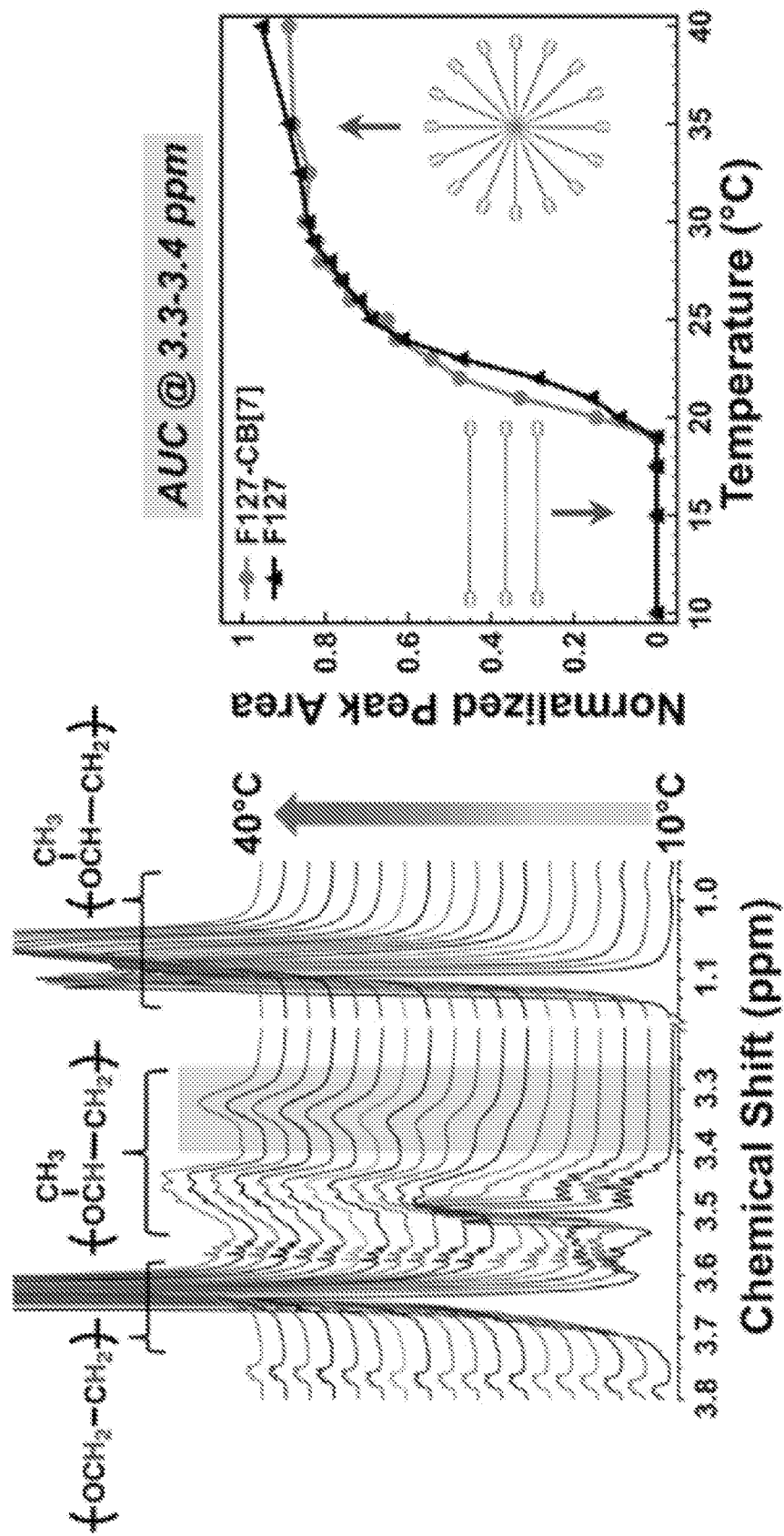

FIG. 6A, FIG. 6B, FIG. 6C, FIG. 6D, FIG. 6E, FIG. 6F, FIG. 6G, FIG. 6H and FIG. 6I show the design of a thermoresponsive supramolecular hydrogel for localized drug homing. Pluronic F127 is end-modified with cucurbit[7]uril (CB[7]) through copper-catalyzed click chemistry (FIG. 6A). Variable temperature $^1$H-NMR of F127-CB[7], with PPO-specific signal (purple shaded region), quantify micelle formation compared to unmodified F127 (FIG. 6B).

Figure 6C:
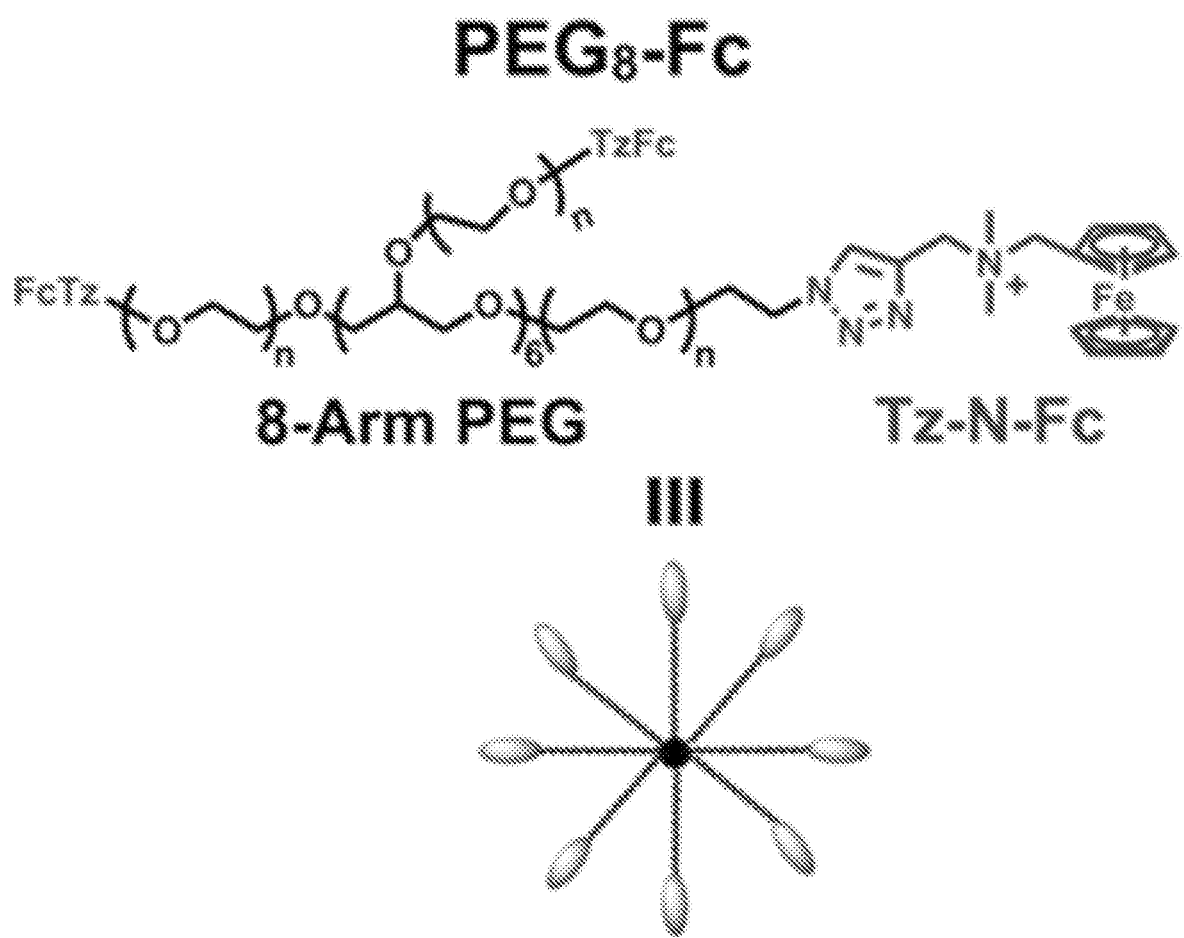
Figure 6D:
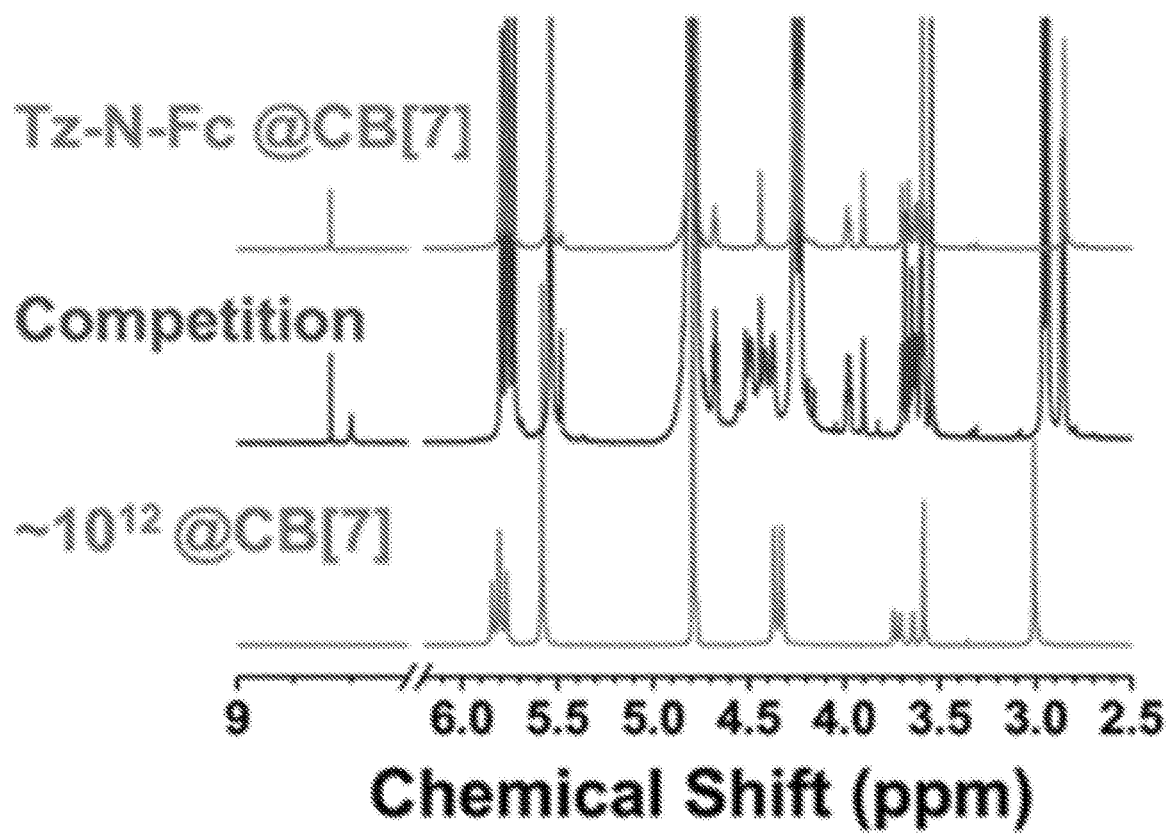
Figure 6E:
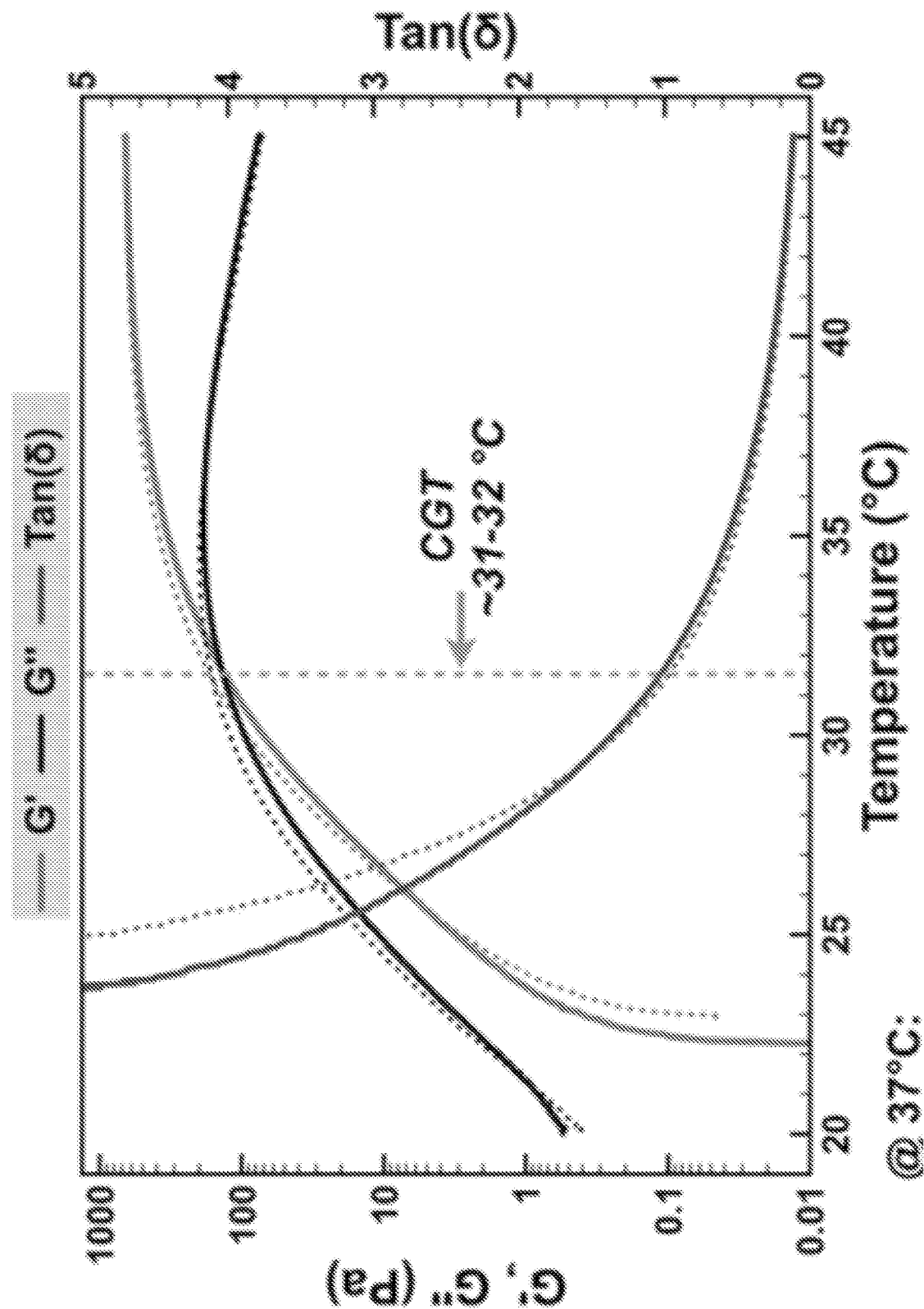
Figure 6F:
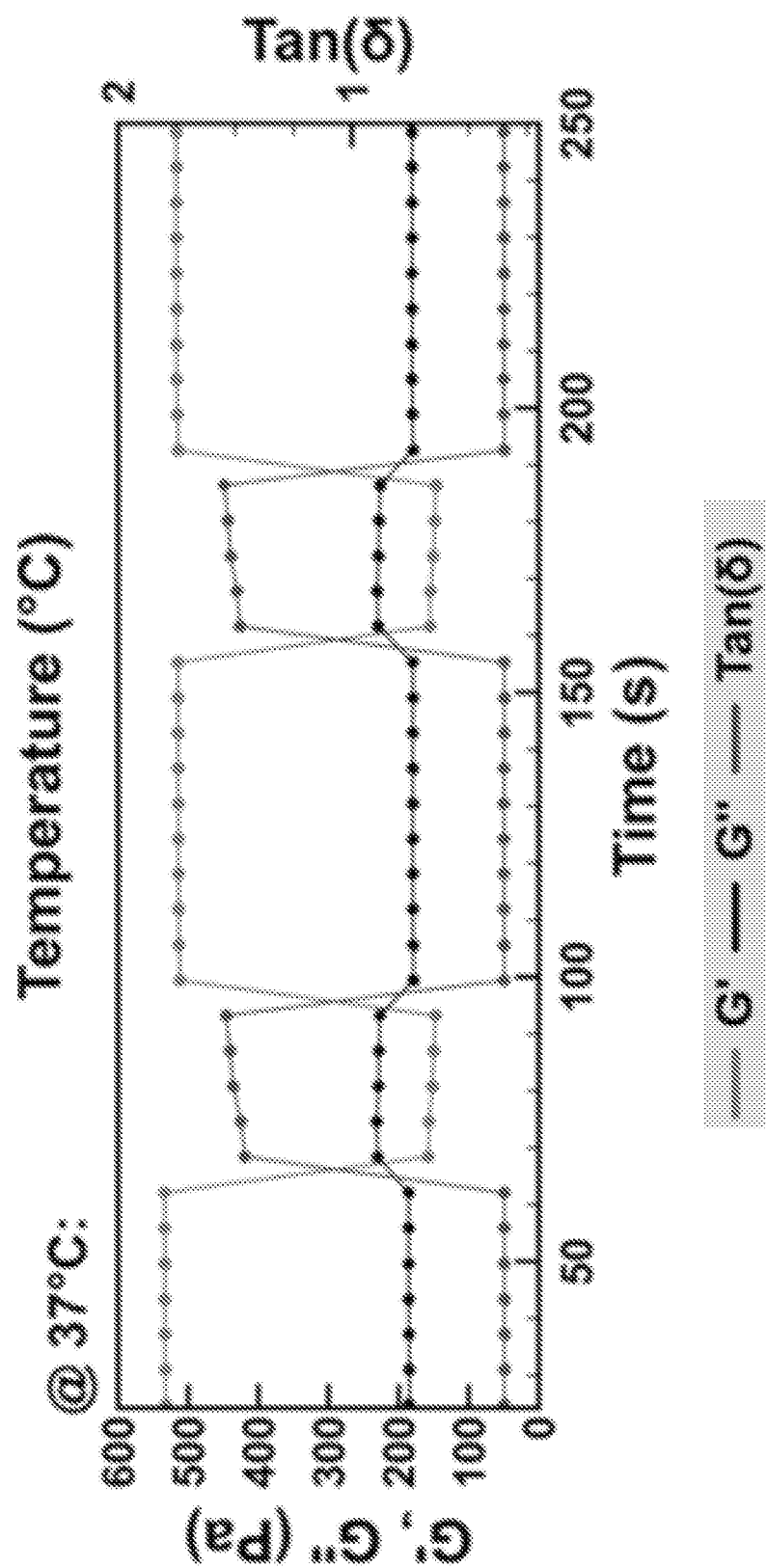

A strong ferrocene guest attached to 8-arm polyethylene glycol (PEG$_8$-Fc) crosslink F127 micelles and form a percolated network (FIG. 6C). The guest molecule presented on PEG$_8$-Fc was determined by competition $^1$H-NMR to bind CB[7] with an affinity of $3.5\times10^{12}$ M$^{-1}$ (FIG. 6D). Variable temperature oscillatory rheology determined the critical gelation temperature for F127-CB[7] and PEG$_8$-Fc at 10 wt % solids, mixed at a CB[7]:Fc ratio of 3:1 (FIG. 6E). Shear-thinning and self-healing was demonstrated for the same hydrogels at 37° C., alternating between 2% and 200% strain (FIG. 6F). Evidence for instant gelation upon injection of a sol of F127-CB[7]:PEG$_8$-Fc into a 37° C. bath (FIG. 6G) was compared to injection (FIG. 6H) of the same sol into a 23° C. bath. Proposed mechanism (FIG. 6I) for thermo-responsive gelation entails a "loop-rich" precursor with limited crosslinking at ambient temperatures, which transitions to a percolated hydrogel upon crosslinking of F127 micelles at physiologic temperatures.

Figure 7A:
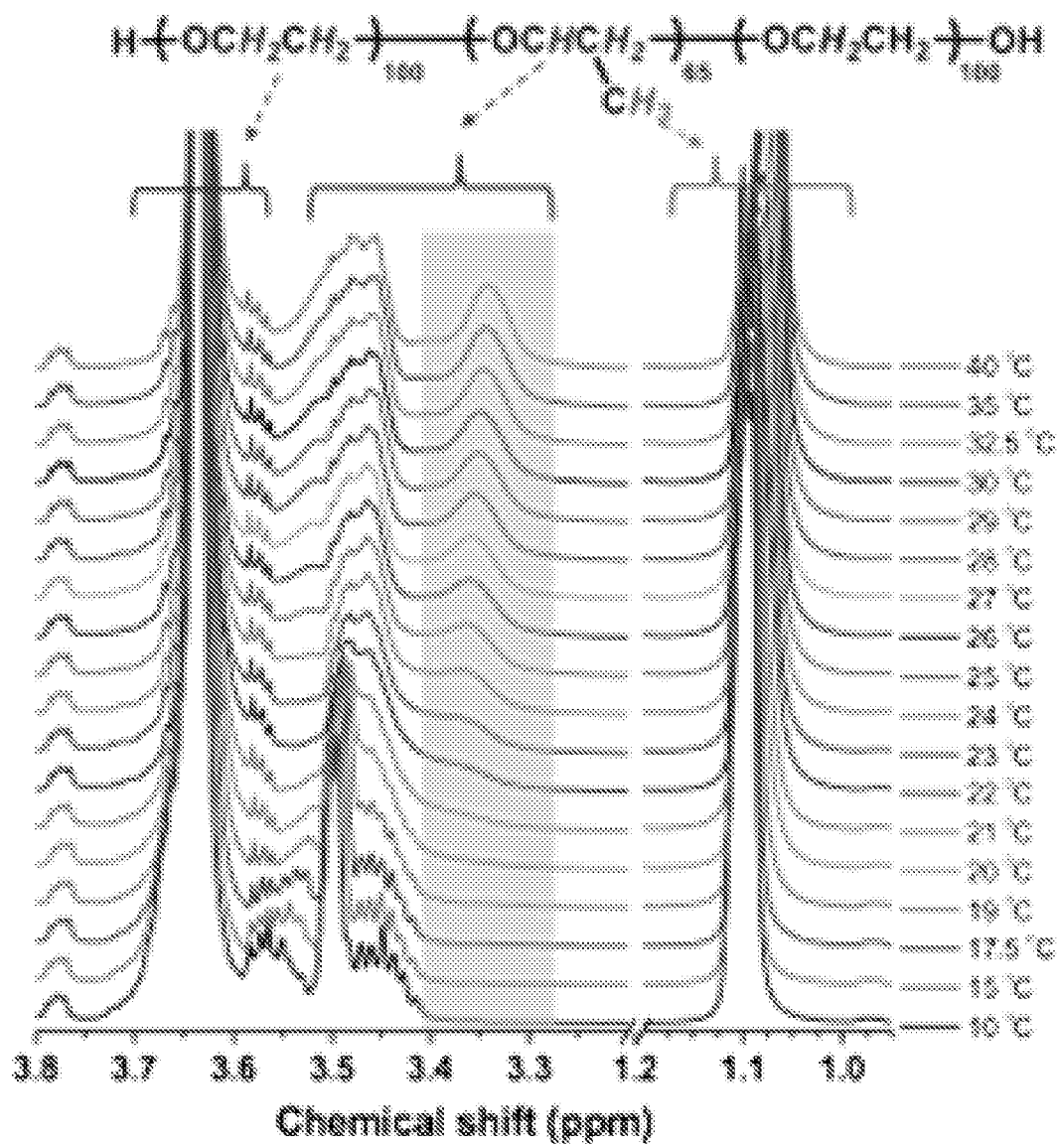
Figure 7B:
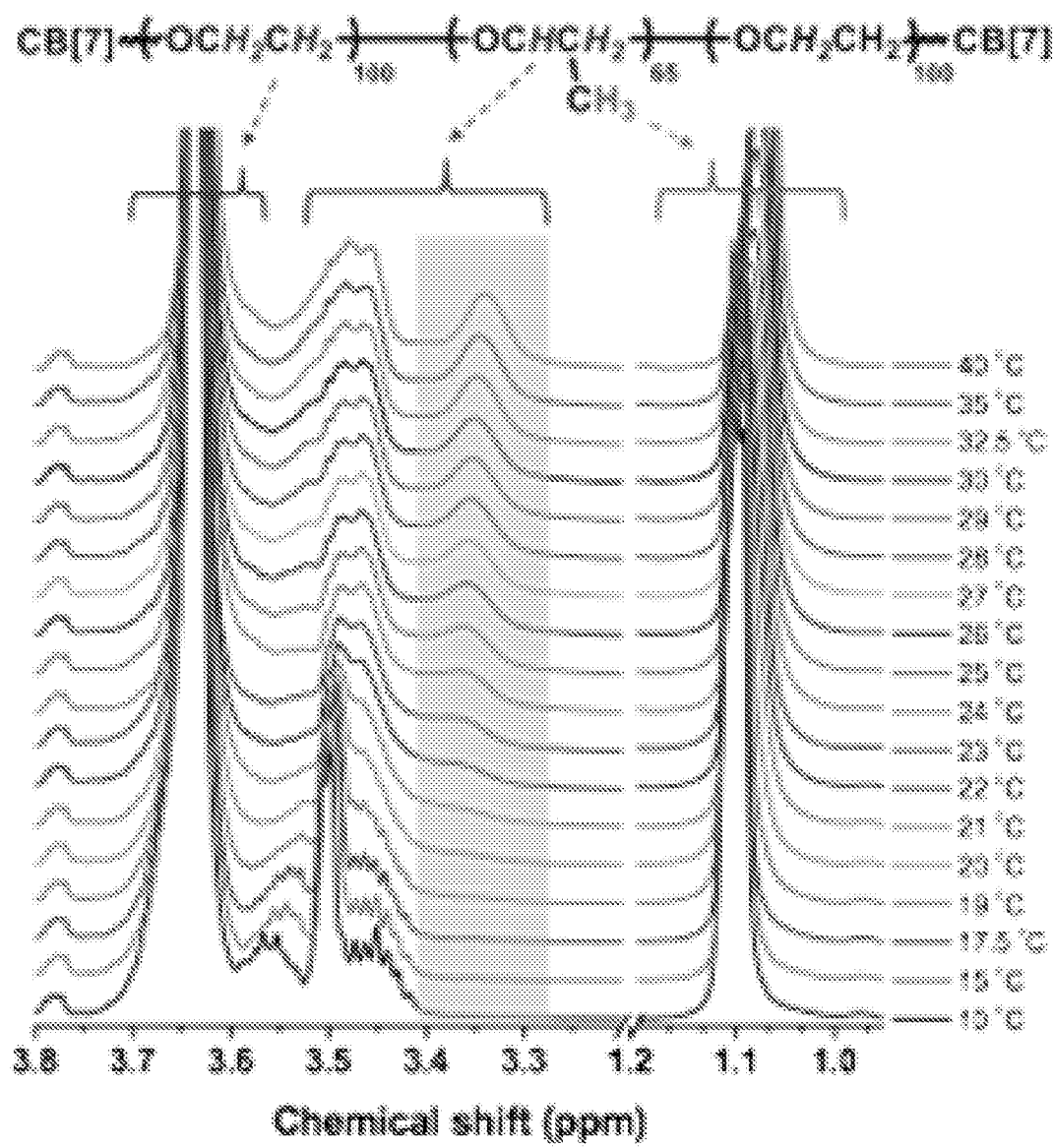
Figure 7C:
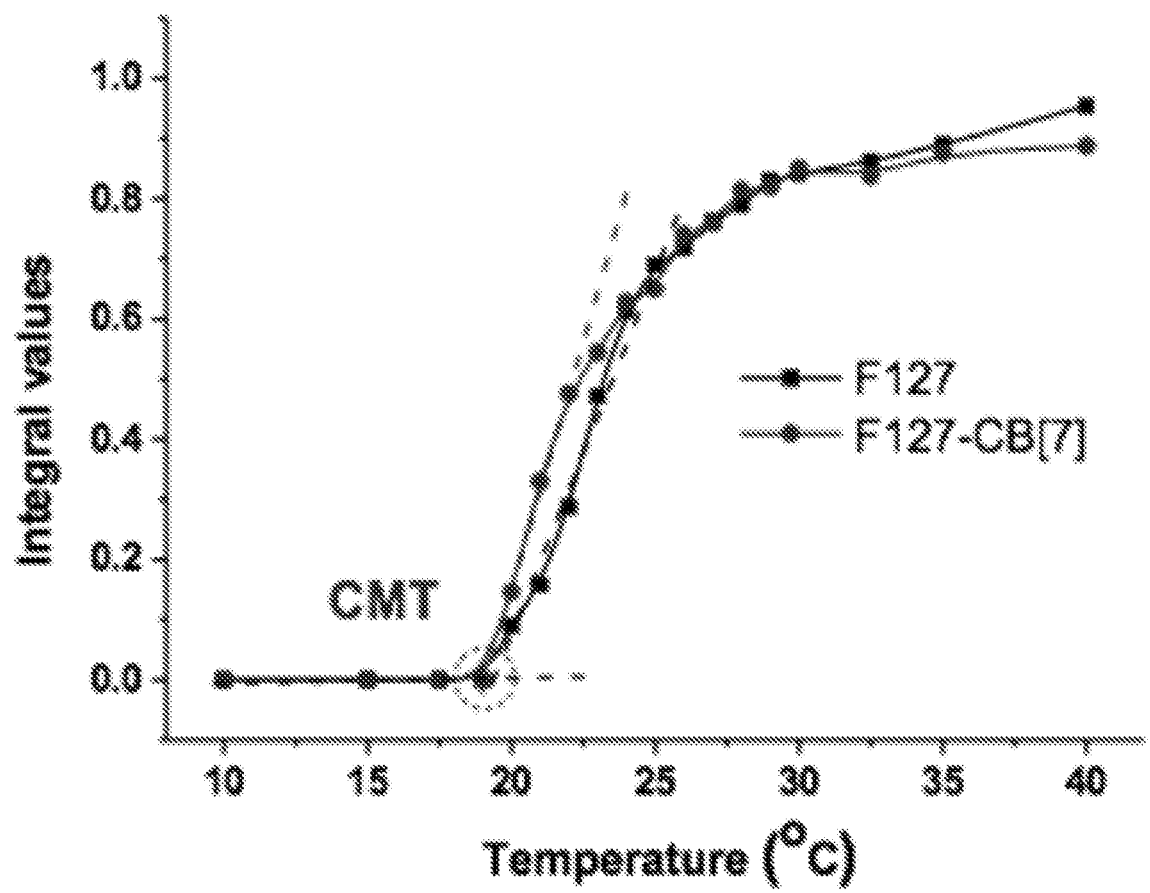

FIG. 7A, FIG. 7B and FIG. 7C are graphs of the temperature-dependent $^1$H-NMR in D$_2$O of F127 (FIG. 7A) and F127-CB[7] (FIG. 7B) and the critical micelle temperature (CMT) (FIG. 7C).

Figure 8:
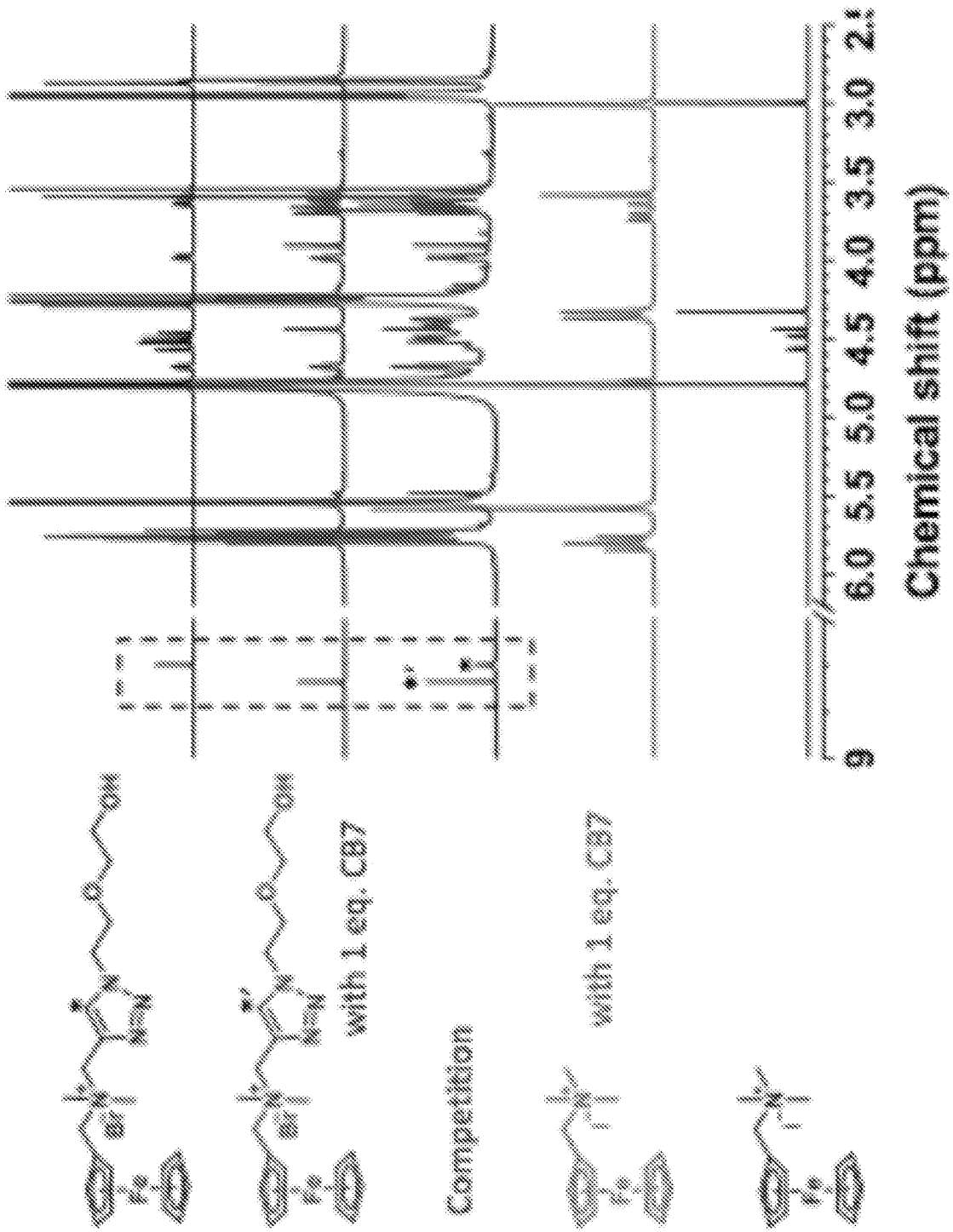

FIG. 8 is an example $^1$H-NMR spectra from guest competition studies to determine $K_{eq}$ for PEG$_{8a}$-Fc. Model guest OEG-Tz-N-Fc (Top), model guest OEG-Tz-N-Fc with 1 eq. CB[7] (Second from Top), model guest OEG-Tz-N-Fc (1.356 mM) and competitive guest (2.887 mM) with CB[7] (1.911 mM) (Middle), competitive guest with CB[7] (Second from Bottom) and competitive guest in D$_2$O (Bottom). $K_{rel}$ value of 0.87 was obtained from averaging three different competition experiments with different ratios of guest, competitor, and CB[7]. Comparing to the literature-reported value of $K_{eq}$ of $3.98\times10^{12}$ M$^{-1}$ for the competitor, the $K_{eq}$ for this guest OEG-Tz-N-Fc was determined at $3.46\times10^{12}$ M$^{-1}$. (*'-bound signal, *-free signal used for the calculation of bound and free guest species).

Figure 9A:
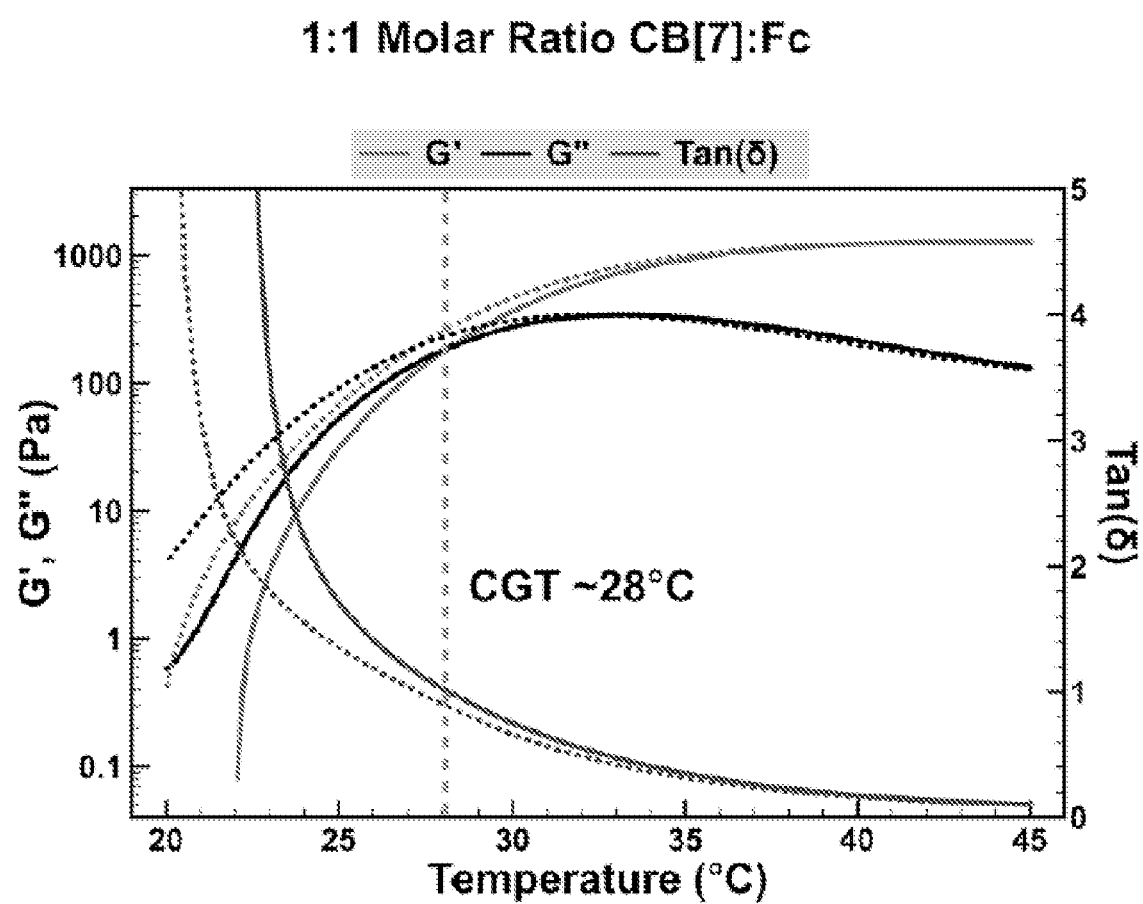
Figure 9B:
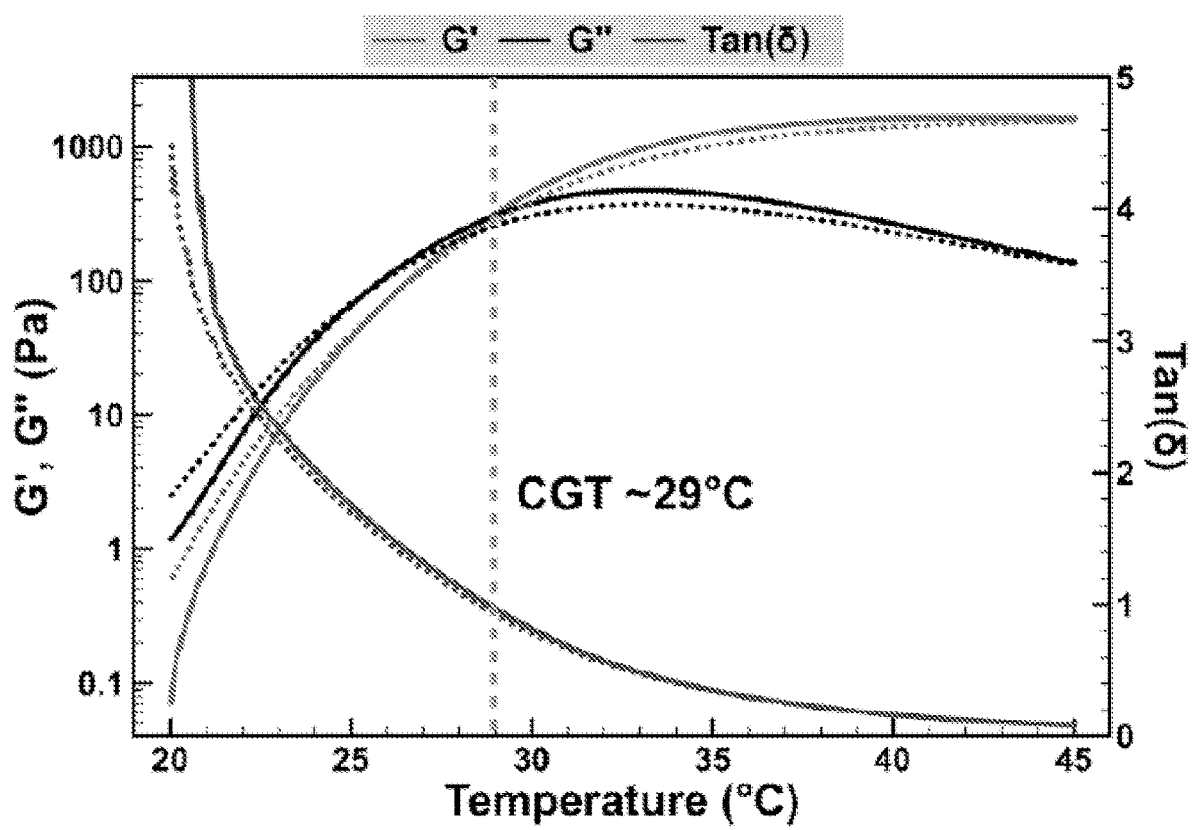
Figure 9C:
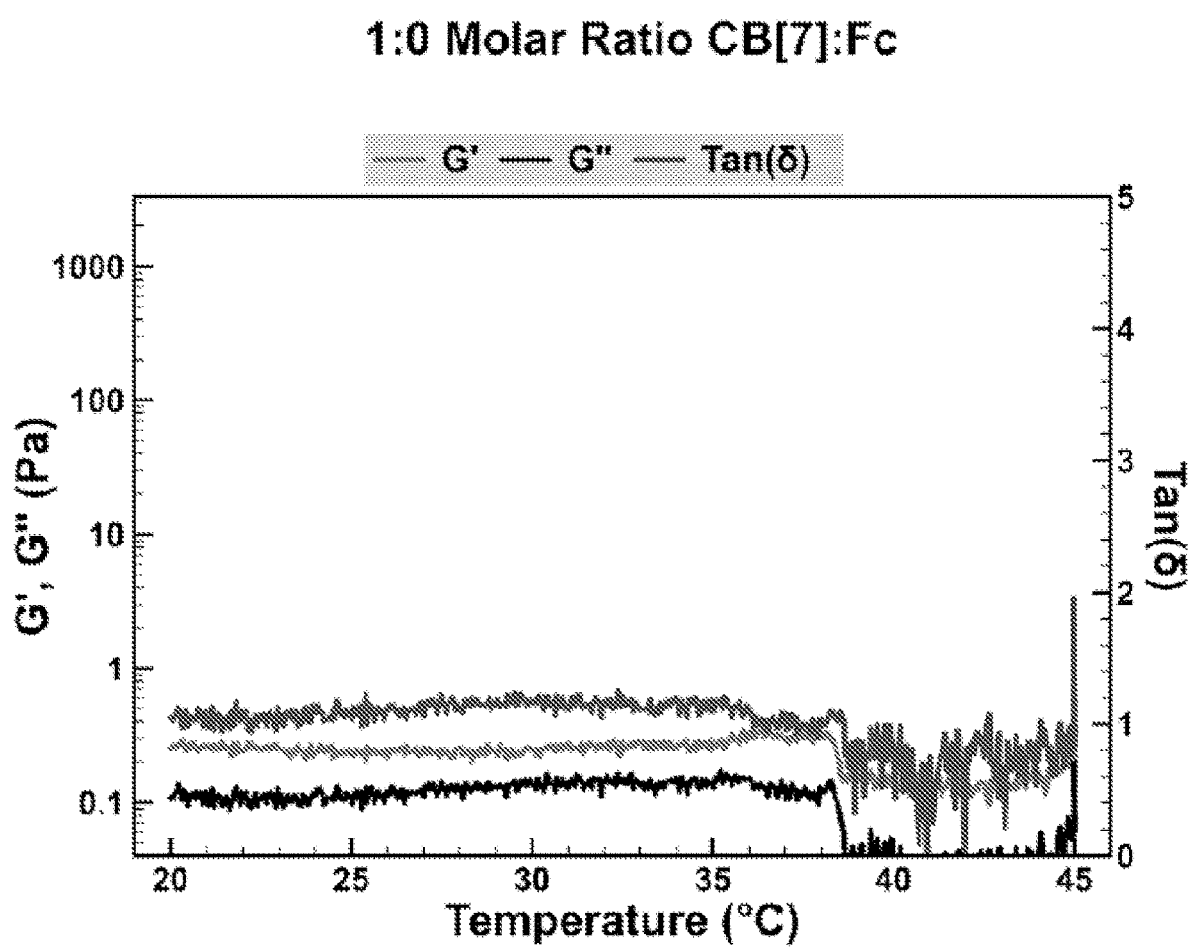

FIG. 9A, FIG. 9B and FIG. 9C are graphs of the control variable temperature rheology experiments with PEG$_8$-Fc and F127-CB[7] at different CB[7]:Fc molar ratios while keeping the total dissolved solids constant. A thermal sweep was performed, with solid lines (heating) and dashed lines (cool) plotted.

Figure 10A:
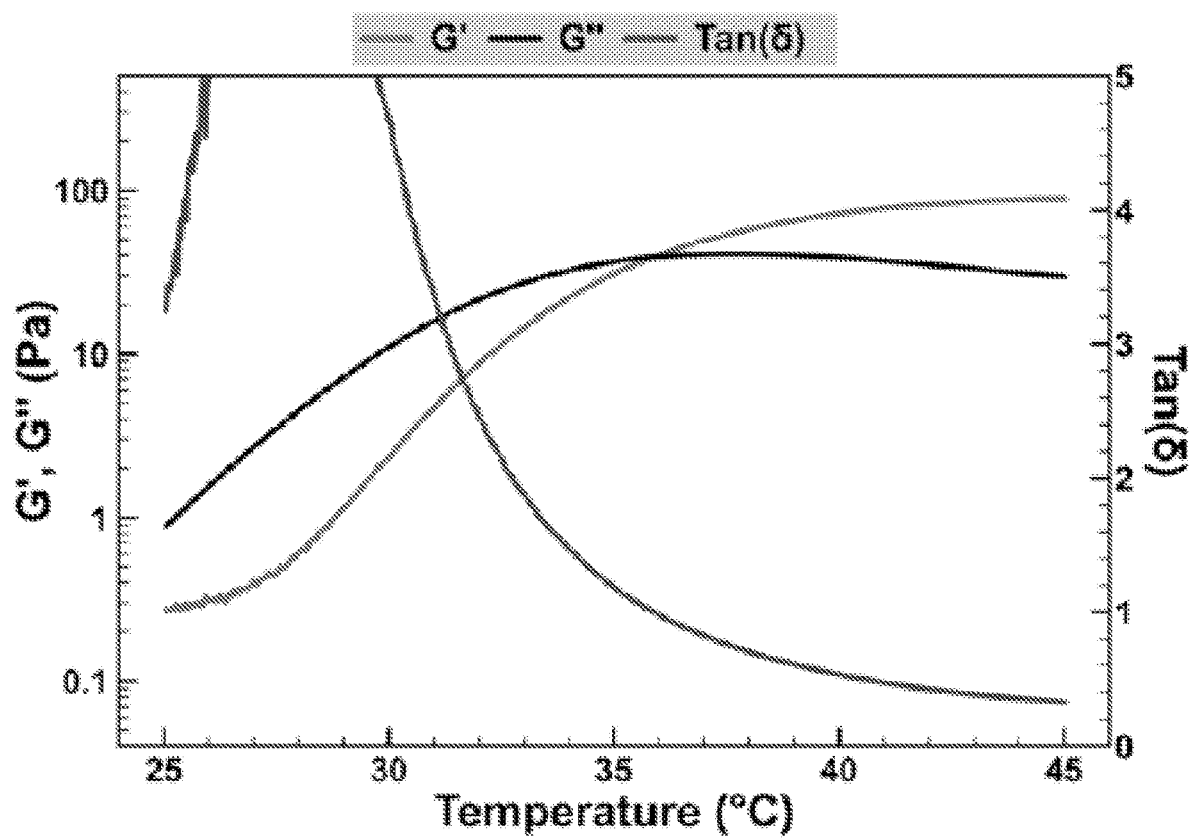
Figure 10B:
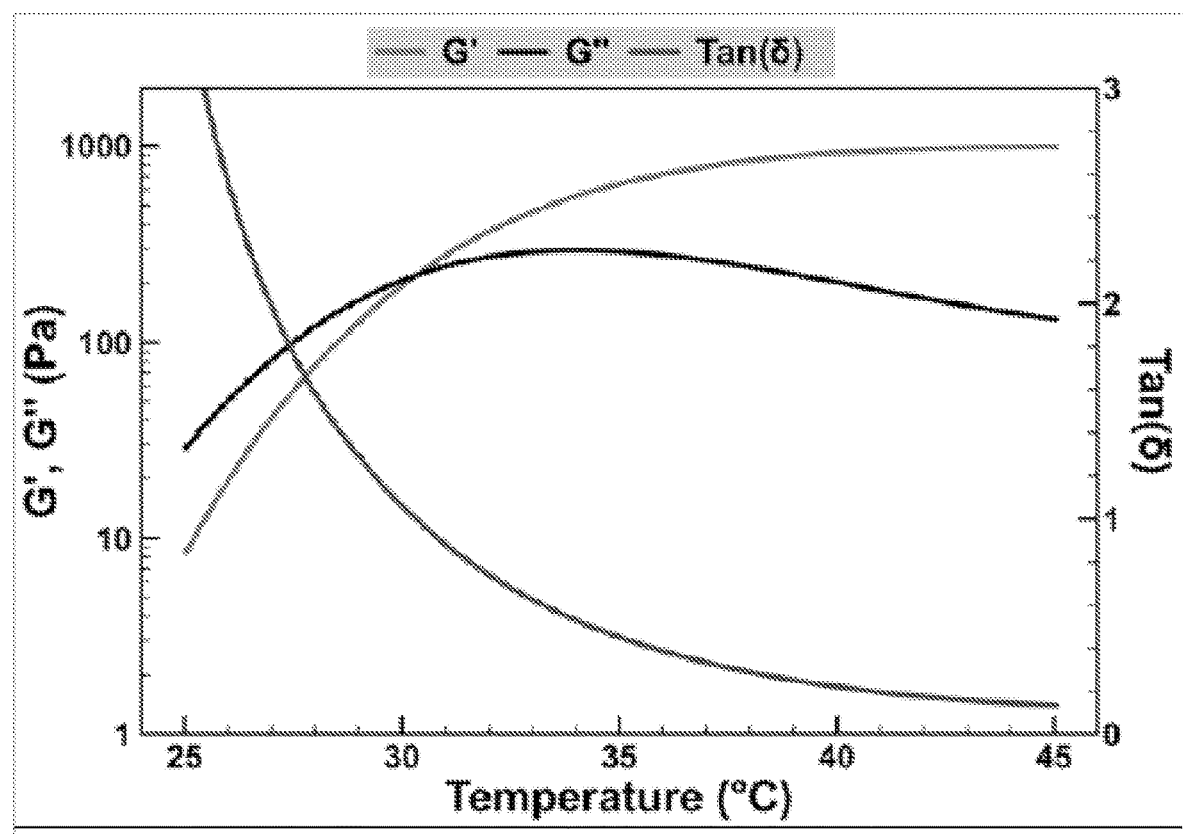

FIG. 10A and FIG. 10B are graphs of control rheology experiments altering the valency of the Fc guest macromer, using a linear (2-arm) macromer, PEG$_2$-Fc (FIG. 10A) and a 4-arm macromer PEG$_4$-Fc (FIG. 10B) to gel the F127-CB [7] starting material.

Figure 11A:
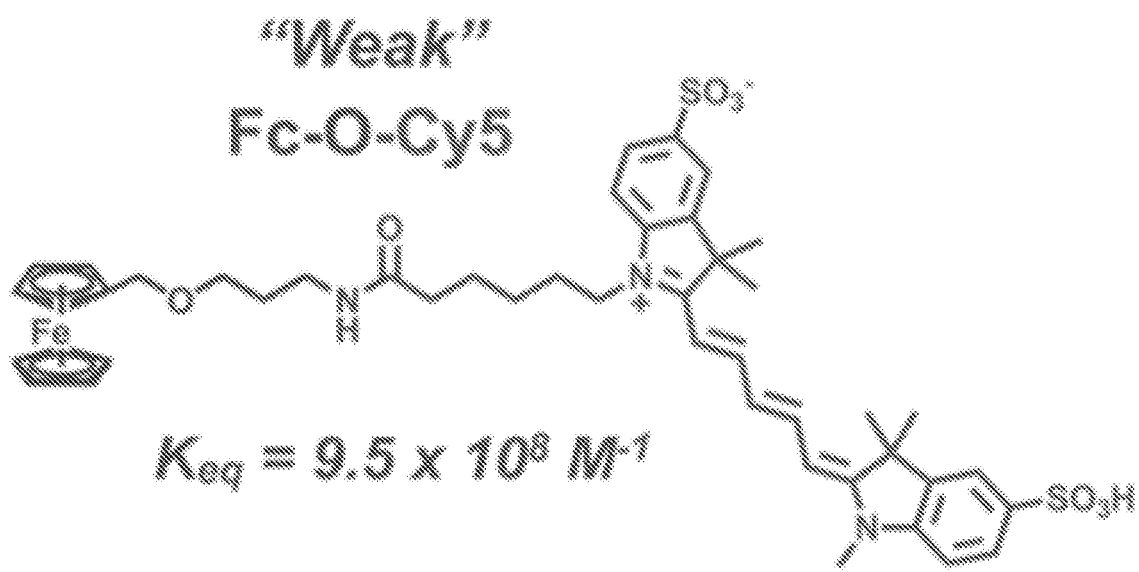
Figure 11B:
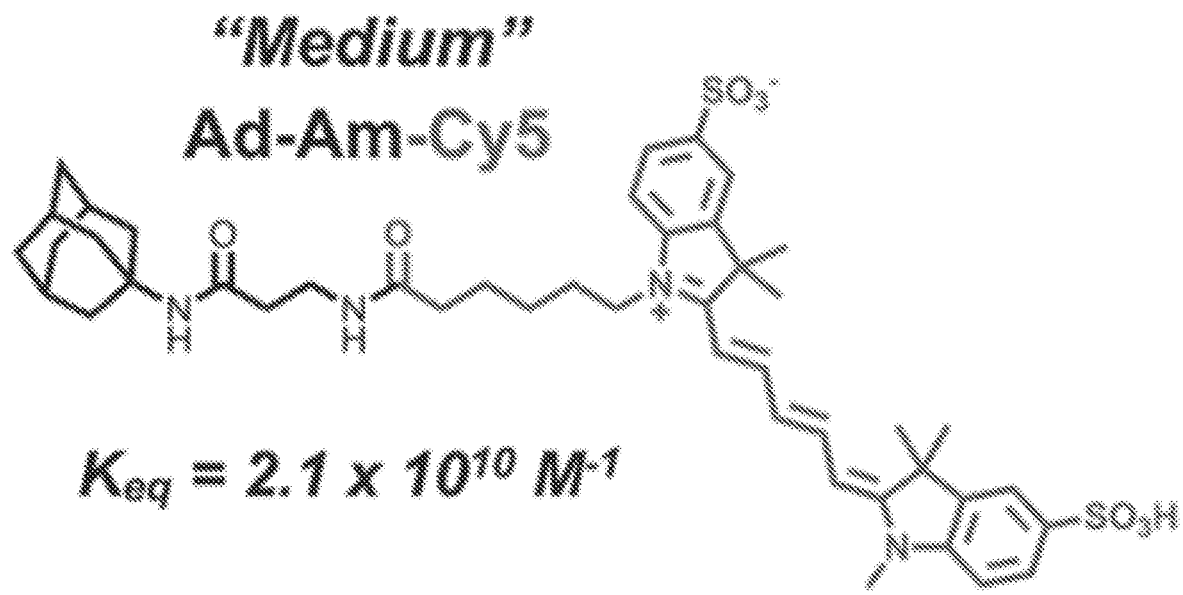
Figure 11C:
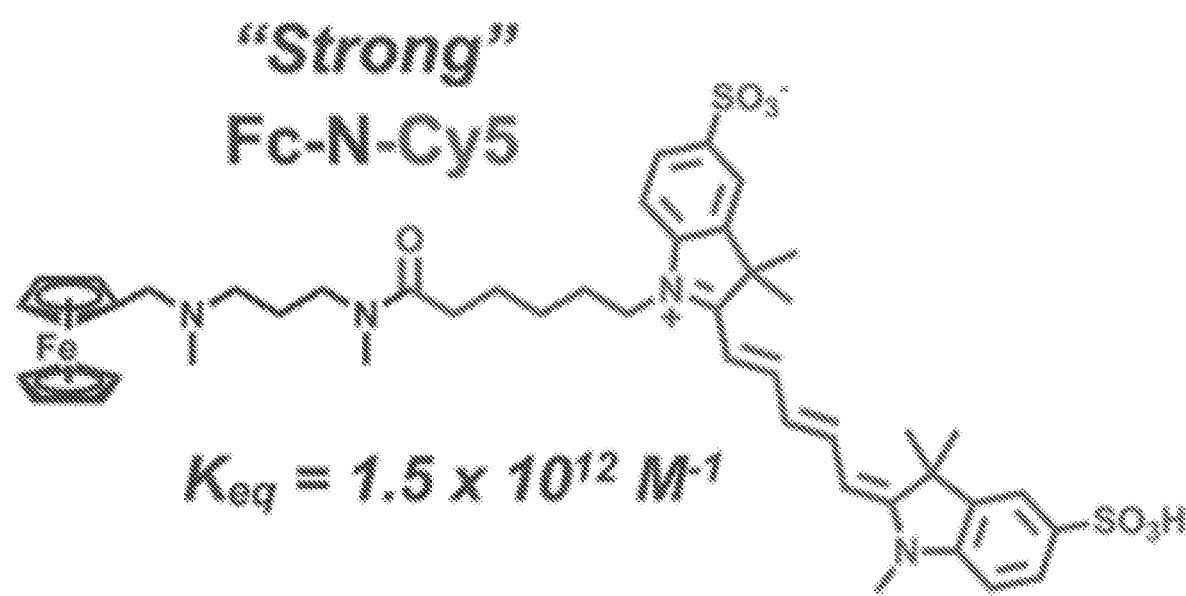
Figure 11D:
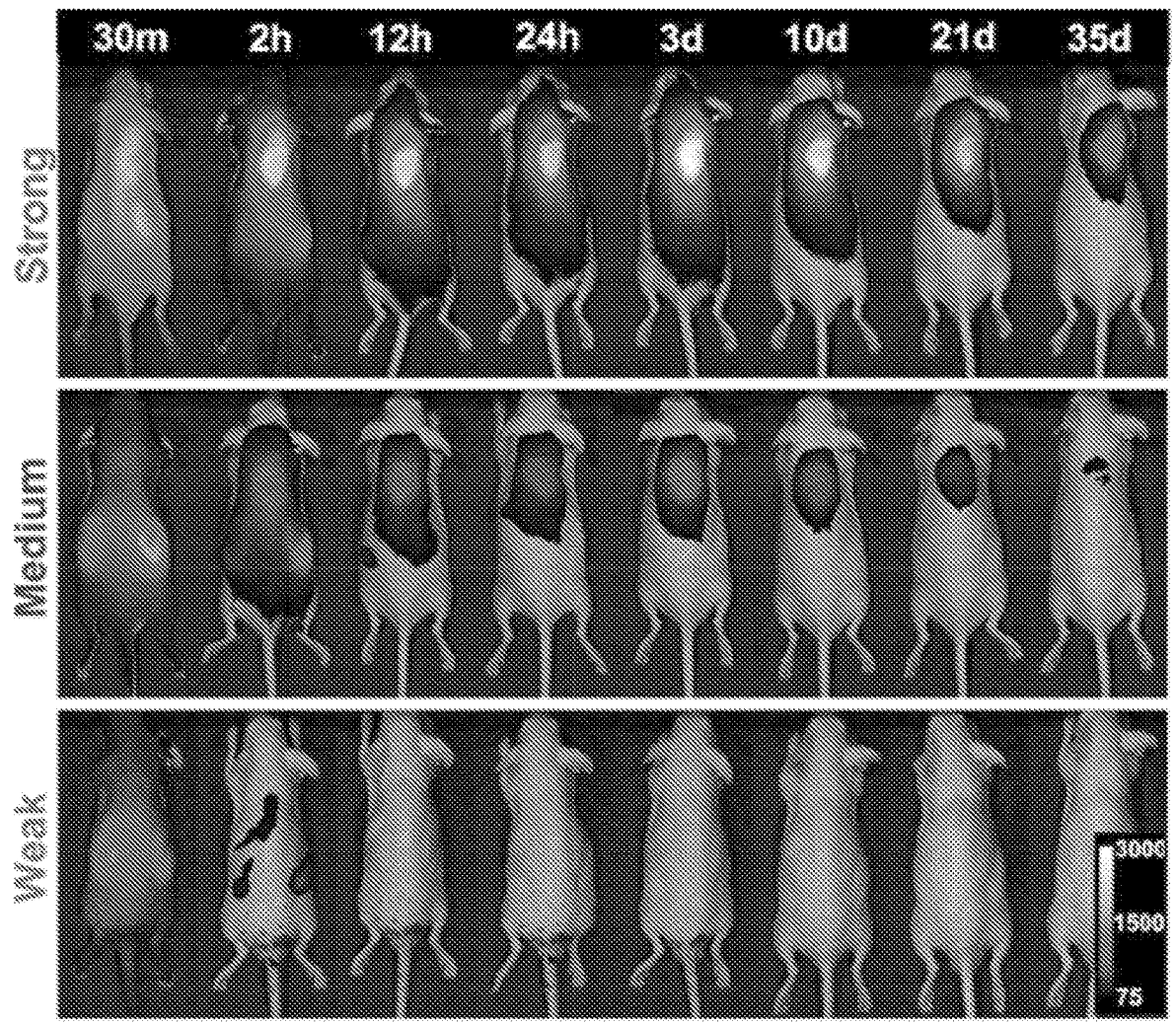
Figure 11E:
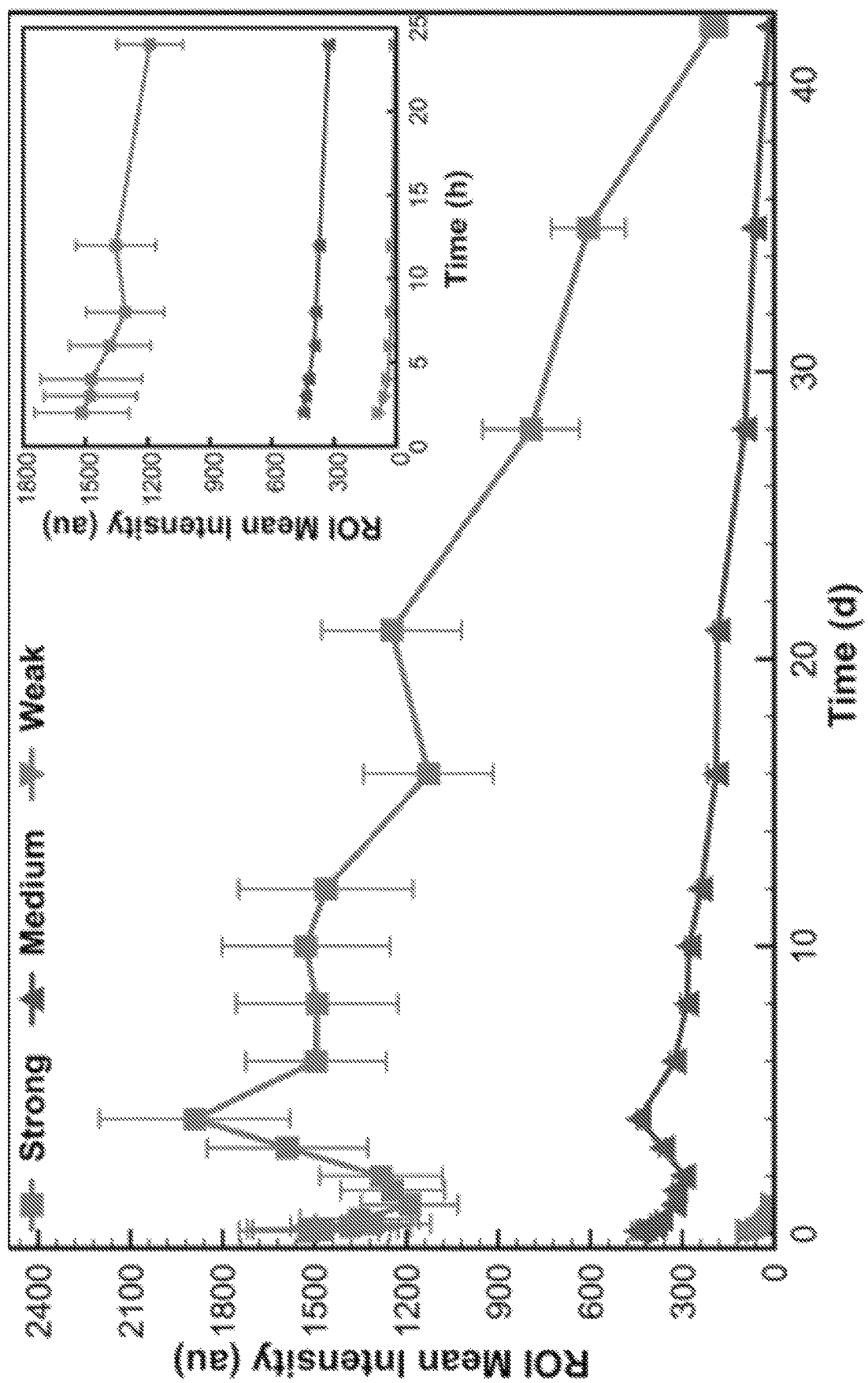
Figure 11F:
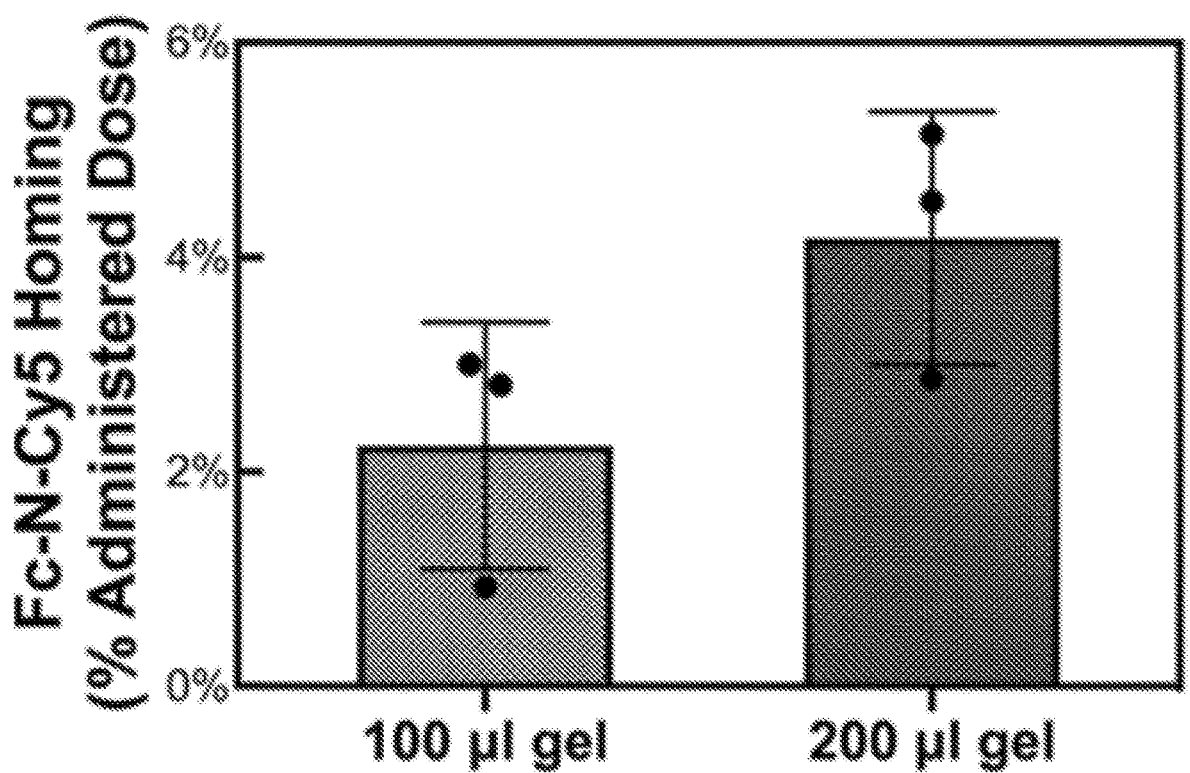
Figure 11G:
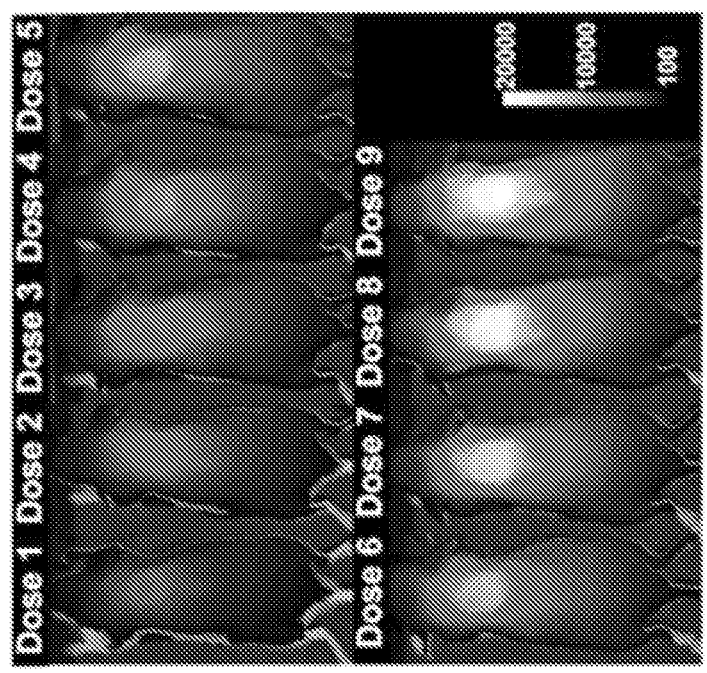
Figure 11G:
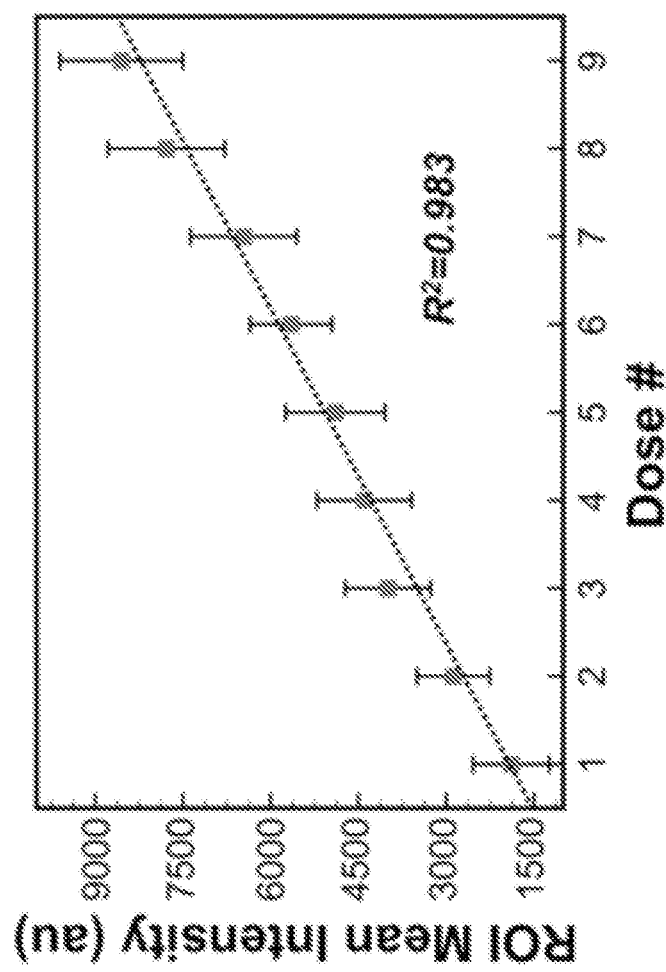

FIG. 11A, FIG. 11B, FIG. 11C, FIG. 11D, FIG. 11E, FIG. 11F, and FIG. 11G show the determination of host-guest affinity required for complex formation in the body after systemic administration. Structure of model prodrug from a ferrocene guest conjugated to a near-infrared cyanine dye (Cy5), termed the "Weak" guest (Fc-O-Cy5), with a measured affinity for CB[7] of $9.5\times10^8$ M$^{-1}$ (FIG. 11A). Structure of model prodrug from an adamantyl guest conjugated to Cy5, termed the "Medium" guest (Ad-Am-Cy5), with a measured affinity for CB[7] of $2.1\times10^{10}$ M$^{-1}$ (FIG. 11B). Structure of model prodrug from a ferrocene guest conjugated to Cy5, termed the "Strong" guest (Fc-N-Cy5), with a measured affinity for CB[7] of $1.5\times10^{12}$ M$^{-1}$ (FIG. 11C). F127-CB[7]:PEG$_8$-Fc hydrogels injected subcutaneously, with subsequent administration of the three model dye-linked guests and representative in vivo fluorescence imaging to quantify dye homing to the site of the hydrogel (FIG. 11D). Quantification of the average intensity in the hydrogel region of interest over time following administration of the three model dye-linked guests (FIG. 11E, n=4). Results from dye quantification following explanation of 100 µl and 200 µl hydrogels, dye extraction, and quantification (FIG. 11F). Studies evaluating serial loading of subcutaneous hydrogels with 9 consecutive doses administered in 12-hour intervals (FIG. 11G).

Figure 12:
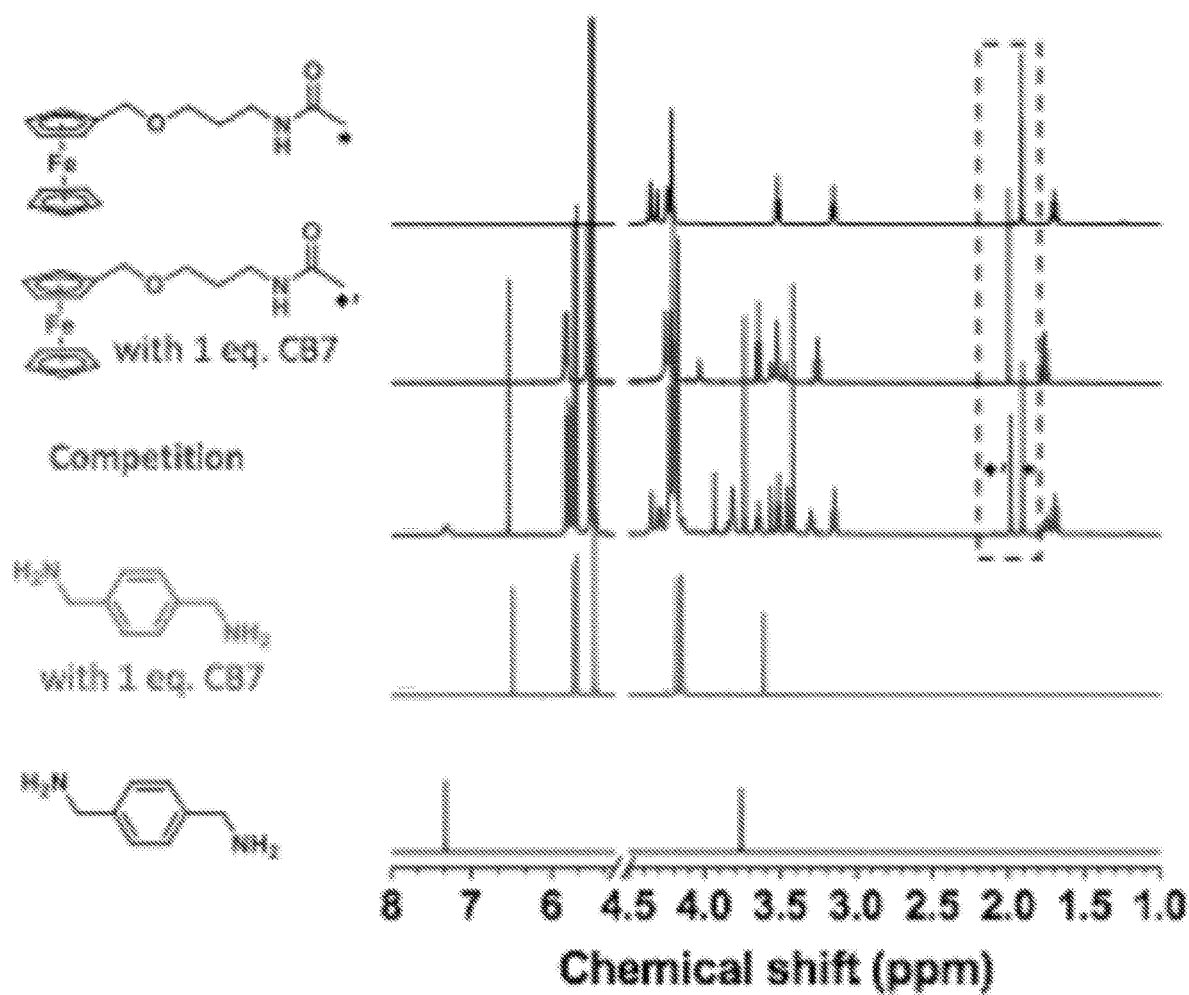

FIG. 12 is an example $^1$H-NMR spectra from guest competition studies to determine $K_{eq}$ for Fc-O-Cy5. Model guest Fc-O-Ac (Top), model guest Fc-O-Ac with CB[7] (Second from Top), model guest Fc-OAc (1.904 mM) and competitive guest p-xylylenediamine (1.96 mM) with CB[7] (2.18 mM) (Middle), competitive guest p-xylylenediamine with CB[7] (Second from Bottom), and competitive guest p-xylylenediamine in D$_2$O (Bottom). $K_{rel}$ value of 0.52 was obtained from averaging three different competition experiments with different ratios of guest, competitor, and CB[7]. Comparing to the literature-reported value of $K_{eq}$ of $1.84\times10$ M$^{-1}$ for the competitor p-xylylenediamine, the $K_{eq}$ for guest moieties Fc-O-Cy5 was determined at $9.5\times10^8$ M. (*'-bound signal, *-free signal for the calculation of bound and free guest species).

Figure 13:
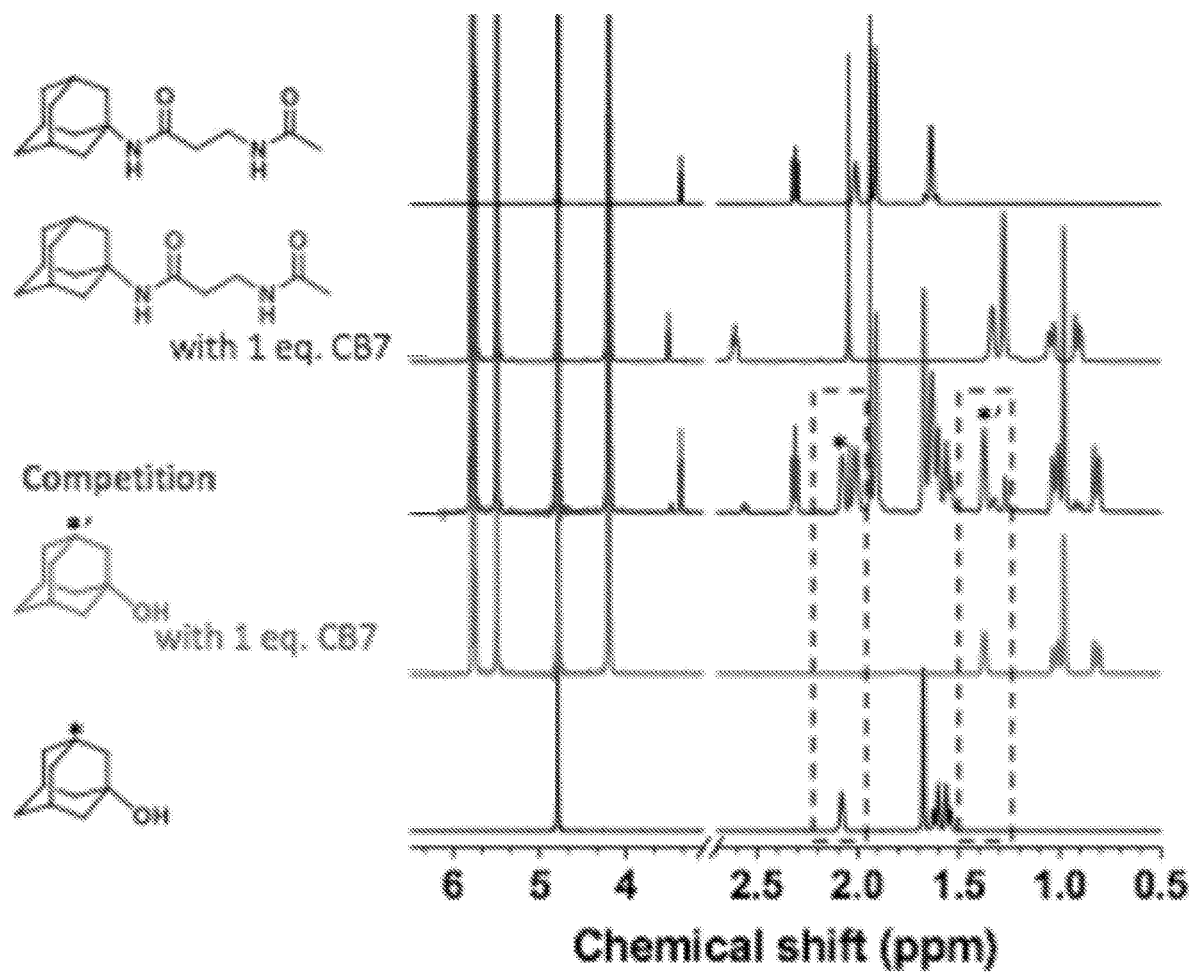

FIG. 13 is an example $^1$H-NMR spectra from guest competition studies to determine $K_{eq}$ for Ada-Am-Cy5. Model guest Ada-Am-Ac (Top), model guest Ada-Am-Ac with CB[7](Second from Top), model guest Ada-Am-Ac (1.893 mM) and competitive guest 1-adamantanol (1.88 mM) with CB[7] (2.595 mM) (Middle), competitive guest 1-adamantanol with CB[7](Second from Bottom), and competitive guest 1-adamantanol in D$_2$O (Bottom). $K_{rel}$ value of 0.89 was obtained from averaging three different competition experiments with different ratios of guest, competitor, and CB[7]. Comparing to the literature-reported value of $K_{eq}$ of $2.3\times10^{10}$ M$^{-1}$ for the competitor, the $K_{eq}$ for guest moieties Ada-amide-Cy5 was determined at $2.05\times10^{10}$ M$^{-1}$. (*'-bound signal, *-free signal for the calculation of bound and free guest species)

Figure 14:
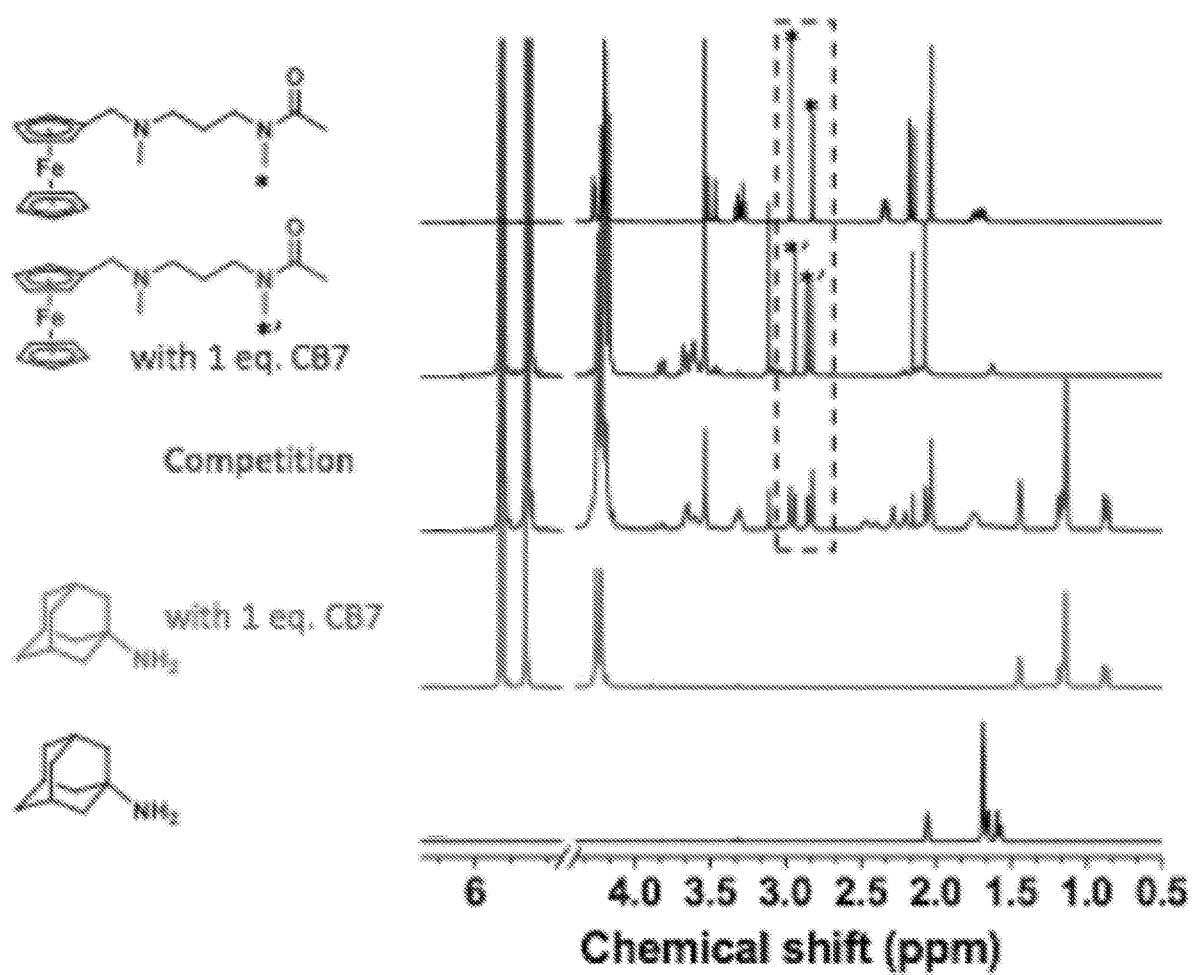

FIG. 14 is an example $^1$H-NMR spectra from guest competition studies to determine $K_{eq}$ for Fc-NCy5. Model guest Fc-N-Ac (Top), model guest Fc-N-Ac with CB[7] (Second from Top), model guest Fc-N-Ac (2.0 mM) and competitive guest (1.257 mM) with CB[7] (2.178 mM) (Middle), competitive guest 1-adamantylamine with CB[7] (Second from Bottom), and competitive guest 1-adamantylamine in D$_2$O (Bottom). $K_{rel}$ value of 0.36 was obtained from averaging three different competition experiments with different ratios of guest, competitor 1-adamantylamine, and CB[7]. Comparing to the literature-reported value of $K_{eq}$ of $4.17\times10$ M-1 for the competitor 1-adamantylamine, the $K_{eq}$ for guest moieties Fc-N-Cy5 was determined at $1.5\times1012$ M$^{-1}$. (*'-bound signal, *-free signal for the calculation of bound and free guest species)

Figure 15:
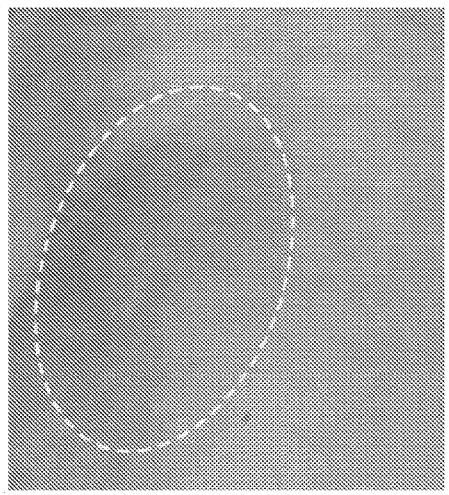

FIG. 15 is a photograph of subcutaneous F127-CB[7]: PEG$_8$-Fc gel, demonstrating the blue color that emerges following system administration of Fc-N-Cy5.

Figure 16:
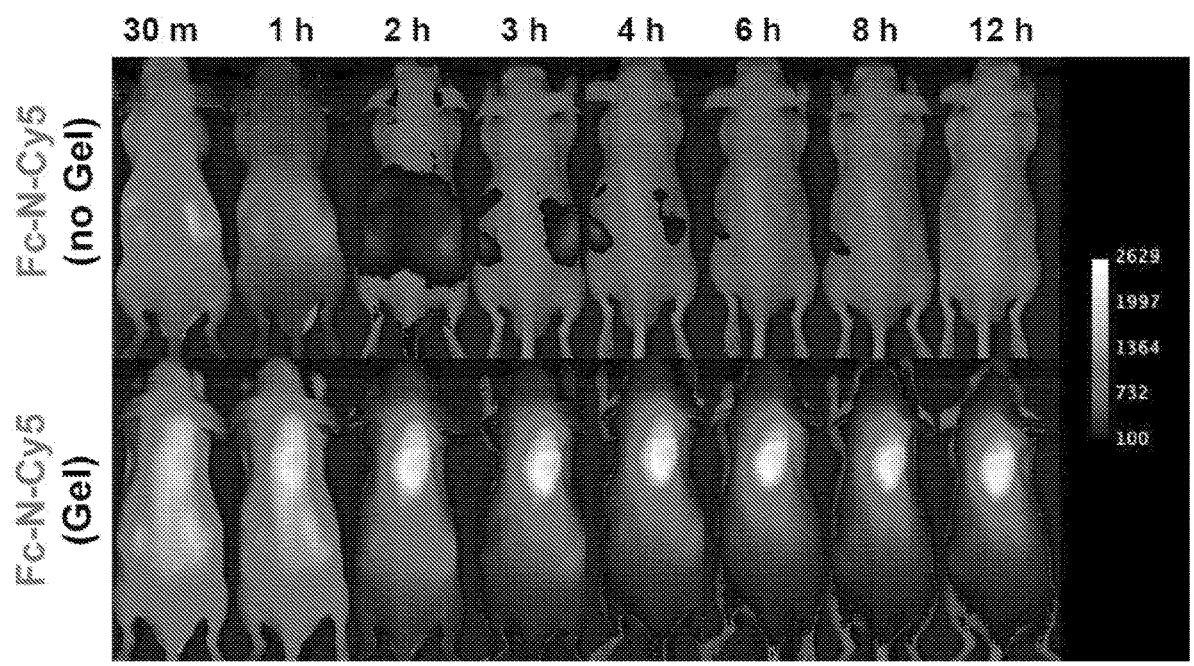

FIG. 16 is images showing the optical clearance profile for Fc-N-Cy5 in animals without (top) compared to with (bottom) the F127-CB[7]:PEG$_8$-Fc hydrogel.

Figure 17:
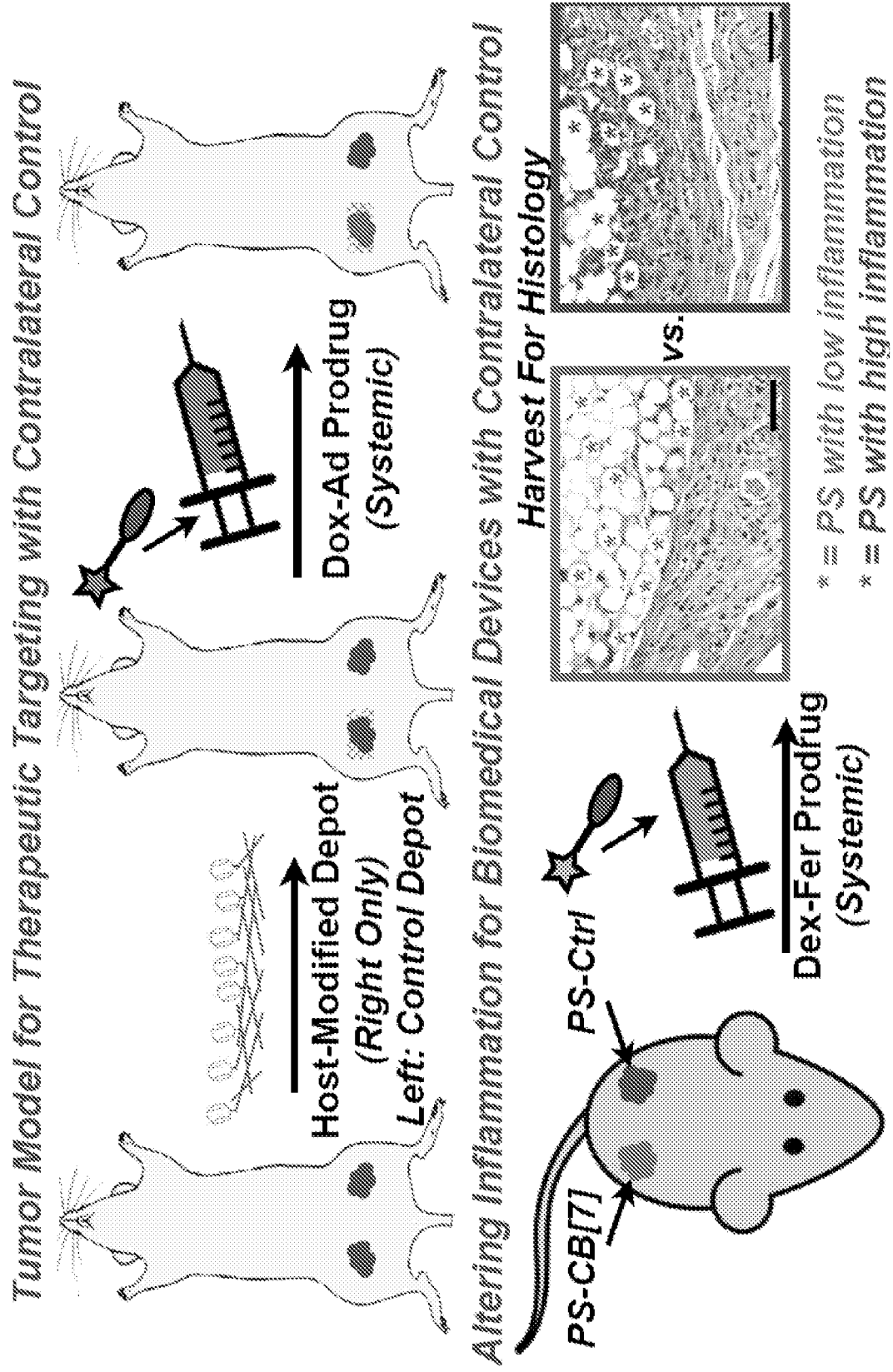

FIG. 17 is schematics of the models for valuating efficacy of the Dox-Ad prodrug, with CB[7]-modified depot injected proximal to a tumor and a control depot injected proximal to contralateral tumor. Relative tumor growth was monitored to validate targeting (Top) and localized anti-inflammatory therapy for an implanted biomedical device, using polystyrene (PS) beads modified with CB[7] compared to a contralateral control bead (Bottom). Histology of the implant bed was assessed for function of Dex-Fer (images from Webber et al. Biomaterials 2012, 33 (28), 6823-6832, incorporated herein by reference).

Figure 18A:
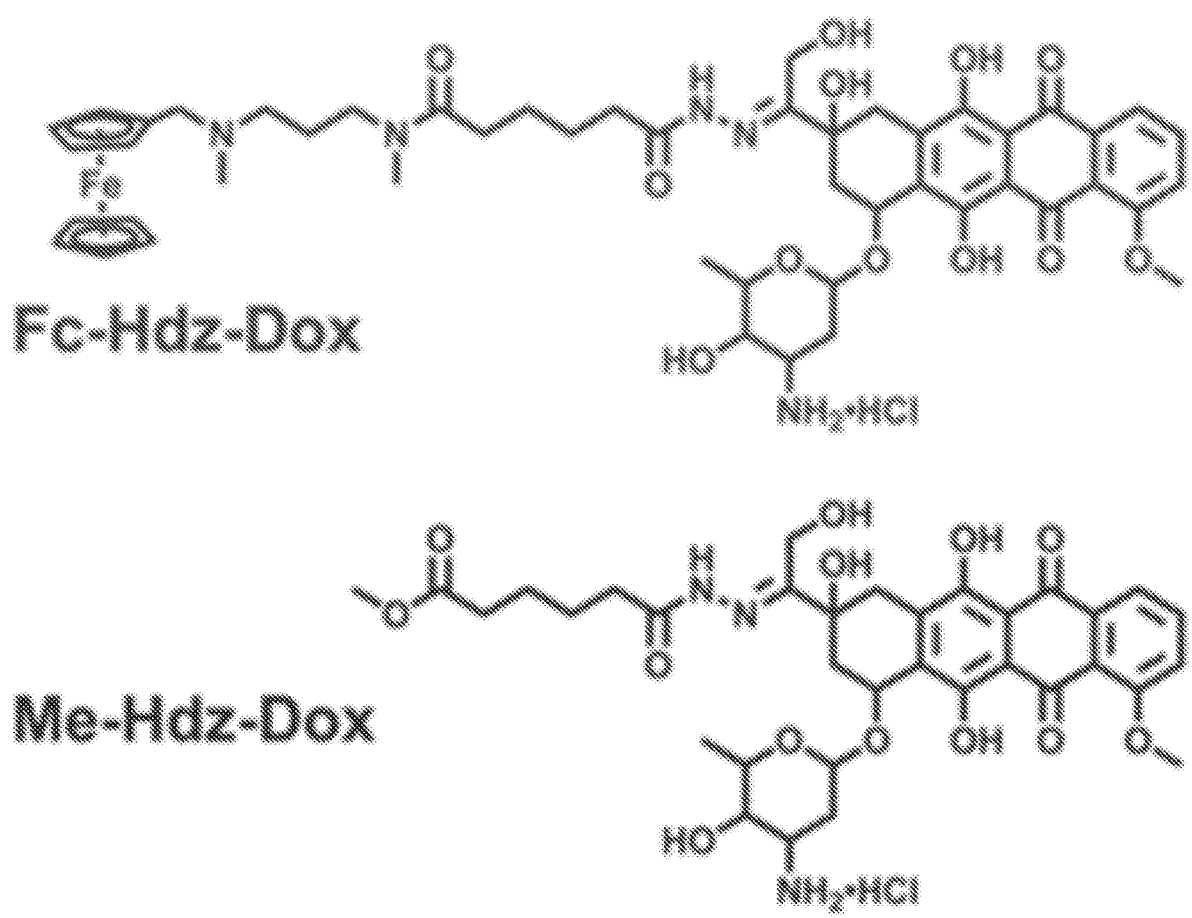
Figure 18B:
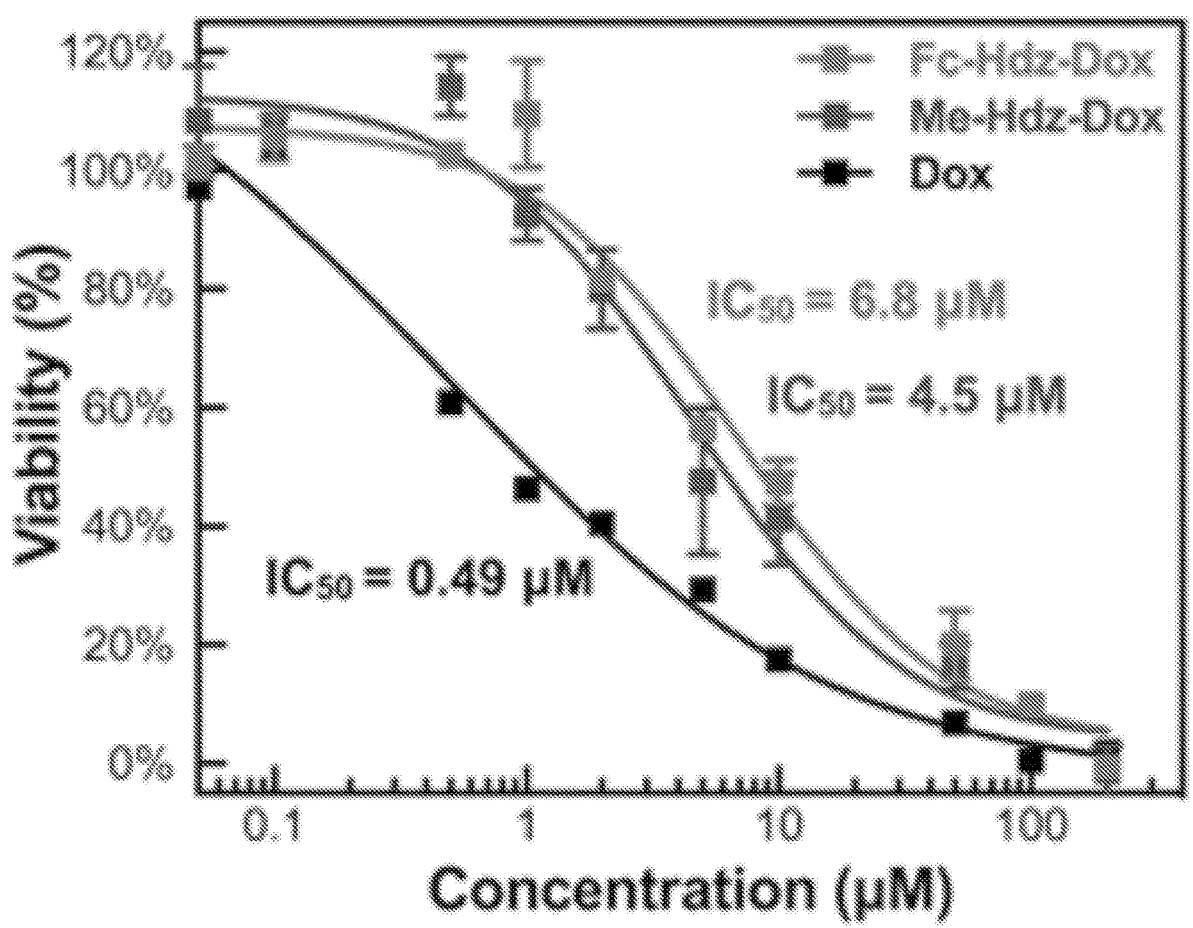
Figure 18C:
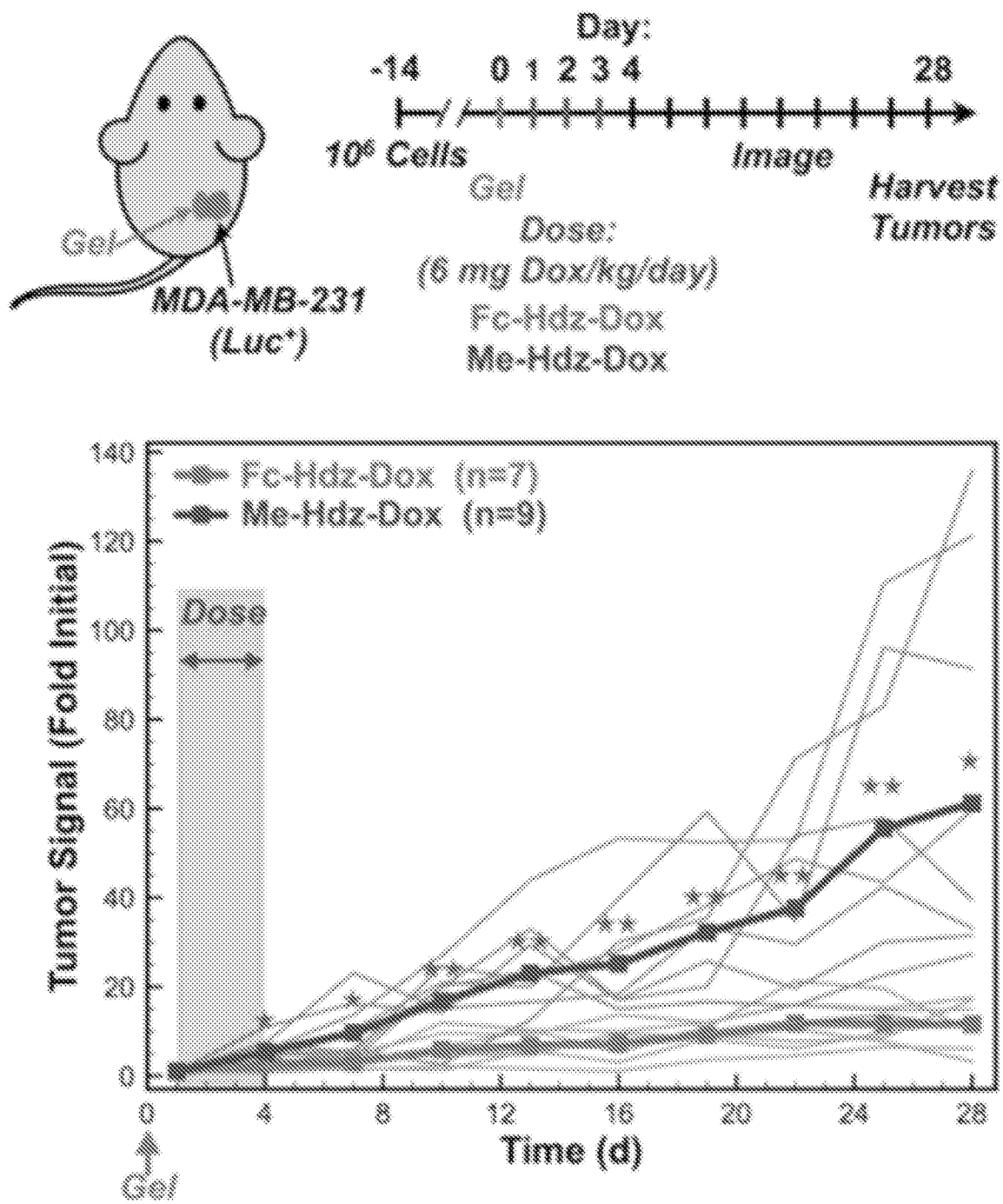

FIG. 18A, FIG. 18B and FIG. 18C show the supramolecular homing applied to therapeutic design. Doxorubicin was modified with a strong ferrocene guest through a hydrazone linkage (Fc-Hdz-Dox) as well as a control of doxorubicin modified with a hydrazone but lacking a CB[7]-binding guest (Me-Hdz-Dox) (FIG. 18A). Potency of doxorubicin and hydrazone conjugates in vitro in MDA-MB-231 cancer cells (FIG. 18B). Tumor model evaluated supramolecular homing of Fc-Hdz-Dox compared to Me-Hdz-Dox following application of F127-CB[7]:PEG$_8$-Fc hydrogel adjacent to a tumor prepared from MDA-MB-231 (luc+) cells (FIG. 18C, *P<0.05, **P<0.01).

Figure 19:
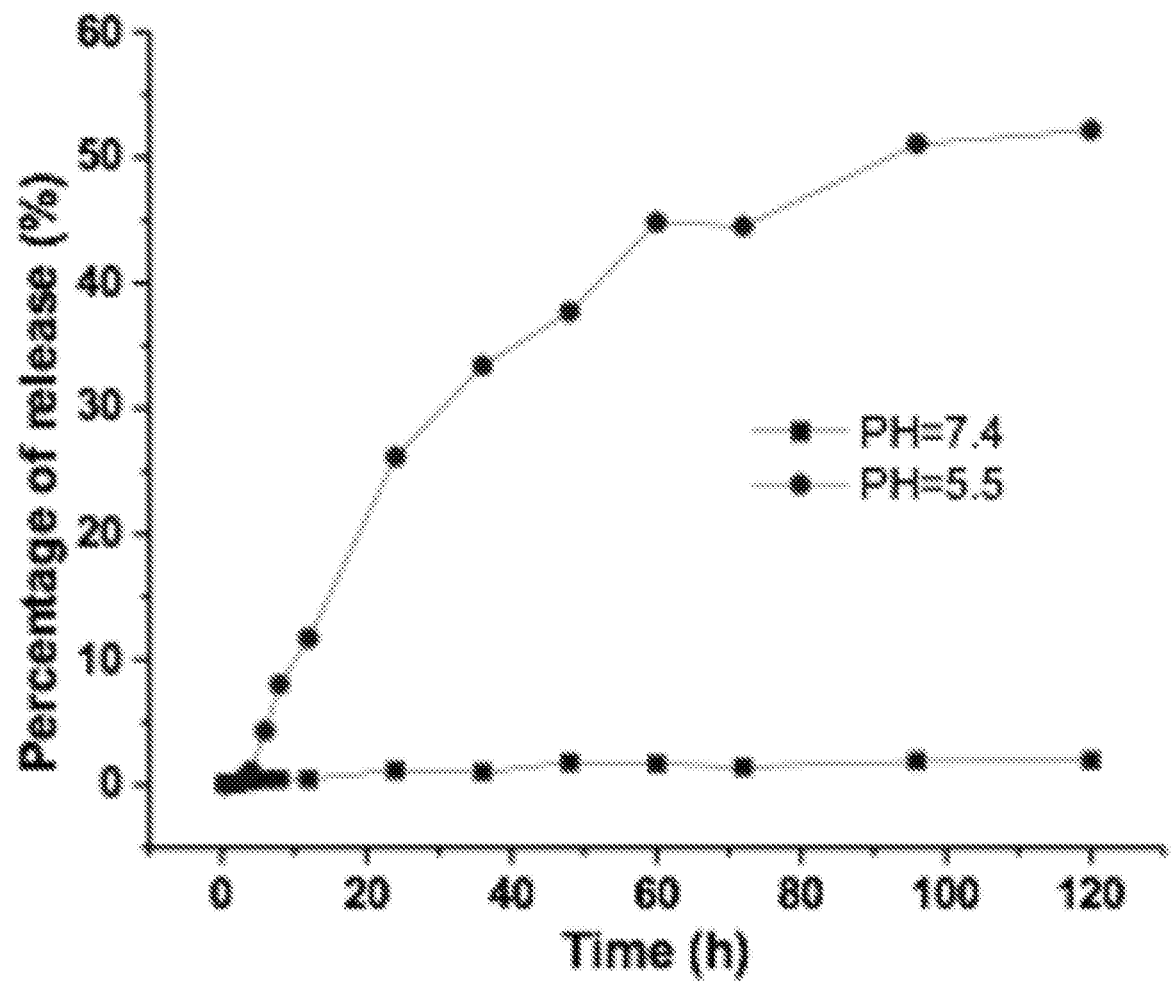

FIG. 19 is a graph showing doxorubicin release from F127-CB[7]:PEG$_8$-Fc hydrogels loaded with Fc-Hdz-Dox over time at pH 5.5 (circles) and 7.4 (squares).

Figure 20:
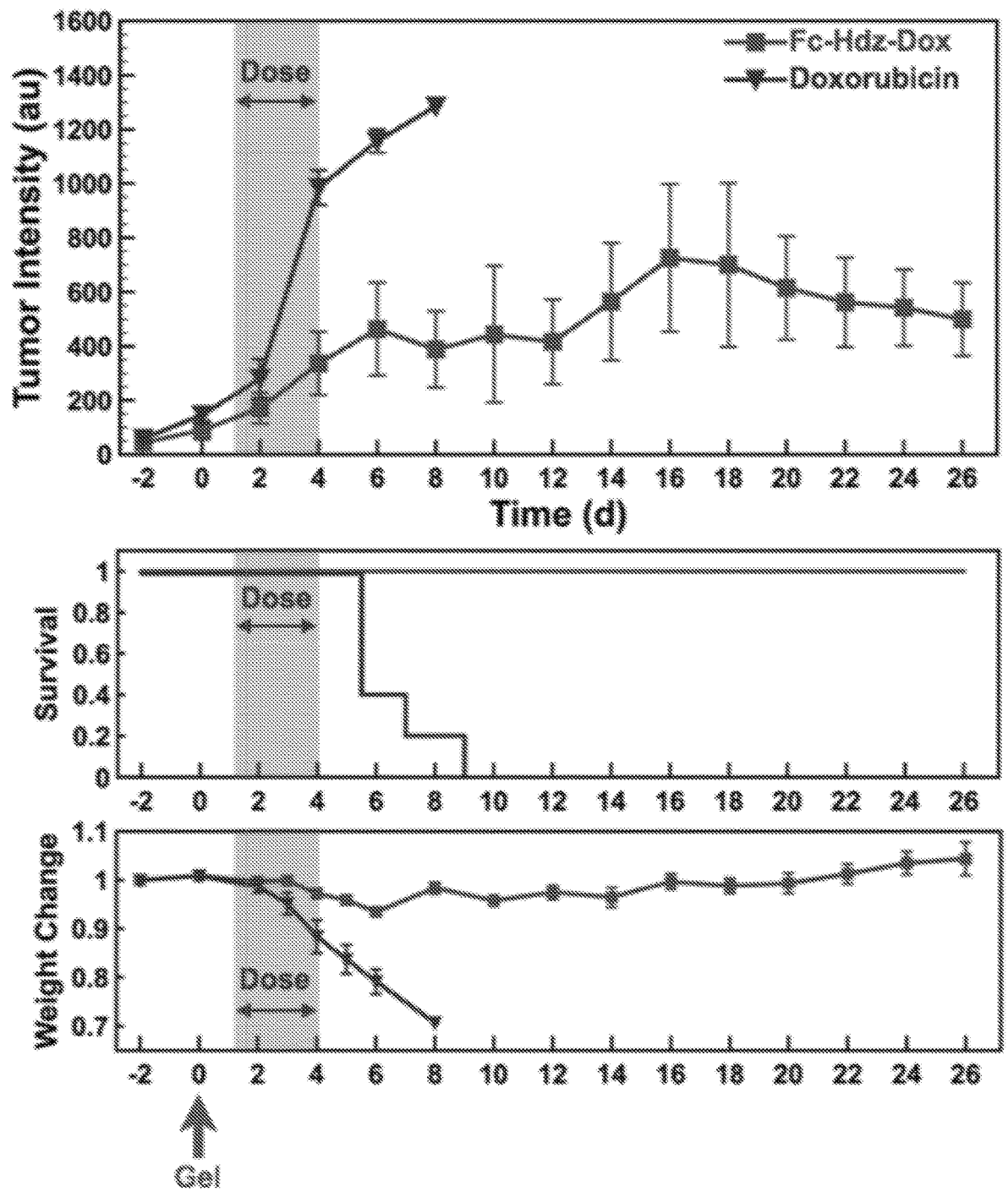

FIG. 20 is graphs of the preliminary studies comparing Fc-Hdz-Dox to Doxorubicin in MDA-MB-231 tumor models for tumor intensity, survival and weight change, dosed at 3 mg/kg doxorubicin equivalent on days 1, 2, and 3.

Figure 21:
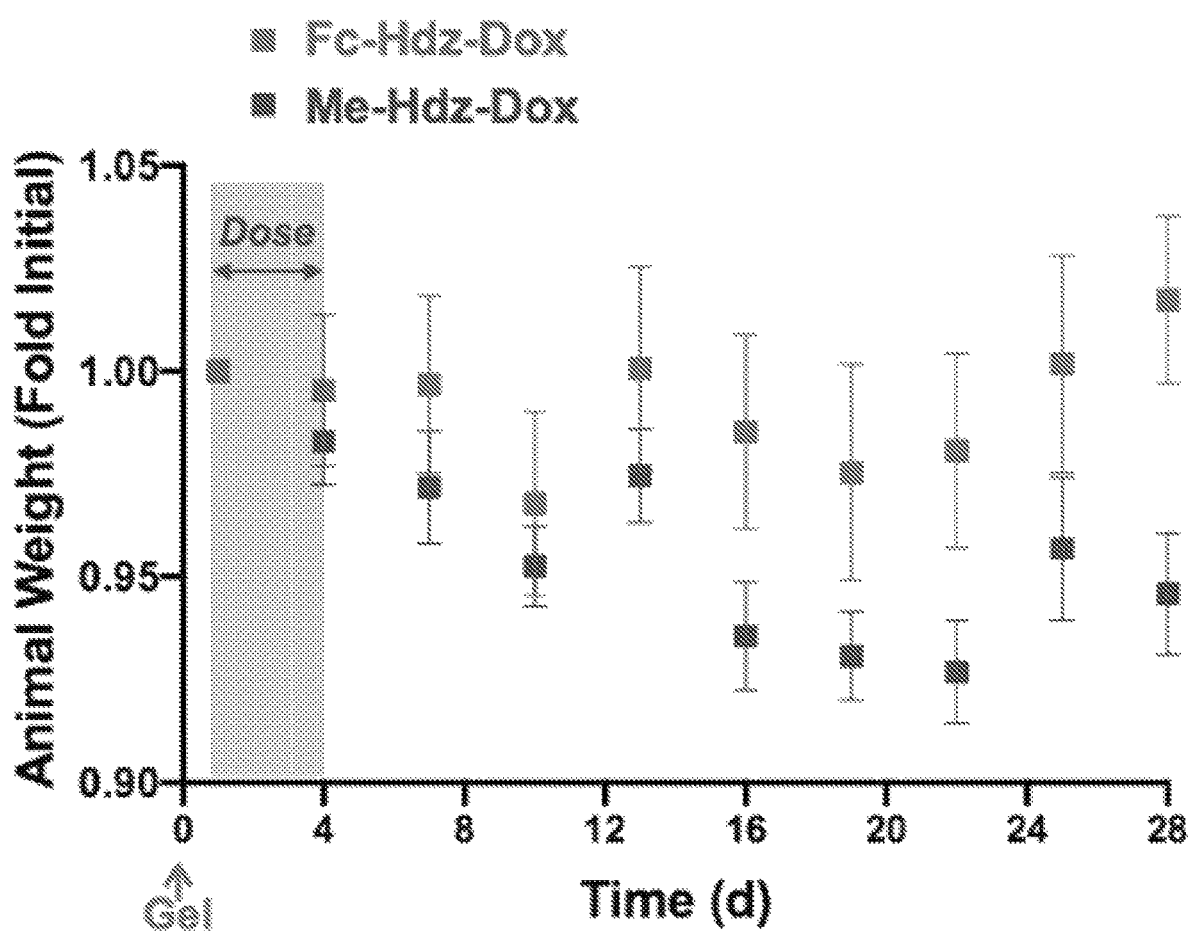

FIG. 21 is a graph showing animal weight from tumor studies comparing Fc-Hdz-Dox to Me-Hdz-Dox.

Figure 22A:
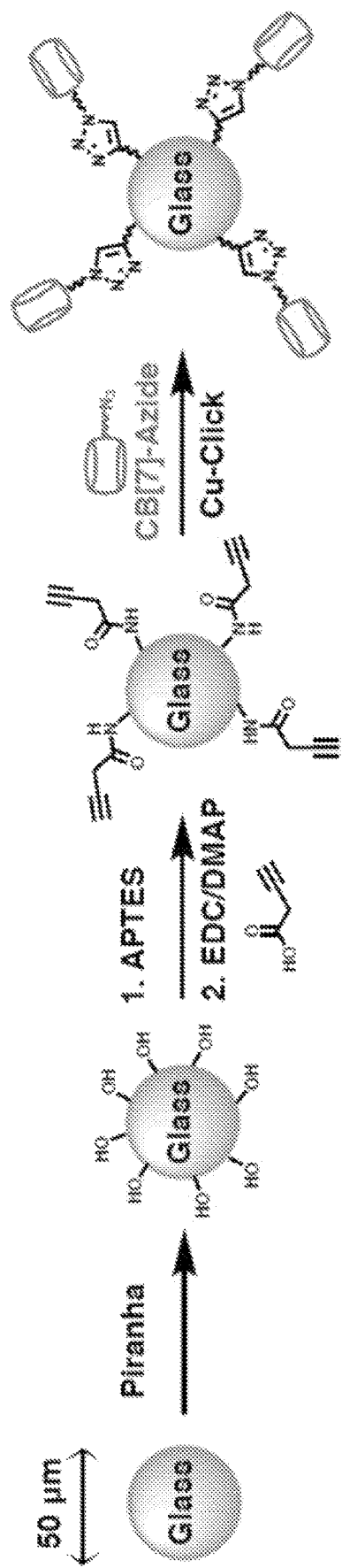
Figure 22B:
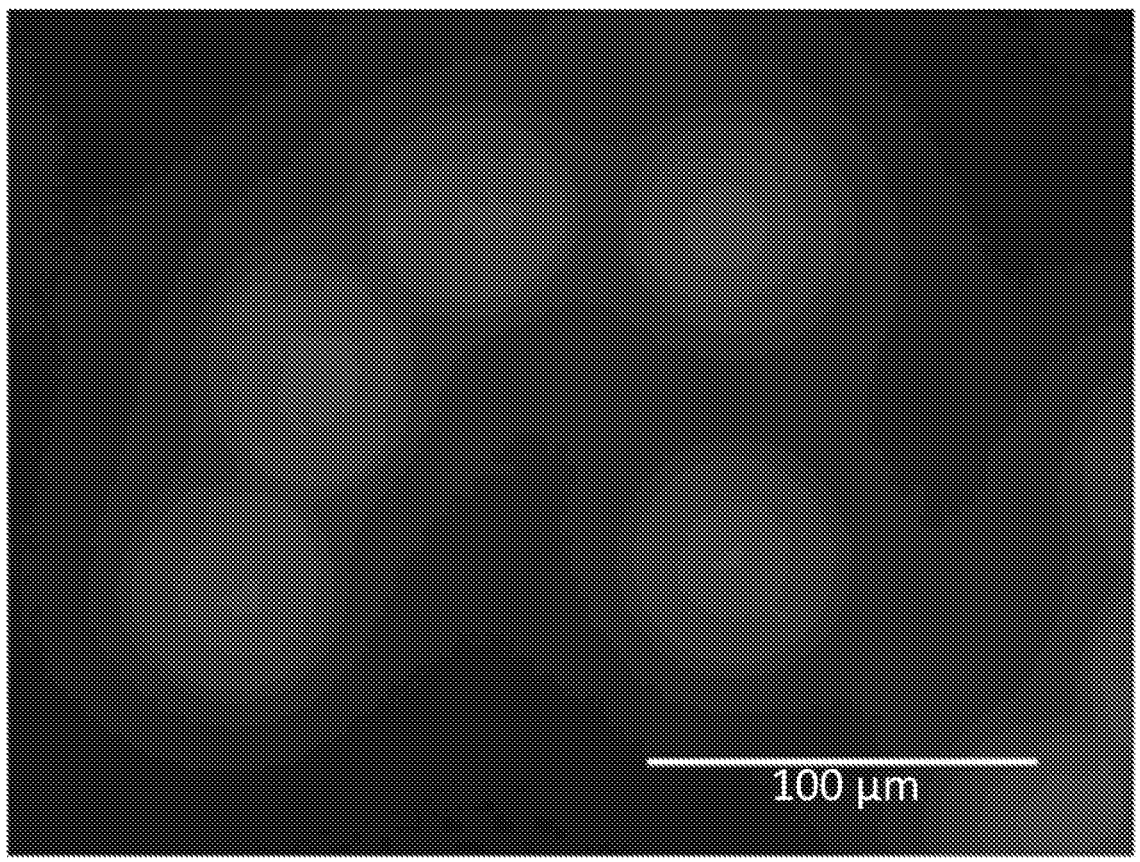
Figure 22C:
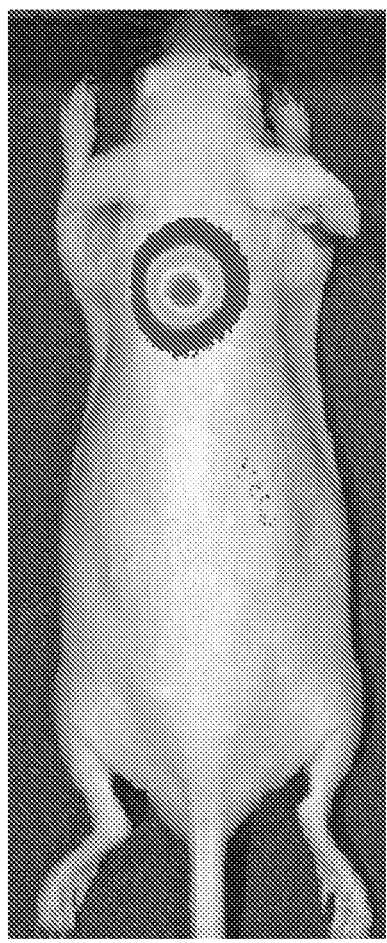
Figure 22D:
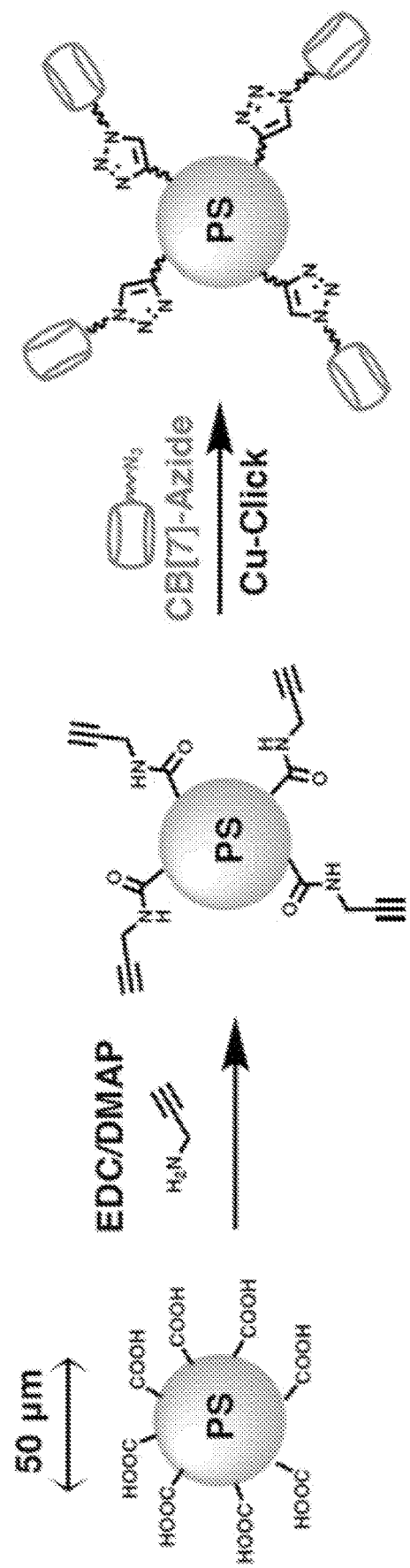
Figure 22E:
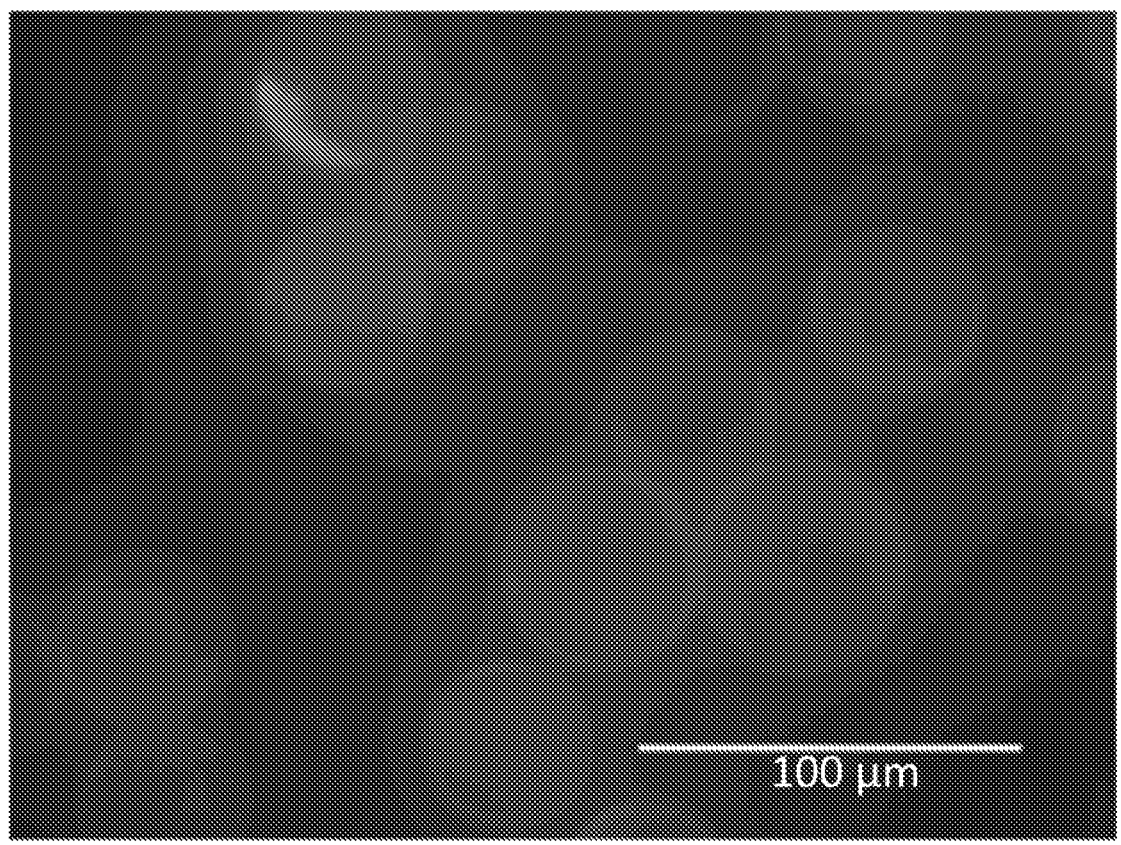
Figure 22F:
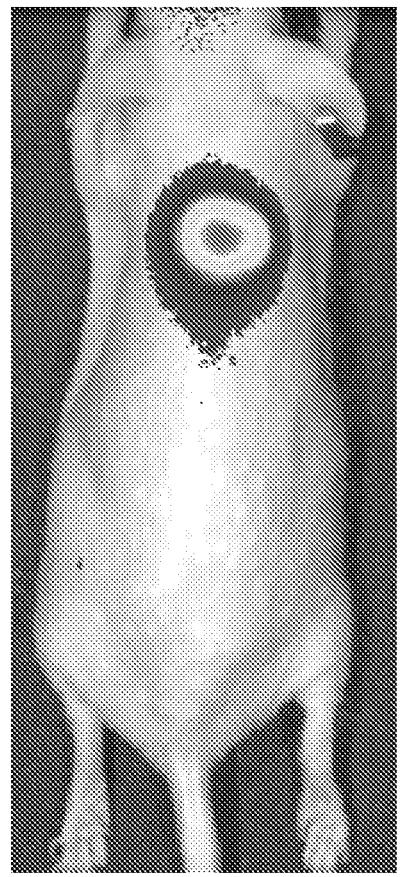

FIG. 22A, FIG. 22B, FIG. 22C, FIG. 22D, FIG. 22E, and FIG. 22F show the use of CB[7] homing with beads. Scheme for CB[7] modification of glass beads (FIG. 22A). Fluorescence microscopy showing Fc-N-Cy5 bound to the surface of glass beads (FIG. 22B). In vivo imaging demonstrating homing of Fc-N-Cy5 to a subcutaneous site where glass beads have been injected following systemic administration of the dye (FIG. 22C). Scheme for CB[7]modification of polystyrene beads (FIG. 22D). Fluorescence microscopy showing Fc-N-Cy5 bound to the surface of polystyrene beads (FIG. 22E). In vivo imaging demonstrating homing of Fc-N-Cy5 to a subcutaneous site where polystyrene beads have been injected following systemic administration of the dye (FIG. 22F).

Figure 23:
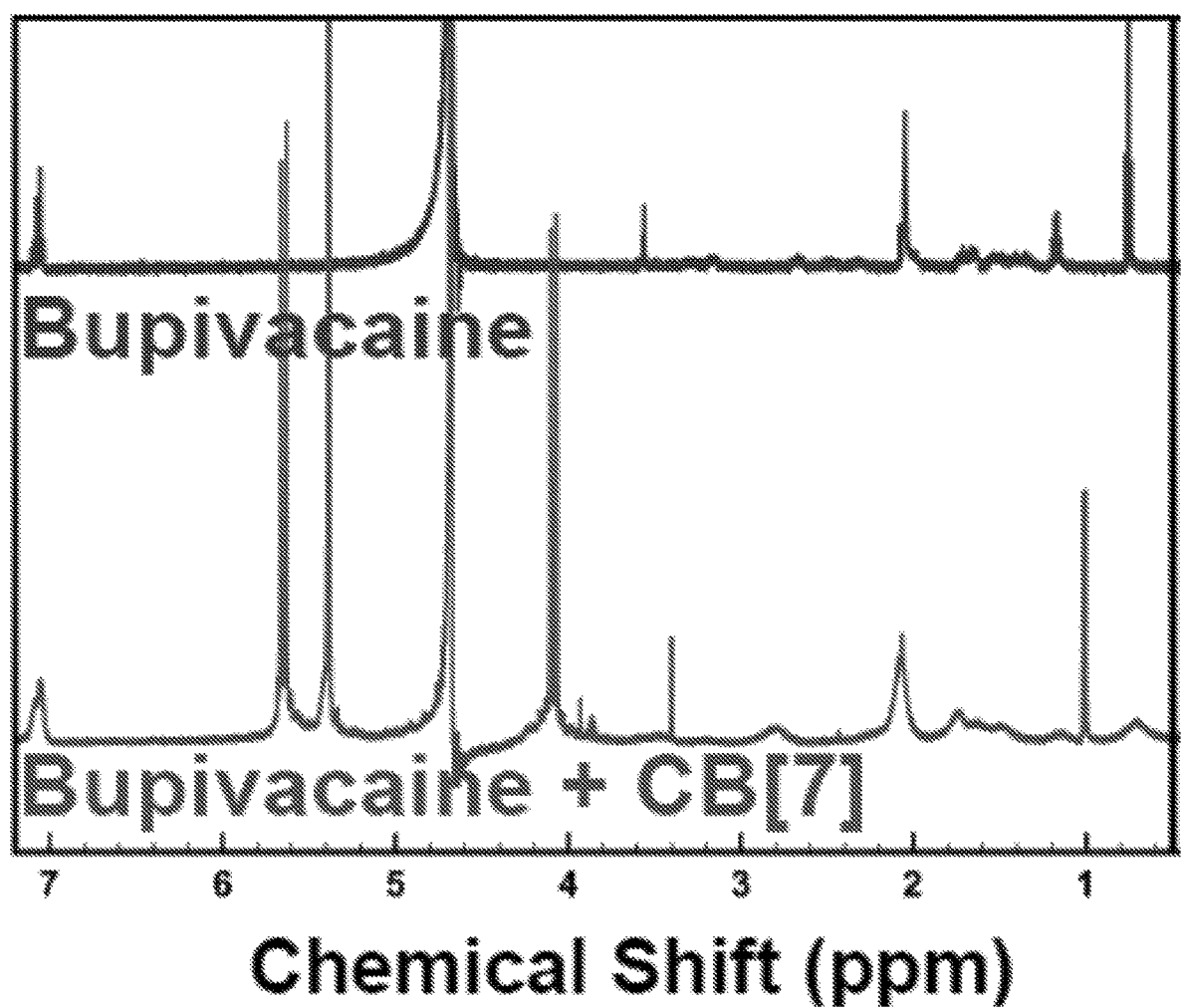

FIG. 23 is an NMR spectra comparing bupivacaine and bupivacaine bound to CB[7].

Figure 24:
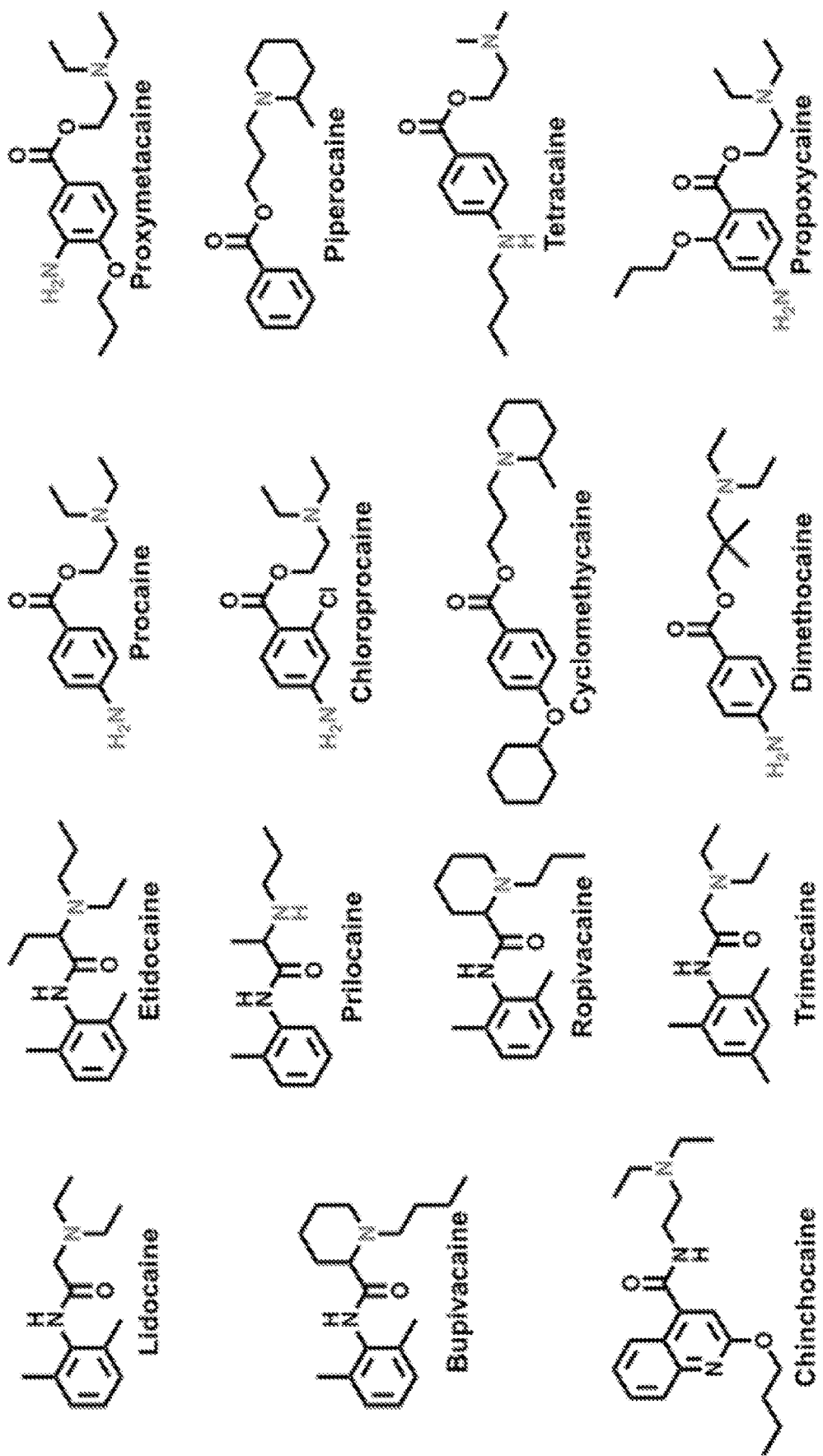

FIG. 24 is structures of sodium channel blockers, with structural motifs of protonating amines near aliphatic and/or aromatic groups, typical of strong-binding CB[7] guests.

Figure 25A:
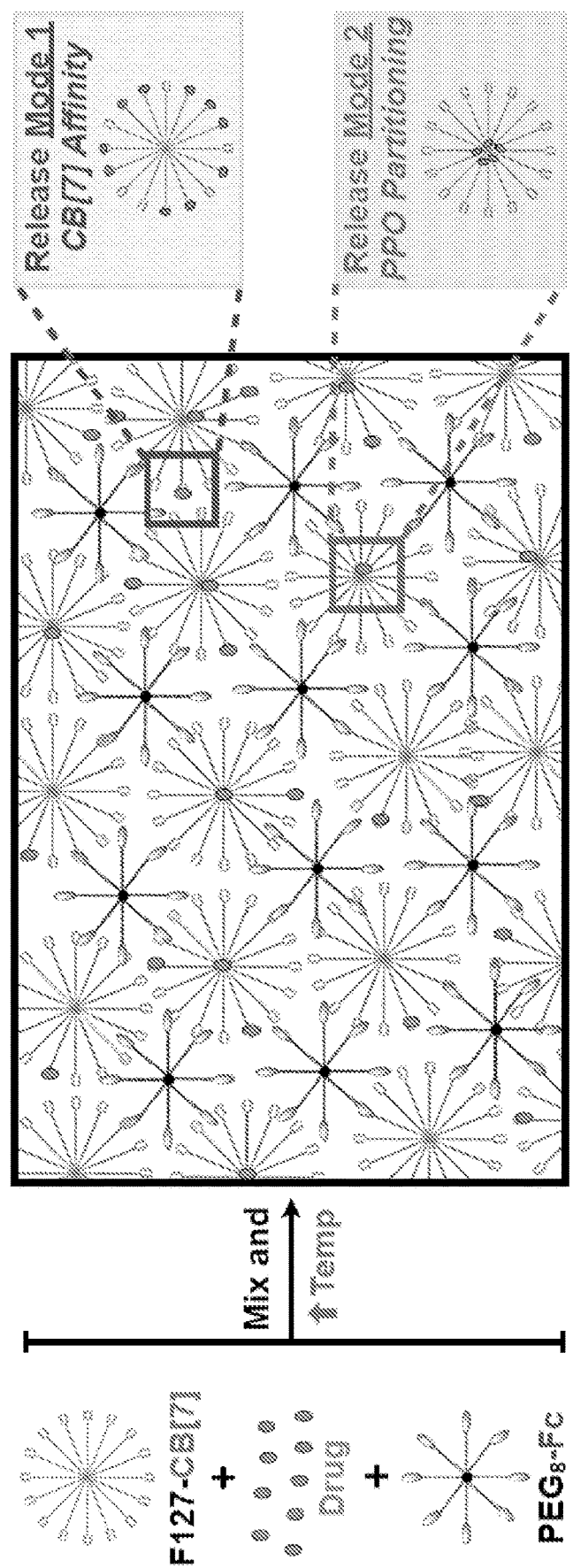
Figure 25B:
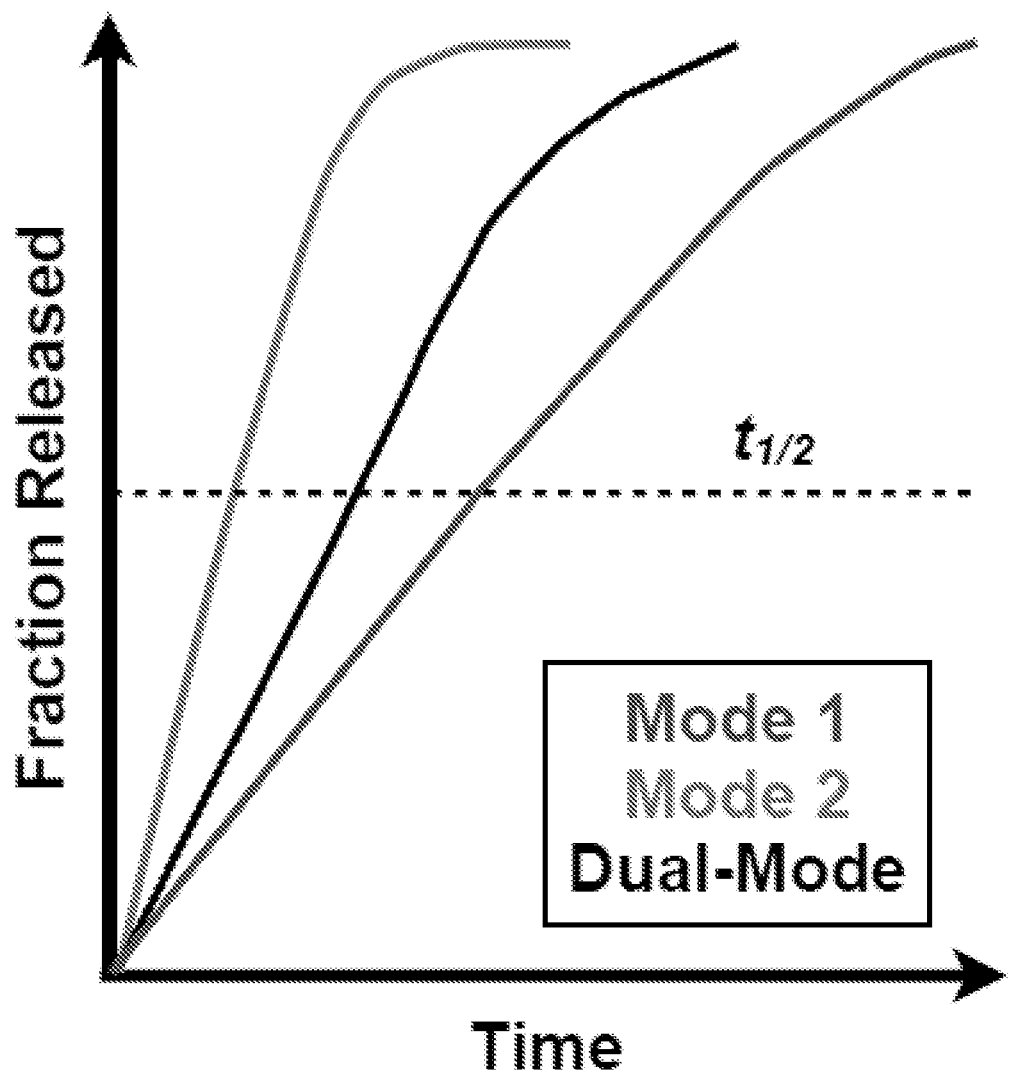

FIG. 25A and FIG. 25B show a model of the route to the encapsulation and release of drugs from CB[7]-F127 hydrogels, including the possibility of CB[7]-affinity-mediated release as well as PPO micelle encapsulation.

Figure 26A:
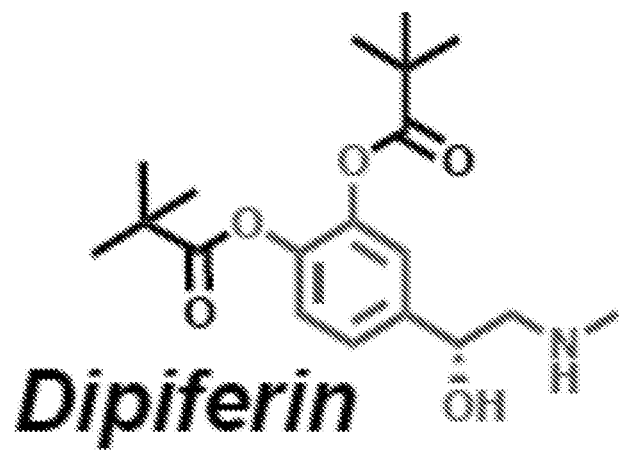
Figure 26B:
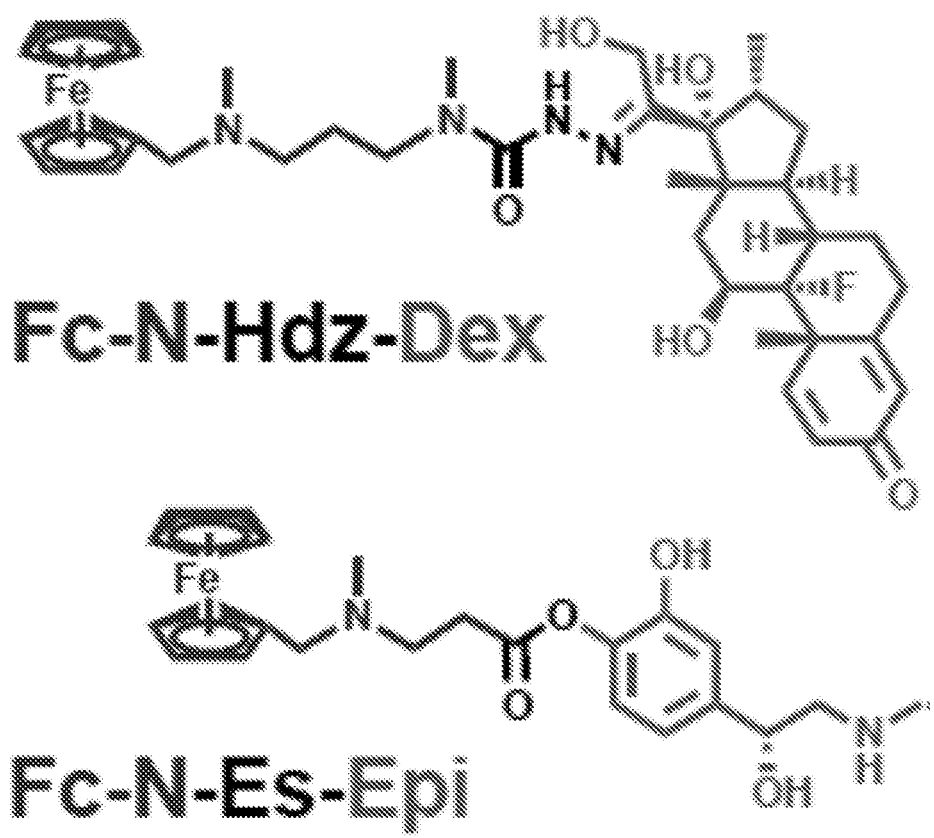

FIG. 26A and FIG. 26B show structures of epinephrine prodrug dipivefrin (FIG. 26A) and guest-linked prodrugs (FIG. 26B) which load by CB[7] affinity.

Figure 27:
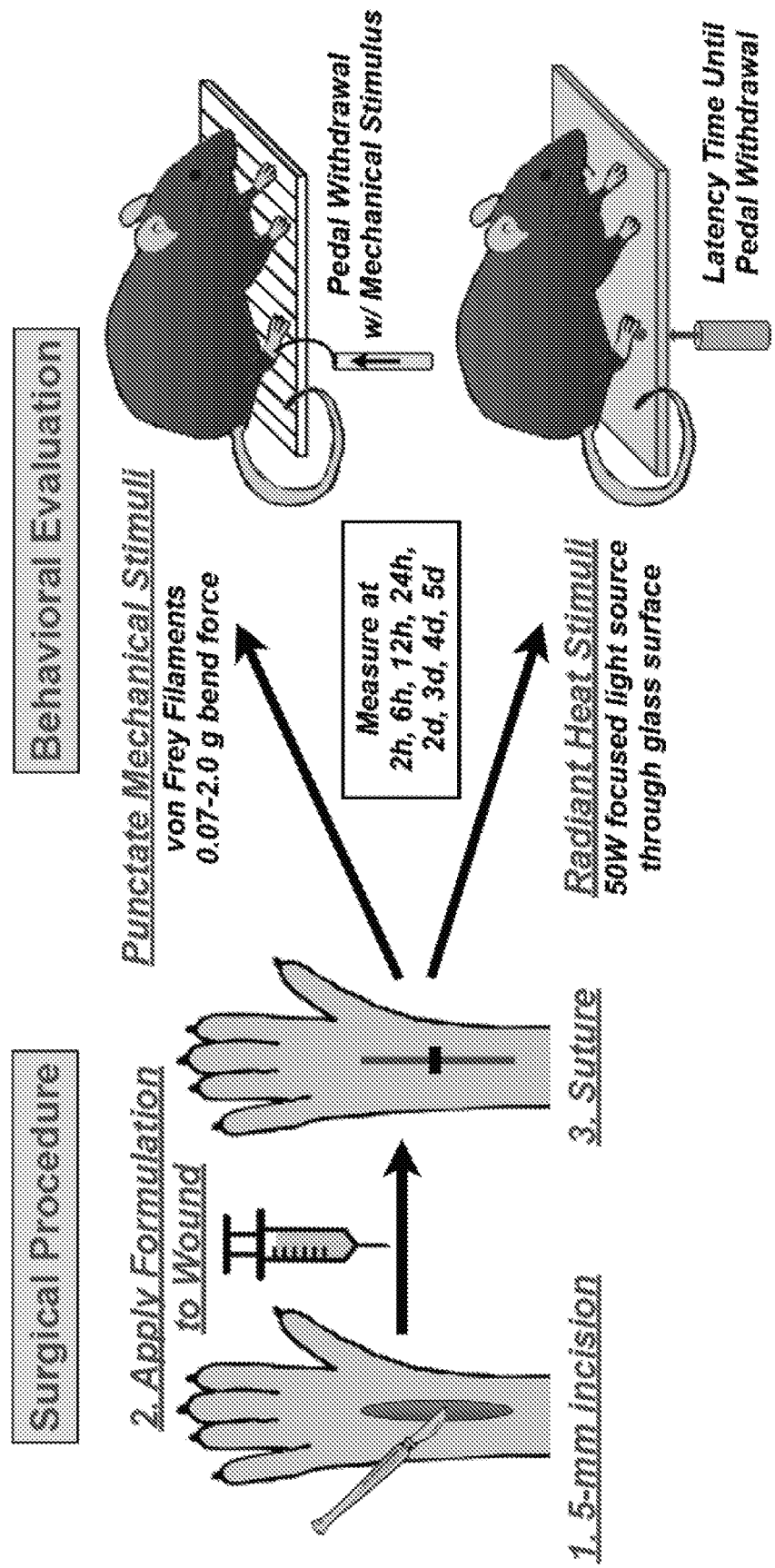

FIG. 27 is a schematic for the use of the mouse model of incision-associated pain and the plan to use it to assess the hydrogel-based formulations. Following the surgical procedure and material application, mice will be assessed for behavioral indicators of pain including the use of punctate mechanical stimuli and radiant heat stimuli.

Figure 28A:
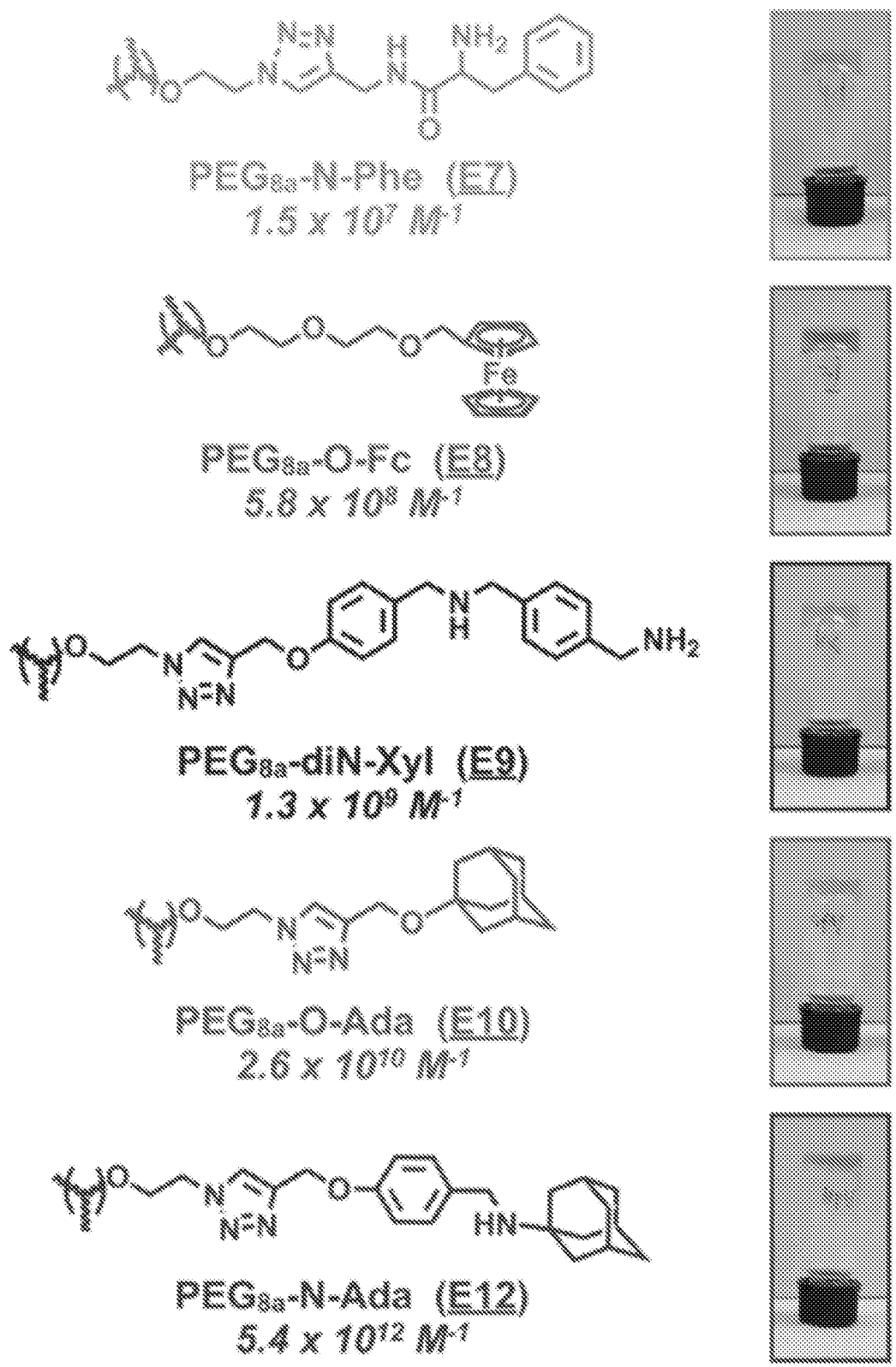
Figure 28B:
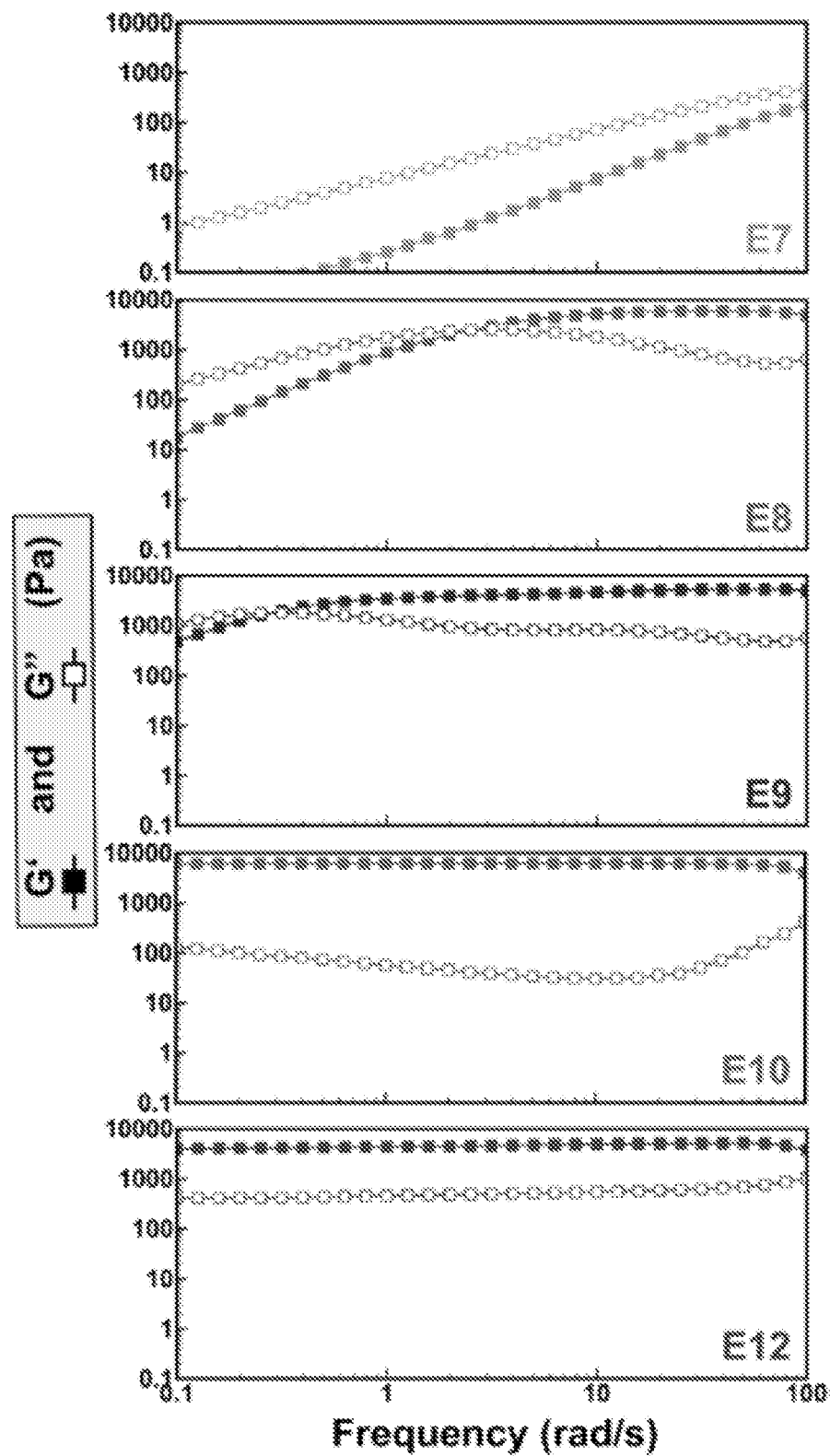
Figure 29A:
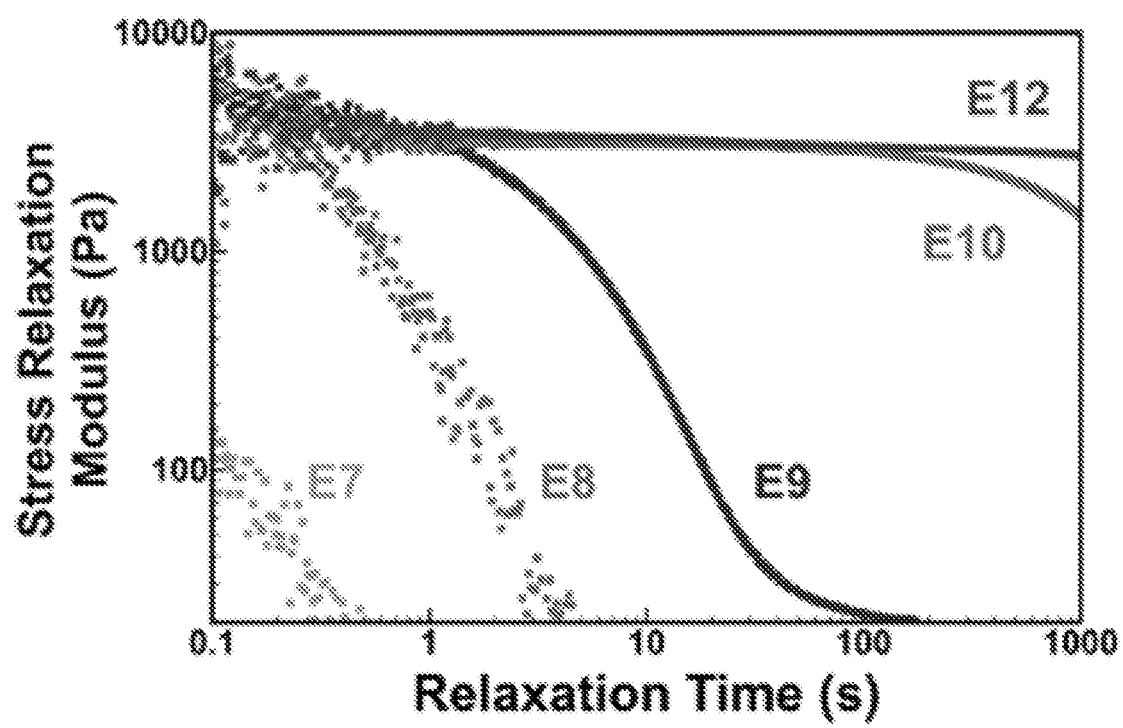

FIG. 28A and FIG. 28B show the materials and test to guest chemistry affinity on hydrogel rheology. FIG. 29A is structures of Five 8-arm PEG macromers were synthesized presenting guest chemistries with a range of affinities, listed from the lowest affinity (E7) to highest affinity (E12). All five macromers form self-supporting hydrogels when mixed with PEG$_{8a}$-CB[7] at stoichiometric proportion of host and guest in water at a macromer concentration of 5 wt %. FIG. 28B is frequency traces from oscillating rheology at constant 2% strain correlate to the time over which cross-links are dynamic in these hydrogels by the observed G'-G" crossover point.

Figure 29B:
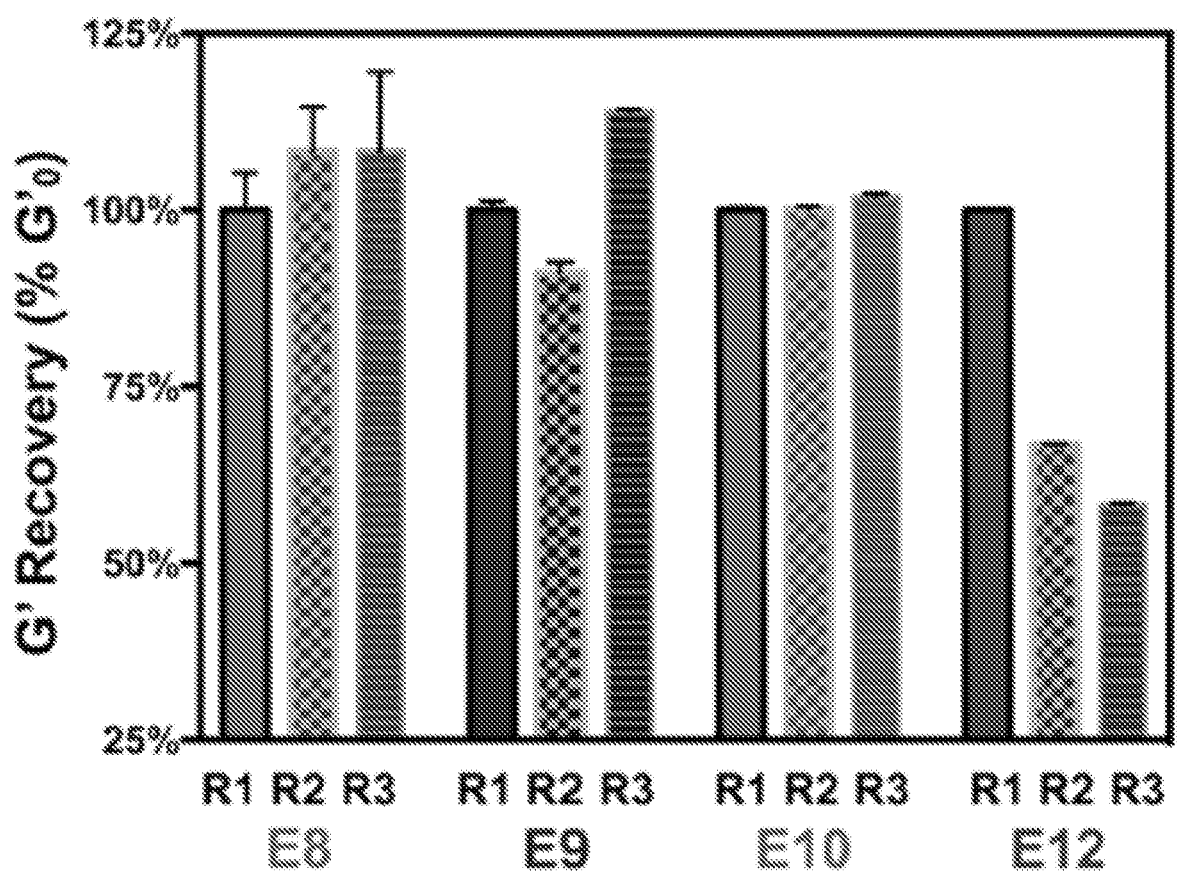
Figure 29C:
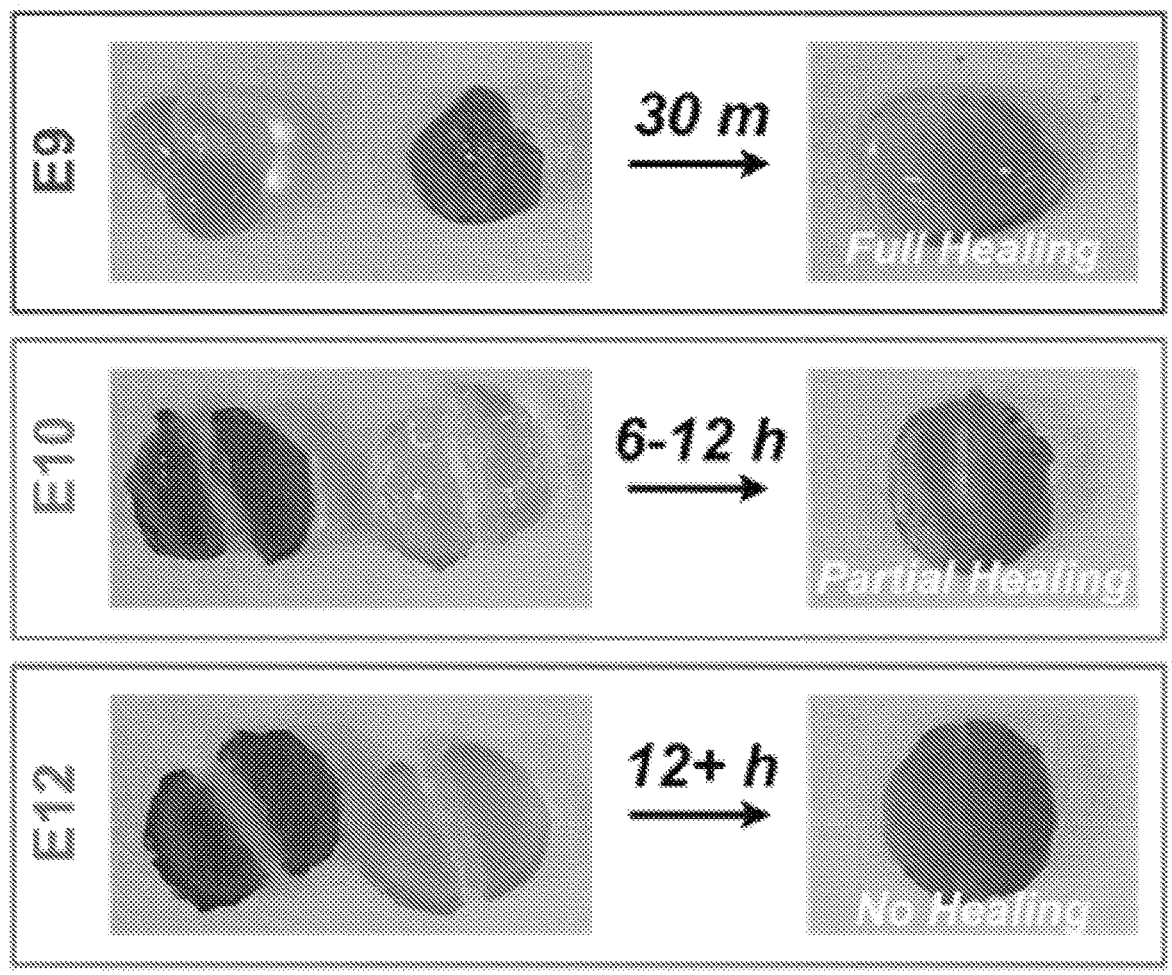
Figure 29D:
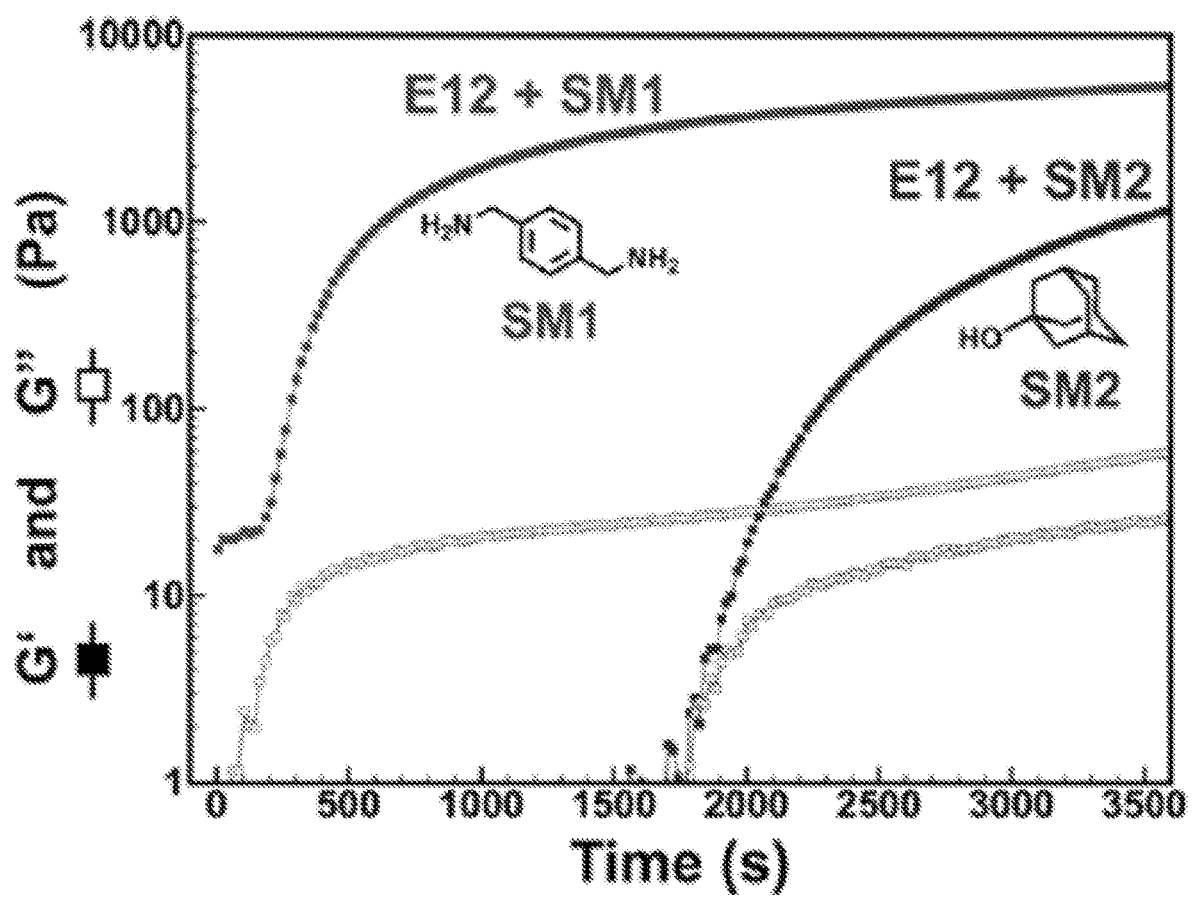

FIG. 29A, FIG. 29B, FIG. 29C, and FIG. 29D show the measurements of other hydrogel characteristics using guest chemistries of varying affinity. FIG. 29A is a graph showing the measurement of the stress relaxation modulus with 2% strain for hydrogels of varying affinity. FIG. 29B is a graph showing the step-strain studies, cycling between 2 and 200% strain, were conducted to measure self-healing upon each round (R1, R2, R3) of shear-thinning mechanical perturbation. FIG. 29C are images of bulk hydrogels cut and placed into contact, with a dye included in one-half to verify fluid contact. At various times, the gel was mechanically manipulated to determine the extent of defect healing. FIG. 29D is a graph showing the gelation kinetics for E12 in the presence of a soluble small molecule competitor that binds to CB[7] with affinity of $\sim 1 \times 10^9$ M$^{-1}$ (SM$^{-1}$) or $\sim 1 \times 10^{10}$ M$^{-1}$ (SM2).

Figure 30A:
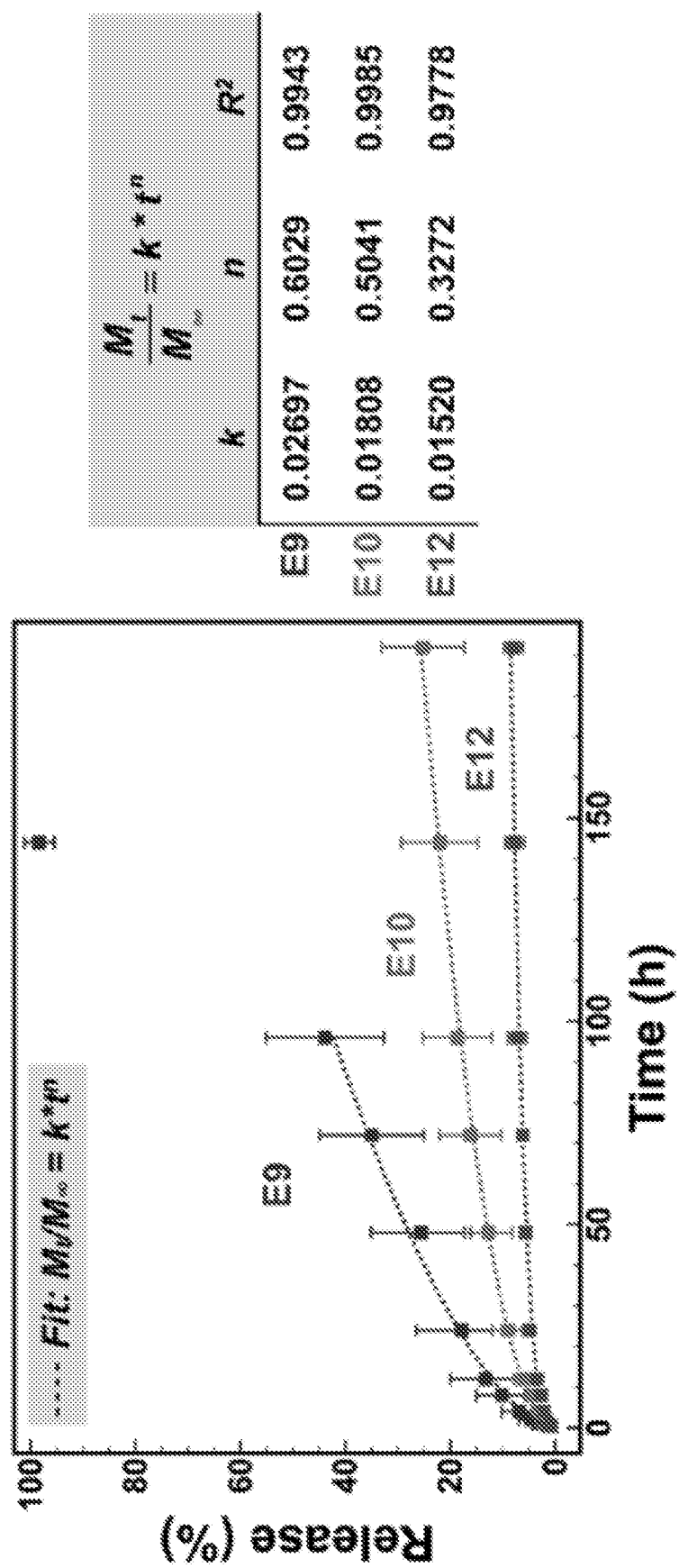
Figure 30B:
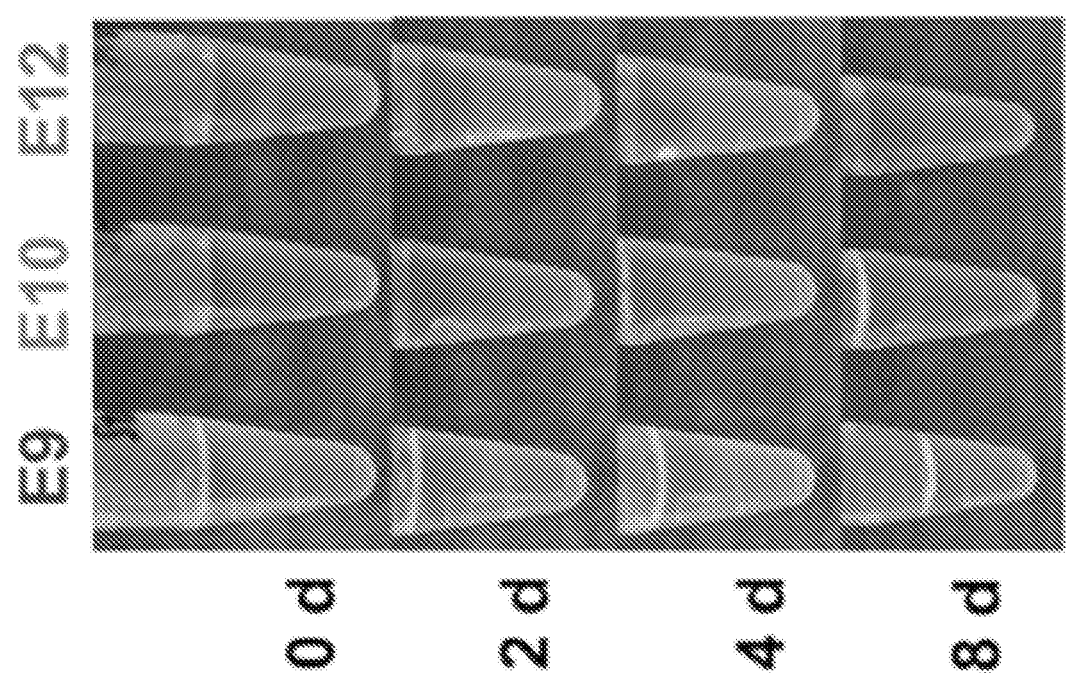
Figure 30C:
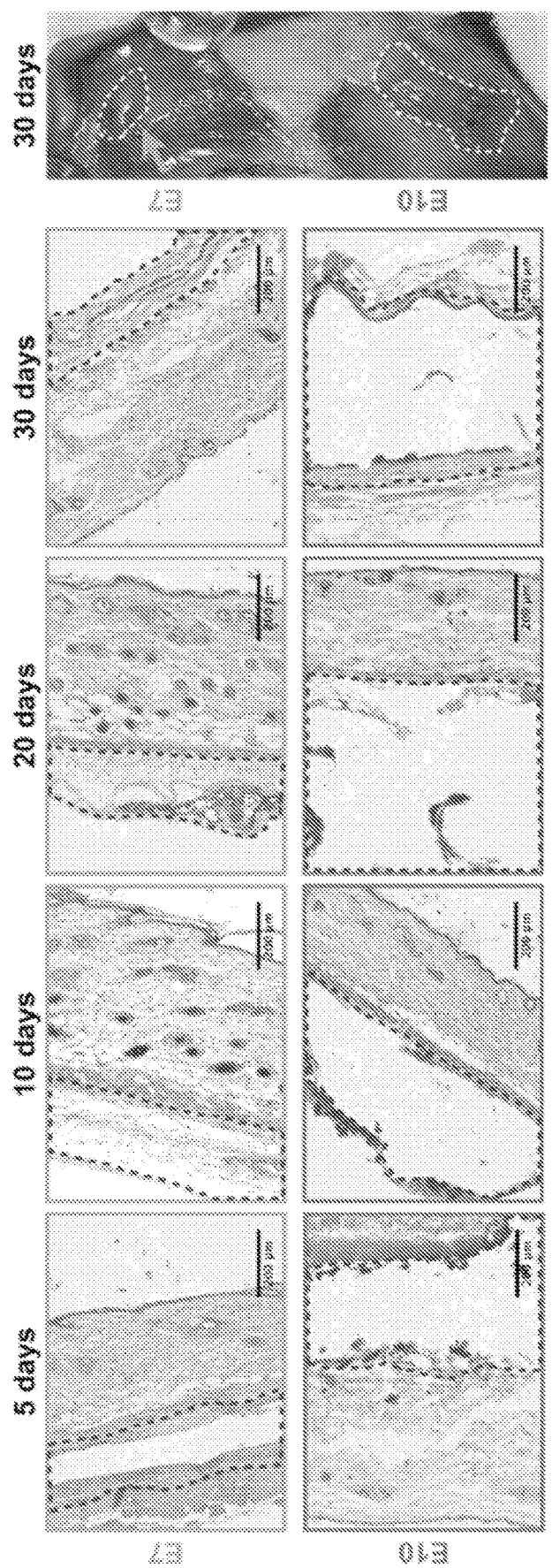

FIG. 30A, FIG. 30B and FIG. 30C show the in vivo analysis of hydrogels using guest chemistries of varying affinity. FIG. 30A is a graph and table showing the release over time of encapsulated 70 kDa FITC-dextran from E9, E10, and E12 hydrogels; data was fit to the Korsmeyer-Peppas equation and the fitting parameters for each hydrogel are shown. E9 data at 144 h was excluded from fitting as hydrogels had dissipated completely by this time. FIG. 30B are representative images from the release studies illustrating hydrogel erosion and macromolecule release from E9, E10, and E12 hydrogels. FIG. 30C is the H&E histology over 30 days for E7 and E10 hydrogels injected subcutaneously into mice, with the hydrogel outlined in blue dots on the underside of the skin. A corresponding photograph of one sample at 30 days is included to show the relative hydrogel volume remaining for each sample with the hydrogel outlined in white.

DETAILED DESCRIPTION OF THE INVENTION

Disclosed herein is a hybrid platform that aims to remotely modulate the function of any biomedical device or implant through systemic drug refilling, modular drug combinations, and/or temporal tuning of activity would advance small molecule therapy in both the pharmaceutical and biomedical device market.

Figure 1:
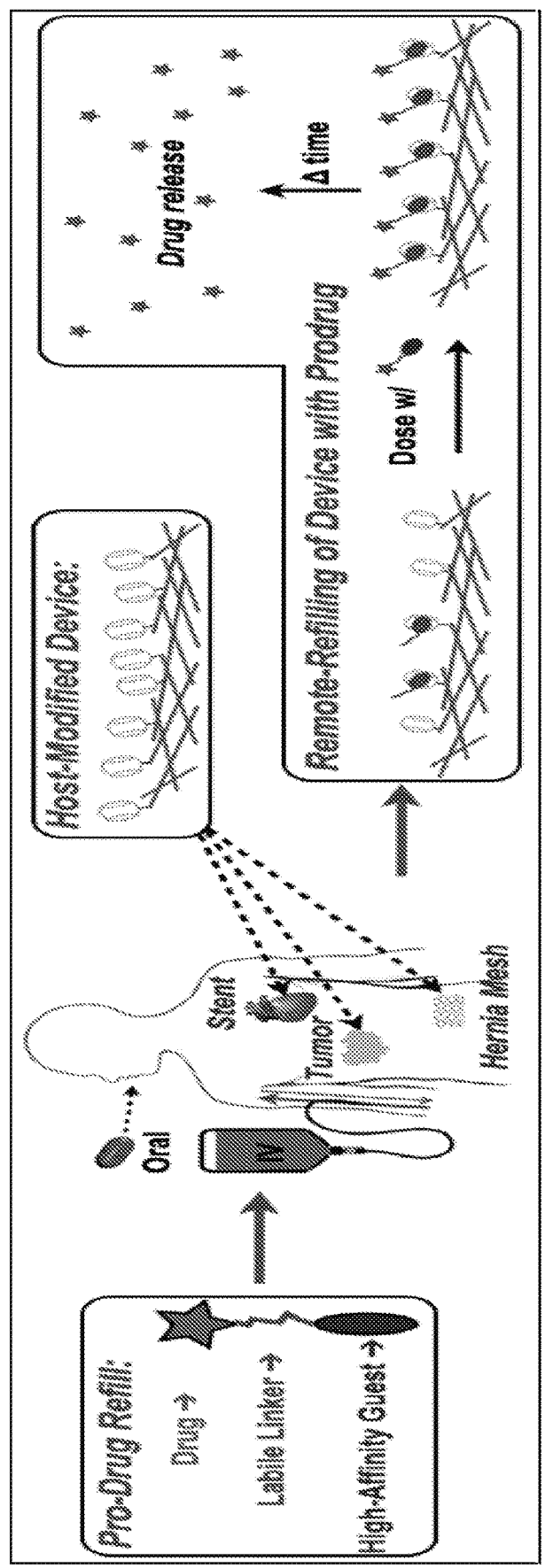

Two components bearing complimentary affinity motifs allow targeting of small molecule pharmaceutical by supramolecular affinity as a homing axis (FIG. 1). The first component consists of a drug depot or biomedical device that is injected or implanted in a desired site in the body where drug action is needed. This component was decorated with a supramolecular "host" macrocycle, cucurbit[7]uril (CB[7]), to serve as a homing signal. The second component consisted of systemically administered therapeutic prodrug—created by fusing a drug to a high-affinity "guest"—intended to home to the site of device in the body through supramolecular affinity for the presented host. The linker of this prodrug was then tailored for rupture over time to release the free drug molecules.

This technology combines benefits from systemic targeted drug carriers and localized implanted depots to enable a hybrid approach; a locally administered depot that can be refilled systemically via affinity-driven homing. The approach also reduces the risk of overdose and off-site activity, as the drug molecule would only be active once the linker is ruptured, and the kinetics of this release can be adjusted through linker selection, while simultaneously targeting the biodistribution of active drug spatially to the area of need.

In addition, this technology furthermore affords modularity in drug selection. This is especially important in the context of combination drug therapy in overcoming drug resistance; because this phenomenon can lead to diseases such as cancer becoming more difficult to treat overtime. Once an injectable depot is applied proximal to a site of need (e.g., a tumor), multiple small molecule pharmaceuticals can be dosed concurrently or in sequence, with the biodistribution for any prodrug biased to the site of the depot by virtue of affinity for presented macrocycles.

This hybrid platform technology enables temporal alteration of a drug on board as a function of affinity. Many issues arise in the implantation of biomedical devices, including specific and localized cell-mediated inflammatory reactions in the acute stage following implant. Additionally, in this acute stage the risk of infections peak. However, once these acute issues subside, it may preferable for the device to undergo pro-healing integration within the host tissue. The drug delivery device, disclosed herein may be loaded with anti-inflammatory and antibiotic drug function in the acute stage, and then subsequently switched this to pro-healing agents at a later time, allowing modulation through systemic drug refilling, modular drug combinations, and/or temporal tuning of activity thus advances therapy in a variety of scenarios.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein may be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

As used herein, the terms "administering," "providing" and "introducing" are used interchangeably and refer to the placement of the compositions of the disclosure into a subject by a method or route that results in at least partial localization of the composition to a desired site. The compositions may be administered by any appropriate route that results in delivery to a desired location in the subject.

As used herein, the term "chemotherapeutic" or "anti-cancer drug" includes any drug used in cancer treatment or any radiation sensitizing agent. Chemotherapeutics may include alkylating agents (including, but not limited to, cyclophosphamide, mechlorethamine, chlorambucil, melphalan, dacarbazine, nitrosoureas, and temozolomide), anthracyclines (including, but not limited to, daunorubicin, doxorubicin, epirubicin, idarubicin, mitoxantrone, and valrubicin), cytoskeletal disruptors or taxanes (including, but not limited to, paclitaxel, docetaxel, abraxane, and taxotere), epothilones, histone deacetylase inhibitors (including, but not limited to, vorinostat and romidepsin), topoisomerase inhibitors (including, but not limited to, irinotecan, topotecan, etoposide, tenoposide, and tafluposide), kinase inhibitors (including, but not limited to, bortezomib, erlotinib, gefitinib, imantinib, vemurafenib, and vismodegib), nucleotide analogs and precursor analogs (including, but not limited to, azacitidine, azathioprine, capecitabine, cytarabine, doxifluridine, fluorouracil, gemcitabine, hydroxyurea, mercaptopurine, methotrexate, and tioguanine), peptide antibiotics (including, but not limited to, bleomycin and actinomycin), platinum-based agents (including, but not limited to, carboplatin, cisplatin and oxaliplatin), retinoids (including, but not limited to, tretinoin, alitretinoin, and bexarotene), *vinca* alkaloids and derivatives (including, but not limited to, vinblastine, vincristine, vindesine, and vinorelbine), or combinations thereof. The chemotherapeutic may in any form necessary for efficacious administration and functionality.

As used herein, the terms "effective amount" or "therapeutically effective amount," refer to a sufficient amount of an agent or a composition or combination of compositions being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a composition as disclosed herein that may provide a clinically significant decrease in disease symptoms. An appropriate "effective" amount in any individual case may be determined using techniques, such as a dose escalation study. The dose could be administered in one or more administrations. However, the precise determination of what would be considered an effective dose may be based on factors individual to each patient, including, but not limited to, the patient's age, size, type or extent of disease, stage of the disease, route of administration of the regenerative cells, the type or extent of supplemental therapy used, ongoing disease process and type of treatment desired (e.g., aggressive vs. conventional treatment).

As used herein, the term "hydrogel" is intended to connote that meaning normally associated with that term—i.e., a three-dimensional hydrophilic polymeric network that are hydrophilic, in which water is the dispersion medium, and are capable of maintaining their structural integrity. Hydrogels are highly swollen (they can contain over 99.9% water) natural or synthetic polymers. Hydrogels also possess a degree of flexibility very similar to natural tissue, due to their significant water content.

A "peptide" or "polypeptide" is a linked sequence of two or more amino acids linked by peptide bonds. The polypeptide may be natural, synthetic, or a modification or combination of natural and synthetic. Domains are portions of a polypeptide or protein that form a compact unit and are typically 15 to 350 amino acids long.

As used herein, the term "preventing" refers to partially or completely delaying onset of an infection, disease, disorder and/or condition; partially or completely delaying onset of one or more symptoms, features, or clinical manifestations of a particular infection, disease, disorder, and/or condition; partially or completely delaying onset of one or more symptoms, features, or manifestations of a particular infection, disease, disorder, and/or condition; partially or completely delaying progression from an infection, a particular disease, disorder and/or condition; and/or decreasing the risk of developing pathology associated with the infection, the disease, disorder, and/or condition.

The term, "repeat unit", "repeating unit", or "block" as used herein refers to the moiety of a polymer that is repetitive. The repeat unit may comprise one or more repeat units, labeled as, for example, repeat unit A, repeat unit B, repeat unit C, etc. Repeat units A-C, for example, may be covalently bound together to form a combined repeat unit. Monomers or a combination of one or more different monomers can be combined to form a (combined) repeat unit of a polymer or copolymer.

A "subject" or "patient" may be human or non-human and may include, for example, animal strains or species used as "model systems" for research purposes, such a mouse model as described herein. Likewise, patient may include either adults or juveniles (e.g., children). Moreover, patient may mean any living organism, preferably a mammal (e.g., human or non-human) that may benefit from the administration of compositions contemplated herein. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

As used herein, "treat," "treating" and the like, mean a slowing, stopping or reversing of progression of a disease or disorder when provided a composition described herein to an appropriate control subject. The terms also mean a reversing of the progression of such a disease or disorder to a point of eliminating or greatly reducing the cell proliferation. As such, "treating" means an application or administration of the compositions described herein to a subject, where the subject has a disease or a symptom of a disease, where the purpose is to cure, heal, alleviate, relieve, alter, remedy, ameliorate, improve or affect the disease or symptoms of the disease. As used herein, "treatment," "therapy" and/or "therapy regimen" refer to the clinical intervention made in response to a disease, disorder or physiological condition manifested by a patient or to which a patient may be susceptible. The aim of treatment includes the alleviation or prevention of symptoms, slowing or stopping the progression or worsening of a disease, disorder, or condition and/or the remission of the disease, disorder or condition.

2. Thermoresponsive Hydrogel

Provided herein is a thermoresponsive hydrogel comprising a cucurbit[n]uril moiety, wherein n is an integer from 5-8, and a polymer. The thermoresponsive hydrogel may have phase transition behavior such that it reversibly forms a gel at or above the gelation temperature.

The thermoresponsive hydrogel may have a gelation temperature between 25° C. and 35° C. The thermoresponsive hydrogel may have a gelation temperature above 25° C., above 26° C., above 27° C., above 28° C., above 29° C., above 30° C., above 31° C., above 32° C., above 33° C., or above 34° C. The thermoresponsive hydrogel may have a gelation temperature below 35° C., below 34° C., below 33° C., below 32° C., below 31° C., below 30° C., below 29° C., below 28° C., below 27° C., or below 26° C.

i. Cucurbit[n]uril

The thermoresponsive hydrogel may comprise a cucurbit[n]uril moiety. The cucurbit[n]uril moiety may be modified or unmodified. For example, the cucurbit[n]uril moiety may be modified with at least one halide, such as chloride, at least one epoxide, at least one azide, at least one maleimide, or a combination thereof. An epoxide modified cucurbit[n]uril moiety may be reactive with amines, frequently found on protein and peptides, thereby forming a secondary amine in the linkage. An azide modified cucurbit[n]uril moiety may be reactive with thiol groups, and may be used to introduce a maleimide group.

The thermoresponsive hydrogel may comprise a cucurbit[n]uril moiety, where n is 7, yielding a cucurbit[7]uril moiety (CB[7]).

ii. First Polymer

The thermoresponsive hydrogel may comprise a first polymer.

In some embodiments, the first polymer may be a thermoresponsive polymer. The thermoresponsive polymer may be any polymer that forms aggregates or changes phases as a function of temperature. Thermoresponsive polymers may possess regions of hydrophobic and hydrophilic character. The thermoresponsive polymer may be linear or branched.

Suitable thermoresponsive polymers may include polyoxyalkylene polymers, such as block copolymers of different oxyalkylene units. At least one polyoxyalkylene unit may have hydrophobic characteristics and at least one polyoxyalkylene unit may have hydrophilic characteristics. A block copolymer of polyoxyethylene and polyoxypropylene may be used. Other suitable thermoresponsive polymers may include Pluronic® triblock polyol polymers (BASF) having the general formula (POE)c (POP)d (POE)c, where POP is polyoxypropylene and represents the hydrophobic portion of the polymer and POE is polyoxyethylene and represents the hydrophilic portion of the polymer. Other exemplary polyoxyalkylene polymers may include alkyl polyols, which are a product of alcohol condensation reactions with a terminal alkyl or arylalkyl group. The alkyl group may have hydrophobic character, such as butyl, hexyl and the like. An alkyl polyol may have the general formula $R—(OCH_2 CH_2)n$ OH, where R is a nonpolar pendant group such as alkyl and arylalkyl and the like, and n is in the range of 5-1000. A preferred alkylpolyol is polyethylene glycol mono(nonylphenyl)ether. Still other exemplary thermoresponsive polymers may include cellulosic, cellulose ethers and guar gums which possess hydrophobic and hydrophilic regions along the polymer backbone which permit aggregation behavior. One or more thermoresponsive polymer may be used in the thermoresponsive hydrogel.

In some embodiments, the thermoresponsive polymer may be a block copolymer of polyethylene oxide (PEO) and polypropylene oxide (PPO). In some embodiments, the thermoresponsive polymer is a triblock copolymer with the formula (PEO)a(PPO)b(PEO)a, wherein a is an integer between 20 and 200 and b is an integer between 50 and 100. In exemplary embodiments, the thermoresponsive polymer is a triblock copolymer with the formula (PEO)a(PPO)b (PEO)a in which a has an average value of approximately 100 and b has an average value of approximately 65.

In some embodiments, the thermoresponsive polymer may reversibly form micelles at or above a critical micelle temperature. The critical micelle temperature of the thermoresponsive conjugate may be between 20° C. and 35° C. The critical micelle temperature of the thermoresponsive conjugate may be above 20° C., above 21° C., above 22° C., above 23° C., above 24° C., above 25° C., above 26° C., above 27° C., above 28° C., above 29° C., above 30° C., above 31° C., above 32° C., above 33° C., or above 34° C. The critical micelle temperature of the thermoresponsive conjugate may be below 35° C., below 34° C., below 33° C., below 32° C., below 31° C., below 30° C., below 29° C., below 28° C., below 27° C., below 26° C., below 25° C., below 24° C., below 23° C., below 22° C., or below 21° C.

In some embodiments, the thermoresponsive polymer may comprise a plurality of thermoresponsive conjugates. The thermoresponsive conjugate may comprise at least one cucurbit[n]uril moiety linked to the thermoresponsive polymer. In exemplary embodiments, each thermoresponsive conjugate comprises two cucurbit[n]uril moieties.

The thermoresponsive conjugate may have phase transition behavior such that it reversibly forms micelles at or above a critical micelle temperature. The critical micelle temperature of the thermoresponsive conjugate may be between 20° C. and 35° C. The critical micelle temperature of the thermoresponsive conjugate may be above 20° C., above 21° C., above 22° C., above 23° C., above 24° C., above 25° C., above 26° C., above 27° C., above 28° C., above 29° C., above 30° C., above 31° C., above 32° C., above 33° C., or above 34° C. The critical micelle temperature of the thermoresponsive conjugate may be below 35° C., below 34° C., below 33° C., below 32° C., below 31° C., below 30° C., below 29° C., below 28° C., below 27° C., below 26° C., below 25° C., below 24° C., below 23° C., below 22° C., or below 21° C.

In some embodiments, the thermoresponsive polymer is configured to bind the cucurbit[n]uril moiety. The thermoresponsive polymer may comprise at least one functional group configured to bind the cucurbit[n]uril moiety. The at least one functional group may be selected from the group consisting of ferrocene, phenylalanine, xylylenediamine, and adamantane.

iii. Second Polymer

In some embodiments, the thermoresponsive gel may include a second polymer. The second polymer may be any polymer compatible with the first polymer to form the thermoresponsive hydrogel. The second polymer may be straight or branched. In some embodiments, the second polymer is branched.

The second polymer may be a multi-arm polyether polyol including, but not limited to, comb and star polyether polyols. It should be recognized that the multi-arm polyether polyols are generally a somewhat heterogeneous mixture having a distribution of arm lengths and in some cases, a distribution of species with different numbers of arms. When a polyether polyol has a distribution of species having different numbers of arms, it can be referred to based on the average number of arms in the distribution. Typically, multi-arm polyether polyols are made by condensing ethylene oxide, propylene oxide or mixtures thereof with a polyol core, such as glycerol, polyglycerol, or triethanolamine, or with a polyamine core such as ethylenediamine, under basic conditions. In some embodiments, the second polymer is a multi-arm polyethylene glycol.

In some embodiments, the second polymer is configured to bind the cucurbit[n]uril moiety. The second polymer may comprise at least one functional group configured to bind the cucurbit[n]uril moiety. The second polymer may comprise at least two, at least 4, at least 6, at least 9, or at least 10 functional groups configured to bind the cucurbit[n]uril moiety.

Any functional group capable of binding to the cucurbit[n]uril moiety may be used. The functional group may have an affinity ($K_r$) for the cucurbit[n]uril moiety of at least $1.0 \times 10^8$ $M^{-1}$. The at least one functional group may be selected from the group consisting of ferrocene, phenylalanine, xylylenediamine, adamantane, and derivatives or combinations thereof. In some embodiments, the at least functional group is ferrocene.

In some embodiments, the second polymer is conjugated to at least one cucurbit[n]uril moiety. When the second polymer is branched or a multi-arm polymer, each or any arm or branch may be conjugated to a cucurbit[n]uril moiety.

The hydrogels described herein may have low total polymer concentration. The high water content of the hydrogel makes it highly attractive for biomedical applications, for example due to improved biocompatibility. In some embodiments, the thermoresponsive hydrogel comprises 1 to 20% by weight total solids of the cucurbit[n]uril moiety, the first polymer, and the second polymer. The thermoresponsive hydrogel may comprise about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20% by weight total solids of the cucurbit[n]uril moiety, the first polymer, and the second polymer.

The thermoresponsive hydrogel may comprise a ratio of the cucurbit[n]uril moiety to the at least functional group as necessary to form the gel required. One of skill in the art will be able to vary the amounts of the cucurbit[n]uril moiety to the at least functional group based on the desired method of use and the first and second polymers comprising the thermoresponsive hydrogel. In some embodiments, the thermoresponsive hydrogel comprises a ratio of the cucurbit[n]uril moiety to the at least functional group of between 1:1 and 3:1.

3. Drug Delivery System

Also provided herein is a drug delivery system. The drug delivery system may comprise a thermoresponsive hydrogel as described herein and at least one therapeutic agent reversibly bound to the thermoresponsive hydrogel.

The at least one therapeutic agent may be coupled to a guest ligand with a labile linker. The guest ligand may be any ligand that will reversibly bind to the cucurbit[n]uril moiety of the thermoresponsive hydrogel. In some embodiments, the guest ligand has an affinity of greater than $10^{10}$ $M^{-1}$ for the cucurbit[n]uril moiety. The guest ligand may be selected from the group consisting of ferrocene, phenylalanine, xylylenediamine, adamantane, and combinations thereof.

The labile linker may be any moiety or combination of moieties that links the guest ligand to the therapeutic agent that may be cleaved under a given set of conditions or by a metabolic or enzymatic process to release a free therapeutic agent and a free guest ligand. For example, the labile ligand may be cleaved and release the therapeutic agent by hydrolysis of the labile linker, metabolism of the labile linker, enzymatic cleavage of the labile linker, or a combination thereof. The labile linker may comprise an ethylene glycol moiety, a hydrazone moiety, an ester moiety, a imine moiety, a cis-aconityl moiety, an ether moiety, a peptide, a disulfide moiety, a thioester moiety, an oxime moiety, a carbonate moiety, an amide moiety, an orthoester moiety, a urethane moiety, an anhydride moiety, an acetal moiety, or a ketal moiety.

The labile linker may have a rate of hydrolysis or a rate of metabolism greater than the off-rate of the guest ligand bound to the thermoresponsive hydrogel.

The at least one therapeutic agent may be an anti-cancer drug, an anti-infective drug, an anti-inflammatory drug, an analgesic, a cardiovascular drug, a tissue regenerating drug, an anti-diabetic drug, a vaccine antigen, a peptide, a protein, an ocular drug, or a nanoparticle formulation, or a combination thereof. In some embodiments, the at least one therapeutic agent is an anti-cancer drug, an analgesic, an anti-inflammatory drug, or a combination thereof.

In some embodiments, the analgesic is a sodium channel blocking analgesic. The sodium channel blocking analgesic may be selected from the group consisting of lidocaine, etidocaine, prilocaine, bupivacaine, ropivacaine, chinchocaine, trimecaine, procaine, proxymetacaine, chloroprocaine, piperocaine, cyclomethycaine, tetracine dimethocaine, propxycaine, and a combination thereof.

The at least one therapeutic agent may be an anti-cancer drug. In exemplary embodiments, the anti-cancer drug is doxorubicin.

The at least one therapeutic agent may be an anti-inflammatory drug. Anti-inflammatory drugs reduce inflammation, including redness, swelling, and pain, in the body. The anti-inflammatory drug may be a steroidal or nonsteroidal anti-inflammatory drug. Commonly used steroidal anti-inflammatory drugs include, for example, betamethasone, prednisone, dexamethasone, cortisone, hydrocortisone, methylprednisolone, and prednisolone. Some examples of nonsteroidal anti-inflammatory drugs include aspirin, ibuprofen, and naproxen. In addition, about half of analgesics are anti-inflammatory drugs. In some embodiments, the anti-inflammatory drug is epinephrine or dexamethasone.

4. Methods of Use

The present disclosure also provides methods of treating a disease or disorder in a subject. The method may comprise implanting a thermoresponsive hydrogel as described herein at a desired location in a subject and administering at least one dose of a first therapeutic agent to the subject. The method may further comprise administering at least one dose of a second therapeutic agent to the subject. The first and/or second therapeutic agents may reversibly bind to the thermoresponsive hydrogel.

The thermoresponsive hydrogel may be implanted by techniques well known to those skilled in the medical arts taking into consideration such factors as the age, sex, weight, and condition of the particular subject and desired location for implantation. In some embodiments, the thermoresponsive hydrogel is implanted by injection.

The first therapeutic agent may be an anti-cancer drug, an anti-infective drug, an anti-inflammatory drug, an analgesic, a cardiovascular drug, a tissue regenerating drug, an anti-diabetic drug, a vaccine antigen, a peptide, a protein, an ocular drug, or a nanoparticle formulation, or a combination thereof.

In some embodiments, the analgesic is a sodium channel blocking analgesic. The sodium channel blocking analgesic may be selected from the group consisting of lidocaine, etidocaine, prilocaine, bupivacaine, ropivacaine, chinchocaine, trimecaine, procaine, proxymetacaine, chloroprocaine, piperocaine, cyclomethycaine, tetracine dimethocaine, propxycaine, and a combination thereof. In some embodiments, the anti-inflammatory drug is epinephrine or dexamethasone. In exemplary embodiments, the anti-cancer drug is doxorubicin.

The first therapeutic agent may be coupled to a guest ligand with a labile linker. The guest ligand may be any ligand that will reversibly bind to the cucurbit[n]uril moiety of the thermoresponsive hydrogel. In some embodiments, the guest ligand has an affinity of greater than $10^{10}$ $M^{-1}$ for the cucurbit[n]uril moiety.

The guest ligand may be selected from the group consisting of ferrocene, phenylalanine, xylylenediamine, adamantane, and combinations thereof.

The labile linker may be any moiety or combination of moieties that links the guest ligand to the therapeutic agent that may be cleaved under a given set of conditions or by a metabolic or enzymatic process to release a free therapeutic agent and a free guest ligand. For example, the labile ligand may be cleaved and release the therapeutic agent by hydrolysis of the labile linker, metabolism of the labile linker, enzymatic cleavage of the labile linker, or a combination thereof. The labile linker may comprise an ethylene glycol moiety, a hydrazone moiety, an ester moiety, a imine moiety, a cis-aconityl moiety, an ether moiety, a peptide, a disulfide moiety, a thioester moiety, an oxime moiety, a carbonate moiety, an amide moiety, an orthoester moiety, a urethane moiety, an anhydride moiety, an acetal moiety, or a ketal moiety.

The labile linker may have a rate of hydrolysis or a rate of metabolism greater than the off-rate of the guest ligand bound to the thermoresponsive hydrogel.

The second therapeutic agent may reversibly bind to the thermoresponsive hydrogel. The second therapeutic agent may be coupled to a guest ligand with a labile linker. The guest ligand may be any ligand that will reversibly bind to the cucurbit[n]uril moiety of the thermoresponsive hydrogel. The second therapeutic agent may bind to the hydrogel without the addition of a guest ligand.

The second therapeutic agent may be an anti-cancer drug, an anti-infective drug, an anti-inflammatory drug, an analgesic, a cardiovascular drug, a tissue regenerating drug, an anti-diabetic drug, a vaccine antigen, a peptide, a protein, an ocular drug, or a nanoparticle formulation, or a combination thereof.

a. Treating Cancer

The methods as detailed herein may be used to treat cancer. The cancer may be any cancer type or subtype. The cancer may be a carcinoma, sarcoma, lymphoma, leukemia, melanoma, mesothelioma, multiple myeloma, or seminoma. The cancer may be a cancer of the bladder, blood, bone, brain, breast, cervix, colon/rectum, endometrium, head and neck, kidney, liver, lung, muscle tissue, ovary, pancreas, prostate, skin, spleen, stomach, testicle, thyroid or uterus. In some embodiments, the cancer is a solid tumor. Examples of cancers that are solid tumors include, but are not limited to, brain, pancreatic, bladder, non-small cell lung cancer (NSCLC), breast and ovarian cancers.

In the methods as detailed herein to treat cancer, the first therapeutic may be an anti-cancer drug. In some embodiments, the anti-cancer drug is doxorubicin.

In some embodiments, the desired location of hydrogel implantation is proximal to the solid tumor.

b. Administration and Dosing

The disclosed therapeutic agents may be incorporated into pharmaceutical compositions suitable for administration to a subject (such as a patient, which may be a human or non-human) well known to those skilled in the pharmaceutical art. The pharmaceutical compositions may be prepared for administration to a subject. Such pharmaceutical compositions may be administered in dosages and by techniques well known to those skilled in the medical arts taking into consideration such factors as the age, sex, weight, and condition of the particular subject, and the route of administration.

The pharmaceutical compositions may include pharmaceutically acceptable carriers. The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants may also be present in the composition, according to the judgment of the formulator. The route by which the composition is administered and the form of the composition will dictate the type of carrier to be used.

The therapeutic agents or pharmaceutical compositions comprising the therapeutic agents may be administered prophylactically or therapeutically. In prophylactic administration, the therapeutic agents or pharmaceutical compositions comprising the therapeutic agents may be administered in an amount sufficient to induce a response. In therapeutic applications, the therapeutic agents or pharmaceutical compositions comprising the therapeutic agents are administered to a subject in need thereof in an amount sufficient to elicit a therapeutic effect. An amount adequate to accomplish this is defined as "therapeutically effective dose." Amounts effective for this use will depend on, e.g., the particular composition of the conjugate regimen administered, the manner of administration, the stage and severity of the disease, the general state of health of the patient, and the judgment of the prescribing physician.

The therapeutic agents or pharmaceutical compositions comprising the therapeutic agents may be administered by methods well known in the art as described in Donnelly et al. (*Ann. Rev. Immunol.* 1997, 15, 617-648); Felgner et al. (U.S. Pat. No. 5,580,859, issued Dec. 3, 1996); Felgner (U.S. Pat. No. 5,703,055, issued Dec. 30, 1997); and Carson et al. (U.S. Pat. No. 5,679,647, issued Oct. 21, 1997). One skilled in the art would know that the choice of a pharmaceutically acceptable carrier, including a physiologically acceptable compound, depends, for example, on the route of administration. The therapeutic agents may be administered locally or systemically by enteral or parenteral routes. In some embodiments, the therapeutic agents are administered systemically.

The therapeutic agents disclosed herein may conveniently be presented in a single dose or as divided doses administered at appropriate intervals, for example, as two, three, four or more sub-doses per day. The sub-dose itself may be further divided, e.g., into a number of discrete loosely spaced administrations.

As will be readily apparent to one skilled in the art, the useful in vivo dosage to be administered and the particular mode of administration will vary depending upon the age, weight, the severity of the affliction, and mammalian species treated, the particular compounds employed, and the specific use for which therapeutic agents are employed. The determination of effective dosage levels, that is the dosage levels necessary to achieve the desired result, can be accomplished by one skilled in the art using routine methods, for example, human clinical trials, in vivo studies and in vitro studies.

Dosage amount(s) and interval(s) may be adjusted individually to provide levels of the molecule which are sufficient to maintain the modulating effects, or minimal effective concentration (MEC). The MEC will vary for each therapeutic agents but can be estimated from in vivo and/or in vitro data. Dosages necessary to achieve the MEC will depend on individual characteristics and route of administration. Dosage intervals can also be determined using MEC value.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the symptoms to be treated and the route of administration. Further, the dose, and perhaps dose frequency, will also vary according to the age, body weight, and response of the individual patient. A program comparable to that discussed above may be used in veterinary medicine.

A therapeutically effective amount of the compositions may be administered alone or in combination with a therapeutically effective amount of other additional therapeutic agents. In some embodiments, effective combination therapy is achieved with a single composition or pharmacological formulation that includes both agents, or with two distinct compositions or formulations, administered at the same time, wherein one composition includes a compound of this invention, and the other includes the second agent(s). Alternatively, in other embodiments, the therapy precedes or follows the other agent treatment by intervals ranging from minutes to months.

A wide range of second therapies may be used in conjunction with methods the present disclosure. The second therapy may be a combination of a second therapeutic agent or may be a second therapy not connected to administration of another agent. Such second therapies include, but are not limited to, surgery, immunotherapy, or radiotherapy

5. Kit

In another aspect, the disclosure provides a kit comprising a thermoresponsive hydrogel as disclosed herein and at least one therapeutic agent, or pharmaceutical composition(s) comprising at least one therapeutic agent.

The at least one therapeutic agent may be an anti-cancer drug, an anti-infective drug, an anti-inflammatory drug, an analgesic, a cardiovascular drug, a tissue regenerating drug, an anti-diabetic drug, a vaccine antigen, a peptide, a protein, an ocular drug, or a nanoparticle formulation, or a combination thereof. In some embodiments, the at least one therapeutic agent is an anti-cancer drug, an analgesic, an anti-inflammatory drug, or a combination thereof.

The therapeutic agent may be capable of reversibly binding to the thermoresponsive hydrogel.

In some embodiments, the at least one therapeutic agent is coupled to a guest ligand with a labile linker, wherein the guest ligand is capable of binding to the cucurbit[n]uril moiety of the thermoresponsive hydrogel. The guest ligand may be selected from the group consisting of ferrocene, phenylalanine, xylylenediamine, and adamantane. The labile linker may comprise an ethylene glycol moiety, a hydrazone moiety, an ester moiety, a imine moiety, a cis-aconityl moiety, an ether moiety, a peptide, a disulfide moiety, a thioester moiety, an oxime moiety, a carbonate moiety, an amide moiety, an orthoester moiety, a urethane moiety, an anhydride moiety, an acetal moiety, or a ketal moiety, and wherein the therapeutic agent is released from the drug delivery device by hydrolysis of the labile linker, metabolism of the labile linker, or a combination thereof.

In some embodiments, the thermoresponsive hydrogel and the at least one therapeutic agent are co-formulated. In some embodiments, the thermoresponsive hydrogel and the at least one therapeutic agent are co-packaged. The kits can also comprise additional agents and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

That the disclosed kits can be employed in connection with disclosed methods of use.

The kits may further comprise information, instructions, or both that use of the kit will provide treatment for a disease or disorder in mammals (particularly humans). The information and instructions may be in the form of words, pictures, or both, and the like. In addition or in the alternative, the kit may include the therapeutic agent, the thermoresponsive hydrogel, or both; and information, instructions, or both, regarding methods of administration or implantation of the therapeutic agent, the thermoresponsive hydrogel, or both, preferably with the benefit of treating or preventing a disease or disorder in mammals (e.g., humans).

6. Examples

It will be readily apparent to those skilled in the art that other suitable modifications and adaptations of the present disclosure described herein are readily applicable and appreciable, and may be made using suitable equivalents without departing from the scope of the present disclosure or the aspects and embodiments disclosed herein. Having now described the present disclosure in detail, the same will be more clearly understood by reference to the following examples, which are merely intended only to illustrate some aspects and embodiments of the disclosure, and should not be viewed as limiting to the scope of the disclosure. The disclosures of all journal references, U.S. patents, and publications referred to herein are hereby incorporated by reference in their entireties.

Example 1: Compound Synthesis

Abbreviations used in the Schemes and descriptions that follow include the following: Boc is tert-butyloxycarbonyl; DCM is dichloromethane; DMAP is 4-dimethylaminopyridine; DMF is dimethylformamide; EDC is 1-Ethyl-3-(3-dimethylaminopropyl)carbodiimide; Et$_3$N is triethylamine; MeOH is methanol; PEG is polyethylene glycol; PEO is polyethylene oxide; PMDETA is N,N,N',N'',N''-pentamethyldiethylenetriamine; PPO is polypropylene oxide; TFA is trifluoro acetic acid; and THF is tetrahydrofuran.

A. Synthesis of F127 End-Modified with Cucurbit[7]uril (F127-CB[7])

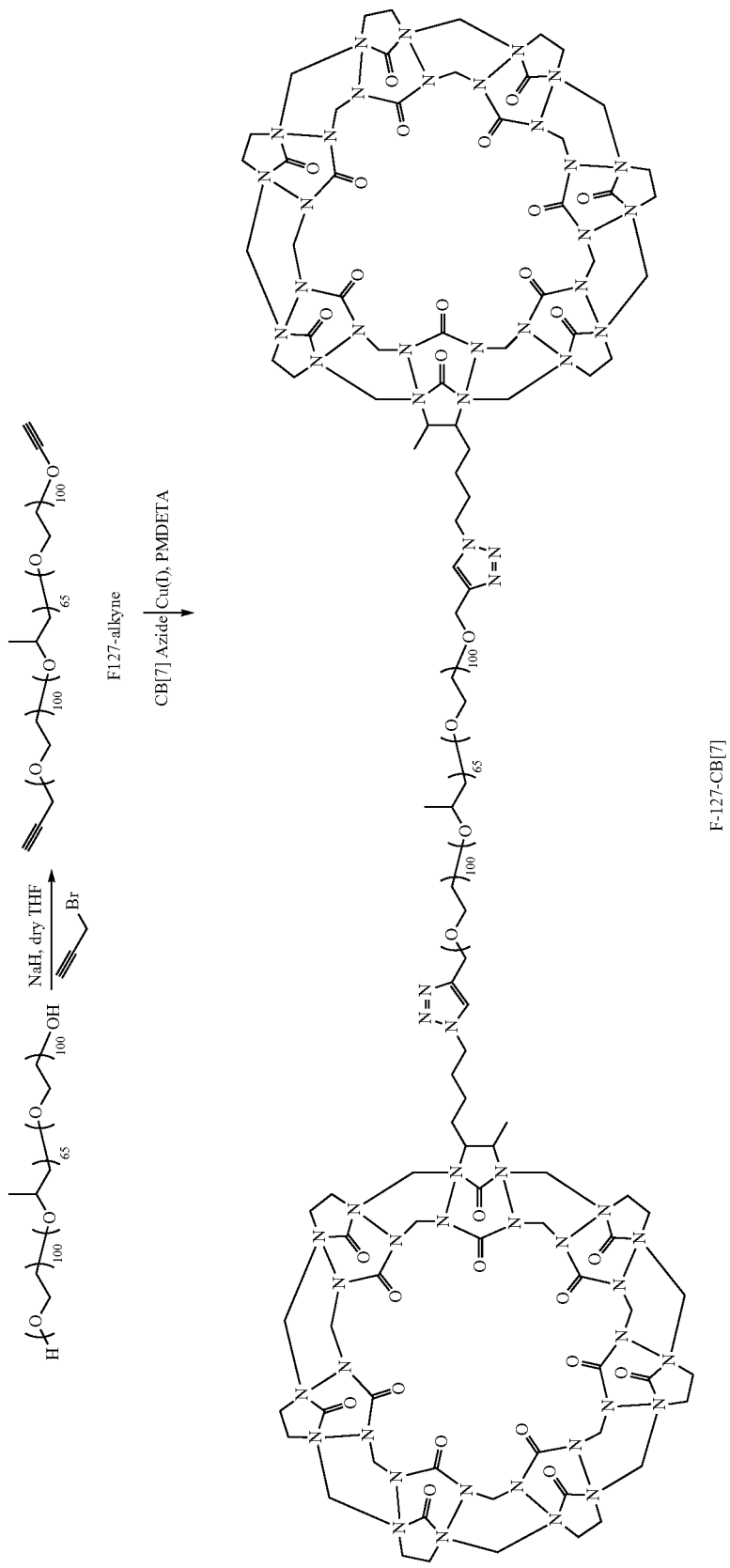

Synthesis of F127 terminated with alkyne group (F127-alkyne). In a dry round-bottom flask, sodium hydride (0.27 g, 60% dispersion in mineral oil, Beantown Chemical) was slowly added to a solution of Pluronic F127 (PEG-PPO-PEG, Mn=12600, 2.20 g, Sigma-Aldrich) in dry THF (20 mL). The mixture was stirred for 20 minutes at room temperature until no hydrogen gas release was evident. Then, propargyl bromide (0.20 mL, 80 wt. % solution in toluene, Beantown Chemical) was added and the reaction mixture was stirred at room temperature for 100 hours. After quenching with a small volume of water, the reaction mixture was transferred to a 50 mL centrifuge tube. The supernatant was collected by centrifuge. The solid residue was washed with THF three times (20 mL each), combined with the supernatant, and the mixture was evaporated under reduced pressure. The residue was dissolved in 100 mL DCM and washed with brine once (100 mL). The organic layer was dried over anhydrous $Na_2SO_4$ and evaporated under reduced pressure into a small volume which was precipitated into cold diethyl ether. The pure product was obtained as light yellow solid (1.96 g, 86% yield). $^1$H-NMR (500 MHz Bruker, 25° C., $CDCl_3$): δ (ppm)=4.20 (d, J=2.4 Hz, 3H), 3.80-3.27 (m, PPO main chain and PEG chain), 2.43 (t, J=2.4 Hz, 1H), 1.17-1.08 (m, PPO methyl side chain).

Synthesis of F127-CB[7]. CB[7]-azide (CB[7]-$N_3$) (101.84 mg) was synthesized according to previously published methods. The pure CB[7]-$N_3$ (127.3 mg) product was combined with F127-alkyne (633.8 mg), p-xylylenediamine (27.2 mg, 99%, TCI), copper(II) sulfate pentahydrate ($CuSO_4 \cdot 5H_2O$, 2.5 mg, BDH, ACS grade) and N,N,N',N'',N'''-pentamethyldiethylenetriamine (PMDETA, 98%, 2 uL, Acros) and dissolved in 9 mL DMF/water (½, v/v) in a Schlenk flask. The flask was degassed with three freeze-pump-thaw cycles. On the last cycle, the flask was opened to quickly add sodium ascorbate (20.0 mg) into the flask before re-capping the flask. The flask was vacuumed and backfilled with $N_2$ for 5 cycles before immersion in a 50° C. oil bath to thaw the solution and initiate the 'click' reaction with stirring. After 48 h, the reaction was quenched by exposure to air. The reaction mixture was then transferred into dialysis tubing (MWCO=3500, Thermo Scientific) and dialyzed against 3 L water over 24 h with water changed every 2 h. To remove residual p-xylylenediamine, the obtained solid after lyophilization was treated with excess acetic anhydride and triethylamine in 10 mL DMF for 24 h. Then the mixture was again transferred into dialysis tubing (MWCO=3500, Thermo Scientific) and dialyzed against 3 L water over 24 h with water change for every 2 h. The pure product was obtained after lyophilization as light yellow solid (760.0 mg, 100% yield) and was determined to be fully substituted with CB[7].

$^1$H-NMR (500 MHz Bruker, 25° C., $D_2O$, with >1 equiv of p-xylylenediamine added as probe to quantify CB[7]): δ (ppm)=8.07 (s, 1H), 7.52 (s, free probe), 6.62 (s, threaded probe), 5.83-5.62 (m, 14H), 5.61-5.42 (m, 12H), 4.70 (s, 2H), 4.49 (t, J=6.5 Hz, 2H), 4.35-4.13 (m, 14H), 4.21 (s, free probe), 3.92 (s, threaded probe), 3.86-3.42 (m, PEG and PPO main chain), 2.33 (m, 2H), 2.04 (m, 2H), 1.78 (s, 3H), 1.22-1.08 (m, PPO-Me).

B. Synthesis of 8-Arm PEG End-Modified with a Ferrocene Guest ($PEG_8$-Tz-N-Fc)

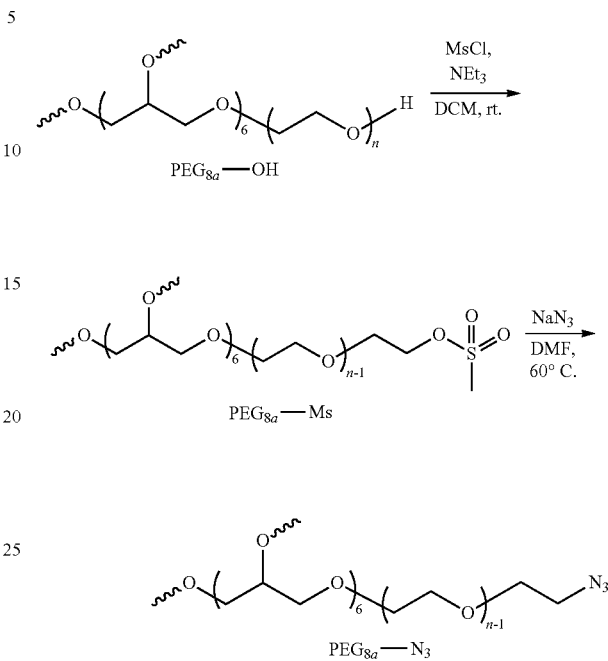

Synthesis of 8-arm PEG terminated with mesylate ($PEG_{8a}$-Ms). In a dry round-bottom flask, hydroxyl-terminated 8-arm PEG (Mn=20747, 4.00 g, Creative PEGWorks) was dissolved in 20 mL DCM with triethylamine (2.20 mL). The solution was cooled to 0° C. in an ice bath and methanesulfonyl chloride (MsCl, 1.20 mL, Beantown Chemical) was added slowly. The flask was then removed from the ice bath and the reaction mixture was stirred for 2 d at room temperature. After quenching with a small volume of water, the reaction mixture was diluted into 200 mL of DCM and washed with brine three times (200 mL each). The organic layer was dried over anhydrous $Na_2SO_4$ and evaporated under reduced pressure into a small volume which was precipitated into cold diethyl ether. The product was obtained as a colorless powder (4.03 g, 98% yield).

$^1$H-NMR (500 MHz Bruker, 25° C., $CDCl_3$): δ (ppm)=4.37 (m, 2H), 3.83-3.43 (m, PEG chain), 3.07 (s, 3H).

Synthesis of 8-arm PEG terminated with azido group ($PEG_{8a}$-$N_3$). Sodium azide (0.52 g, high purity, VWR) and $PEG_{8a}$-Ms (1.10 g) were suspended in DMF (10 mL) and stirred at 60° C. for 2 d. The reaction mixture was then diluted into 200 mL of DCM and washed with brine three times (200 mL each). The organic layer was dried over anhydrous $Na_2SO_4$ and evaporated under reduced pressure into a small volume which was precipitated into cold diethyl ether. The product was obtained as a white powder (0.98 g, 91% yield).

$^1$H-NMR (500 MHz Bruker, 25° C., $CDCl_3$): δ (ppm)=3.81-3.43 (m, PEG chain), 3.38 (t, J=10.1 Hz, 2H).

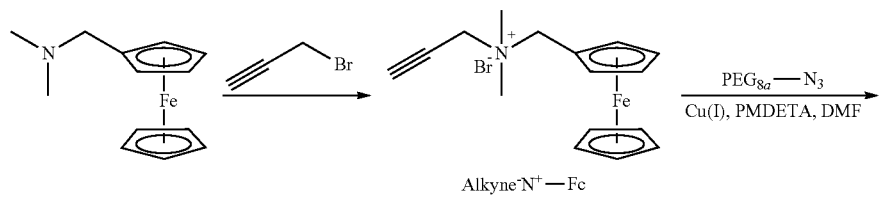

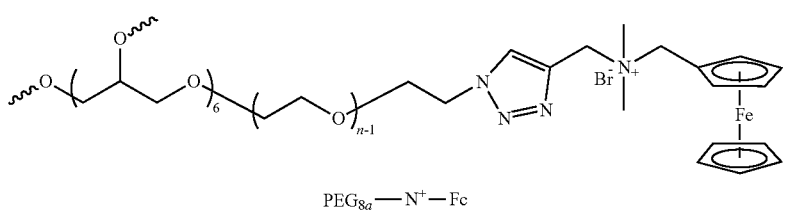

PEG$_{8a}$—N$^+$—Fc

Synthesis of Alkyne-N-Fc. Propargyl bromide (186 ul, 80 wt. % solution in toluene, Beantown Chemical) was added slowly to a solution of (dimethylaminomethyl)ferrocene (0.405 g, 98+%, Alfa Aesar) in 2.5 mL acetonitrile and the reaction mixture was stirred at room temperature. After 30 min, the entire mixture was precipitated into 20 mL diethyl ether. Yellow solid (0.593 g, 99% yield) was collected by centrifuge and further washed twice with diethyl ether (10 mL).

$^1$H-NMR (500 MHz Bruker, 25° C., CDCl$_3$): δ (ppm)=4.92 (s, 2H), 4.56 (d, J=2.3 Hz, 2H), 4.55 (t, J=1.7 Hz, 2H), 4.37 (t, J=1.7 Hz, 2H), 4.30 (s, 5H), 3.34 (s, 6H), 2.87 (t, J=2.3 Hz, H).

Synthesis of PEG$_8$-Tz-N-Fc. Alkyne-N-Fc (0.1158 g), PEG$_{8a}$-N$_3$ (0.8388 g), CuSO$_4$·5H$_2$O (4.0 mg) and PMDETA (3.2 uL) were dissolved in DMF (8 mL) in a Schlenk flask. The flask was degassed with three freeze-pump-thaw cycles. On the last cycle, the flask was opened to quickly add sodium ascorbate (20 mg) before re-capping. The flask was vacuumed and backfilled with N$_2$ over 5 cycles before immersion in a 40° C. oil bath to thaw the solution and initiate the 'click' reaction. After 24 h, the reaction was quenched by exposure to air. The reaction mixture was diluted with 20 mL of DCM and passed through a short Al$_2$O$_3$ column. The resulting liquid was evaporated under reduced pressure, following which the solution was precipitated into cold diethyl ether. The fully substituted product was obtained as white powder (0.42 g, 89% yield).

$^1$H-NMR (500 MHz Bruker, 25° C., CDCl$_3$): δ (ppm)=8.70 (s, 1H), 5.02 (s, 2H), 4.69 (s, 2H), 4.61 (t, J=5.3 Hz, 2H), 4.60 (s, 2H), 4.39 (t, J=1.7 Hz, 2H), 4.27 (s, 5H), 3.92 (t, J=5.3 Hz, 2H), 3.75-3.48 (m, PEG chain), 3.10 (s, 6H).

Using these same methods, a linear (2-arm) macromer, (PEG$_2$-Fc), was prepared from 6 kDa PEG.

C. Synthesis of Model Guest Resembling PEG$_8$-Tz-N-Fc (OEG-Tz-N-Fc)

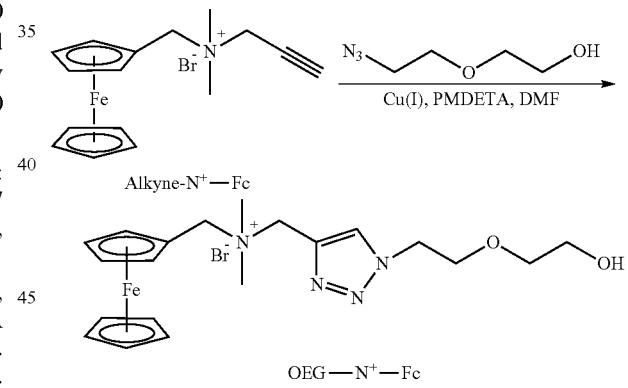

A model compound, OEG-Tz-N-Fc, was prepared by combining Alkyne-N-Fc (0.181 g), 2-(2-azidoethoxy)ethan-1-ol (0.066 g), CuSO$_4$·5H$_2$O (6.25 mg) and PMDETA (5 uL) in DMF (5 mL) in a Schlenk flask. The flask was degassed with three freeze-pump-thaw cycles. On the last cycle, the flask was opened to quickly add sodium ascorbate (20 mg) before re-capping. The flask was vacuumed and backfilled with N$_2$ for 5 cycles before warming up to room temperature to thaw the solution and initiate the 'click' reaction. After 3 days, the reaction was quenched by exposure to air. The reaction mixture was diluted with 20 mL of DCM and passed through a short Al$_2$O$_3$ column. The combined fractions were evaporated under reduced pressure and precipitated into cold ether. The fully substituted product was obtained as yellow powder (0.150 g, 61% yield).

$^1$H-NMR (500 MHz Bruker, 25° C., D$_2$O): δ (ppm)=8.33 (s, 1H), 4.68 (t, J=5.0 Hz, 2H), 4.57 (t, J=1.8 Hz, 2H), 4.52 (s, 2H), 4.50 (s, 2H), 4.46 (t, J=1.8 Hz, 2H), 4.29 (s, 5H), 3.98 (t, J=5.0 Hz, 2H), 3.66-3.62 (m, 2H), 3.60-3.57 (m, 2H), 2.87 (s, 6H).

D. Synthesis of "Weak" Model Prodrug, Fc-O-Cy5

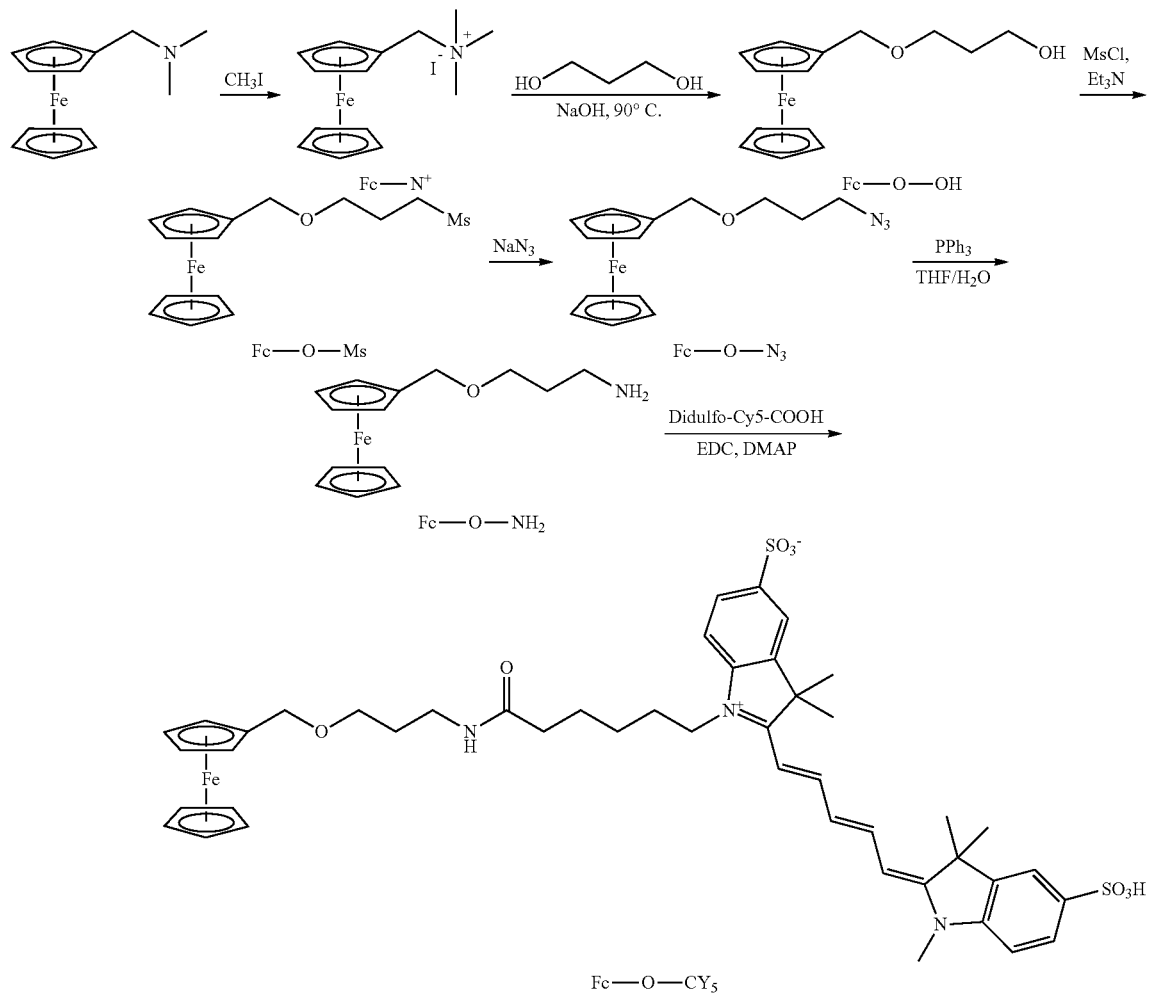

Fc—O—CY5

Synthesis of compound Fc-N+. A solution of (dimethylaminomethyl)ferrocene, (2.43 g) in 20 mL of ether stirred in a vial on ice was combined with iodomethane (2.00 g, 99%, Alfa Aesar) in 5 ml of ether by dropwise addition. After the addition, the reaction mixture was stirred for 30 min at room temperature. The precipitate product Fc-N+(3.65 g, 95% yield) was collected by filtration, washed with ether (10 mL) three times, and dried.

$^1$H-NMR (500 MHz Bruker, 25° C., $D_2O$): δ (ppm)=4.56 (t, J=3.6 Hz, 2H), 4.48 (t, J=3.6 Hz, 2H) 4.44 (s, 2H), 4.33 (s, 5H), 3.0 (s, 9H).

Synthesis of compound Fc-O—OH. A mixture of compound Fc-N+(0.475 g) and NaOH (0.90 g) in 10 mL of 1,3-propandiol was stirred at 90° C. for 24 hours. After cooling to room temperature, the mixture was partitioned between DCM (200 mL) and water (200 mL). The DCM layer was further washed with water five times (100 mL each), dried over anhydrous $Na_2SO_4$, and concentrated under reduced pressure to give an orange oil (0.344 g, 100% yield) that crystalized upon cooling.

$^1$H-NMR (500 MHz Bruker, 25° C., $CDC_3$): δ (ppm)=4.40 (s, 2H), 4.33 (t, J=1.7 Hz, 2H), 4.26 (t, J=1.7 Hz, 2H), 4.25 (s, 5H), 3.86 (td, J1=5.7 Hz, J2=5.4 Hz, 2H), 3.74 (t, J=5.7 Hz, 2H), 2.52 (t, J=5.4 Hz, 1H), 1.92 (m, 2H).

Synthesis of compound Fc-O-Ms. Methanesulfonyl chloride (MsCl, 0.25 mL) was added slowly into a solution of compound Fc-O—OH (0.34 g) and triethylamine (0.45 mL) in 20 mL DCM on an ice bath. The flask was then removed from the ice bath and the reaction mixture was stirred for 24 hours at room temperature. After quenching with a small volume of water, the reaction mixture was partitioned between DCM/diethyl ether (1/1 (v/v), 200 mL) and water (200 mL). The organic layer was further washed with water five times (100 mL each), dried over anhydrous $Na_2SO_4$, and evaporated under reduced pressure into an orange solid. The product (0.38 g, 91% yield) was used for next step without further purification.

$^1$H-NMR (500 MHz Bruker, 25° C., $CDCl_3$): δ (ppm)=4.29 (t, J=5.8 Hz, 2H), 4.28 (s, 2H), 4.21 (m, 2H), 4.15 (m, 2H), 4.13 (s, 5H), 3.52 (t, J=5.9 Hz, 2H), 2.94 (s, 3H), 1.97 (m, 2H).

Synthesis of compound Fc-O—$N_3$. Sodium azide (0.70 g, high purity, VWR) and compound Fc-O-Ms (0.38 g) were suspended in DMF (20 mL) and stirred at 50° C. for 2 d. After cooling to room temperature, the reaction mixture was then partitioned between DCM/diethyl ether (1/1 (v/v), 200 mL) and water (200 mL). The organic layer was further washed with water at least five times (100 mL each), dried over anhydrous $Na_2SO_4$, and concentrated under reduced pressure to give orange solid (0.33 g, 98% yield) which was used for next step without further purification.

$^1$H-NMR (500 MHz Bruker, 25° C., $CDCl_3$): δ (ppm)=4.28 (s, 2H), 4.22 (m, 2H), 4.15 (m, 2H), 4.13 (s, 5H), 3.49 (t, J=6.0 Hz, 2H), 3.36 (t, J=6.7 Hz, 2H), 1.81 (m, 2H).

Synthesis of compound Fc-O—$NH_2$. A reaction mixture of compound Fc-O—$N_3$ (0.33 g), triphenylphosphine (0.35 g, 99%, Sigma-Aldrich) and water (1 mL) in 9 mL of THF was stirred at room temperature overnight. The solvent was then removed under reduced pressure and the residue was purified on a silica column, eluting with a mixture of DCM/MeOH/$Et_3N$ (10/1/0.1, v/v/v). The target product was obtained as an orange oil (0.24 g, 80% yield).

$^1$H-NMR (500 MHz Bruker, 25° C., $CDCl_3$): δ (ppm)=4.27 (s, 2H), 4.22 (m, 2H), 4.14 (m, 2H), 4.13 (s, 5H), 3.50 (t, J=6.2 Hz, 2H), 2.77 (t, J=6.7 Hz, 2H), 1.70 (m, 2H).

Synthesis of Fc-O-Cy5—A mixture of compound Fc-O—$NH_2$ (29.8 mg), disulfo-Cy5-COOH (63.2 mg), EDC·HCl (60.1 mg, 95+%, Matrix Scientific) and DMAP (3.2 mg, 95+%, Matrix Scientific) in 1.5 mL of DMF was stirred at room temperature for 36 h. After 36 h, most of the solvent was removed under reduced pressure and the residue was purified on a silica column, eluting with a mixture of DCM/MeOH (3/1, v/v). The target product was obtained as blue solid (72.0 mg, 81% yield).

$^1$H-NMR (500 MHz Bruker, 25° C., DMSO-d6): δ (ppm)=8.34 (t, J=13.0 Hz, 2H), 7.80 (s, 2H), 7.62 (m, 2H), 7.30 (t, J=6.6 Hz, 2H), 6.55 (t, J=12.4 Hz, 2H), 6.25 (dd, J1=13.0 Hz, J2=12.4 Hz, 2H), 4.19 (m, 2H), 4.16 (s, 2H), 4.11 (m, 5H), 4.10 (m, 2H), 4.06 (t, J=7.5 Hz, 2H), 3.57 (s, 3H), 3.01 (m, 2H), 2.97 (m, 2H), 1.99 (m, 2H), 1.67 (m, 16H), 1.53 (m, 2H), 1.30 (m, 2H).

Model "Weak" Guest for Determination of Binding Constant.

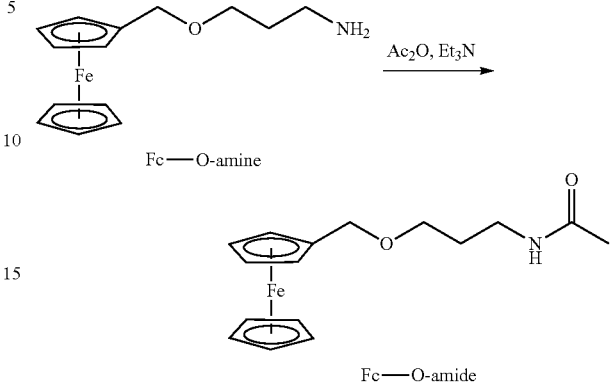

Acetic anhydride (33 μL) was slowly added into a solution of compound Fc-O-Amime (95 mg) and triethylamine (59 μL) in 2 mL of DCM. The reaction mixture was stirred for 1 hour, then diluted with 5 mL DCM and washed with a 5% $K_2CO_3$ aqueous solution four times (5 mL each). The DCM layer was passed through a short $Al_2O_3$ column and evaporated under reduced pressure to give orange crystals.

$^1$H-NMR (500 MHz Bruker, 25° C., $D_2O$): δ (ppm)=4.36 (s, 2H), 4.31 (m, 2H), 4.25 (m, 2H), 4.22 (s, 5H), 3.52 (t, J=6.4 Hz, 2H), 3.15 (t, J=6.7 Hz, 2H), 1.70 (m, 2H).

The binding affinity for this model agent to CB[7] was then determined using competition $^1$H-NMR (FIG. 12)

E. Synthesis of "Medium" Model Prodrug, Ada-Am-Cy5

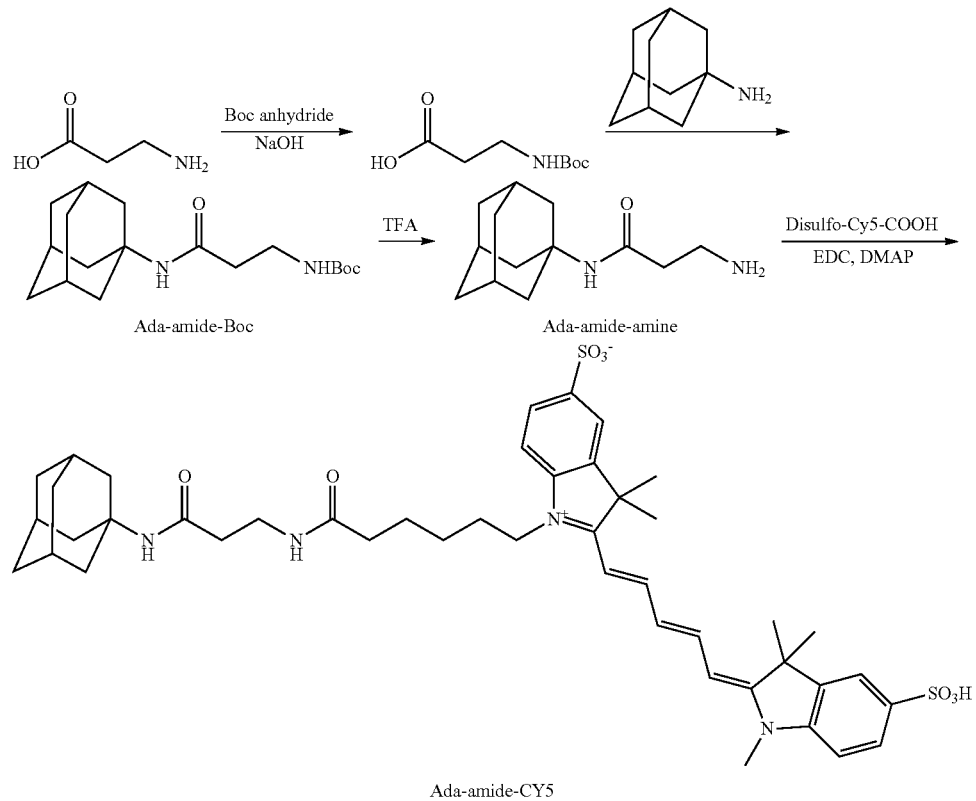

Synthesis of Boc protected β-alanine. Boc anhydride (16.00 g, 99%, Sigma-Aldrich) was slowly added to a mixture of p-alanine (6.10 g, 98%, BeanTown Chemical) and NaOH (3.00 g) in dioxane/water (100 mL, 1/1, v/v). The reaction mixture was stirred overnight. Most of the dioxane was then evaporated under reduced pressure and 200 mL of water was added. The pH value of the aqueous mixture was adjusted to around 3 by the addition of formic acid and was then washed twice with hexane (100 mL each). The mixture was extracted by DCM twice (100 mL each). The DCM extracts were combined, washed by water (100 mL) once, dried over anhydrous $Na_2SO_4$ and concentrated under reduced pressure to give colorless sticky liquid which crystalized slowly (13.55 g, 100% yield). The product was used for next step without further purification.

$^1$H-NMR (500 MHz Bruker, 25° C., CDCl$_3$): δ (ppm)=6.21(bs) and 5.07 (bs) (1H), 3.40 (bs, 2H), 2.56 (bs, 2H), 1.46 (bs, 9H).

Synthesis of compound Ada-Am-Boc. A mixture of Boc protected β-alanine (1.89 g), 1-adamantylamine (1.51 g, TCI), EDC·HCl (3.01 g) and DMAP (30 mg) in 50 mL of DCM was stirred at room temperature for 24 h. The reaction mixture was diluted in 200 mL of DCM, washed with water (100 mL) five times, dried over anhydrous $Na_2SO_4$, and concentrated under reduced pressure to give a colorless solid (3.20 g, 100% yield). The product was used for next step without further purification.

$^1$H-NMR (500 MHz Bruker, 25° C., CDC$_3$): δ (ppm)=5.24 (s, 1H), 5.21 (s, 1H), 3.36 (m, 2H), 2.31 (m, 2H), 2.07 (m, 3H), 1.98 (m, 6H), 1.67 (m, 6H), 1.43 (bs, 9H).

Synthesis of compound Ada-Am-amine. Compound Ada-Am-Boc (3.20 g) was dissolved in 30% TFA in DCM (50 mL) and stirred for 3 hours at room temperature. Then, most of the contents were evaporated under reduced pressure to give a sticky residue. The residue was dissolved in 200 mL DCM, washed with aqueous NaOH (100 mL, pH=12) three times, dried over anhydrous $Na_2SO_4$, and concentrated under reduced pressure to give colorless liquid (1.75 g, 79% yield). The product was used for next step without further purification.

$^1$H-NMR (500 MHz Bruker, 25° C., CDCl$_3$): δ (ppm)=6.26 (s, 1H), 2.95 (t, J=5.9 Hz, 2H), 2.21 (t, J=5.9 Hz, 2H), 2.05 (m, 3H), 1.99 (m, 6H), 1.66 (m, 6H).

Synthesis of Ada-Am-Cy5. A mixture of compound Ada-Am-amine (32.0 mg), disulfo-Cy5-COOH (64.2 mg), EDC·HCl (60.0 mg) and DMAP (3.0 mg) in 2 mL of DMF was stirred at room temperature for 24 h. After 24 h, most of the solvent was removed under reduced pressure and the residue was purified on a silica column, eluting with a mixture of ethyl acetate/MeOH (3/2, v/v). The target product was obtained as blue solid (62.0 mg, 73% yield).

$^1$H-NMR (500 MHz Bruker, 25° C., DMSO-d6): δ (ppm)=8.34 (t, J=13.0 Hz, 2H), 7.80 (s, 2H), 7.62 (m, 2H), 7.30 (t, J=6.6 Hz, 2H), 6.54 (t, J=12.4 Hz, 2H), 6.26 (dd, J1=13.0 Hz, J2=12.4 Hz, 2H), 4.06 (m, 2H), 3.57 (s, 3H), 3.13 (m, 2H), 2.11 (t, J=7.1 Hz, 2H), 2.00 (t, J=7.2 Hz, 2H), 1.94 (m, 3H), 1.87 (m, 6H), 1.67 (m, 16H), 1.56 (m, 6H), 1.51 (m, 2H), 1.30 (m, 2H).

Model "Medium" Guest for Determination of Binding Constant.

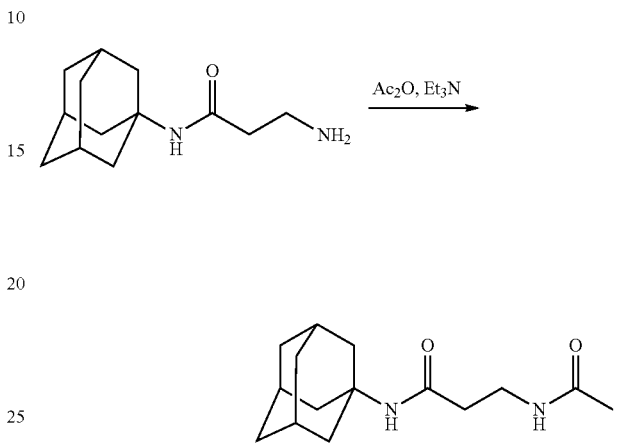

Acetic anhydride (0.14 mL) was slowly added into a solution of Ada-amide-amine (0.20 g) and triethylamine (0.20 mL) in 5 mL of DCM. The reaction mixture was stirred for 3 days, then diluted with 10 mL of DCM and washed with 5% $K_2CO_3$ aqueous solution for four times (15 mL each). The DCM layer was dried over anhydrous $Na_2SO_4$ and evaporated under reduced pressure to give white crystal (0.21 g, 88% yield).

$^1$H-NMR (500 MHz Bruker, 25° C., D$_2$O): δ (ppm)=6.43 (s, 1H), 5.27 (s, 1H), 3.47 (m, 2H), 2.32 (t, J=5.9 Hz, 2H), 2.07 (m, 3H), 1.98 (m, 6H), 1.67 (m, 6H).

The binding affinity for this model agent to CB[7] was then determined using competition $^1$H-NMR (FIG. 13).

F. Synthesis of "Strong" Model Prodrug, Fc-N-Cy5

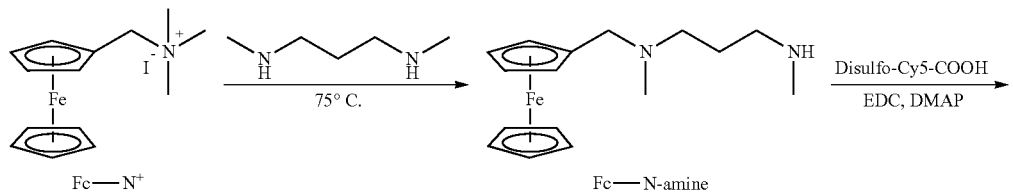

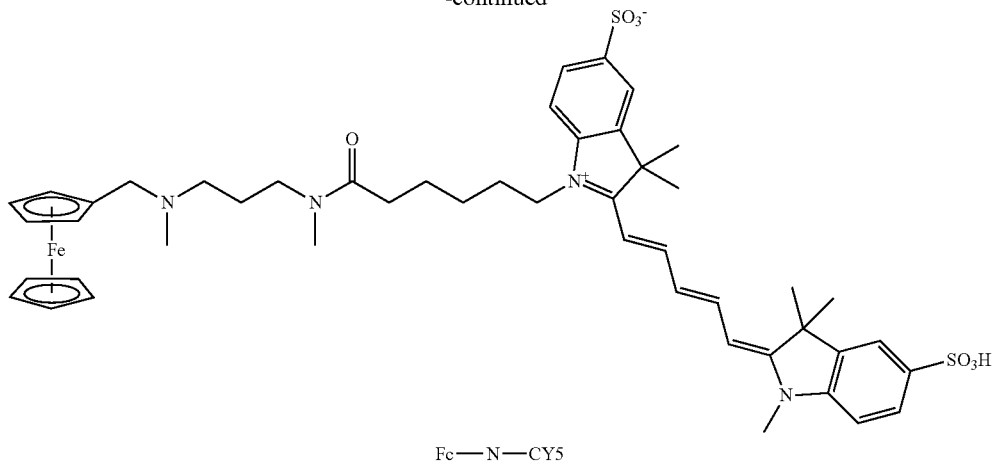

Fc—N—CY5

Synthesis of compound Fc-N-amine. A mixture of compound Fc-N+(1.22 g), N,N'-dimethyl-1,3-propanediamine (1.26 g, 97%, Alfa Aesar) and $K_2CO_3$ (0.43 g) in 10 mL of acetonitrile was stirred at 75° C. for 4 days. After cooling to room temperature, 20 mL DCM was added to the mixture and the solid was removed by centrifuge. The supernatant was passed through a short $Al_2O_3$ column, evaporated under reduced pressure, and resuspended in 20 mL DCM. The insoluble solid was removed by centrifuge and the DCM solution was evaporated under reduced pressure to give orange oil (0.81 g, 85% yield). The product was used for next step without further purification.

$^1$H-NMR (500 MHz Bruker, 25° C., $CDCl_3$): δ (ppm)=4.15 (m, 2H), 4.10 (m, 7H), 4.38 (s, 2H), 2.58 (t, J=6.8 Hz, 2H), 2.40 (s, 3H), 2.34 (t, J=7.2 Hz, 2H), 2.15 (s, 3H), 1.66 (m, 2H).

Synthesis of Fc-N-Cy5. A mixture of compound Fc-N-amine (45.0 mg), disulfo-Cy5-COOH (66.4 mg), EDC·HCl (40.0 mg) and DMAP (2.0 mg) in 1.5 mL of DMF was stirred at room temperature for 24 h. After 24 h, the solvent was removed under reduced pressure and the residue was purified on a C18 column, eluting with a gradient mixture of water/MeOH (7/3 to 4/6, v/v). The target product was obtained as blue solid (60.0 mg, 62% yield).

$^1$H-NMR (500 MHz Bruker, 25° C., DMSO-d6): δ (ppm)=8.35 (t, J=13.0 Hz, 2H), 7.80 (s, 2H), 7.62 (m, 2H), 7.30 (t, J=6.6 Hz, 2H), 6.53 (t, J=12.4 Hz, 2H), 6.27 (dd, J1=13.0 Hz, J2=12.4 Hz, 2H), 4.38 (s, 2H), 4.26 (s, 2H), 4.26 (s, 2H), 4.20 (s, 5H), 4.16-4.0 (m, 4H), 3.58 (s, 3H), 3.21 (m) and 3.16 (m) (2H), 2.90-2.68 (m, 6H), 2.55 (m, 2H), 2.20 (m) and 2.15 (m) (2H), 1.67 (m, 16H), 1.47 (m, 2H), 1.29 (M, 2H). ESI-MS: 925.33 (expected [M]+), 925.20 (observed [M]+).

Model "Strong" Guest for Determination of Binding Constant

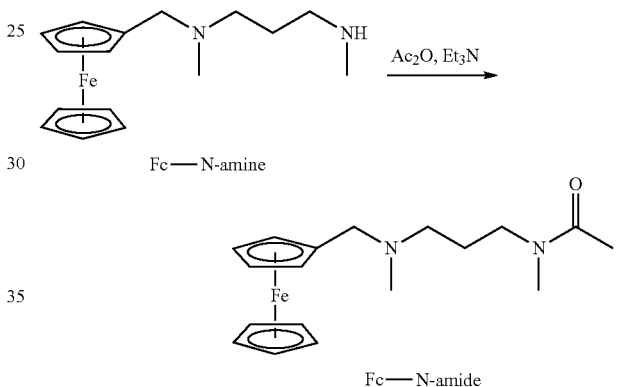

A reaction mixture of Fc-N-amine (60.0 mg), acetic anhydride (19 μL) and triethylamine (28 μL) in 3 mL of DCM was stirred at room temperature for 3 hours. After 3 hours, the reaction mixture was diluted with 3 mL of DCM and washed with 5% $K_2CO_3$ aqueous solution four times (5 mL each). The DCM layer was dried over anhydrous $Na_2SO_4$ and evaporated under reduced pressure. The residue was purified by C18 column, eluting with a gradient mixture of water/MeOH (8/2 to 2/8, v/v). The target product was obtained as orange solid (17.0 mg, 25% yield).

$^1$H-NMR (500 MHz Bruker, 25° C., $D_2O$): δ (ppm)=4.29-4.26 (m, 2H), 4.24-4.18 (m, 7H), 3.52 (s) and 3.47 (s) (2H), 3.34-3.27 (m, 2H), 2.96 (s) and 2.82 (s) (3H), 2.37-2.30 (m, 2H), 2.18 (s) and 2.15 (s) (3H), 2.04 (s) and 2.03 (s) (3H), 1.77-1.64 (m, 2H).

The binding affinity for this model agent to CB[7] was then determined using competition $^1$H-NMR (FIG. 14).

G. Synthesis of Fc-Hdz-Dox

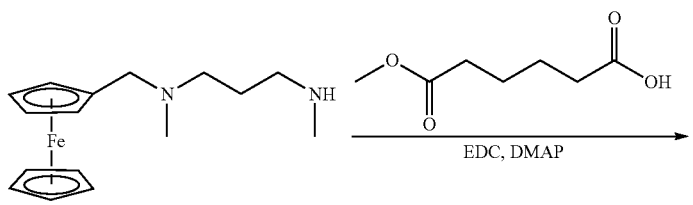

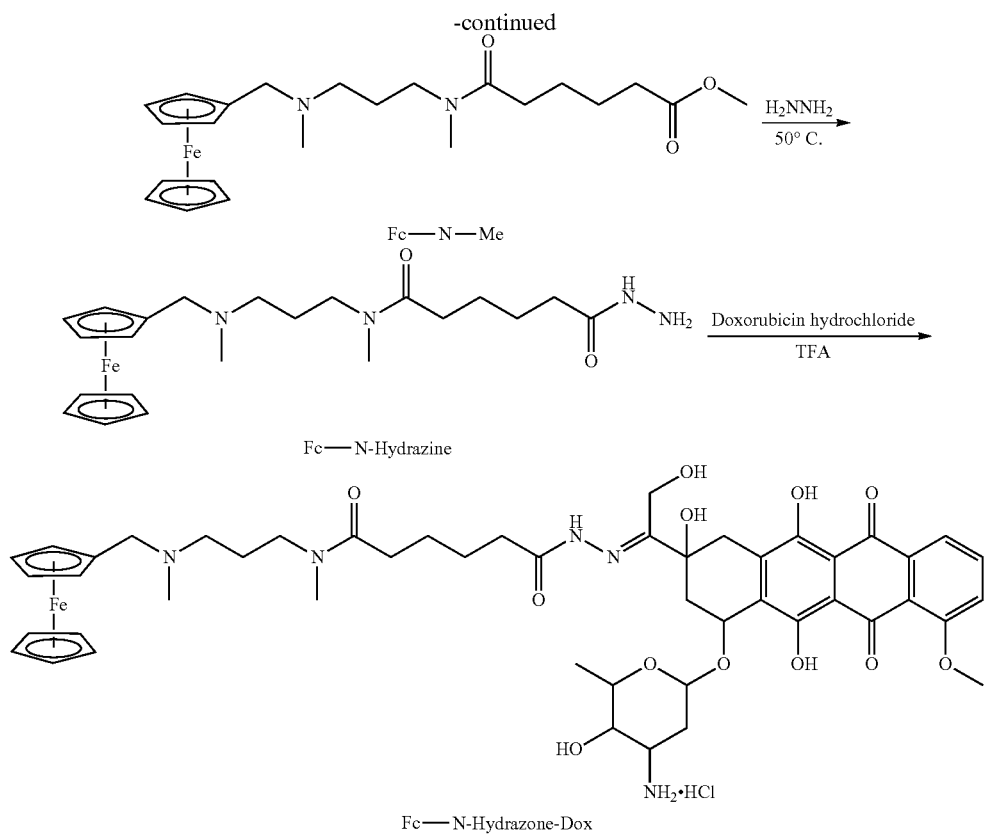

Synthesis of compound Fc-N-Me. A mixture of compound Fe—N-amine (300.0 mg), monomethyl adipate (200.0 mg, 98%, Ark Pharm), EDC·HCl (300.0 mg), and DMAP (5.0 mg) in 10 mL of DCM was stirred at room temperature for 36 h. After 36 h, the reaction mixture was diluted with 10 mL of DCM and washed with 5% $K_2CO_3$ aqueous solution four times (10 mL each). The DCM layer was dried over anhydrous $Na_2SO_4$ and evaporated under reduced pressure. The residue was purified on a C18 column, eluting with a gradient mixture of water/MeOH (6/4 to 0/100, v/v). The target product was obtained as orange solid (300.0 mg, 69% yield).

$^1$H-NMR (500 MHz Bruker, 25° C., $CDCl_3$): δ (ppm)=4.15-4.08 (m, 9H), 3.66 (s) (3H), 3.36 (s) and 3.35 (s) (2H), 3.33(t, J=7.3 Hz) and 3.26(t, J=7.3 Hz) (2H), 2.93 (s) and 2.88 (s) (3H), 2.38-2.30 (m, 3H), 2.30-2.22 (m, 3H), 2.13 (s) and 2.12 (s) (3H), 1.70-1.62 (m, 6H).

Synthesis of compound Fc-N-Hydrazine. A mixture of compound Fc-N-Me (300.0 mg) and hydrazine monohydrate (0.66 mL, 98%, BeanTown Chemical) in 10 mL of MeOH was stirred at 50° C. for 24 hours. After cooling to room temperature, the sample was evaporated under reduced pressure and the residue was purified on a C18 column, eluting with a gradient mixture of water/MeOH (8/2 to 2/8, v/v). The target product was obtained as orange solid (300.0 mg, 100% yield).

$^1$H-NMR (500 MHz Bruker, 25° C., $CDC_3$): δ (ppm)=7.60 (s) and 7.51 (s) (1H), 4.16-4.06 (m, 9H), 3.36 (s) and 3.37 (s) (2H), 3.35 (t, J=7.3 Hz) and 3.26 (t, J=7.3 Hz) (2H), 2.93 (s) and 2.89 (s) (3H), 2.37-2.19 (m, 6H), 2.13 (s) and 2.12 (s) (3H), 1.71-1.61 (m, 6H).

Synthesis of Fc-Hydrazone-Dox (Fc-Hdz-Dox). Compound Fc-N-Hydrazine (75.0 mg) and Doxorubicin hydrochloride (14.0 mg, 98%, Bide Pharmatech) were dissolved in 1 mL of dry MeOH. Then trifluoroacetic acid (40 μL) was added to the solution and the reaction mixture was stirred for 2 days in the dark. The entire reaction solution was precipitated into 40 mL of dry ethyl acetate. The dark red precipitate was collected by centrifugation and washed with dry ethyl acetate two times (5 mL each). The product (24 mg, 100% yield) was obtained as dark red solid after dried under high vacuum.

$^1$H-NMR (500 MHz Bruker, 25° C., DMSO): δ (ppm)=10.31 (s, 1H), 7.92-7.90 (m, 4H), 7.82 (m, 6H), 7.65 (m, 2H), 5.77 (m, 1H), 5.49-5.43 (m, 3H), 5.32-5.27 (m, 2H), 4.95 (m, 1H), 4.44-4.35 (m, 6H), 4.31-4.23 (m, 4H), 4.22-4.02 (m), 3.97 (s, 3H), 3.49 (s, 3H), 3.28-3.14 (m), 2.30-2.67 (m), 2.63-2.53 (m), 2.32-2.01 (m), 1.91-1.25 (m), 1.15 (d, J=6.5 Hz, 3H). ESI-MS: 968.37 (expected [M]+), 968.28 (observed [M]+).

H. Synthesis of Me-Hdz-Dox

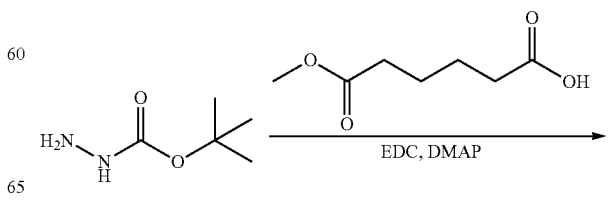

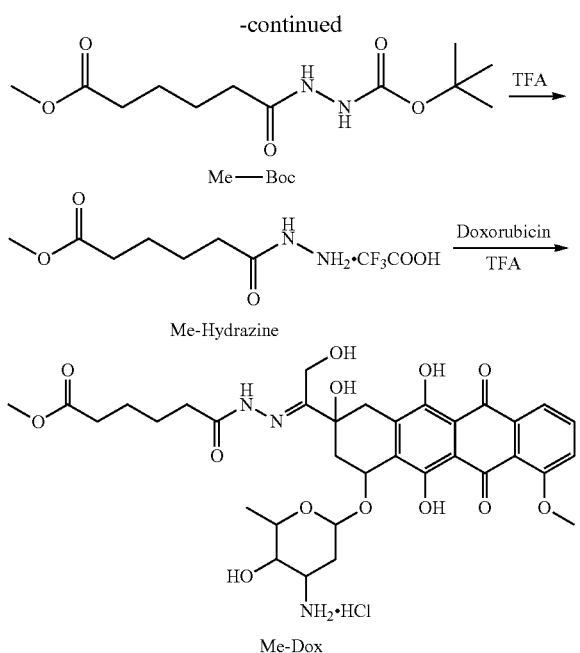

Synthesis of compound Me-Boc. A mixture of tert-butyl carbazate (1.32 g, 95+%, Matrix Scientific), monomethyl adipate (1.66 g), EDC·HCl (2.00 g), and DMAP (20.0 mg) in 20 mL of DCM was stirred at room temperature for 12 h. The reaction mixture was then diluted with 20 mL of DCM and washed with 5% $K_2CO_3$ aqueous solution four times (40 mL each). The DCM layer was dried over anhydrous $Na_2SO_4$ and evaporated under reduced pressure. The residue was purified with silica column, eluting with DCM/ethyl acetate (9/1, v/v). The target product was obtained as colorless sticky liquid (2.51 g, 92% yield).

$^1$H-NMR (500 MHz Bruker, 25° C., CDCl$_3$): δ (ppm)=7.59 (s, 1H), 6.58 (s, 1H), 3.66 (s, 3H), 2.34 (m, 2H), 2.24 (m, 2H), 1.79-1.63 (m, 4H), 1.46 (s, 9H).

Synthesis of compound Me-Hydrazine. A solution of compound Me-Boc (1.00 g) in 5 mL of 20% TFA in DCM was stirred at room temperature for 2 hours. After 2 hours, the volatiles were evaporated under reduced pressure to give colorless sticky liquid (100% yield).

$^1$H-NMR (500 MHz Bruker, 25° C., CDCl$_3$): δ (ppm)=9.30 (s, 3H), 3.66 (s, 3H), 2.38-2.31 (m, 4H), 1.69-1.56 (m, 4H).

Synthesis of Me-Dox. Compound Me-Hydrazine (144.0 mg) and Doxorubicin hydrochloride (29.0 mg) were dissolved in 2 mL of dry MeOH. Trifluoroacetic acid (30 µL) was added to the solution and the reaction mixture was stirred for 2 days in the dark. The reaction solution was then precipitated into 40 mL of dry ethyl acetate. The dark red precipitate was collected by centrifugation and washed with dry ethyl acetate two times (5 mL each). The product was dried under high vacuum and obtained as a dark red solid (21 mg, 57% yield).

$^1$H-NMR (500 MHz Bruker, 25° C., DMSO): δ (ppm)=10.31 (s, 1H), 7.92-7.90 (m, 4H), 7.82 (m, 6H), 7.65 (m, 2H), 5.75 (m, 1H), 5.48 (m, 1H), 5.45 (s, 1H), 5.44 (s, 1H), 5.30-5.26 (m, 2H), 4.95 (t, J=6.6 Hz, 1H), 4.42-4.33 (m, 2H), 4.05-3.95 (m, 2H), 3.96 (s, 3H), 3.56 (m, 4H), 3.49 (s, 3H), 3.30 (d, J=17.0 Hz, 1H), 2.76 (d, J=17.0 Hz, 1H), 2.37-2.05 (m, 6H), 1.87 (m, 1H), 1.70 (m, 1H), 1.63-1.45 (m), 1.33 (m), 1.15 (d, J=6.5 Hz, 3H). ESI-MS: 700.10 (expected [M]+), 700.15 (observed [M]+).

I. Synthesis of diSulfo-Cy5-COOH

The fluorescent cyanine dye, diSulfo-Cy5-COOH, was synthesized according to published methods as a starting material. The recorded $^1$H-NMR spectrum was identical to that of the authentic commercial sample.

$^1$H-NMR (500 MHz Bruker, 25° C., DMSO-d6): δ (ppm)=8.36 (t, J=13.1 Hz, 2H), 7.79 (s, 2H), 7.61 (m, 2H), 7.29 (d, J=8.1 Hz, 2H), 6.55 (t, J=12.3 Hz, 1H), 6.27 (m, 2H), 4.07 (t, J=7.1 Hz, 2H), 3.58 (s, 3H), 2.17 (t, J=7.2 Hz, 2H), 1.67 (s, 14H), 1.53 (m, 2H), 1.35 (m, 2H).

Example 2: Methods

Thermal Transition and Micelle Formation of F127 vs. F127-CB[7]. NMR samples in $D_2O$ were prepared by dissolving F127-CB[7] at concentration of 100 mg/mL dissolved solids. A control of F127 was similarly prepared at an equivalent molar concentration, accounting for the molecular weight difference attributable to CB[7]. Temperature-dependent $^1$H-NMR was conducted (500 MHz Bruker) in sealed tubes, beginning from 10° C., with incremental heating and equilibration until a temperature of 40° C. was reached. At least 5 minutes of dwell time was provided after the set temperature was reached prior to collecting measurements. Data for F127-CB[7] and F127 is included in FIG. 6B and FIG. 7.

Determination of Keq by $^1$H-NMR competition experiments. $^1$H-NMR competition experiments were performed on a 500 MHz Bruker NMR spectrometer, according to the method described by Isaacs and colleagues. Briefly, NMR samples were prepared at three different ratios of a) a model compound for the PEG-appended guest, b) a competitive guest with a previously reported binding constant, and c) free unmodified CB[7]. Samples were prepared in $D_2O$ and allowed to reach equilibrium for times ranging from ~30 minutes for the weakest guest to 4 days for the strongest guests. Equilibrium was verified by tracking the measured $^1$H-NMR resonances until the spectra became constant. $^1$H-NMR spectra were then acquired for each sample. The resonances which could be clearly assigned to the bound (marked as *' in FIGS. 8, 12, 13, and 14) and the free (marked as * in FIGS. 8, 12, 13, and 14) guest and did not overlap with any other signals were integrated. The concentrations of the bound and free guest were obtained by this method, also yielding the concentration for the bound and the free form of the competing guest as well. In these equilibrium mixture, the $K_{rel}$ values were calculated using the relationships below. $K_{rel}$ values for 3 independent experiments with varying and known ratios of each of three components were averaged to obtain the final estimated $K_{eq}$ values.

$$K_{rel,test/known} = \frac{[test]_{bound}[known]_{free}}{[test]_{free}[known]_{bound}}$$

$K_{rel}$ can alternatively be expressed as follows:

$$K_{rel,test/known} = \frac{K_{eq,test}}{K_{eq,known}}$$

Rearranging yields the following expression for $K_{eq}$:

$$K_{rel,test} = K_{rel,test/known} \times K_{eq,known}$$

Rheological Testing. Viscoelastic properties of the hydrogels were studied using TA Instruments Discovery HR-2 rheometer fitted with a Peltier stage. All hydrogels were prepared as described at a consistent 10 w/v % solids, altering the molar ratio of CB[7]:Fc to be 1:0, 1:1, 2:1, and 3:1. Oscillatory frequency sweep measurements from 0.1 rad/s to 100 rad/s were conducted at 2% strain, a value verified to be in the linear viscoelastic region by a strain sweep conducted for all hydrogels. Thermal ramps were conducted, first raising the temperature slowly (0.5° C. per minute) from 20° C. to 45° C., and then cooling at the same rate over the same range. To study self-healing, step-strain experiments were conducted at 10 rad/s, cycling between 2% and 200% strain. All measurements were performed using a 20 mm 1.9880 cone plate and the solvent trap accessory was used to minimize sample drying during testing.

In vivo Implantation and Imaging. F127-CB[7]:PEG$_8$-Fc (0.1 mL, 10 wt % solid content, 3:1 ratio of CB[7]:Fc) was injected subcutaneously into the dorsal region, between the scapulae, of 7-8 week old female mice. For analysis by histology, C57BL/6J mice were used. For in vivo imaging, hairless but immunocompetent SKH1-E mice were used. Transcutaneous injections were performed using a 25G needle attached to a 1 mL syringe. For histology studies, animals were euthanized at 3, 7, 14, 30, 45, and 60 days following implantation, animals were euthanized and the implantation bed was excised, analyzed by gross necropsy for gel content, and then fixed in formalin and subjected to routine histological processing, sectioning, and staining with H&E. Tissue sections were imaged for gel content and cellular infiltration and clearance. For imaging studies, 48 hours after gel administration mice were intraperitoneally injected with 200 μL guest-linked dye in PBS at a concentration of 1 mM. Equimolar concentration in these dye samples was further verified by measuring the fluorescent emission intensity (Tecan M200Pro Plate Reader) to ensure fluorescence levels were equal between all dye solutions. At serial timepoints following administration, mice were imaged under inhaled anesthesia using an IVIS Lumina Imager with a Cy5 filter set. For studies exploring repeated dosing, Fc-N-Cy5 was administered every 12 hours, with images collected immediately prior to the next dose administration for a total of 9 dye administrations. All in vivo fluorescence images were processed, analyzed, and quantified using ImageJ.

Dye Extraction and Quantification. F127-CB[7]:PEG$_8$-Fc (0.1 mL or 0.2 mL, 10 wt % solid content, 3:1 ratio of CB[7]:Fc) was injected subcutaneously into the dorsal region, between the scapulae, of 7-8 week old female SKH1-E mice. Fc-N-Cy5 was intraperitoneally injected in a volume of 200 μL in PBS at a concentration of 1 mM. After 24 hours, animals were euthanized and the hydrogels were explanted. The hydrogels were dissolved and dye was extracted into PBS (15 mL) by sonication on ice for approximately 2 hours and fluorescence of the extract was measured using a Tecan M$^{200}$Pro Plate Reader with the readings converted to concentrations using a standard curve of Fc-N-Cy5 dissolved in PBS.

Surface Modification of Glass Beads. Borosilicate glass beads (2.00 g, D=45-53 m, Cospheric) were treated with Piranha solution at 80° C. for 1 hour. The glass beads were sequentially washed with water (20 mL×4), ethanol (20 mL×4), and acetone (20 mL×4) and then dried with a stream of N$_2$. A mixture of 3-aminopropyl)triethoxysilane (APTES, 0.3 mL, 99%, Sigma-Aldrich), 95% ethanol aqueous solution (15 mL), and acetic acid (0.3 mL) was stirred for 5 min and transferred to the vial containing the Piranha-treated beads. The reaction mixture was gently stirred for 10 min at room temperature. The supernatant was decanted and the beads were sequentially washed with ethanol (20 mL×4) and acetone (20 mL×4). The beads were then dried with a stream of N$_2$ and heated at 110° C. for 10 min. Then, the beads were gently stirred in a mixture of 4-pentynoicacid (0.20 g), EDC (0.50 g), and DMAP (40.0 mg) in 5 mL of DMF for 24 hours. The beads were sequentially washed with ethanol (20 mL×4) and acetone (20 mL×4) and then dried with a stream of N$_2$. Finally, the beads (1.00 g), CB[7]-azide (28.0 mg), CuSO$_4$·5H$_2$O (2.0 mg) and PMDETA (98%, 1.6 μL) were suspended in DMF/water (1/1, v/v, 10 mL) in a Schlenk flask. The flask was degassed with three freeze-pump-thaw cycles. On the last cycle, the flask was opened to quickly add sodium ascorbate (10 mg) before re-capping. The flask was vacuumed and backfilled with N$_2$ for 5 cycles before warming up to room temperature to thaw the solution and initiate the 'click' reaction with gentle stirring. After 3 days, the reaction was quenched by exposure to air. The beads were sequentially washed with water (20 mL×4), ethanol (20 mL×4), and acetone (20 mL×4) and then dried with a stream of N$_2$. To verify CB[7] surface functionalization, 10.0 mg beads were soaked an aqueous solution of Fc-N-Cy5 (0.01 mg/mL) for 5 minutes and washed with large amount of water at least 10 times until the supernatant was colorless. By naked eyes, the beads were blue. These beads were further analyzed by fluorescence microscopy and compared to control beads which had undergone all other processing steps apart from CB[7] functionalization. These control beads did not have a blue color and showed no signal by fluorescence microscopy. A schematic of functionalization and example data from fluorescence microscopy are shown in FIG. 22. Subsequently, these beads were injected subcutaneously into SKH1-E mice, and systemic homing studies with Fc-N-Cy5 were performed as before with the use of in vivo imaging.

Surface Modification of Polystyrene Beads. Carboxy-modified solid polystyrene beads (0.10 g, D=45-53 μm, Spherotech) were gently stirred in a mixture of propargylamine (50 uL), EDC (0.20 g), and DMAP (18.0 mg) in 10 mL of THF for 24 hours. The beads were sequentially washed with methanol (15 mL×4) and acetone (15 mL×4) and dried under a stream of air. Beads (80.0 mg), CB[7]-azide (6.0 mg), CuSO$_4$·5H$_2$O (1.0 mg), and PMDETA (98%, 0.8 μL) were suspended in DMF/water (1/1, v/v, 4 mL) in a Schlenk flask. The flask was degassed with three freeze-pump-thaw cycles. On the last cycle, the flask was opened to quickly add sodium ascorbate (5.0 mg) before re-capping. The flask was vacuumed and backfilled with N$_2$ for 5 cycles before warming up to room temperature to thaw the solution and initiate the 'click' reaction with gentle stirring. After 3 days, the reaction was quenched by exposure to air. The beads were sequentially washed with water (5 mL×4), ethanol (5 mL×4), and acetone (5 mL×4) and dried under a stream of air. The successful functionalization of CB[7] on the surface was verified by loading Fc-N-Cy5 and observed by naked eye and by fluorescence microscopy compared to controls, as described above for glass beads. A schematic of functionalization and example data from fluorescence microscopy are shown in FIG. 22. Subsequently, these beads were injected subcutaneously into SKH1-E mice, and systemic homing studies with Fc-N-Cy5 were performed as before with the use of in vivo imaging.

Fc-Hdz-Dox Release Studies. F127-CB[7]:PEG$_8$-Fc hydrogels (0.56 mL, 10 w/v % solid content, 3:1 molar ratio of CB[7] and guest) were preloaded with 0.933 mg Fc-N-Hdz-Dox by mixing at 4° C. Then the hydrogel was divided into mini-dialysis kit and dialyzed against 45 mL PBS at pH=7.4 or 5.5 and 37° C. At serial times, 0.5 mL of the dialysis solution was samples and replaced with fresh buffer. The doxorubicin content was examined by measuring the fluorescence on a TECAN Infinite M200 PRO microplate reader, fitting to a standard curve established from pure doxorubicin in buffer.

In Vitro Drug Functional Assay. A standard MTT assay was used to measure and compare in vitro cytotoxiciy of Fc-N-Hdz-Dox and Me-Hdz-Dox. Briefly, MDA-MB-231 cells were seeded in 96 well plates at a density of 20,000 cells per well in 200 µL complete growth media (DMEM with 10% FBS) and cultured for 24 hrs. Assorted concentrations of Fc-Hdz-Dox, Me-Hdz-Dox and free doxorubicin were prepared in fresh growth media were prepared and added to each well. The cells were incubated for 72 hrs. Controls consisted of cells grown in the same volume of normal media, and background was collected from wells with media only. The media in each well were replaced with 100 uL of 3-(4,5-dimethylthiazol-2-yl)-2,5-diphenyltetrazolium bromide (MTT) salt in PBS solution at a concentration of 2 mg/mL. After incubation at 37° C. for 1 hr, the supernatant was replaced with 100 µL of dimethyl sulfoxide (DMSO) and plates were agitated for 15 minutes at room temperature. Absorbance readings were collected on a TECAN Infinite M200 PRO microplate reader at 570 nm. Results were expressed as viability relative to the cell number in the untreated wells. Samples were fit to a standard dose-response function (GraphPad Prism v8) to extract the IC50 for each compound.

In Vivo Tumor Model. Luciferase-expressing MDA-MB-231 cells (Gen Target Inc) were received and passaged 3 times under sterile conditions in standard growth media (DMEM with 10% FBS). Tumors were induced by the injection of 106 cells suspended in 50% growth factor-reduced Matrigel (BD Biosciences) to a total volume of 200 µL (100 µL PBS and 100 µL Matrigel) subcutaneously onto the shaved right flank of NSG mice under sterile conditions. After 14 days, mice without palpable tumors were culled from the study. Remaining mice were treated by injection of F127-CB[7]:PEG$_8$-Fc hydrogels (0.1 mL, 10 w/v % solid content, 3:1 molar ratio of CB[7] and guest) immediately adjacent to the tumor using a 22G syringe. This day was considered as 'day 0' throughout the study. One day after gel injection (day 1), tumors started being tracked using in vivo bioluminescence imaging using an IVIS Lumina Imager. Mice were intraperitoneally injected with 0.1 ml of 30 mg/ml D-Luciferin in 1×DPBS 10 min before imaging, determined from control experiments to be sufficient to capture luminescent signal at its plateau. Mice were randomized into groups. Treated animals received Fc-Hdz-Dox or Me-Hdz-Dox (6 mg/kg Dox-equivalent dose) by i.p. injection in 0.1 ml saline 1, 2, and 3 days after hydrogel application. PBS was injected in the same way into control animals. Throughout the study, in vivo bioluminescence imaging and body weight was collected for treated mice every three days. At day 28, mice were euthanized and tumors were excised and weighed.

Example 3: Supramolecular Affinity as a Homing Mechanism

A suite of supramolecular macrocycles endow medical or implantable devices with an affinity-driven homing signal for capture and local concentration of systemically administered drugs.

The extraordinarily high binding affinity of CB[7] for a number of small molecule guests inspired its selection as the motif of the new drug targeting axis. CB[7] is known to be responsible for the highest ever-recorded affinity of any host-ligand interaction. Though not used as often in medicine as the family of cyclodextrin macrocycles, CB[7] affords binding affinities ($K_{eq}$) that can be as much as 8-12 orders of magnitude higher for the same guest than is possible with cyclodextrin. A number of specialized guest molecules have been reported, based on adamantyl and ferrocene groups, with affinities in the range of $K_{eq}=10^{12}$-$10^{15}$ M$^{-1}$. Binding in such high-affinity regimes offer thermodynamic and kinetic benefits to effectively combat dissociative processes in the body arising from dilution in serum and competition by ubiquitous hydrophobic compounds. For an approximation of the kinetics of guest binding to CB[7], if $k_{on}$ is diffusion controlled ($\sim 10^8$ M$^{-1}$s$^{-1}$), high-affinity binding ($K_{eq}$: $10^{12}$-$10^{11}$ M$^{-1}$) is expected to have $k_{off}$ of approximately $10^{-4}$-$10^{-7}$ s$^{-1}$, meaning once formed these complexes would be stable for hours to months or more. Importantly, the molecular weight of CB[7] is 1163 Da, and its minimal footprint combined with very good water solubility (solubility limit >250 mM in water) suggesting CB[7] remains solvent accessible when displayed on a device. CB[7] is not appreciably degraded in vivo, is small enough for renal clearance, and has limited toxicity (LD50>250 mg/kg in rats). Given its remarkable affinity for certain guests, relative biological inertness, and ease of synthesis, CB[7] may be the only supramolecular macrocycle capable of homing drug to target in the dilute and competitive conditions present in the body using a monovalent interaction.

Figure 2A:
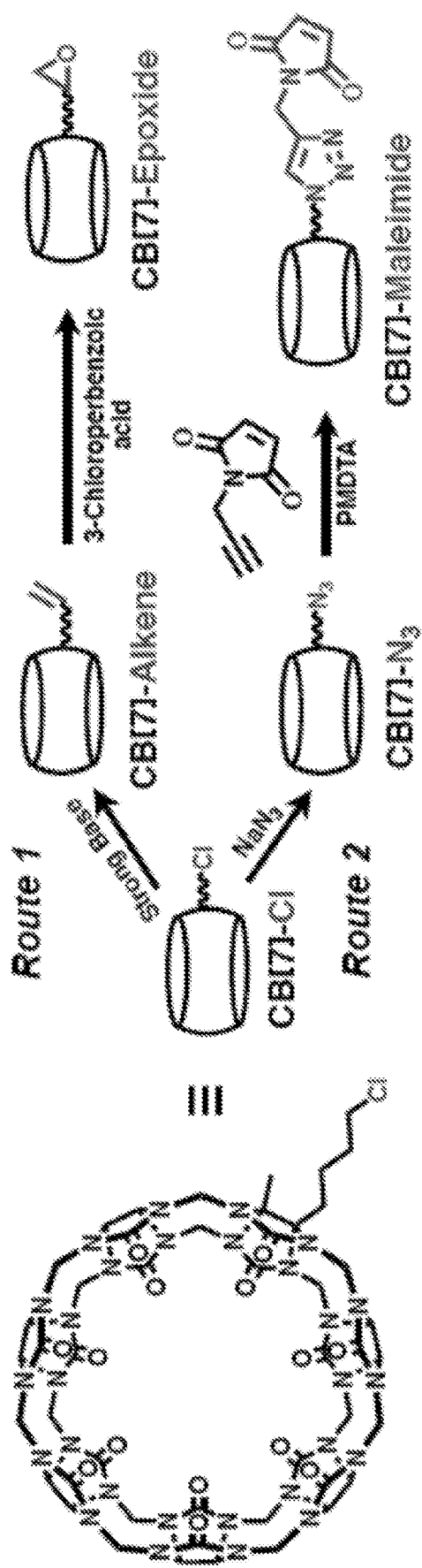
Figure 2B:
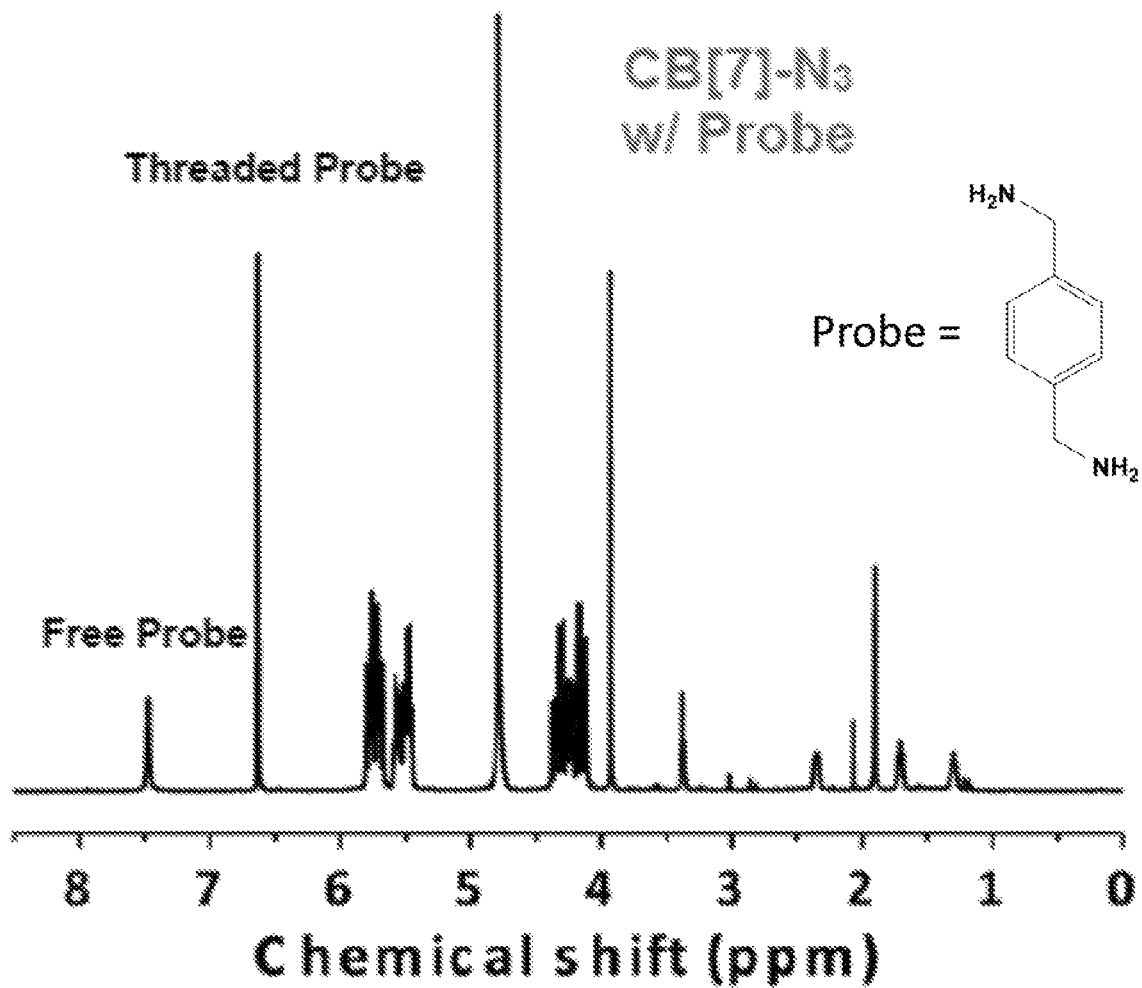
Figure 2C:
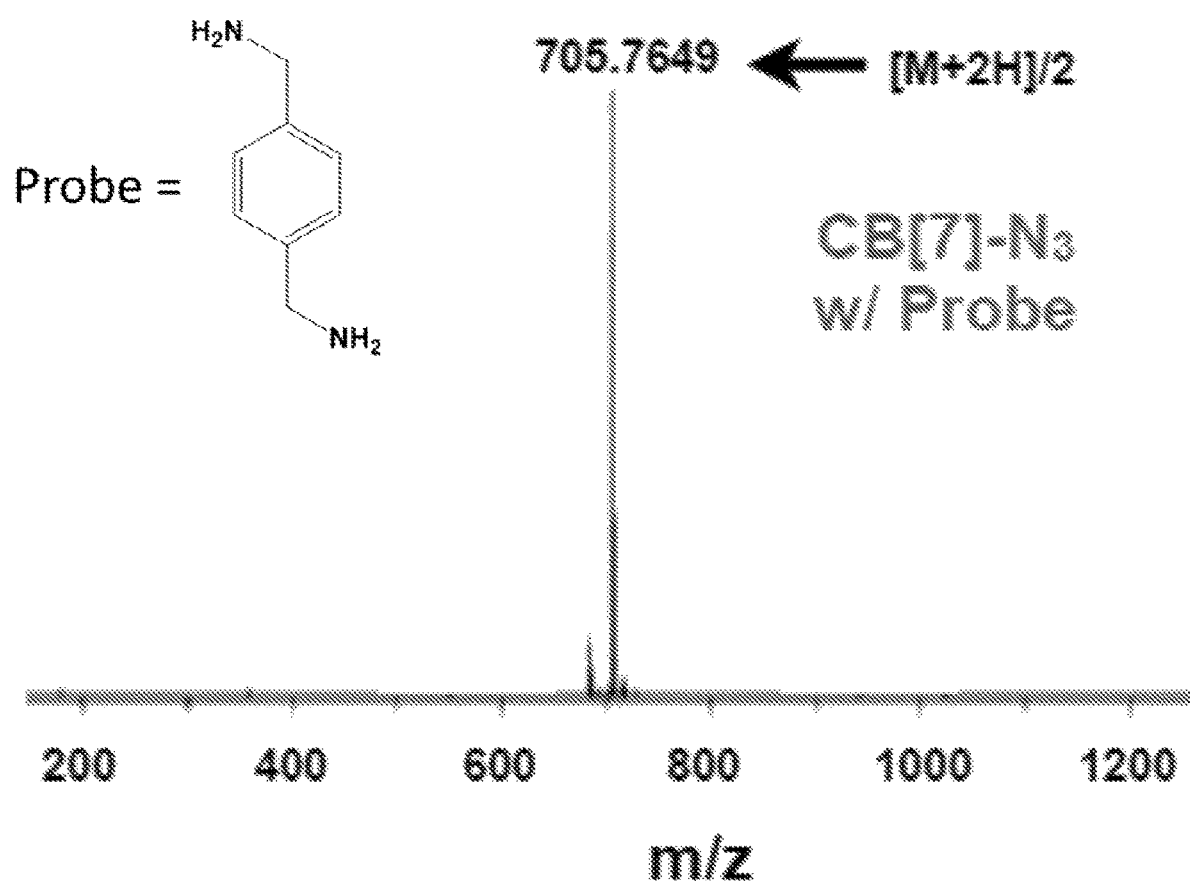

Presenting CB[7] on materials has been challenging due to a lack of reactive groups on the macrocycle and the stability of the urea-based structure. Monofunctional CB[7] entities were generated that can be conjugated to reactive groups on materials (FIG. 2A). In the first route, the alkyl-halide was converted to an alkene, and from there oxidized to afford an epoxide (CB[7]-Epoxide). Epoxides are useful in reacting to amines which are frequently found on protein-based materials or biomaterials made from chitosan. An advantage of using an epoxide, relative to more commonly used EDC/NHS bioconjugation chemistry, is that the product is a secondary amine rather than an amide. Thus, the conjugation site would retain the ability to be protonated, thus maintaining its charge character. In the second route, a thiol-reactive CB[7] was generated from an azide derivative of CB[7] (CB[7]-N$_3$) and from there a maleimide group was introduced (CB[7]-Maleimide) through a conventional thiol-maleimide Michael-type reaction. These macrocycles were characterized by $^1$H-NMR and ESI-mass spectrometry (FIGS. 2B and 2C). A number of synthetic procedures were created to access a diverse group of modified CB[7]macrocycles for use in modifying materials or biomedical devices.

Figure 2D:
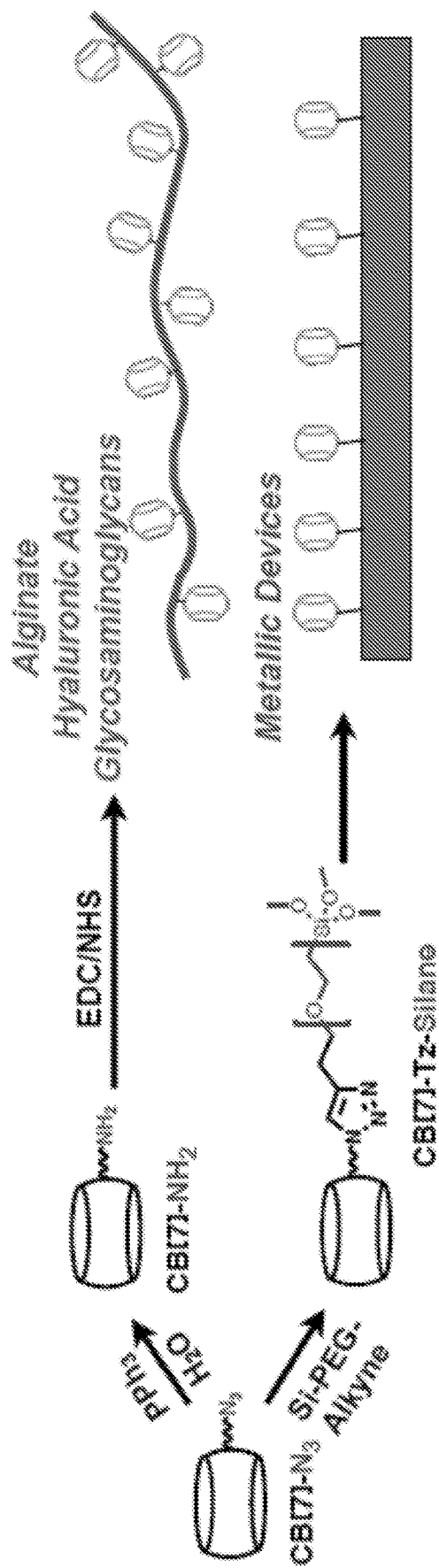

In order to further expand the option of functionalized CB[7] materials to modify other biomedical devices, two more modified CB[7] macrocycles were synthesized beginning from a CB[7]-N$_3$ starting material (FIG. 2D). The first converted the azide to an amine through a Staudinger reduction with triphenylphosphine, giving an amine-modified CB[7] (CB[7]-NH$_2$). This macrocycle would be useful in modifying common biomaterials based on biopolymers such as alginate, hyaluronic acid, and certain glycosaminoglycans. In an alternate route beginning with the same CB[7]-N$_3$ starting material, "click" chemistry was performed to attach a commercially available silane with an oligo ethylene glycol spacer terminated with an alkyne (CB[7]-Tz-Silane). Silane groups may be used for surface modification of metals, including stainless steel biomedical devices. Material characterization techniques, including NMR, atomic force microscopy, and FT-IR spectroscopy, were used to verify modification of these materials with CB[7]. CB[7] remained accessible for guest binding in these different materials as determined using a model fluorescent guest molecule (Acridine Orange, $K_{eq}=2\times10^5$ M$^{-1}$ binding to CB[7]) in combination with fluorescence microscopy.

Example 4: High-Affinity Guest Binding to Supramolecular Macrocycles

Figure 3A:
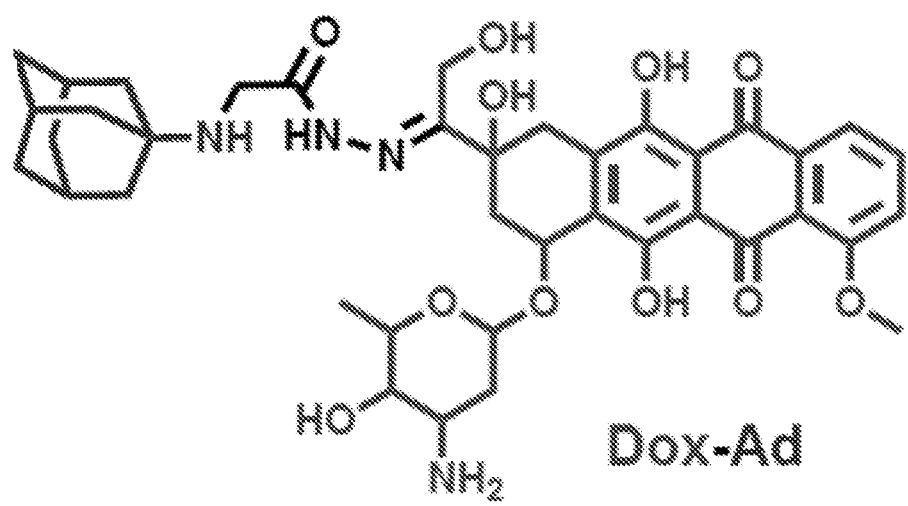
FIG. 3A, FIG. 3B and FIG. 3C show a doxorubicin prodrug (Dox-Ad, FIG. 3A) its NMR spectra (FIG. 3B) and a graph of the rupture rate of the hydrazone linkage as a function of pH as determined by HPLC (FIG. 3C).
Figure 3B:
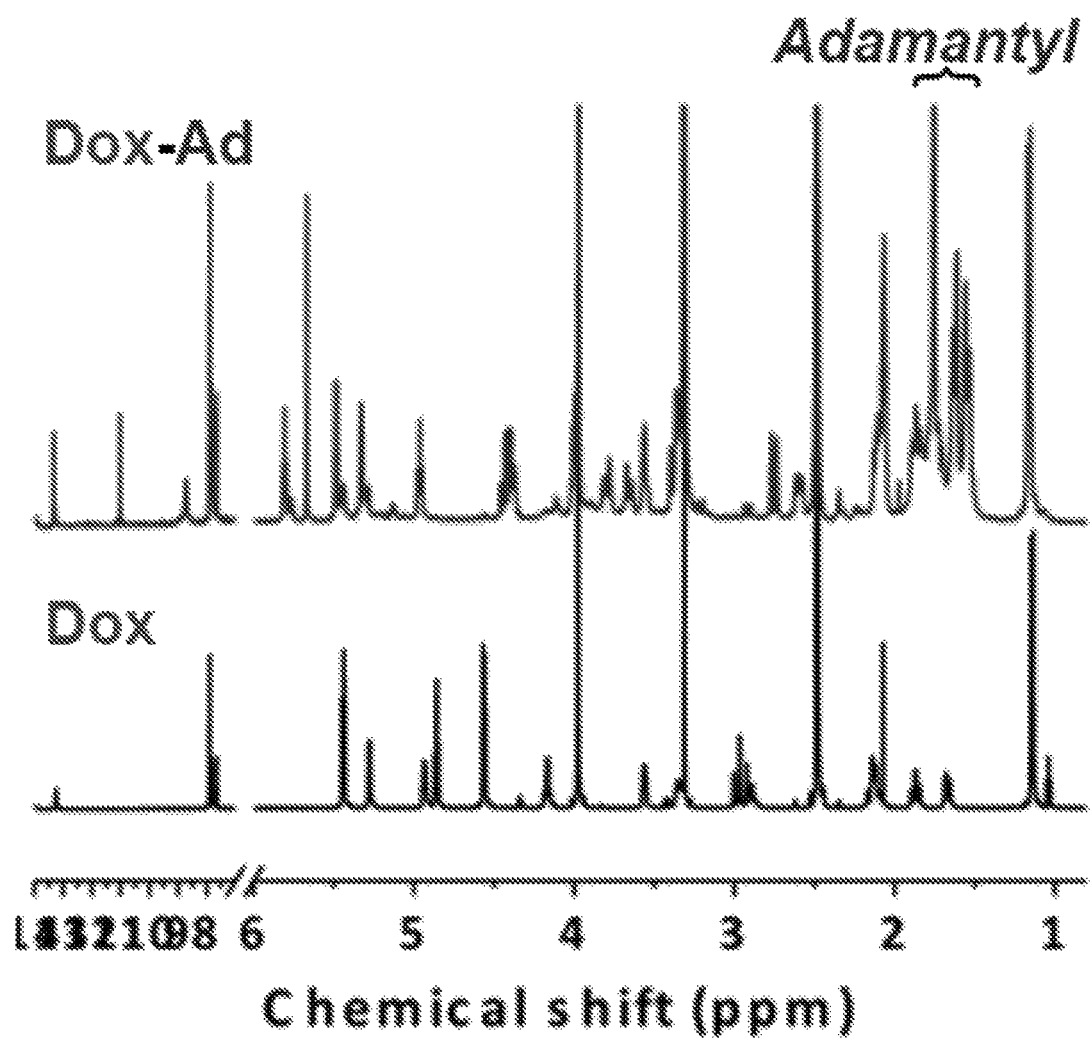
Figure 3C:
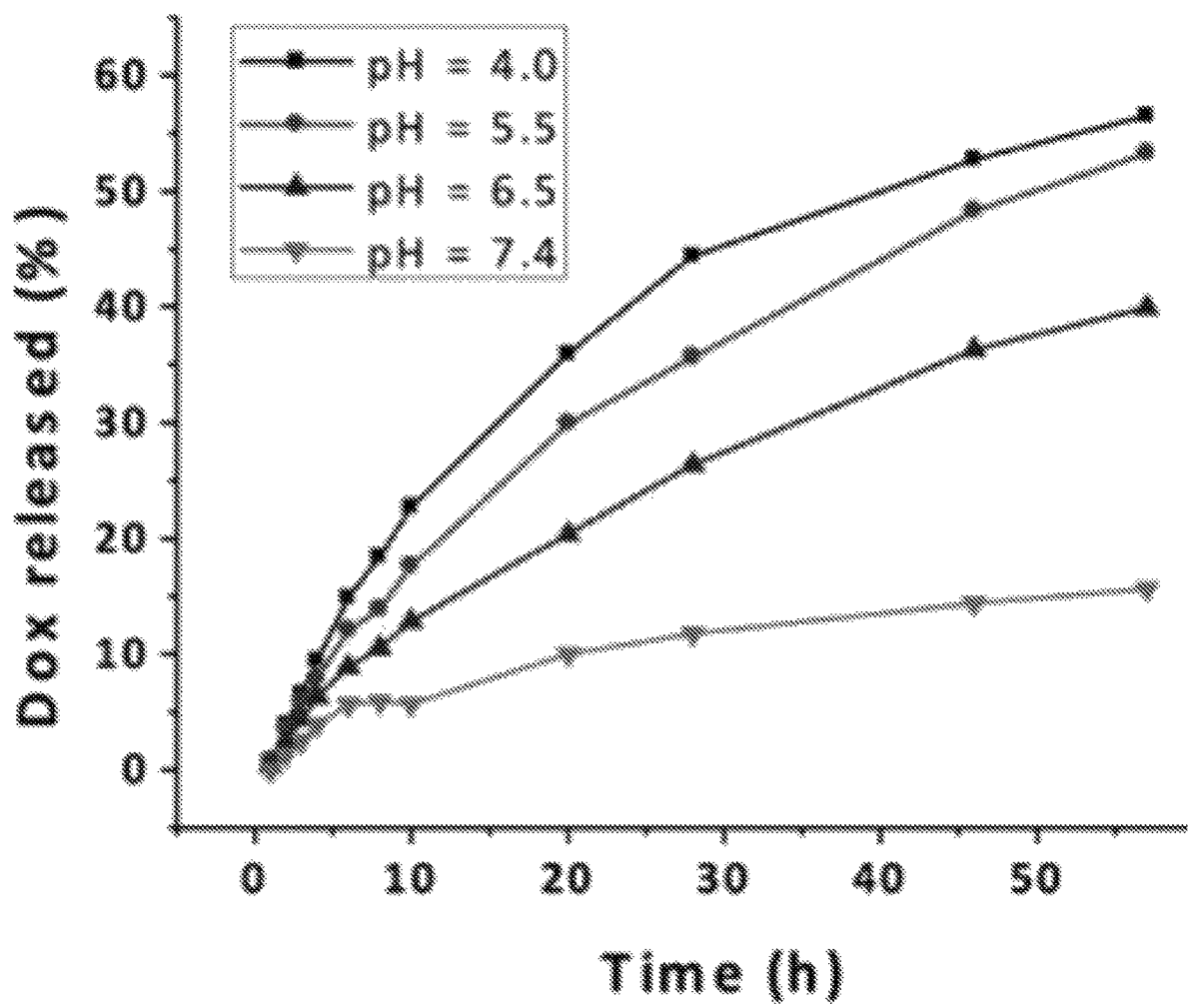

A model set of therapeutic small molecules fused to corresponding high-affinity guests recognized and bound to supramolecular macrocycles under dilute conditions. To demonstrating the new targeting paradigm, a method was created to produce therapeutic agents that can home to CB[7]-modified medical devices for subsequent release. Model prodrugs were synthesized for these purposes. The general design strategy of the prodrugs was as follows: a drug of interest was fused to a high-affinity guest for CB[7] by way of a labile linker, which can be used to tune the rate of release of free drug from the device. Using this approach, a synthetic prodrug variant of the chemotherapeutic, Doxorubicin, was generated by fusing the drug to a high-affinity adamantyl guest using a labile hydrazone (Dox-Ad). The structure of this prodrug (FIG. 3A) was validated by 1-D and 2-D $^1$H-NMR (FIG. 3B) and ESI-MS. The hydrazone linker was cleaved in water, with a rate dictated by pH (FIG. 3C). Using competition NMR experiments, the $K_{eq}$ for Dox-Ad binding to CB[7] was calculated at $4.2\times10^{12}$ M$^{-1}$, consistent with expectations for this adamantyl guest. Affinities in this range are suitable to effectively overcome dissociative processes in vivo as well as outcompete ubiquitous low-affinity binders in the body, such as cholesterol. Dox-Ad was used in conjunction with CB[7]-modified nanoparticles and demonstrated quantitative supramolecular drug loading, cell uptake, and drug function following rupture of the hydrazone linker. As such, CB[7]-binding prodrugs from drugs of interest holds promise in creating a suite of drug molecules for CB[7]-mediated delivery.

Figure 3D:
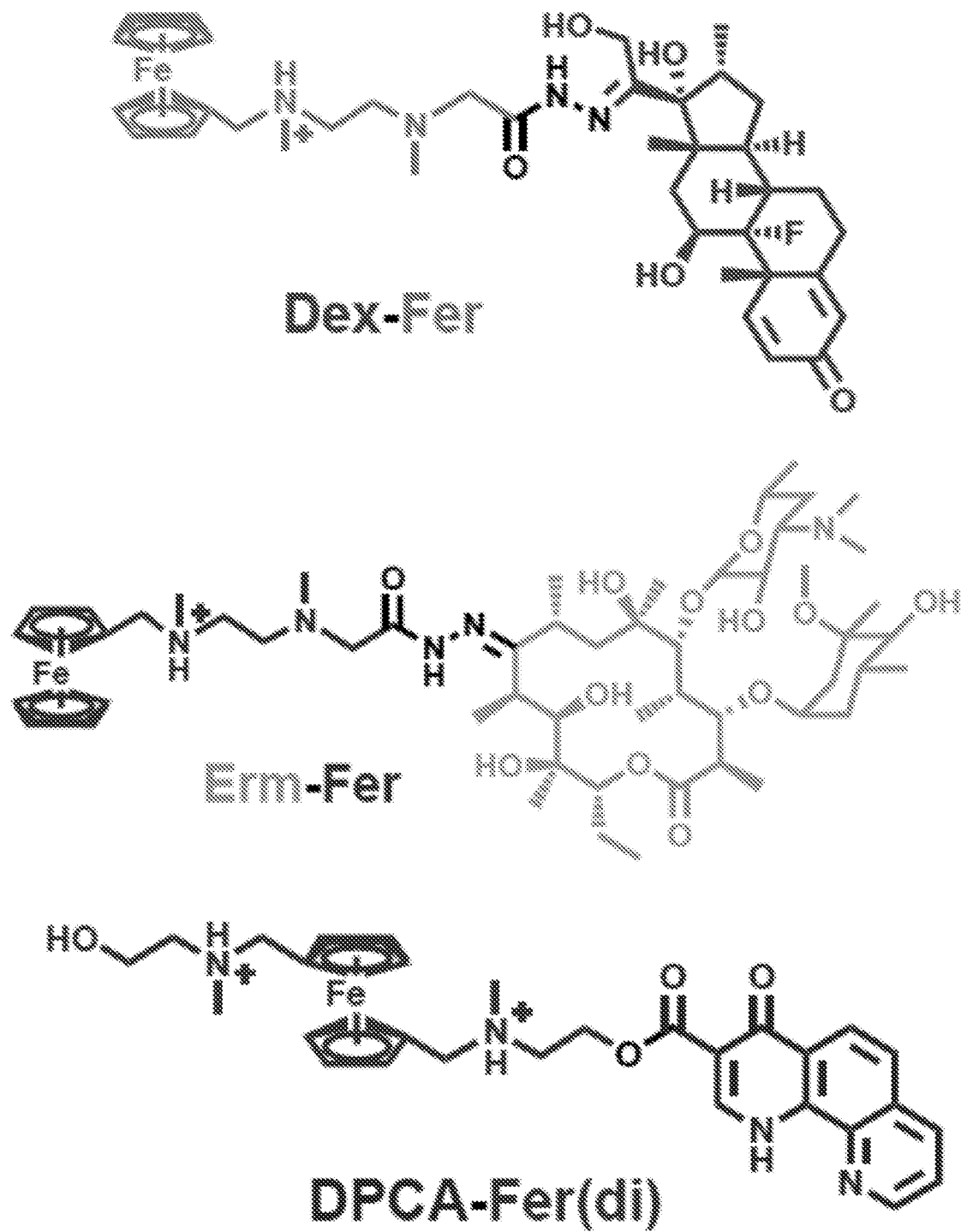
FIG. 3D is prodrug structures for dexamethasone (Dex-Fer), erythromycin (Erm-Fer) and 1,4-DPCA (DPCA-Fer (di)) to address complications in medical devices.

The prodrug, Dox-Ad, was created to evaluate this in the context of adjuvant chemotherapy. In order to create prodrugs with relevance for the challenges encountered in biomedical device applications, the synthetic efforts were expanded to include model drugs that control inflammation, infection, and tissue regeneration (FIG. 3D). Improved methodology has been developed using ferrocene guests; offering comparable affinity (~$10^{12}$-$10^{14}$ M$^{-1}$) as adamantyl derivatives, but with increased synthetic ease.

The first prodrug was based on dexamethasone, a common anti-inflammatory and immune-suppressing steroid. Like doxorubicin, dexamethasone offers a ketone for use in creating a hydrazone linker. The prodrugs were created through attachment of this drug to a high-affinity ferrocene guest for CB[7] using a hydrazone linker (Dex-Fer).

The second drug tested was erythromycin, a common antibiotic with specific relevance in treating *Staphylococcus aureus*, a pathogen often associated with device-related infection. This drug molecule also has a ketone, which was used to attach erythromycin to a ferrocene guest using a hydrazone (Erm-Fer).

A third drug molecule evaluated was 1,4-DPCA (1,4-dihydrophenonthrolin-4-one-3-carboxylic acid), which has been shown to promote scarless pro-regenerative healing following injury. This drug has an available carboxylate group, and a prodrug was formed through attachment of a guest to 1,4-DPCA using a labile ester linkage (DPCA-Fer (di)). For this third design, a ferrocene-diamine guest known to have a higher binding affinity than the mono-amino ferrocene was used. Once acute complications of inflammation and infection have been combated, it may be desirable to switch drug-mediated activity of the device to a prohealing function. The high affinity of DPCA-Fer(di) may supplant the other drugs to localize pro-regenerative drug action to the site of implantation-associated injury.

All the prodrugs were characterized by NMR and ESI-MS. In addition, traceless linkers, or those that when cleaved release the authentic drug molecule, were used to ensure the active drug would be available upon bond rupture. The rupture rate of labile bonds was determined by HPLC quantification. The alteration of the kinetics of bond rupture can be modulated by many other labile chemistries.

The type of fused guest can be used to modulate the affinity for CB[7]. A magnitude of affinities can be observed by competition NMR. A final component of the design involved attenuating the potency of the prodrugs to limit off-target activity, such that prodrugs with attenuated activity either home to the desired site in tissue or are cleared before they transform to an active form. In one example, this enabled a substantial elevation of administered dose to increase drug at the target. In vitro assays were developed to quantify the activity of drugs in free vs. prodrug form. This included measuring cytotoxicity in cancer cells (Dox-Ad), protective effects in oxidatively stressed primary cells (Dex-Fer), dose-dependent colony forming unit assays in *S. aureus* in vitro biofilms (Erm-Fer), and HIF-1α expression in primary fibroblasts (DPCA-Fer(di)).

Example 5: Mode of Targeting in Driving Accumulation of Model Prodrugs

Affinity between host and guest as a homing axis drove modified prodrugs to biomaterials and medical devices modified with CB[7]. A novel hydrogel material decorated with CB[7] that exhibited thermo-responsive gelation when placed into physiologic temperature (FIGS. 4A-4C) was used in vivo. The materials were based on a shear-thinning, affinity-crosslinked Pluronic F127 polymer terminally modified with CB[7] using CB[7]-N$_3$ and "click" chemistry. The reaction to attach CB[7] was quantitative, yielding a thermoresponsive polymer (CB[7]-F127-CB[7]). Pluronic F127 was chosen for its relevance in use as a biomaterial and its general biocompatibility. Pluronic F127 undergoes a well-characterized thermal transition around physiologic temperature, as the polypropylene oxide mid-block becomes more hydrophobic, collapsing into micellar structures with PEG blocks forming a hydrated shell. In order to form hydrogels, the terminal CB[7] units on these thermally responsive polymers were crosslinked with multivalent branched PEG chains appended with high-affinity guests for CB[7]. The material thus resembled a polymer-nanoparticle hydrogel, with CB[7]-decorated Pluronic micelles connected by guest-linked PEG chains to form a percolated network. The composition of this material ensured a significant excess of available CB[7], beyond that used for cross-linking.

Affinity-mediated drug loading was shown using a near-IR model prodrug generated by fusing Cy5 to a high-affinity ferrocene guest for CB[7] (FIG. 4D). A Cy5 dye was chosen due to its versatility for in vivo optical imaging, as near-IR probes excite and emit at longer wavelengths, increasing the penetration depth for visibility in tissue, and are far-removed from the absorbance spectrum for hemoglobin and background autofluorescence of tissue and metabolites. Excitingly, remote-controlled drug loading was demonstrated by first transcutaneously injecting CB[7]-F127-CB[7] hydrogels under the skin, which gelled instantly in situ (FIG. 4E). After 2 hours, Cy5-Fer was administered systemically by intraperitoneal injection. By fluorescent in vivo imaging, fluorescence localized to the subcutaneous hydrogel was observed after 5 hours, and signal intensity at this site was maintained at 24 hours. Therefore, the interaction between CB[7] and a high-affinity guest was sufficient to drive systemically administered small molecules to specific sites in the body.

The efficiency of drug loading was quantified, the kinetics of both uptake in the depot and clearance of unbound drug in the urine was characterized, and the lifetime over which the drug remained in the device and to what extent drug was serially refilled was determined. Initially these properties were established for non-labile drug linkers to further understand the importance of linker rupture rate on drug depot homing, retention, and release.

Another property established was the ability to tune affinity of the guest molecule linked to a payload in order to switch the drug loaded in a depot at a desired time. To this end, a near-IR Cy7 dye was synthesized with the ferrocene diamine guest described previously (Cy7-Fer(di)) and its binding to CB[7] was, in initial studies, verified with a measured affinity of $3 \times 10^{14}$ $M^{-1}$. The kinetics of loading and clearance of the Cy5-Fer dye helped determine the opportunities for switching the drug on board in the device at a desired time by introducing a second drug with higher affinity. This expands the utility of the approach by enabling remote-control of drug-loaded devices, using affinity to tune the identity and function of a drug on board.

Example 6: Hydrogel Platform for Supramolecular Homing Device

By first pre-targeting a desired site with a localized supramolecular "homing" cue, such as a CB[7]-rich injectable hydrogel, affinity between host and guest could be used to facilitate drug localization (FIG. 5). Contrasting with methods which have used antibodies and related large biomolecules, this approach instead used small molecules which offer improved tissue distribution and more rapid clearance from circulation. In addition, small molecule approaches should circumvent risks of immunogenicity and expensive large-scale production that may limit the use of antibodies. Host-guest complexes are typically diffusion-governed ($k_{on}$ ~$10^8$ $M^{-1}$ $s^{-1}$), affording a key advantage over pre-targeting methods based on in situ 'click' chemistry reactions that are more kinetically limited ($k_{on}$ ~$10^0$-$10^4$ $M^{-1}$ $s^{-1}$). Furthermore, supramolecular affinity does not permanently consume a targeted site and in principle the same host site may be subsequently retargeted. In spite of the affinity offered by CB[7]-guest interactions, leveraging its recognition as an axis for therapeutic targeting has not been studied extensively in the contaminated and dilute milieu of a living animal.

Building on the initial studies in Example 5 and to afford a high concentration of locally applied CB[7] for use as a supramolecular "homing" device, an azide-modified monofunctional CB[7] was created and Pluronic® F-127 (F127, 12.6 kDa) was end-modified with CB[7] by azide-alkyne copper 'click' chemistry (F127-CB[7], FIG. 6A). As described above, F127 is an FDA-approved poly(ethylene oxide)/poly(propylene oxide)/poly(ethylene oxide) tri-block co-polymer that undergoes thermally triggered micelle formation near physiologic temperatures. CB[7] modification was quantitative, resulting in F127 end-modified with two CB[7] macrocycles. Temperature-dependent $^1$H-NMR revealed limited impact on F127 micelle formation resulting from CB[7] appendage (FIGS. 6B and 7), with a critical micelle temperature of ~19° C. and full maturation of micelles once temperatures reached ~30° C. The number of surface-presented CB[7] groups on these micelles was estimated from the aggregation number of F127, reported to be in the range of yielding ~70-100 CB[7] macrocycles per micelle or two CB [7] per F127.

Figure 6G:
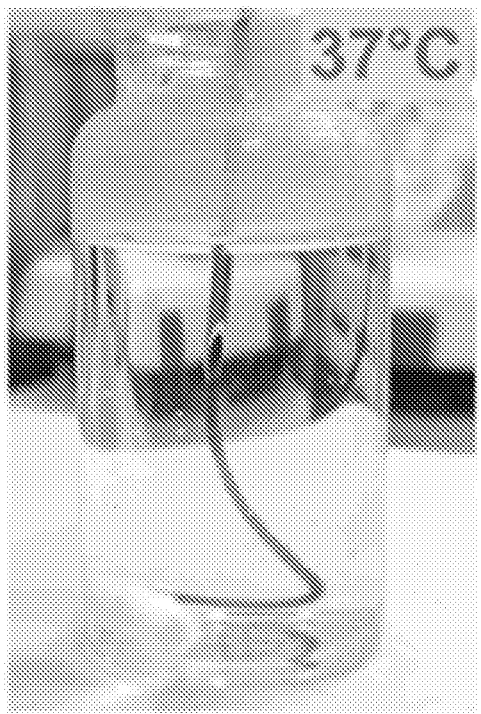
Figure 6H:
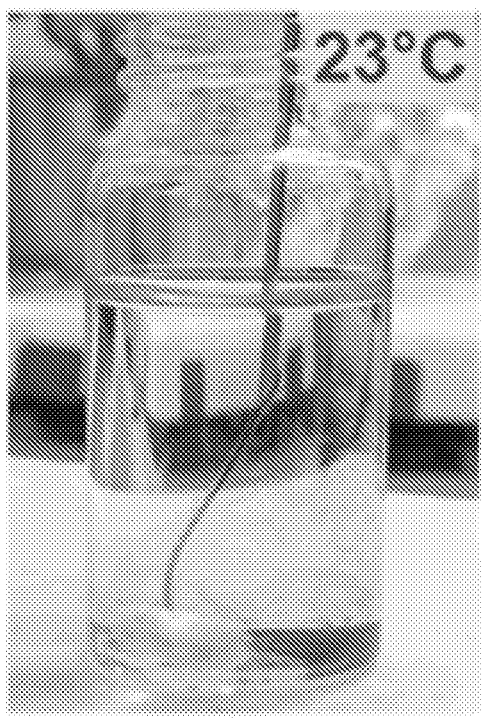

To crosslink F127-CB[7] micelles and form a percolated hydrogel network, 8-arm polyethylene glycol macromers (20 kDa) were end-functionalized with a ferrocene (Fc) guest for CB[7] (PEG$_8$-Fc, FIG. 6C). CB[7] binding to a model compound of this ferrocene guest (FIG. S6) was measured at $3.5 \times 10^{12}$ $M^{-1}$ by competition $^1$H-NMR (FIGS. 6D and 8). By mixing F127-CB[7] with PEG$_8$-Fc at a CB[7]:Fc molar ratio of 3:1 and a concentration of 10 wt % total solids, a thermally reversible hydrogel formed with a critical gelation temperature of ~31-32° C. (FIG. 6E). Hydrogels prepared from alternate ratios of CB[7]:Fc (2:1 and 1:1) with concentration maintained at 10 wt % total solids showed similar thermally reversible hydrogel formation, while F127-CB[7] alone at 10 wt % did not form a hydrogel (FIG. 9). The formed network from 3:1 CB[7]:Fc exhibited instantaneous self-healing properties under step-strain perturbation at physiologic temperature (FIG. 6F). Thermally-induced gelation was effectively instant when the sol was injected into a 37° C. solution (FIG. 6G). By comparison, the hydrogel did not form when the viscous sol was injected into a 23° C. bath (FIG. 6H).

Figure 6I:
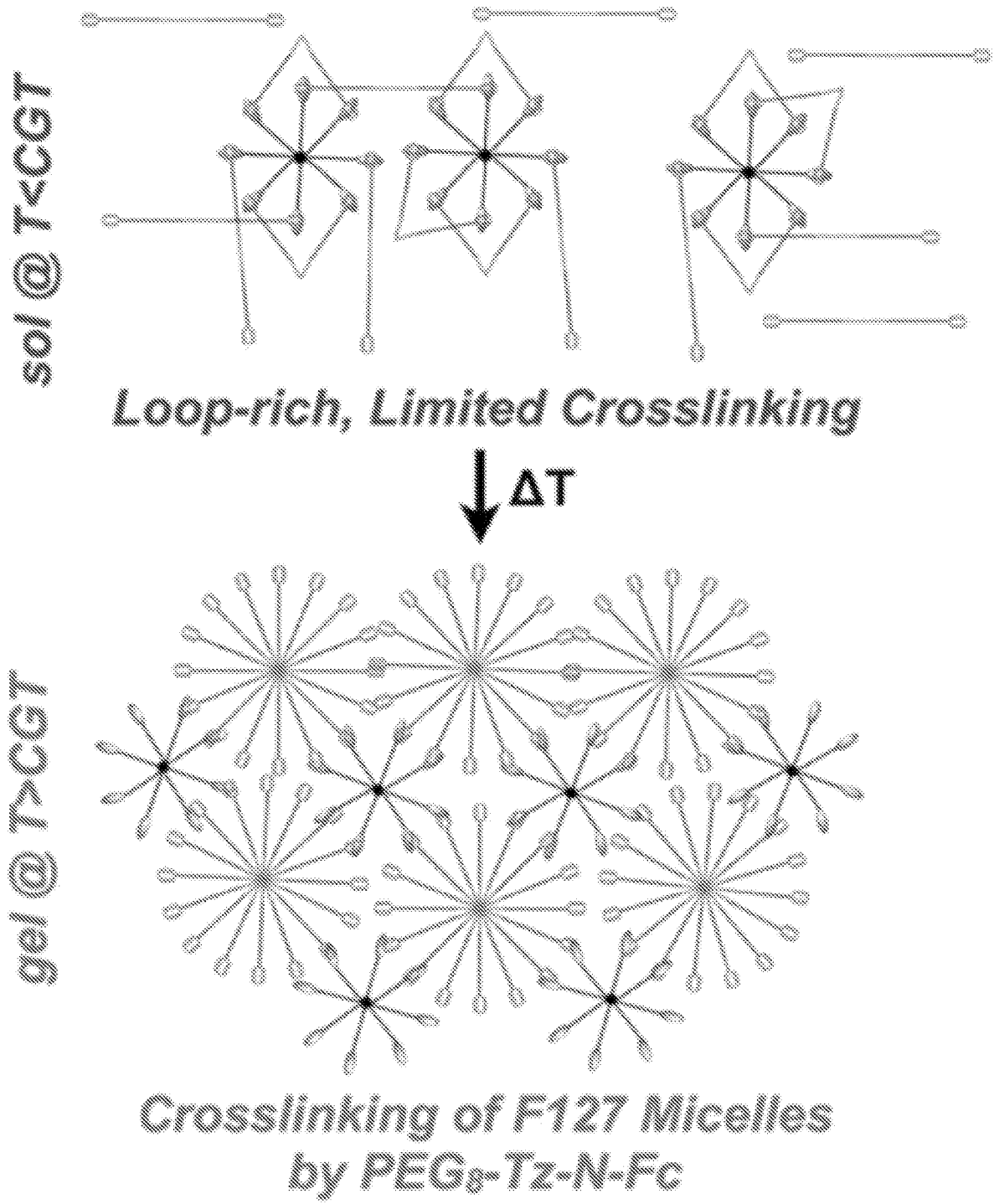

From these rheology studies, hydrogel network formation depended on host-guest crosslinking between CB[7] and the Fc guests appended from the 8-arm PEG macromer. This was supported by a lack of gel formation in F127-CB[7] alone, in spite of its formation of micelles upon heating. F127 formed hydrogels alone at concentrations of >20 wt %. The interaction between CB[7] and PEG-appended Fc guests should be essentially independent of temperature, and at these concentrations an affinity of ~$10^2$ M4 predicted complete guest inclusion in CB[7] portals. When then assessing these findings in the context of Flory-Stockmayer theory, it would be expected that F127-CB[7] (f=2) and PEG$_8$-Fc (f=8) would form a hydrogel network regardless of temperature. Yet this was not observed in the data presented. Temperature-dependent hydrogel formation was furthermore not a result of excess CB[7]contributing to extensive network defects, as hydrogels prepared from a 1:1 ratio of CB[7]:Fc also showed temperature-dependent network formation. As such, the temperature dependence observed was likely the result of extensive "loop" formation in the low temperature sol, wherein macrocycles on the bi-functional F127-CB[7] interacted primarily with Fc guests on the same PEG$_8$-Fc macromere (FIG. 6I).

Without being bound by theory, this could be explained according to principles of avidity; once the first CB[7] binds to an Fc guest, the other CB[7] may be more likely to bind an Fc guest on the same macromer. Hydrogelation thus arises upon thermally induced aggregation of PPO segments, with host-guest supramolecular interactions then serving to crosslink these micelles to form a network. This mechanism was supported by an observation of thermo-responsive hydrogel formation upon mixing F127-CB[7] with linear (PEG$_2$-Fc, f=2) and 4-arm (PEG$_4$-Fc, f=4) guest macromers of molecular weight affording similar arm lengths as PEG$_8$-Fc (FIG. 10). In addition, the rapid self-healing of these hydrogels further supported a mechanism in which PPO aggregation, rather than high-affinity host—guest complexation, governs hydrogel formation.

Instant thermally-induced gelation, coupled with shear-thinning and self-healing character, are desirable traits for injectable biomaterials as it would allow a low viscosity sol to be administered using a syringe and gel at the site of injection. This function was demonstrated for F127-CB[7]:PEG$_8$-Fc hydrogels, which were easily injected as a sol subcutaneously into mice using a 26G syringe and showed clear evidence by palpation of immediate hydrogel formation. Visual inspection of the hydrogel by gross necropsy and tissue histology (H&E) performed at 3, 7, 14, 30, 45, and 60 days revealed a very mild inflammatory response to the injected material which consisted in the acute phase of infiltrating neutrophils and gave rise to macrophages at later times. The gel volume showed an apparent decrease with time implanted, until 60 days when hydrogels were no longer visible by necropsy or recoverable for histology. At 10 wt %, hydrogels with a CB[7]:Fc ratio of 3:1 afforded 7.8 mM free CB[7], assuming 100% CB[7]:Fc complexation. Thus, there remained a significant concentration of free CB[7] within the formed hydrogel to enable its use in the spatially defined capture of systemically administered guest-linked small molecules envisioned here. These CB[7]-rich hydrogels were well-suited to serve as an injectable hydrogel "homing beacon" and facilitate drug localization on the basis of supramolecular affinity.

Example 7: Systemic Small Molecule Administration Targets Hydrogel Platform In Vivo The monovalent affinity required to home a systemically administered small molecule to the site of the hydrogel in the complex physiologic milieu was next evaluated using a model set of small molecules offering a range of affinity for CB[7]. From methods to afford sulfonated cyanine dyes, disulfo-Cy5 with a single pendant carboxylate was synthesized. Sulfonate groups enhance solubility and were included to facilitate rapid clearance in the body, while the near-infrared fluorescence of the dye was intended to enable in vivo imaging with moderate tissue penetration and limited background interference. From this dye, different guests for CB[7] were attached to create model "prodrugs" with expected affinities informed by literature precedent. The first compound, Fc-O-Cy5, termed here as the "weak" guest, bound CB[7] with a measured $K_{eq}$ of $9.5 \times 10^8$ M$^{-1}$ (FIGS. 11A and 12), determined using competition $^1$H-NMR. In spite of nomenclature, this "weak" guest still bound CB[7] with an affinity roughly 3 orders of magnitude higher than cyclodextrin binds virtually any guest. Next, an adamantyl (Ad) variant, Ad-Am-Cy5, was synthesized as a "medium" guest with a measured $K_{eq}$ of $2.1 \times 10^{10}$ M$^{-1}$ for binding to CB[7] (FIGS. 11B and 13). Finally, Fc-N-Cy5, termed the "strong" guest, was prepared and found to bind CB[7] with $K_{eq}$ of $1.5 \times 10^{12}$ M$^{-1}$ (FIGS. 11C and 14).

Dorsal subcutaneous injection in mice of F127-CB[7]:PEG$_8$-Fc hydrogels with a CB[7]:Fc ratio of 3:1 was followed 48 hours later by systemic intraperitoneal administration of the three guest-linked model agents at equal dose. Within only 30 minutes of administration, there was already a dramatic affinity-dependent difference in dye accumulation at the site of hydrogel implantation, as observed by in vivo imaging (FIGS. 11D-11E). The "strong" conjugate, Fc-N-Cy5, showed rapid accumulation and retention at the site of the hydrogel, with the hydrogel even adopting a blue color that was apparent through the skin (FIG. 18). By comparison, and on the basis of fluorescence, 3-fold less of the "medium" conjugate accumulated at the site of the hydrogel while the "weak" conjugate showed no hydrogel accumulation by imaging. A small increase in signal was observed between days 3 and 5, which was attributed to the observation of some hydrogel swelling in the early stages following injection. Swelling would reduce self-quenching from nearby cyanine dyes and increase the size of the gel within the region of interest quantified in the course of image analysis.

Subsequent studies explanted hydrogels 24 h after systemic administration of the "strong" Fc-N-Cy5 conjugate. Extracting the dye from these hydrogels revealed 2.2% (±1.1%) of the total administered dye localized to the site of a 100 µl hydrogel, while 4.2% (±1.2%) localized to a 200 µl hydrogel (FIG. 11F). This level of homing was exciting when compared to the typical accumulation seen in previously mentioned reports using antibody-based targeting. Though there was correlation between hydrogel volume and the percent of agent which homed to the site, these hydrogels were far from saturated upon a single injection of the Fc-N-Cy5 conjugate. This was evident by studying repeat dosing in mice bearing a 100 µl hydrogel (FIG. 11G). Dosing nine consecutive times, with 12 hour spacing between doses and follow-up imaging, resulted in a linear increase in signal at the hydrogel site up to the limit where the detector of the imaging instrument was saturated.

With $k_{on}$ roughly diffusion-limited (~$10^8$ M$^{-1}$ s$^{-1}$) for host-guest interactions of small molecules, $k_{off}$ for the "strong" Fc-N-Cy5 conjugate is ~$10^{-4}$ s$^{-1}$. As such, there should be limited release of dye once bound to CB[7]. The signal reduction observed over 45 d furthermore corresponded to observations for gel clearance made in necropsy and histology. Taken together, this supported a mechanism wherein dye clearance occurred primarily in the course of material erosion and clearance rather than dye releasing from its CB[7]-bound state.

The homing of Fc-N-Cy5 to the site of the CB[7]-rich hydrogel was remarkably efficient, especially in light of the rapid clearance of these small molecules. If no CB[7] hydrogel was present, within hours fluorescent signal in mice returned to the pre-injected baseline (FIG. 16). The majority of dye cleared quickly by renal excretion, as evidenced by fluorescent signal from the kidneys in early imaging times as well as a distinct blue color of urine and bedding evident within 30 minutes of dye administration. Rapid renal clearance suggested that only a fraction of administered dose was even exposed to the hydrogel. As such, the finding that 2-4% of Fc-N-Cy5 homed to the site of the hydrogel was even more impressive. In the case of Fc-N-Cy5, its affinity of ~$10^{12}$ M$^{-1}$ ensured rapid binding and retention at the site for any agent which was exposed to the hydrogel in the course of its distribution in the body. Comparatively weaker-binding guests would have more rapid exchange ($k_{off}$) in their binding to CB[7], impacting their retention at the site even when their distribution resulted in exposure to the hydrogel. The equilibrium state of weaker-binding agents was similarly more highly impacted by dilution in the body as well as competition from native physiologic binders of CB[7]; among the best-binding competitors present in the body include N-terminal aromatic amino acids on proteins ($K_{eq}$~$10^6$ M$^{-1}$).

Example 8: Injectable Depots for Adjuvant Chemotherapy

Homing to injectable depots may be particularly useful in the practice of adjuvant chemotherapy, wherein a chemotherapeutic regimen is followed either pre- or post-operatively to address micro-metastases and locally advanced disease, predictors of disease recurrence and mortality, or to reduce tumor mass for more addressable surgical resection. In adjuvant chemotherapy, doxorubicin has been used, though this drug has many off-target side-effects including cardiotoxicity.

Dox-Ad delivery was initially validated in a breast cancer animal model using a proximally implanted depot (FIG. 17). For this model, tumors of identical size were induced by seeding two million MDA-MB-231 human breast cancer cells in each of the L4 and R4 mammary tissue of NSG (SCID) mice. Following establishment of tumors measuring an average size of 150 mm$^3$ on each side, CB[7]-modified hydrogels were injected into the right mammary fat pad adjacent to the tumor. A control gel was administered into the left mammary fat pad. Following gel implantation, the Dox-Ad prodrug was administered serially through systemic injection via tail vein. This was compared to controls of free doxorubicin. In addition, by incorporating a contralateral control tumor, whether drug homing to the depot had implications on local therapeutic activity was assessed by monitoring tumor size and growth rates in each fat pad with the use of calipers. At the conclusion of the study, tumors were explanted and evaluated for size and examined histologically for signs of drug activity.

Subsequent confirmative studies used doxorubicin modified with the same N-linked ferrocene used to enable homing in the "strong" Fc-N-Cy5 conjugate. Given the expected slow off-rate of the guest once bound to CB[7], a labile hydrazone linker was included between drug and guest, yielding a prodrug referred to here as Fc-Hdz-Dox (FIG. 18A). Hydrazones are common linkers used in the modification of drugs, even including some doxorubicin variants evaluated clinically. Hydrazones are fairly stable at neutral pH, but rupture more quickly under acidic conditions, making these useful linkers for controlled drug delivery in treating cancer. To validate pH-responsive cleavage of the Fc-linked prodrug, F127-CB[7]:PEG$_8$-Fc hydrogels with a 3:1 ratio of CB[7]:Fc were loaded with Fc-Hdz-Dox and the release of free doxorubicin was monitored over time at pH 5.5 and 7.4 (FIG. 19). Drug release progressed quickly over the course of 100 h at pH 5.5, but only a small percentage of drug was released at pH 7.4. Modification of doxorubicin through a hydrazone linkage has been shown to result in attenuation of its potency. Indeed, Fc-Hdz-Dox was found to have an IC$_{50}$ of 6.8 µM for human breast cancer cells (MDA-MB-231) in culture (FIG. 18B); an order of magnitude less potent than unmodified doxorubicin (IC$_{50}$ '$_2$ 0.49 µM) in vitro.

In order to demonstrate a role for supramolecular homing in therapy with Fc-Hdz-Dox, an orthotopic xenograft tumor model was deployed in immunocompromised mice as described for Dox-Ad. Once tumors had formed, the F127-CB[7]:PEG$_8$-Fc hydrogel was applied adjacent to the tumor and animals were dosed with 3 mg/kg/day of unmodified doxorubicin or a doxorubicin equivalent dose of Fc-Hdz-Dox for three consecutive days (FIG. 20). While this dose of doxorubicin is below its reported LD$_{50}$ in mice (11.2 mg/kg i.p. from RTECS database), three consecutive doses proved detrimental to health of these mice and resulted in weight loss and poor survival outcomes. Fc-Hdz-Dox was well-tolerated by these same measures. Furthermore, Fc-Hdz-Dox slowed the rate of tumor growth relative to doxorubicin treatment alone, for which tumors continued to grow in spite of treatment.

To probe supramolecular homing to tumors while limiting drug toxicity, another hydrazone-modified doxorubicin variant was synthesized, termed Me-Hdz-Dox (FIG. 18A). When evaluated for toxicity in MDA-MB-231 cells in culture, this new variant had an IC$_{50}$ of 4.5 µM (FIG. 18B), and as such was comparable to the in vitro potency of Fc-Hdz-Dox. In addition, this new appending group did not facilitate measurable binding to CB[7]. This compound was thus explored for the explicit purpose of evaluating supramolecular homing of doxorubicin for treating cancer (FIG. 18C). Fc-Hdz-Dox and Me-Hdz-Dox were evaluated on the basis of their ability to control the growth of tumors adjacent to F127-CB[7]:PEG$_8$-Fc hydrogels, dosing at 6 mg/kg/day doxorubicin equivalence for three consecutive days. This dose was chosen following pilot studies to determine the maximum Fc-Hdz-Dox dose without eliciting outward morbidity in these mice (~8-10 mg/kg/day). Indeed, weight remained stable throughout the study, suggesting both compounds were well tolerated (FIG. 21). Excitingly, mice treated with Fc-Hdz-Dox showed a significant and sustained reduction in the rate of tumor growth that lasted well beyond the initial period where compounds were dosed (FIG. 18C). This finding suggests a mechanism entailing initial homing on the basis of supramolecular affinity, and prolonged drug presence near the tumor as hydrazone linkers slowly rupture. Though some have postulated the peri-tumoral environment to be of somewhat acidic pH, release studies suggested the rupture rate of the hydrazone may yet be too slow and as such might limit free drug concentrations reaching the level needed for complete tumor regression.

These models showed that the function of doxorubicin was enhanced by employing supramolecular homing to direct it to the region of a primary tumor. Unlike other similar depots, such as the Gliadel® wafer, this implanted material can be periodically refilled in order to restock drug supply. Moreover, this approach reduced the systemic toxicity of compounds such as doxorubicin, and thus the maximum tolerated dose of the Dox-Ad prodrug compared to free drug was improved.

Example 9: Supramolecular Affinity for Biomedical Devices

Supramolecular affinity could also be a versatile approach to facilitate spatially controlled accumulation of small molecules to other desired sites. As an example, biomedical devices are plagued by a number of interface-mediated modes of failure. Supramolecular homing was thus explored for its ability to enable homing to the interface of an implanted device.

To evaluate the utility of homing to other materials, solid glass and polystyrene beads were surface-modified with CB[7]. Following implantation of the beads, administered Fc-N-Cy5 dye localized to the site of these CB[7]-modified biomaterials (FIG. 22). This example points to a possible broader use for this approach in the context of biomedical device coatings.

In another model to establish utility of the disclosed paradigm in drug targeting, a subcutaneous biomaterial implant was used to study and assess inflammation and fibrosis (FIG. 17). Specifically, the surface of 20 µm amine-modified polystyrene microparticles were decorated with CB[7] using CB[7]-epoxide to react to surface amines. Control particles were modified with an epoxy-ethylene glycol to preserve the charge and relative hydrophilicity of the modification. CB[7]-decorated microparticles were injected subcutaneously into the right flank and the non-CB

[7] control particles into the left flank as a contralateral control. the dexamethasone prodrug was administered systemically via tail vein injection. At various points following administration, the microparticles and surrounding implant bed were harvested, and the tissue was processed for histological staining using H&E and Mason's Trichrome. A blinded scoring protocol was developed to assess the degree of immune cell infiltration into the implant bed as well as the thickness of fibrotic capsule formed around the implant. This example showed that the function of dexamethasone can be localized immediately to the site of an inflammatory insult.

As demonstrated herein, pre-targeting with an injectable CB[7]-rich hydrogel served to spatially define the desired site of drug action by localizing a systemically administered guest-linked small molecule on the basis of supramolecular affinity. There are several advantages to this approach. Small molecules, such as the guest-modified variants shown here, should have more extensive tissue distribution than larger antibodies or even larger nanoscale carriers. At the same time, if they do not find their desired site of action, these small molecules should clear rapidly, as opposed to alternative strategies that have challenges arising from toxic drug molecules which are shed from a carrier in the course of prolonged circulation. Synthetic modification of a drug with a guest motif may also attenuate its potency and enable higher dosing without concomitant issues from off-site toxicity, as was demonstrated here when modifying doxorubicin. Host-guest complexes associate at the diffusion limit, contrasting with many in situ chemical ligation strategies which can be kinetically limited. Though the host-guest interactions used here have a very slow off-rate, there are opportunities more generally with this approach to explore the "regeneration" of host macrocycles so that these may be subsequently re-targeted to increase the longevity of a device. This is a possibility not afforded by common methods for in situ chemical ligation.

Example 10: Pharmaceutical Dosage Forms

The following formulations illustrate representative pharmaceutical dosage forms that may be used for the therapeutic or prophylactic administration of a compound or prodrug described herein, a compound or prodrug specifically disclosed herein, or a pharmaceutically acceptable salt or solvate thereof (hereinafter referred to as 'Compound X'):

| (i) Tablet 1 | mg/tablet |
|---|---|
| Compound X | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/mL) | mg/mL |
|---|---|
| Compound X (fee acid form) | 1.0 |
| Dibasic sodium phosphate | 12.0 |
| Monobasic sodium phosphate | 0.7 |
| Sodium chloride | 4.5 |
| 1.0N sodium hydroxide solution (pH adjustment to 7.0-7.5) | q.s |
| Water for injection | q.s. ad 1 mL |

| (v) Injection 2 (10 mg/mL) | mg/mL |
|---|---|
| Compound X (fee acid form) | 10.0 |
| Dibasic sodium phosphate | 1.1 |
| Monobasic sodium phosphate | 0.3 |
| Polyethylene glycol 400 | 200.0 |
| 0.1N sodium hydroxide solution (pH adjustment to 7.0-7.5) | q.s |
| Water for injection | q.s. ad 1 mL |

| (vi) Aerosol | mg/can |
|---|---|
| Compound X | 20 |
| Oleic acid | 10 |
| Trichloromonofluoromethane | 5,000 |
| Dichlorodifluoromethane | 10,000 |
| Dichlorotetrafluoroethane | 5,000 |

| (vii) Topical Gel 1 | wt % |
|---|---|
| Compound X | 5 |
| Carbomer 934 | 1.25 |
| Triethanolamine (pH adjustment to 5-7) | q.s |
| Methyl paraben | 0.2 |
| Purified water | q.s. to 100 g |

| (viii) Topical Gel 2 | wt % |
|---|---|
| Compound X | 5 |
| Methylcellulose | 2 |

| (viii) Topical Gel 2 | wt % |
|---|---|
| Methyl paraben | 0.2 |
| Propyl paraben | 0.02 |
| Purified water | q.s. to 100 g |

| (ix) Topical Ointment | wt % |
|---|---|
| Compound X | 5 |
| Propylene glycol | 1 |
| Anhydrous ointment base | 40 |
| Polysorbate 80 | 2 |
| Methyl paraben | 0.2 |
| Purified water | q.s. to 100 g |

| (x) Topical Cream 1 | wt % |
|---|---|
| Compound X | 5 |
| White bees wax | 10 |
| Liquid paraffin | 30 |
| Benzyl alcohol | 5 |
| Purified water | q.s. to 100 g |

| (xi) Topical Cream 2 | wt % |
|---|---|
| Compound X | 5 |
| Stearic acid | 10 |
| Glyceryl monostearate | 3 |
| Polyoxyethylene stearyl ether | 3 |
| Sorbitol | 5 |
| Isopropyl palmitate | 2 |
| Methyl paraben | 0.2 |
| Purified water | q.s. to 100 g |

These formulations may be prepared by conventional procedures well known in the pharmaceutical art. It will be appreciated that the above pharmaceutical compositions may be varied according to well-known pharmaceutical techniques to accommodate differing amounts and types of active ingredient 'Compound X'. Aerosol formulation (vi) may be used in conjunction with a standard, metered dose aerosol dispenser. Additionally, the specific ingredients and proportions are for illustrative purposes. Ingredients may be exchanged for suitable equivalents and proportions may be varied, according to the desired properties of the dosage form of interest.

Example 11: Affinity Hydrogels as Opioid Replacements in Pain Management

The use of the hydrogel may be explored for loading and prolonged release of sodium channel blocking anesthetics combined with analgesic and anti-inflammatory drugs. Using this approach can facilitate localization and control release of active pain-managing agents at surgical sites. This material can be easily applied, and will offer tunable drug availability over the time-frame appropriate for post-surgical pain management and advance the practice of continuously available local anesthesia for post-surgical pain management compatible with at-home care, without requiring infusion pumps of repeated physician intervention.

Emerging methods in anesthesiology have explored the use of regional and/or local anesthetics to limit pain and obviate the need for opioids. Yet, these methods often rely on repeat physician administration, sometimes automated by transcutaneous pumps; both introduce added complication in pursuit of alternative pain management. The field of drug delivery may offer a solution to this challenge, with reports of controlled release technology for local application at the surgical site. Relative to the different drug delivery technologies explored thus far, the hydrogel described herein offers some key and innovative advantages:it combines typical hydrophobic drug encapsulation with supramolecular affinity-based drug carriers to facilitate more specific drug loading and tunable, multi-modal release kinetics; the modularity from these two mechanisms for drug loading and release affords combination of standard anesthetic agents with supportive analgesic and anti-inflammatory agents to enhance and improve pain management locally; and the hydrogels are prepared from safe and biocompatible materials that clear from tissue, thus limiting the possible impact on tissue healing from long-term material presence or a material-associated tissue reaction at the injury site.

Agents that block sodium channels on neurons are commonly used pain relievers as they prevent membrane depolarization and signal transduction to the central nervous system to inhibit transmission of distal sensory inputs including pain. The duration of action for this approach can vary by agent, but ranges from 30-60 minutes for short-acting agents like 2-chloroprocaine, 1-2 hours for intermediate-acting agents like lidocaine, and upwards of 12+ hours for long-acting agents like bupivacaine. These non-addictive agents have a long history of safe use for short-term pain management. Several approaches have been explored to extend their duration of action through continuous application at the site. However, the need for repeated physician administrations, sometimes automated by transcutaneous perfusion pumps, introduces additional complications such as increased infection risk, increased cost of care, and sometimes reduced mobility.

The mechanism for high-affinity guest binding by CB[7], as described above, may be due to hydrophobic interactions by guest inclusion in the cavity, typical of other host-guest complexes. Sodium channel blocking anesthetics are characterized by structures with protonating amines adjacent to aliphatic groups, predicting high-affinity CB[7] binding. The affinity for CB[7] by a variety of sodium channel blocking agents will be explored, so as to enable their delivery with the CB[7]-rich hydrogels. These molecules may bind CB[7] with affinity of ~$10^8$-$10^9$ $M^{-1}$, given known binding affinities of other similar compounds with CB[7]. To estimate the kinetics of such binding, $k_{on}$ for a CB[7]-guest complex occurs approximately at the diffusion limit (~$10^7$ $M^{-1}$ $s^{-1}$); binding with $K_{eq}$=$10^8$-$10^9$ $M^{-1}$ has an approximate $k_{off}$ of ~$10^{-2}$ $s^{-1}$. In other words, binding in the range anticipated for some of these drugs will dictate a reasonably stable complex that will remain preferentially bound, yet release over time to facilitate drug availability in tissue. The best competitors reported to bind to CB[7] in biological milieu, N-terminal aromatic amino acids on proteins, bind with $K_{eq}$ of $10^6$ $M^{-1}$. Thus, these molecules should bind with greater affinity than “background” competitors in the body. Moreover, the high density of CB[7] on the hydrogel makes it likely that a drug releasing from one bound site will find another, further extending release beyond that dictated by pure 1:1 binding stoichiometry kinetics. Model compounds with affinities approximately in this range home to CN[7]-rich hydrogels in the body (FIGS. 11A-11C).

First, a dye exclusion assay will be performed placing drugs in competition with acridine orange (AO, $K_{eq}$=2×$10^5$ $M^{-1}$) for CB[7] binding. AO undergoes a photo-physical shift in fluorescence between its CB[7]-bound and free forms, with AO displacement from drug binding to CB[7] reducing its fluorescence. At comparable concentrations of dye and drug, reduced AO fluorescence suggests drug affinity $\geq 10^5$ $M^{-1}$. Promising compounds, which in this assay display affinity considerably higher than AO (i.e., out-compete AO for CB[7] binding when at relative dilution) will be further characterized for binding using more rigorous methods. Isothermal titration calorimetry (ITC) can provide in-depth thermodynamic profiling and simultaneously determine all binding parameters in a single experiment. ITC will enable drug binding to be characterized and compared on the basis of binding constant ($K_{eq}$), reaction stoichiometry (n), binding enthalpy (ΔH), and binding entropy (ΔS). In parallel, competition $^1$H-NMR will be used to determine drug binding.

To quantify binding affinity, drugs will be studied in competition with 1,6-diaminohexane ($K_{eq}$=8.9×10$^7$ $M^{-1}$) and p-xylylenediamine (1.78×10$^9$ $M^{-1}$), and the relative ratio of CB[7]-bound drug will be compared to the known binding for these two model compounds to determine $K_{eq}$. As shown in preliminary work, binding to CB[7], resulted in shifts to encapsulated protein. The binding of the sodium-channel blocker bupivacaine to CB[7] was assessed using NMR with results suggesting binding of ~10$^8$ $M^{-1}$ based on prior experience (FIG. 23). Bupivacaine is sparingly soluble on its own, but has very good water solubility when combined with CB[7], supporting its interaction as a guest inside CB[7].

Following identification of CB[7] binding agents, the loading and release from the CB[7]-rich hydrogels will be quantified. Drug molecules will be added to the pre-gelled solutions where these will complex with some of the available CB[7]. Hydrogels will be formed upon heating to 37° C. Upon F127 micelle formation, some hydrophobic drugs may partition into the PPO mid-block of the micelles, facilitating possibly two independent modes of release (FIG. 25). The common sodium channel blocker, lidocaine, has been found to selectively partition into the core of F127 micelles, leading to its controlled release. These hydrogels will be incubated in physiologic buffer with and without the addition of serum. Maximal loading will be measured by drug extraction and quantification with HPLC-MS. The theoretical maximum loading of the material would have drug at ~6% of the weight of the material if all CB[7] are occupied, before considering the possibility for additional drug in the PPO mid-block which would substantially increase drug loading and perhaps offer bi-modal release kinetics. Clinically used injectable suspensions of these drugs are often on the order of 0.2-0.5% drug, a loading that should be easily achieved with the materials. Release will be measured through sampling the bulk phase and quantifying by analytical HPLC-MS. With each bulk phase sampling, fresh release media will be added to simulate dilution and clearance in vivo. The kinetics of release will be fit to standard mathematical models, with an expectation that the best formulations will have minimal burst release and first-order kinetics to ensure drug release decreases over time. Release lasting on the order of ~3-5 days is expected to be preferred for this application. To further probe PPO encapsulation-mediated release, experiments will be repeated with a stoichiometric excess of drug:CB[7]. In addition, formulations wherein a high-binding competitor is added to "block" available CB[7] binding sites to force drug to solely occupy the PPO micellar core will be performed.

Drug loading and controlled release from CB[7]-rich hydrogels will be further explored in vivo for sodium channel blockers which show CB[7] binding and/or PPO encapsulation with ideal release kinetics. Using C57BL6J mice, release and local tissue concentration will be quantified. Drug-loaded hydrogels will be injected (s.c.) after loading with drug. At serial timepoints over the next 3 days, blood will be drawn by cardiac puncture and the hydrogel and surrounding tissue will be explanted. Targeted HPLC-MS on a triple quadrupole instrument (Agilent) will be used to quantify remaining drug within the hydrogel as well as its regional tissue concentration and serum concentration over time.

Example 12: Combination of Analgesic and Anti-Inflammatory Agents with Anesthetics for Pain Management The procedure of infiltration anesthesia not only relies on sodium channel blockers, as explored in Example 11, but includes co-delivered agents such as epinephrine and dexamethasone to help in managing pain and inflammation at the site. Epinephrine is a hormone and neurotransmitter involved in the "fight or flight" response that acts peripherally on α-adrenergic vascular receptors to mediate the contraction of vascular smooth muscle cells and reduce local blood flow. The co-delivery of epinephrine in local infiltration anesthesia has been found to extend duration of action of sodium channel blockers and contribute to improved efficacy and potency. This finding is thought to result from, among other actions, reduced clearance of the anesthetic agent in the tissue. Dexamethasone is a corticosteroid anti-inflammatory agent that functions by inhibiting the production of cyclooxygenase (COX) enzymes which are responsible for producing prostaglandins that, among other roles, serve to sensitize neurons to pain stimuli. Co-delivery of dexamethasone has also been found to prolong the effect of agents such as bupivacaine. The dosing and ratios for inclusion of these agents will be informed by clinical precedent.

The first route we will explore is encapsulation of these agents within the hydrophobic PPO core of F127 micelles in the hydrogel for their controlled release. A prodrug of epinephrine has been used in ocular applications and consist of protection on the catechol of the parent drug by pivalate esters (FIG. 26A) to render the compound lipophilic; esters are subsequently cleaved by endogenous esterases to reveal the functioning drug. This prodrug may partition within the PPO block of F127 micelles of the hydrogels. Similarly, dexamethasone preferentially partitions into the PPO block of F127, a feature which has been explored for ocular drug delivery applications. The loading capacity and kinetics of release for these compounds within the hydrogel materials will be explored.

In preliminary work, the systemic loading of CB[7]-containing hydrogels with model prodrugs was demonstrated (FIGS. 23A and 23B). This clearly illustrated that affinity between CB [7] and certain strong guests (>10$^{10}$ $M^{-1}$) can overcome dilution and competition in realizing complex formation in physiological conditions. Similar prodrug methods will be applied to ephinephrine and dexamethasone to facilitate combination delivery with sodium channel blockers from CB[7] hydrogels. By including motifs for CB[7] affinity on these agents, it will combine affinity-directed loading with PPO partitioning for controlled drug release. The attachment of a high-affinity guest to a drug using these methods may facilitate recognition by CB[7] for affinity-driven loading onto the hydrogels to control the release kinetics. The drugs of interest will be modified with a guest for CB[7] via a labile linker (FIG. 26B). To prepare a dexamethasone prodrug (Fc-N-Hdx-Dox), the drug will be conjugated to a ferrocene guest via a labile hydrazone bond by reaction of a hydrazine-modified ferrocene guest with the available ketone on dexamethasone. This route will similarly enable loading and controlled release of dexamethasone. For epinephrine, a prodrug using a labile ester linkage (Fc-N-Es-Epi) will be created, which ruptures by hydrolysis and also by action of esterase enzymes in tissue. An ester linkage will be created from a hydroxy-terminated Fc-N guest by DCC coupling with catalytic DMAP. Both prodrugs, are derived from a strong ferrocene guest to enable expected $K_{eq}$ for binding to CB[7] of $10^{12}$ $M^{-1}$. Strong binding to CB[7] will be assured using competition $^1$H-NMR. The rupture rate of each labile linkage across a range of pH (e.g., 4-9) will be assessed, and for the ester linkage studies in the presence of physiologic concentrations (7-10 U/ml) of commercial recombinant cholesterol esterase or lipase will be conducted. HPLC-MS will be used determine rupture kinetics of these labile linkages across different conditions.

Like with the release of sodium channel blockers, successful delivery strategies are envisions that would entail release over the course of ~3-5 days with first-order release kinetics. Drug loading and controlled release from CB[7]-rich hydrogel will be established for the parent drugs, the dipivefrin analogue of epinephrine, and the proposed prodrug variants, and measured at physiologic pH and esterase concentrations in serum-containing media. Drug release will be quantified using HPLC-MS, and the impact of formulation parameters on release will be explored by changing the hydrogel concentration, density or availability of CB[7] (by blocking), and other design parameters. From here, experiments will be conducted in C57BL6J mice to determine release, local tissue concentration in vivo, and serum concentrations of drug and/or prodrug. Similar to the plan described of the sodium channel blockers, these studies will determine drug release and/or prodrug linker rupture and effective concentrations of each over the 3 days following implantation.

Two separate routes will be explored to include co-delivery of agents known to extend the activity of anesthetics and improve pain management outcomes. Additionally, a variety of other linkers, beyond the hydrazone and ester may be used, to render labile prodrugs for release from materials with altered kinetics or rates. The combination of both F127-encapsulated agent and CB[7]-bound prodrug agent may offer ideal first-order kinetics arising from dual-mode release with these materials, and can be additionally explored to tune the release kinetics.

Example 13: Pain Management following Surgical Incision

As the first exposure to opioids for many patients happens in the course of routine surgery, the design of formulations will be evaluated for use in the context of pain management in the acute post-surgical period. As such, the formulations are designed from a moldable and injectable thermo-responsive hydrogel that could be placed at the site of an incision or within deeper sites of surgical trauma. When in contact with tissue at physiologic temperature, this material adheres well to the tissue and remains in place with slow degradation and clearance over the course of weeks. Furthermore, promising biocompatibility of this material in preliminary studies supports its planned use here. It is important to note that to evaluate this material was chosen for use at the site of surgical trauma, in a manner similar to the procedure of local infiltration anesthesia. An alternative approach could seek to use the technology described herein for post-surgical pain management in a manner resembling regional anesthesia (e.g., a nerve block). In this case, injection of the formulations at proximal sites of innervating bundles would, in principle, enable prolonged drug action. However, in the context of outpatient use this approach may have unwanted complications of impaired motor function.

To assess performance of the envisioned technology in managing pain, an incisional model that mimics acute pain associated with surgery will be used. Plantar incision in rats and mice is especially common for these purposes, and studies in C3H mice will be performed to evaluate the performance of the hydrogel technology described herein. Formulations will be chosen from those that afford first order release kinetics over 3-5 days following implantation (t1/2~1-2 days) to correspond to the timeframe over which post-surgical pain must be managed, and which provide drug availability at a dose and a ratio between agents corresponding to clinical precedent for effective pain management. This timeframe also aligns with the model, where pain-related outcomes return to baseline within ~5-7 days following surgical incision. Formulations may include some of the most efficacious sodium channel blockers as determined in initial studies, and these will be evaluated with or without the addition of augmenting agents, as described above. The surgical model (FIG. 27) will be performed according to previously reported methods; a 5-mm longitudinal incision will be made through the skin, fascia, and muscle of the plantar foot. The incision will begin 2-mm from the proximal edge of the heel and extend toward the toe on the right hind-paw. Following incision, a volume of ~25-50 µl of the various hydrogel formulations will be applied by extrusion (not injection) with a syringe into the surgical wound. The wound will then be secured with a single mattress suture.

At serial time-points (2 h, 6 h, 12 h, 24 h, 2 d, 3 d, 4 d, 5 d) following incision and treatment, mice will be assessed for behavioral indicators of heightened pain sensation in the pedal tissue. The first method to assess pain threshold will be by punctate mechanical stimulation from calibrated von Frey filaments, which bend under a pre-determined normal force. A set of calibrated filaments offers accuracy over a range of applied stimuli in order to quantify mechano-sensitivity in animal models of pain as well as in human clinical sue. Mice will be placed on a wire support to enable access from below. In ascending order of bending force, von Frey filaments will then be applied sequentially to the foot immediately adjacent to the surgical incision site and pressure maintained for is. Stimuli-associated withdrawal of the foot will be considered a positive withdrawal response and five measurements will be collected from each mouse with each filament, with these measurements taken with 10 s spacing. Treatments will be assessed and compared on the basis of response frequency at each applied force (i.e., #withdrawals per 5 measurements per force). In this method, untreated mice with pedal incision respond to applied forces that are a fraction of what is needed for a response in a healthy mouse. Success of the treatment will be defined by a reduction in mechano-sensitivity (e.g., greater tolerance to applied force before withdrawal). The second method to assess pain threshold will be by radiant heat stimulation to measure withdrawal latency time in response to an applied thermal stimulus. In this case, mice will be placed on a heat-tempered glass floor, and from below will be subjected to a heat stimulus with a 50-W light source having a 6 mm aperture applied to the injured foot. Using a stopwatch, withdrawal latency, the amount of time before the mouse removes its foot from the applied heat source, will be measured to the nearest 0.1 s. In this method, untreated mice with pedal incision respond to applied heat much more rapidly does a healthy mouse. Success of the treatment will be defined by a reduction in thermal sensitivity (e.g., longer latency times upon applied heat before withdrawal). Control groups will include sham operated (healthy), operated with no treatment, and operated mice treated with systemic buprenorphine (a common veterinary opioid). At the endpoint of the study, tissue in the foot will be excised and analyzed by histology to study inflammation and cell-mediated tissue reaction. Signs of additional tissue damage attributable to the drug or material will also be monitored.

Example 14: Different Guest Molecules Support Hydrogel Formation with CB[7]

To explore the significance of affinity on dynamic properties of supramolecular hydrogels, monofunctional CB[7] with azide functional handles was used as described in Example 3 (FIG. 2A). From this synthetic macrocycle, 20 kDa 8-arm PEG macromers were then modified by "click" chemistry. This "click" reaction proceeds quantitatively, yielding $PEG_{8a}$-CB[7] macromers with ~100% of terminal groups converted to pendant CB[7]. In parallel, 8-arm PEG macromers were synthesized to present five different guests that were expected to offer $K_{eq}$ values over a broad range (FIG. 28A). The same 20 kDa 8-arm PEG macromers were modified with these guests using "click" chemistry or similar high-yielding conjugation reactions. Competition $^1$H NMR, was performed to determine the binding of CB[7] to model guests used for PEG modification in competition with groups of known $K_{eq}$. The guest with the lowest expected binding affinity ($PEG_{8a}$-N-Phe), mimicking an N-terminal phenylalanine, was determined by this method to bind with $K_{eq}$ of $1.5 \times 10^7$ $M^{-1}$. Another macromer was modified with an O-linked ferrocene ($PEG_{8a}$-O-Fc), with the binding of this group measured at $K_{eq}$ of $5.8 \times 10^8$ $M^{-1}$. The next modified macromer was prepared from a derivative of pxylylenediamine ($PEG_{8a}$-diN-Xyl), with its binding measured at $K_{eq}$ of $1.3 \times 10^9$ $M^{-1}$. To increase affinity, another macromere was modified with O-linked adamantane ($PEG_{8a}$-O-Ada) and its binding affinity measured at $K_{eq}$ of $2.6 \times 10^{10}$ $M^{-1}$. Finally, a high-affinity macromer was synthesized with an N-linked adamantane ($PEG_{8a}$-N-Ada), and its binding affinity measured at $K_{eq}$ of $5.4 \times 10^{12}$ $M^{-1}$. Hydrogels resulting from host-guest physical cross-linking by mixing each of these five guest macromers with $PEG_{8a}$-CB[7] will henceforth be abbreviated according to the magnitude of their $K_{eq}$ values: E7, E8, E9, E10, or E12.

Upon stoichiometric mixing (1:1 ratio of guest:CB[7]) of $PEG_{8a}$-CB[7] with the five guest-modified macromers at 5% (w/v) total solids in water, a self-supporting hydrogel formed in all cases (FIG. 28B). Dynamic oscillating rheology at 2% strain was then performed on each hydrogel to assess viscoelastic properties. In this study, $K_{eq}$ values for each guest translated to a shift in crossover between the storage modulus (G') and loss modulus (G"), a point known as the bulk relaxation rate. Hydrogel E7, E10, and E12 did not have G'-G" crossover within the observed frequency range. Specifically, the expected E7 crossover would occur at a frequency beyond the point where measurements break down due to inertia (>300 rad/s), while the expected G'-G" crossover frequency of E10 and E12 are below reasonable time constraints for experiments (<0.1 rad/s). Hydrogel E8 had G'-G" crossover at a frequency of 2.6 rad/s, corresponding to a bulk relaxation rate for this hydrogel of 0.42 Hz. Hydrogel E9 had a G'-G" crossover at a frequency of 0.25 rad/s, corresponding to a bulk relaxation rate of 0.04 Hz. Using these two crossover values as an approximation of $k_{off}$, as well as $K_{eq}$ values for each complex from competition $^1$H NMR studies, $k_{on}$ was estimated to be on the order of $1 \times 10^8$ $M^{-1}$ $s^{-1}$ for E8 and E9 hydrogels. Hydrogels from 5% (w/v) PEG macromers (~24-29 kDa) were in a semi-concentrated and unentangled regime in water, a theta solvent for PEG. Each PEG macromer also has a valency of 8 terminal groups. As such, $k_{on}$ values on the order of $1 \times 10^8$ $M^{-1}$ $s^{-1}$ more closely resemble a diffusion-governed bimolecular interaction between small molecules, rather than requiring macromolecular diffusion or translocation that may be the case for these macromers in a dilute regime, in a poor solvent, or when at lower valency. This was in line with other work showing polymer-appended guests binding to macrocycles with $k_{on}$ near the diffusion limit. Scaling frequency sweep data for the full range of cross-link affinity using $K_{eq}$ values calculated from $^1$H NMR studies and assuming $k_{on}$ of $1 \times 10^8$ $M^{-1}$ $s^{-1}$, the data exhibited a trend conforming to that with coordinatively crosslinked polymer networks. Furthermore, G' values for each hydrogel at their plateau (~5 kPa) were independent of $K_{eq}$, showing network topology for these hydrogels was independent of the choice of guest or its binding affinity to CB[7]. The E7, E8, and E9 hydrogels exhibited frequency-dependent G' behavior, a hallmark of supramolecular hydrogels. The E10 and E12 hydrogels, on the other hand, exhibited G' values that were frequency independent over the range examined, consistent with the typical behavior of covalent hydrogels.

Data from oscillating rheology were supported by measuring the stress relaxation modulus (FIG. 29A). The cross-link exchange dynamics, governed by binding affinity, are directly related to the ability of these materials to dissipate stress under applied strain. Cross-link interactions with lower affinity (higher dynamicity) should relax quickly as cross-links exchange and polymers flow to dissipate stress, whereas those with higher affinity should exhibit very slow relaxation as these cross-links take longer to reorganize. Indeed, a spectrum of hydrogel relaxation was observed. E7 hydrogels relaxed to dissipate stress in under 1 s while E12 hydrogels showed no evidence of relaxation over 1000 s. Here, E12 hydrogels behaved in a manner similar to covalent hydrogels by not dissipating stress over the course of experimental times. Over very long times, however, E12 hydrogels should still remain dynamic (i.e., creep); an order of magnitude approximation would suggest stress relaxation would be visualized by this technique in E12 hydrogels over ~$1 \times 10^4$ to $1 \times 10^5$ s (~3-30 h). However, over such times sample dehydration by solvent expulsion confounds the data.

One often noted benefit of host-guest supramolecular hydrogels in their application is a self-healing ability. A formed hydrogel would flow upon applied shear, such as extrusion through tubing or a syringe. Upon cessation of shear, these materials would reform instantly with complete recovery of their properties, exhibiting so-called shear-thinning, self-healing behavior. Most hydrogels of this class have shown such behavior. Step-strain experiments were conducted with multiple shearing cycles for E8, E9, E10, and E12 hydrogels (FIG. 29B). The change in G' with each shear-thinning cycle demonstrated that E8, E9, and E10 hydrogels undergo complete recovery following reduction in the shear rate. Interestingly, E12 hydrogels demonstrated a progressive decrease in recovered storage modulus following each successive round of shear-thinning. This may be attributed to the slow dynamics of host-guest interactions in these hydrogels combined with the stoichiometric proportion of host and guest. Once a host-guest interaction is broken in the process of shear-thinning, there are limited sites for interactions to reform due to the slow rate at which new sites become available. Thus, a broken cross-link effectively must find its previous binding site to restore full cross-linking in the hydrogel over short times. To explore self-healing differently, a full-thickness cut was made in E9, E10, and E12 hydrogels and the two pieces were contacted to allow healing, with a blue dye added to one piece to verify fluid contact (FIG. 29C). In E9 hydrogels, full defect healing occurred over the course of ~30 min. For E10 hydrogels, the defect between separated pieces was partially healed over a period of ~6-12 h, whereas E12 hydrogels did not heal the defect at all over 12 h and the two pieces could be easily separated along the original cut.

Gel formation kinetics in these hydrogels were also found to be tunable through the addition of a soluble competitor for CB[7] (FIG. 3D). Prior to mixing $PEG_{8a}$-CB[7] macromere with $PEG_{8a}$-N-Ada to make E12 hydrogels, stoichiometric pxylylenediamine (SM1, $K_{eq}=1.84\times10^9$ $M^{-1}$) or 1-adamantanol (SM2, $K_{eq}=2.3\times10^{10}$ $M^{-1}$) were added to "block" CB[7] on the $PEG_{8a}$-CB[7] macromer. The presence of this competitor slowed hydrogel formation at a rate directly related to its affinity. SM1-blocked CB[7] macromers formed hydrogels with previously observed G' values within hundreds of seconds of mixing with $PEG_{8a}$-N-Ada, while SM2-blocked CB[7] macromers formed hydrogels within thousands of seconds of mixing with $PEG_{8a}$-N-Ada. Ultimately, the high stability and slow $k_{off}$ of cross-links in the E12 hydrogel prevailed, but gelation was delayed according to the expected $k_{off}$ of a competing soluble guest. Without a competitor, E12 hydrogels form instantly with no kinetic evolution in the modulus measurable by this technique.

The controlled release of encapsulated macromolecules was dependent on cross-link affinity (FIG. 30A). The release of 70 kDa dextran encapsulated within E9 hydrogels was significantly faster than that from E10 hydrogels, which had slow release over 200+ hours. Meanwhile, E12 hydrogels showed limited release, with a plateau reached following a small initial burst. Release from these hydrogels was likely due to Fickian diffusion coupled with hydrogel swelling and erosion; the latter occurred to a much greater extent for E9 hydrogels, which eroded completely within 6 days, than for E10 or E12 (FIG. 30B). In addition, there would be less steric entrapment within more dynamic networks as cross-links rearrange to allow for the passage and eventual release of confined macromolecules in hydrogels prepared from lower affinity cross-links. Fitting release data to the Korsmeyer-Peppas model, Fickian diffusion was the prevailing mechanism at higher affinity, whereas the E9 hydrogels (n>0.5) had release governed by anomalous mechanisms (e.g., swelling and erosion) instead of pure diffusion.

The impact of cross-link affinity was also explored in the context of applying these hydrogels as injectable biomaterials. For these studies, E7 hydrogels were compared to E10 hydrogels, as this was the maximum range possible in order to explore the impact of affinity with materials that reform into continuous bulk hydrogels following injection. Mice were injected subcutaneously with both E7 and E10 hydrogels, one on each side of the dorsal flank. The skin and implant bed were examined serially by necropsy, and tissue was harvested for histological assessment (FIG. 30C). Both E7 and E10 hydrogels persisted in the tissue for the duration of the 30 day study, though over time the apparent volume of E7 hydrogels decreased. The E7 hydrogel also became increasingly opaque, suggesting cellular infiltration. The apparent volume of the E10 hydrogel did not change noticeably with implant time, and the hydrogel remained transparent for the full 30 day study. Hydrogels were then analyzed by histology. Cell infiltration into E7 hydrogel began by the first time evaluated, 5 days, and by 10 days the hydrogel was completely infiltrated with cells. The cell-infiltrated gel bed decreased in volume over the remainder of the study. During the early stages following implant, the gel was primarily infiltrated with neutrophils. At later times, the fraction of macrophages within the hydrogel increased and many of these cells were found to have internalized portions of the E7 hydrogel. The E10 hydrogel, in contrast, excluded cells at early times; neutrophils were found at very high density at the gel margins at 5 days, indicating mild inflammation of the implant bed. By 10 days, signs of inflammation subsided. The E10 hydrogel had a much larger volume apparent by histology, and remained completely uninfiltrated by cells until 30 days when the margins showed signs of some infiltration into the hydrogel network. Importantly, even though these hydrogels were not infiltrated or cleared, there was no sign of the typical fibrotic foreign body reaction seen for many nondegradable materials. Taken together, more dynamic host-guest cross-linking in these materials corresponded to more extensive cell infiltration and accelerated hydrogel clearance, whereas materials with slowly dynamic cross-links primarily excluded infiltrating cells and were not substantially cleared from the implant bed over 30 days of implantation.

The impact of affinity on the network properties of supramolecular hydrogels is of great interest, yet the vast majority of supramolecular interactions explored to date do not enable the study of a broad range of affinity, nor study of particularly high affinity interactions. The remarkable range of affinities possible from CB[7] recognition of different guest chemistries has been leveraged here to achieve hydrogels with nearly identical composition and network topology, yet with dynamic properties spanning over 5 orders of magnitude. The range of dynamic relaxation rates achieved by this approach surpasses that reported for methods to create tunably dynamic polymeric (~1-2 orders of magnitude) and recombinant (~4 orders of magnitude) materials. Altering affinity, and by extension relaxation rates, furthermore leads to interesting properties in the application of these materials. As such, this method to create dynamic hydrogel materials offers a useful tool in the pursuit of biomimetic and bioinspired synthetic materials.

For reasons of completeness, various aspects of the invention are set out in the following numbered clauses:

Clause 1. A thermoresponsive hydrogel comprising
a cucurbit[n]uril moiety, wherein n is an integer from 5-8; and
a polymer,
wherein the thermoresponsive hydrogel has a gelation temperature between 25° C. and 35° C.

Clause 2. A thermoresponsive hydrogel of clause 1, wherein n is 7.

Clause 3. The thermoresponsive hydrogel of clause 1 or clause 2, wherein the polymer is a first polymer and the thermoresponsive hydrogel comprises a second polymer.

Clause 4. The thermoresponsive hydrogel of any one of clauses 1-3, wherein the first polymer comprises a thermoresponsive polymer.

Clause 5. The thermoresponsive hydrogel of clause 4, wherein the thermoresponsive polymer comprises a plurality of thermoresponsive conjugates, wherein each thermoresponsive conjugate comprises at least one cucurbit[n]uril moiety linked to the thermoresponsive polymer.

Clause 6. The thermoresponsive hydrogel of clause 5, wherein the plurality of thermoresponsive conjugates forms micelles.

Clause 7. The thermoresponsive hydrogel of clause 5 or clause 6, wherein the thermoresponsive conjugate has a critical micelle temperature between 20° C. and 35° C.

Clause 8. The thermoresponsive hydrogel of any one of clauses 5-7, wherein each thermoresponsive conjugate comprises two cucurbit[n]uril moieties.

Clause 9. The thermoresponsive hydrogel of any one of clauses 5-8, wherein the second polymer is configured to bind the cucurbit[n]uril moiety.

Clause 10. The thermoresponsive hydrogel of any one of clauses 5-9, wherein the second polymer comprises at least one functional group configured to bind the cucurbit[n]uril moiety.

Clause 11. The thermoresponsive hydrogel of clause 10, wherein the at least one functional group is selected from the group consisting of ferrocene, phenylalanine, xylylenediamine, adamantane, and combinations thereof.

Clause 12. The thermoresponsive hydrogel of clause 10 or clause 11, wherein the at least functional group is ferrocene.

Clause 13. The thermoresponsive hydrogel of any one of clauses $10^{-12}$, wherein the thermoresponsive hydrogel comprises a ratio of the cucurbit[n]uril moiety to the at least functional group of between 1:1 and 3:1.

Clause 14. The thermoresponsive hydrogel of any one of clauses 5-13, wherein the thermoresponsive hydrogel comprises 1 to 20% by weight total solids of the cucurbit[n]uril moiety, the first polymer, and the second polymer.

Clause 15. The thermoresponsive hydrogel of clause 4, wherein the thermoresponsive polymer is configured to bind the cucurbit[n]uril moiety.

Clause 16. The thermoresponsive hydrogel of clause 15, wherein the thermoresponsive polymer comprises at least one functional group configured to bind the cucurbit[n]uril moiety.

Clause 17. The thermoresponsive hydrogel of clause 16, wherein the at least one functional group is selected from the group consisting of ferrocene, phenylalanine, xylylenediamine, adamantane, and combinations thereof.

Clause 18. The thermoresponsive hydrogel of any one of clauses 15-17, wherein the thermoresponsive polymer forms micelles.

Clause 19. The thermoresponsive hydrogel of any of clauses 15-18, wherein the second polymer is conjugated to at least one cucurbit[n]uril moiety.

Clause 20. The thermoresponsive hydrogel of any one of clauses 4-19, wherein the thermoresponsive polymer comprises a block copolymer of polyethylene oxide (PEO) and polypropylene oxide (PPO).

Clause 21. The thermoresponsive hydrogel of clause 20, wherein the block copolymer has a triblock copolymer formula of $(PEO)_a(PPO)_b(PEO)_a$, wherein a is an integer between 20 and 200 and b is an integer between 50 and 100.

Clause 22. The thermoresponsive hydrogel of clause 21, wherein a has an average value of approximately 100 and b has an average value of approximately 65.

Clause 23. The thermoresponsive hydrogel of any one of clauses 3-23, wherein the second polymer is branched.

Clause 24. The thermoresponsive hydrogel of any one of clauses 3-24, wherein the second polymer comprises a multi-arm polyethylene glycol.

Clause 25. A drug delivery system comprising: a thermoresponsive hydrogel of any one of clauses 1-24; and at least one therapeutic agent reversibly bound to the thermoresponsive hydrogel.

Clause 26. The drug delivery system of clause 25, wherein the at least one therapeutic agent is coupled to a guest ligand with a labile linker.

Clause 27. The drug delivery system of clause 26, wherein the guest ligand is reversibly bound to the cucurbit[n]uril moiety of the thermoresponsive hydrogel.

Clause 28. The drug delivery system of clause 27, wherein the guest ligand has an affinity of greater than $10^{10}$ M for the cucurbit[n]uril moiety.

Clause 29. The drug delivery system of any one of clauses 26-28, wherein the guest ligand is selected from the group consisting of ferrocene, phenylalanine, xylylenediamine, adamantane, and combinations thereof.

Clause 30. The drug delivery system of any one of clauses 26-39, wherein the labile linker comprises an ethylene glycol moiety, a hydrazone moiety, an ester moiety, a imine moiety, a cis-aconityl moiety, an ether moiety, a peptide, a disulfide moiety, a thioester moiety, an oxime moiety, a carbonate moiety, an amide moiety, an orthoester moiety, a urethane moiety, an anhydride moiety, an acetal moiety, or a ketal moiety, and wherein the therapeutic agent is released from the drug delivery device by hydrolysis of the labile linker, metabolism of the labile linker, or a combination thereof.

Clause 31. The drug delivery system of any one of clauses 26-30, wherein the labile linker has a rate of hydrolysis or a rate of metabolism greater than the off-rate of the guest ligand bound to the thermoresponsive hydrogel.

Clause 32. The drug delivery system of any one of clauses 25-31, wherein the at least one therapeutic agent is an anti-cancer drug, an anti-infective drug, an anti-inflammatory drug, an analgesic, a cardiovascular drug, a tissue regenerating drug, an anti-diabetic drug, a vaccine antigen, a peptide, a protein, an ocular drug, or a nanoparticle formulation, or a combination thereof.

Clause 33. The drug delivery system of any one of clauses 25-32, where in the at least one therapeutic agent is an anti-cancer drug, an analgesic, an anti-inflammatory drug, or a combination thereof.

Clause 34. The drug delivery system of clause 32 or clause 33, wherein the analgesic is a sodium channel blocking analgesic selected from the group consisting of lidocaine, etidocaine, prilocaine, bupivacaine, ropivacaine, chinchocaine, trimecaine, procaine, proxymetacaine, chloroprocaine, piperocaine, cyclomethycaine, tetracine dimethocaine, propxycaine, or a combination thereof.

Clause 35. The drug delivery system of clause 32 or clause 33, where in the anti-cancer drug is doxorubicin.

Clause 36. The drug delivery system of clause 32 or clause 33, where in the anti-inflammatory drug is epinephrine or dexamethasone.

Clause 37. A kit comprising: a thermoresponsive hydrogel of any one of clauses 1-24; and at least one therapeutic agent.

Clause 38. The kit of clause 37, wherein the at least one therapeutic agent is selected from an anti-cancer drug, an anti-infective drug, an anti-inflammatory drug, an analgesic, a cardiovascular drug, a tissue regenerating drug, an anti-diabetic drug, a vaccine antigen, a peptide, a protein, an ocular drug, or a nanoparticle formulation, or a combination thereof.

Clause 39. The kit of clause 37 or clause 38, wherein the therapeutic agent is capable of reversibly binding to the thermoresponsive hydrogel.

Clause 40. The kit of any one of clauses 37-39, wherein the at least one therapeutic agent is coupled to a guest ligand with a labile linker, wherein the guest ligand is capable of binding to the cucurbit[n]uril moiety of the thermoresponsive hydrogel.

Clause 41. The kit of any one of clauses 37-40, wherein the guest ligand is selected from the group consisting of ferrocene, phenylalanine, xylylenediamine, adamantane, and combinations thereof.

Clause 42. The kit of any one of clauses 37-41, wherein the labile linker comprises an ethylene glycol moiety, a hydrazone moiety, an ester moiety, a imine moiety, a cis-aconityl moiety, an ether moiety, a peptide, a disulfide moiety, a thioester moiety, an oxime moiety, a carbonate moiety, an amide moiety, an orthoester moiety, a urethane moiety, an anhydride moiety, an acetal moiety, or a ketal moiety, and wherein the therapeutic agent is released from the drug delivery device by hydrolysis of the labile linker, metabolism of the labile linker, or a combination thereof.

Clause 43. A method for treating a disease or disorder in a subject in need thereof, the method comprising implanting the thermoresponsive hydrogel of any one of clauses 1-24 at a desired location in a subject; administering at least one dose of a first therapeutic agent to the subject, wherein the first therapeutic agent reversibly binds to the thermoresponsive hydrogel.

Clause 44. The method of clause 43, wherein the thermoresponsive hydrogel is implanted by injection.

Clause 45. The method of clause 43 or clause 44, wherein the first therapeutic agent is administered systemically.

Clause 46. The method of any one of clauses 43-45, wherein the first therapeutic agent is an anti-cancer drug, an anti-infective drug, an anti-inflammatory drug, an analgesic, a cardiovascular drug, a tissue regenerating drug, an anti-diabetic drug, a vaccine antigen, a peptide, a protein, an ocular drug, or a nanoparticle formulation.

Clause 47. The method of any one of clauses 43-46, wherein the first therapeutic agent is coupled to a guest ligand with a labile linker, wherein the guest ligand binds to the cucurbit[n]uril moiety of the thermoresponsive hydrogel.

Clause 48. The method of clause 47, wherein guest ligand has an affinity of greater than $10^{10}$ M for the cucurbit[n]uril moiety.

Clause 49. The method of clause 47 or clause 48, wherein the guest ligand is selected from the group consisting of ferrocene, phenylalanine, xylylenediamine, and adamantane.

Clause 50. The method of any one of clauses 47-49, wherein the labile linker comprises an ethylene glycol moiety, a hydrazone moiety, an ester moiety, a imine moiety, a cis-aconityl moiety, an ether moiety, a peptide, a disulfide moiety, a thioester moiety, an oxime moiety, a carbonate moiety, an amide moiety, an orthoester moiety, a urethane moiety, an anhydride moiety, an acetal moiety, or a ketal moiety, and wherein the first therapeutic agent is released from the drug delivery device by hydrolysis of the labile linker, metabolism of the labile linker, or a combination thereof.

Clause 51. The method of any one of clauses 47-50, wherein the labile linker has a rate of hydrolysis or a rate of metabolism greater than the off-rate of the guest ligand bound to the thermoresponsive hydrogel.

Clause 52. The method of any one of clauses 43-51, further comprising administering at least one dose of a second therapeutic agent to the subject, wherein the second therapeutic agent reversibly binds to the thermoresponsive hydrogel.

Clause 53. The method of clause 52, wherein the second therapeutic agent is administered systemically.

Clause 54. The method of any one of clauses 43-53, wherein the disease or disorder is cancer.

Clause 55. The method of clause 54, wherein the first therapeutic agent is an anti-cancer drug.

Clause 56. The method of clause 55, wherein the anti-cancer drug is doxorubicin.

Clause 57. The method of any one of clauses 54-56, wherein the cancer is a solid tumor.

Clause 58. The method of any one of clauses 54-57, wherein the desired location is proximal to the solid tumor.

Clause 59. A refillable drug delivery device comprising: a biocompatible substrate covalently modified with a plurality of supramolecular hosts and a prodrug comprising an active pharmaceutical ingredient (API) tethered via a labile linker to a guest ligand having a binding affinity for a supramolecular host of the biocompatible substrate, wherein the prodrug reversibly binds via the guest ligand to the supramolecular host of the biocompatible substrate, thereby forming the refillable drug delivery device.

Clause 60. The device of clause 59 wherein the supramolecular host comprises a cucurbit[n]uril, wherein n is 5 to 8.

Clause 61. The device of clause 59 wherein the labile linker comprises an ethylene glycol moiety, a hydrazone moiety, an ester moiety, a imine moiety, a cis-aconityl moiety, an ether moiety, a peptide, a disulfide moiety, a thioester moiety, an oxime moiety, a carbonate moiety, an amide moiety, an orthoester moiety, a urethane moiety, an anhydride moiety, an acetal moiety, or a ketal moiety, and wherein the API is released from the drug delivery device by hydrolysis of the labile linker, metabolism of the labile linker, or a combination thereof.

Clause 62. The device of clause 59 wherein the rate of hydrolysis or the rate of metabolism of the labile linker is less than the off-rate of the guest ligand reversibly bound to a supramolecular host on the biocompatible substrate.

Clause 63. The device of clause 59 wherein the guest ligand comprises a ferrocene moiety or a adamantane moiety.

Clause 64. The device of clause 59 wherein the biocompatible substrate comprises a polymer, gel, metal, nucleoside, protein, ceramic, glass, cell, tissue, or combination thereof.

Clause 65. A method of delivering an active pharmaceutical ingredient (API) in vivo comprising: implanting within a subject in need thereof a biocompatible substrate covalently modified with a plurality of cucurbit

[n]uril hosts; and administering to the subject a prodrug comprising an API tethered via a labile linker to a guest ligand having a binding affinity for a cucurbit[n]uril host of the biocompatible substrate; wherein the prodrug circulates systemically in the subject and reversibly binds via the guest ligand to fill or refill the cucurbit[n]uril host of the biocompatible substrate, thereby forming a refillable drug delivery device within the subject, wherein the device subsequently releases the API via the labile linker.

Clause 66. The method of clause 65 wherein the refillable drug delivery device is refilled by a subsequent administration of the prodrug.

Clause 67. The method of clause 65 or clause 66 wherein one or more different prodrugs are administered.

Clause 68. The method of clauses 65-68 wherein the biocompatible substrate is implanted by injection and the prodrug comprises an anti-cancer drug, an anti-infective drug, an anti-inflammatory drug, a cardiovascular drug, a tissue regenerating drug, an anti-diabetic drug, a vaccine antigen, a peptide, a protein, an ocular drug, or a nanoparticle formulation.

What is claimed is:

1. A drug delivery system comprising:
   a thermoresponsive hydrogel comprising a cucurbit[n]uril moiety, wherein n is an integer from 5-8, and a first polymer, wherein the first polymer comprises a thermoresponsive polymer, the thermoresponsive polymer comprising a block copolymer of polyethylene oxide (PEO) and polypropylene oxide (PPO), and wherein the thermoresponsive hydrogel has a gelation temperature between 25° C. and 35° C.; and
   at least one therapeutic agent reversibly bound to the thermoresponsive hydrogel.

2. The drug delivery system of claim 1, wherein the at least one therapeutic agent is coupled to a guest ligand with a labile linker.

3. The drug delivery system of claim 2, wherein the guest ligand is reversibly bound to the cucurbit[n]uril moiety of the thermoresponsive hydrogel.

4. The drug delivery system of claim 3, wherein the guest ligand has an affinity of greater than $10^{10}$ $M^{-1}$ for the cucurbit[n]uril moiety.

5. The drug delivery system of claim 2, wherein the guest ligand is selected from the group consisting of ferrocene, phenylalanine, xylylenediamine, adamantane, and combinations thereof.

6. The drug delivery system of claim 2, wherein the labile linker comprises an ethylene glycol moiety, a hydrazone moiety, an ester moiety, a imine moiety, a cis-aconityl moiety, an ether moiety, a peptide, a disulfide moiety, a thioester moiety, an oxime moiety, a carbonate moiety, an amide moiety, an orthoester moiety, a urethane moiety, an anhydride moiety, an acetal moiety, or a ketal moiety, and wherein the therapeutic agent is released from the drug delivery device by hydrolysis of the labile linker, metabolism of the labile linker, or a combination thereof.

7. The drug delivery system of claim 2, wherein the labile linker has a rate of hydrolysis or a rate of metabolism greater than the off-rate of the guest ligand bound to the thermoresponsive hydrogel.

8. The drug delivery system of claim 1, wherein the at least one therapeutic agent is an anti-cancer drug, an anti-infective drug, an anti-inflammatory drug, an analgesic, a cardiovascular drug, a tissue regenerating drug, an anti-diabetic drug, a vaccine antigen, a peptide, a protein, an ocular drug, or a nanoparticle formulation, or a combination thereof.

9. The drug delivery system of claim 1, wherein the at least one therapeutic agent is an anti-cancer drug, an analgesic, an anti-inflammatory drug, or a combination thereof.

10. The drug delivery system of claim 8, wherein the analgesic is a sodium channel blocking analgesic selected from the group consisting of lidocaine, etidocaine, prilocaine, bupivacaine, ropivacaine, chinchocaine, trimecaine, procaine, proxymetacaine, chloroprocaine, piperocaine, cyclomethycaine, tetracine dimethocaine, propxycaine, or a combination thereof.

11. The drug delivery system of claim 8, wherein the anti-cancer drug is doxorubicin.

12. The drug delivery system of claim 8, wherein the anti-inflammatory drug is epinephrine or dexamethasone.

13. The drug delivery system of claim 1, wherein n is 7.

14. The drug delivery system of claim 7, wherein the thermoresponsive hydrogel comprises a second polymer.

15. The drug delivery system of claim 1, wherein the thermoresponsive polymer comprises a plurality of thermoresponsive conjugates, wherein each thermoresponsive conjugate comprises at least one cucurbit[n]uril moiety linked to the thermoresponsive polymer.

16. The drug delivery system of claim 15, wherein the plurality of thermoresponsive conjugates forms micelles.

17. The drug delivery system of claim 15, wherein the thermoresponsive conjugate has a critical micelle temperature between 20° C. and 35° C.

18. The drug delivery system of claim 15, wherein each thermoresponsive conjugate comprises two cucurbit[n]uril moieties.

19. The drug delivery system of claim 15, wherein the second polymer is configured to bind the cucurbit[n]uril moiety.

20. The drug delivery system of claim 15, wherein the second polymer comprises at least one functional group configured to bind the cucurbit[n]uril moiety.

21. The drug delivery system of claim 1, wherein the at least one functional group is selected from the group consisting of ferrocene, phenylalanine, xylylenediamine, adamantane, and combinations thereof.

22. The drug delivery system of claim 20, wherein the at least one functional group is ferrocene.

23. The drug delivery system of claim 20, wherein the thermoresponsive hydrogel comprises a ratio of the cucurbit[n]uril moiety to the at least one functional group of between 1:1 and 3:1.

24. The drug delivery system of claim 15, wherein the thermoresponsive hydrogel comprises 1 to 20% by weight total solids of the cucurbit[n]uril moiety, the first polymer, and the second polymer.

25. The drug delivery system of claim 14, wherein the thermoresponsive polymer is configured to bind the cucurbit[n]uril moiety.

26. The drug delivery system of claim 25, wherein the thermoresponsive polymer comprises at least one functional group configured to bind the cucurbit[n]uril moiety.

27. The drug delivery system of claim 26, wherein the at least one functional group is selected from the group consisting of ferrocene, phenylalanine, xylylenediamine, adamantane, and combinations thereof.

28. The drug delivery system of claim 25, wherein the thermoresponsive polymer forms micelles.

29. The drug delivery system of claim 25, wherein the second polymer is conjugated to at least one cucurbit[n]uril moiety.

30. The drug delivery system of claim 1, wherein the block copolymer has a triblock copolymer formula of (PEO)$_a$(PPO)$_b$(PEO)$_a$, wherein a is an integer between 20 and 200 and b is an integer between 50 and 100.

31. The drug delivery system of claim 30, wherein a has an average value of approximately 100 and b has an average value of approximately 65.

32. The drug delivery system of claim 14, wherein the second polymer is branched.

33. The drug delivery system of claim 14, wherein the second polymer comprises a multi-arm polyethylene glycol.

\* \* \* \* \*